US009296998B2

(12) United States Patent
Unkefer et al.

(10) Patent No.: US 9,296,998 B2
(45) Date of Patent: Mar. 29, 2016

(54) NUCLEIC ACIDS ENCODING PLANT GLUTAMINE PHENYLPYRUVATE TRANSAMINASE (GPT) AND USES THEREOF

(71) Applicants: Los Alamos National Security, LLC, Los Alamos, NM (US); University of Maine System Board of Trustees, Bangor, ME (US)

(72) Inventors: Pat J. Unkefer, Los Alamos, NM (US); Penelope S. Anderson, Los Alamos, NM (US); Thomas J. Knight, Raymond, ME (US)

(73) Assignees: Los Alamos National Security, LLC, Los Alamos, NM (US); University of Maine System Board of Trustees, Bangor, ME (US)

( * ) Notice: Subject to any disclaimer, the term of this patent is extended or adjusted under 35 U.S.C. 154(b) by 180 days.

(21) Appl. No.: 13/734,688

(22) Filed: Jan. 4, 2013

(65) Prior Publication Data
US 2013/0198908 A1 Aug. 1, 2013

Related U.S. Application Data

(63) Continuation of application No. 12/660,506, filed on Feb. 26, 2010, now abandoned, which is a continuation-in-part of application No. 12/551,193, filed on Aug. 31, 2009, now abandoned.

(60) Provisional application No. 61/190,520, filed on Aug. 29, 2008, provisional application No. 61/190,581, filed on Aug. 29, 2008.

(51) Int. Cl.
*C12N 15/82* (2006.01)
*C12N 9/10* (2006.01)

(52) U.S. Cl.
CPC ............ *C12N 9/1096* (2013.01); *C12N 15/827* (2013.01); *C12N 15/8261* (2013.01); *C12N 15/8262* (2013.01); *C12N 15/8269* (2013.01); *C12N 15/8273* (2013.01); *C12Y 206/01064* (2013.01)

(58) Field of Classification Search
None
See application file for complete search history.

(56) References Cited

U.S. PATENT DOCUMENTS 6,084,153 A * 7/2000 Good et al. ................... 800/290
6,486,384 B1 * 11/2002 Zhang et al. .................. 800/293

OTHER PUBLICATIONS

Suzuki et al. GenBank Accession No. AB206815, Sep. 14, 2006, Hordeum vulgare IDI4 mRNA for putative asparate aminotransferase, complete cds.*
Suzuki et al. GenBank Accession No. AB206815, Sep. 14, 2006, Hordeum vulgare 1014 mRNA for putative asparate aminotransferase, complete cds.

* cited by examiner

*Primary Examiner* — Cynthia Collins
(74) *Attorney, Agent, or Firm* — Kilpatrick Townsend & Stockton LLP

(57) ABSTRACT

Glutamine phenylpyruvate transaminase (GPT) proteins, nucleic acid molecules encoding GPT proteins, and uses thereof are disclosed. Provided herein are various GPT proteins and GPT gene coding sequences isolated from a number of plant species. As disclosed herein, GPT proteins share remarkable structural similarity within plant species, and are active in catalyzing the synthesis of 2-hydroxy-5-oxoproline (2-oxoglutaramate), a powerful signal metabolite which regulates the function of a large number of genes involved in the photosynthesis apparatus, carbon fixation and nitrogen metabolism.

23 Claims, 33 Drawing Sheets

```
Hordeum           ----------------------------------------------------------MASAPAS
RICE              ------MNLAGFLATPATATATRHEMPLNPSSSASFLLSSLRRSLVASLRKASPAAAAALS
Zea_mays          ---------MNLAAFSSTLATLPWYEMPSINSSATFSSSLLRRSLCASLRTISHMASAAAP
Cotton            MQAAECTWTHFEMLRPLCFKSPSTTPLFFNFSKHFQKGFSDSSFFRSNRRISNYPSFMAT
GRAPE             ----------------MQLSQCTWTFPELLKRPAFLRRSIDSISSRSRSSSKYPSFMA-
Ricinus_communi   --MQSQCTWTGTRMPLPIILKPSTFSILKHLPTKRTNLFSTRSPISNYPSLMATFSTA--
POPULUS_TRICHOC   ----------------------------------------------------------MAS--
soybean           -------------------------MKFTPSSKFLGFSNHFHSLLAPSFSPTPKFS
Danio_rerio       ------------------------------------------------------------
arabidopsis       ---------------------------MYLDINGVMIKQFSFKASLLPFSSNFRQSSA
Physcomitrella_   -------------------------------------------------------MAS
Chlamy            ------------------------------------------------------------
consensus         ------------------------------------------------------------

Hordeum           ASAALSTAAP---ADNGAAKPTEQRPVQVAKRLEKFKTTIFTQMSMLAVKHGAINLGQGF
RICE              PMASASTVAAENGAAKGAAEKQQQQPVQVAKRLEKFKTTIFTQMSMLAIKHGAINLGQGF
Zea_mays          TSAPVATTE------NGAAKAIEQRPVQVAERLEKFKTTIFTQMSMLAIKHGAINLGQGF
Cotton            ISSLSTHKDPVS--THDATPNITHQPVQVAKRLEKFKTTIFTQMSMLAIKHGAINLGQGF
GRAPE             --SASTVSAPNT--EAEQTHNPPQPLQ-VAKRLEKFKTTIFTQMSMLAIKHGAINLGQGF
Ricinus_communi   --STTEKDAPSG--QNDSTQKSQQPLQ-VAKRLEKFKTTIFTQMSSLAIKHGAINLGQGF
POPULUS_TRICHOC   --SPSLKDAVST--QNESTQKTQQPLQ-VAKRLEKFKTTIFTQMSSLAIKHGAINLGQGF
soybean           SSFSATMSTLST--QNDTVTHKTQQPLQIAKRLEKFQTTIFTQMSLLAIKHGAINLGQGF
Danio_rerio       ----------------------VAKRLEKFKTTIFTQMSMLAIKHGAINLGQGF
arabidopsis       -KIHRPIGATMT--TVSTQNESTQKPVQVAKRLEKFKTTIFTQMSILAVKHGAINLGQGF
Physcomitrella_   LSLSINGVAQES--AMPASQNSDPPRVQVAKRLEQFKTTIFTEISILASKHNAINLGQGF
Chlamy            ----------MAPPPEAGATAAAEPSKPLNELFSSLPTTLFEVMSKLAMEHASVNLGQGF
consensus         -------------------------vakrlekfkTTIFtqmS-LA-kHgaiNLGQGF Hordeum           PNFDGPDFVKDAAIEAIKAGKNQ-YARGYGVPELNSAVAERFLKDSGLHIDPDKEVTVTS
RICE              PNFDGPDFVKEAAIQAINAGKNQ-YARGYGVPELNSAIAERFLKDSGLQVDPEKEVTVTS
Zea_mays          PNFDGPDFVKEAAIQAINAGKNQ-YARGFGVPELNSAIAERFLKDSGLQVDPDKEVTVTS
Cotton            PNFDGPDFVKGAAIQAIKDGKNQ-YARGYGVPDFNNAIAARFKKDTGLVIDPEKEVTVTS
GRAPE             PNFDGPEFVKEAAIQAIKDGKNQ-YARGYGVAVADRFKKDTGLVVDPEKEVTVTS
Ricinus_communi   PNFDGPEFVKEAAIQAIRDGKNQ-YARGYGVPDFNSAIVDRFKKDTGLVVDPEKEVTVTS
POPULUS_TRICHOC   PNFDGPEFVKEAAIQAIKDGKNQ-YARGYGVPDFSSAIAERFKKDTGLVVDPEKEITVTS
soybean           PNFDGPEFVKEAAIQAIRDGKNQ-YARGYGVPDLNIAIAERFKKDTGLVVDPEKEITVTS
Danio_rerio       PNFDGPDFVKEAAIQAIRDGNNQ-YARGYGVPDLNIAISERYKKDTGLAVDPEKEITVTS
arabidopsis       PNFDGPDFVKEAAIQAIKDGKNQ-YARGIPQLNSAIAARFREDTGLVVDPEKEVTVTS
Physcomitrella_   PNFDGPEFVKNAAIEAIRDGGKNQYARGFGVPQLNAAIAESFNKESGIVVDPETHVTVTS
Chlamy            PDAEGPEAMKQIAS-ASMYDFHNQIPSLLGVPELRQAVAAHSEREQGILVDWATETLIRV
consensus         PnfdGP-fvK-aAi-Ai--g-nq-Yarg-GvP--n-A-a-rf-kd-Gl-vDp-ke-tvTs Hordeum           GCTEAIRATILGLINPGDEVILFAPFYDSYEATLSMAGANVKAITLRPPDFAVPLEELKA
RICE              GCTEAIAATILGLINPGDEVLLFAPFYDSYEATLSMAGANVKAITLRPPDFSVPLEELKA
Zea_mays          GCTEAIAATILGLINPGDEVLLFAPFYDSYEATLSMAGANVKAITLRAPDFAVPLEELEA
Cotton            GCTEAIAATMLGLINPGDEVILFAPFYDSYEATLSMAGAKVKCITLCPPDFAVPIDELKS
GRAPE             GCTEAIAATMLGLINPGDEVILFAPFYDSYEATLSMAGAQIKSITLRPPDFAVMDELKS
Ricinus_communi   GCTEAIAATILGLIDPGDEVLLFAPFYDSYEATLSMAGAKIKCVTLQPPDFAVPIDELKS
POPULUS_TRICHOC   GCTEAIAATMLGLINPGDEVILFAPFYDSYEATLSMAGAKIKCITLHPPDFAVPIDELKS
soybean           GCTEAIAATMIGLINPGDEVIMFAPFYDSYEATLSMAGAKVKGITLRPPDFAVPLEELKS
Danio_rerio       GCTEAIAATVLGLINPGDEVIVFAPFYDSYEATLSMAGAKVKGITLRPPDFALFIEELKS
arabidopsis       GCTEAIAAMLGLINPGDEVILFAPFYDSYEATLSMAGAKVKGITLRPPDFSIPLEELKA
Physcomitrella_   GCTEAIAATVLGLVNPGDEIIVFEPFYDSQATVSMSGAILKTVTMRAPEFAVPEEELRA
Chlamy            GATEGLASAFLGLINPGDEVIMFDPMYDSITSMAKRSGAVIVPVRLRLPDFSVPLEELAA
consensus         GcTEaiaat-lGLinPGDEvI-FaPfYDSYeatlsmaGA--k--tl--PdF-vP--EL--

Hordeum           AVSKNTRAIMINTPHNPTGKMFTREELEFIADLCKENDVLLFADEVIDKLAFEADHISM-
RICE              AVSKNTRAIMINTPHNPTGKMFTREELEFIATLCKENDVLLFADEVIDKLVFEADHISM-
Zea_mays          AVSKDTKAIMINTPHNPTGKMFTREELESIAALCKENDVLLFSDEVIDKLVFEADHISM-
Cotton            TISKNTRAILINTPHNPTGKMFTREELNTIASLCIENDVLFTDEVIDKLAFEMDHISM-
GRAPE             AISKNTRAILINTPHNPTGKMFTREELNVIASLCIENDVLFTDEVIDKLAFEMDHISM-
Ricinus_communi   IISKNTRAILINTPHNPTGKMFTREELTTIASCCIENDVLFTDEVIDKLAFEMDHISM-
POPULUS_TRICHOC   AITQDTRAVLINTPHNPTGKMFSREELSTIASREELDHISM-
soybean           TISKNTRAILINTPHNPTGKMFTREELNCIASLCIENDVLFTDEVIDKLAFDMEHISM-
Danio_rerio       TISKNTRAILLNTPHNPTGKMFTPEELNTIASLCIENDVLFSDEVIDKLAFDMEHISI-
arabidopsis       AVTNKTRAILMNTPHNPTGKMFTREELETIASLCIENDVLVFSDEVIDKLAFEMDHISI-
Physcomitrella_   AFSSKTRAILVNTPHNPTGKVFPRHELELIASLCKEHNTLAFCDEVINKLVFKGEHVSL-
Chlamy            AVTPRTKMIMINTPHNPSGKVFTRPELEAIAELCVRHDLIALSDEVIEHLVFGGAAHVSL
consensus         -----Trai--NTPHNPtGKmFtreEL--IA-lC-endvl-f-DEVydkL-F---his--
```

FIG. 2

```
Hordeum              ASIPGMYERTVTMNSLGKTFSLTGWKIGWAIAPPHLTWGVRQAHSFLTFATSTPMQSAAA
RICE                 ASIPGMYERTVTMNSLGKTFSLTGWKIGWAIAPPHLTWGVRQAHSFLTFATCTPMQAAAA
Zea_mays             ASIPGMYERTVTMNSLGKTFSLTGWKIGWAIAPPHLTWGLRQAHSFLTFATCTPMQAAAA
Cotton               ASLPGMYERTVTMNSLGKTFSLTGWKIGWAIAPPHLTWGVRQAHSFLTFATSTPMQYAAT
GRAPE                ASLPGMYERTVTMNSLGKTFSLTGWKIGWTVAPPHLTWGVRQAHSFLTFATCTPMQWAAA
Ricinus_communi      ASLPGMYERTVTLNSLGKTFSLTGWKIGWAIAPPHLTWGVRQAHAFLTFATSTPMQWAAS
POPULUS_TRICHOC      ASLPGMYERTVTLNSLGKTFSLTGWKIGWAIAPPHLTWGVRQAHSFLTFATSTPMQWAAA
soybean              ASLPGMFERTVTLNSLGKTFSLTGWKIGWAIAPPHLSWGVRQAHAFLTFATAHPFQCAAA
Danio_rerio          ASLPGMFERTVTMNSLGKTFSLTGWKIGWAIAPPHLTWGVRQAHAFLTFATSNPMQWAAA
arabidopsis          ASLPGMYERTVTMNSLGKTFSLTGWKIGWAIAPPHLTWGVRQAHSYLTFATSTPAQWAAV
Physcomitrella_      ASLDGMYERTVTMNSLGKTFSLTGWKIGWAVAPPHLTRGIRLAHSYLTFATATPLQWASV
Chlamy               KSLPGMKERCVRLGSAGKTFSFTAWKVGWMTGPARLLNPIVKAHQFLVFTVPSSLQRAVA
consensus            aS-pGM-ERtVt-nSlGKTFSlTgWKiGWa-aPphLtwg-rqAH-fLtFat--p-Q-Aa- Hordeum              AALRAPDSYFEELKRDYGAKKALLVDGLKAAGFIVYPSSGTYFIMVDHTPFGFDNDVEFC
RICE                 AALRAPDSYYEELRRDYGAKKALLVNGLKDAGFIVYPSSGTYFVMVDHTPFGFDNDIEFC
Zea_mays             AALRAPDSYYDELKRDYSAKKAILLEGLEAAGFIVYPSSGTYIMVDHTPFGFDSDVEFC
Cotton               VALQAPDSYFAELKRDYMAKKAILVQGLKDVGFKVFPSSGTYFVVVDHTPFGLENDIAFC
GRAPE                TALRAPDSYYEELKRDYSAKKAILVEGLKAVGFRVYPSSGTYFVVVDHTPFGLKDDIAFC
Ricinus_communi      VALRAPDSYFEELKRDYMAKKAILVEGLKAVGFKVFPSSGTYFVVVDHTPFGLENDIAFC
POPULUS_TRICHOC      VALRAPESYFELKRDYMAKKEILVEGLKAVGFKVFPSSGTYFVVVDHTPFGLENDIAFC
soybean              AALRAPDSYYVELKRDYMAKRAILIEGLKAVGFKVFPSSGTYFVVVDHTPFGLENDVAFC
Danio_rerio          VALRAPDSYYTELKRDYMAKRSILVEGLKAVGFKVFPSSGTYFVVVDHTPFGHENDIAFC
arabidopsis          AALKAPESYFKELKRDYNVKKETLVKGLKEVGFTVFPSSGTYFVVADHTPFGMENDVAFC
Physcomitrella_      EALRAPDSFYAELIKSYSAKKDILVEGLNSVGFEVYPEGTYFVVDHTPFGFENDVAFC
Chlamy               HGLDKEADFYHSLGPSLEAKRRYLEAELTALGFDCLPAHGAYFLVADFQRPGE-DDADFA
consensus            -aL-ap-sy--eL-rdy-aK---L--gL---GF-v-pssGtYf--vDhtpfG---D--Fc Hordeum              EYLIREVGVVAIPPSVFYLNPEDGKNLVRFTFCKDDDTLRAAVDRMKAKLRKK------S
RICE                 EYLIREVGVVAIPPSVFYLNPEDGKNLVRFTFCKDDETLRAAVERMKTKLRKK------S
Zea_mays             EYLIREVGVCAIPPSVFYLDPEEGKKLVRFTFSKDEGTLRAAVERLKAKLRRK------S
Cotton               EYLIKEVG-----------------------------------------------S
GRAPE                EYLIKEVGVVAIPTSVFYLHPEDGKNLVRFTFCKDEGTLRAAVERMKEKLKPKQ-----S
Ricinus_communi      EHLIKEVGVVAIPTSVFYLNPEEGKNLVRFTFCKDEGTLRTAVERMKEKLKRK------S
POPULUS_TRICHOC      EYLIKEVGVVAIPTSVFYLNPEDGKNLVRFTFCKDEGTLRAAVDRMKEKLKRK------S
soybean              EYLVKEVGVVAIPTSVFYLNPEEGKNLVRFTFCKDEETIRSAVERMKAKLRK-------S
Danio_rerio          EYLVKEVGVVAIPTSVFYLNPEEGKNLVRFTFCKDEGTLRAAVDRMKEKLRK-------S
arabidopsis          EYLIEEVGVVAIPTSVFYLNPEEGKNLVRFAFCKDEETLRGAIERMKQKLKRKV-----S
Physcomitrella_      KYLIEEVGIAAIPPSVFYTNPEDGKNLVRFAFCKDEETLKTAVERLRTKLKKAVSLSS-S
Chlamy               KRLTAEGGVTTIPISGFYVGPRPPTHLVRFCYCKEDIKLQAAVERLKAYVGPGGKGAPQV
consensus            eyL--EvGv-aip-svfy--pe-gk-lvrf-fckd--tl--av-r-k-kl---------s Hordeum              GCTEAIAATILGLINPGDEVILFAPFYDSYEATLSMAGANVKAITLRPFDFAVPLEELKA
RICE                 GCTEAIAATILGLINPGDEVILFAPFYDSYEATLSMAGANVKAITLRPFDFSVPLEELKA
Zea_mays             GCTEAIAATILGLINPGDEVILFAPFYDSYEATLSMAGANVKAITLRAFDFAVPLEELEA
Cotton               GCTEAIAATMLGLINPGDEVILFAPFYDSYEATLSMAGAKVKCITLCPFDFAVPIDELKS
GRAPE                GCTEAIAATMLGLINPGDEVILFAPFYDSYEATLSMAGAQIKSITLRPFDFAVPMDELKS
Ricinus_communi      GCTEAIAATILGLIDPGDEVILFAPFYDSYEATLSMAGAKIKCVTLQPFDFAVPIDELKS
POPULUS_TRICHOC      GCTEAIAATMLGLINPGDEVILFAPFYDSYEATLSMAGAKIKCITLHPFDFAVPIDELKS
soybean              GCTEAIAATMIGLINPGDEVIMFAPFYDSYEATLSMAGAKVKGITLRPFDFAVPLEELKS
Danio_rerio          GCTEAIAATVLGLINPGDEVIVFAPFYDSYEATLSMAGAKVKGITLRPFDFALPIEELKS
arabidopsis          GCTEAIAAAMLGLINPGDEVILFAPFYDSYEATLSMAGAKVKGITLRPFDFSIPLEELKA
Physcomitrella_      GCTEAIAATVLGLVNPGDEIIVFEPFYDSYQATVSMSGAILKTVTMRAPEFAVPEEELRA
Chlamy               GATEGLASAFLGLINPGDEVIMFDFMYDSITSMAKRSGAVIVPVRLRLPDFSVPLEELAA
consensus            GcTEaiAat-lGLinPGDEvI-FaPfYDSYeatlsmaGA--k--tl--PdF-vP--EL--

Hordeum              AVSKNTRAIMINTPHNPTGKMFTREELEFIADLCKENDVLLFADEVYDKLAFEADHISM-
RICE                 AVSKNTRAIMINTPHNPTGKMFTREELEFIATLCKENDVLLFADEVYDKLAFEADHISM-
Zea_mays             AVSKDTKAIMINTPHNPTGKMFTREELESIAALCKENDVLLFSDEVYDKLVFEADHISM-
Cotton               TISKNTRAILINTPHNPTGKMFTREELNTIASLCIENDVLVFTDEVYDKLAFEMDHISM-
GRAPE                AISKNTRAILINTPHNPTGKMFTREELNVIASLCIENDVLVFTDEVYDKLAFEMDHISM-
Ricinus_communi      IISKNTRAILINTPHNPTGKMFTREELTTIASCCIENDVLVFTDEVYDKLAFEMDHISM-
POPULUS_TRICHOC      AITQDTRAVLINTPHNPTGKMFSREELSTIASLCIENDVLVFTDEVYDKLAFELDHISM-
soybean              TISKNTRAILINTPHNPTGKMFTREELNCIASLCIENDVLVFTDEVYDKLAFDMEHISM-
Danio_rerio          TISKNTRAILLNTPHNPTGKMFTPEELNTIASLCIENDVLVFSDEVYDKLAFDMEHISI-
arabidopsis          AVTNKTRAILMNTPHNPTGKMFTREELETIASLCIENDVLVFSDEVYDKLAFEMDHISI-
Physcomitrella_      AFSSKTRAILVNTPHNPTGKMFVPRHLELIASLCKEHNTLAFCDEVYNKLVFKGEHVSL-
Chlamy               AVTPRTKMIMINTPHNPSGKVFTRPELEAIAELCVRHDLIALSDEVYEHLVFGGAAHVSL
consensus            -----Trai--NTPHNPtGKmFtreEL--IA-lC-endvl-f-DEVYdkL-F---his--
```

FIG. 2 (CONT.)

```
Cotton            MQAAECTWTHFEMLRPLCFKSPSTTPLFFNFSKHFQKGFSDSSFFRSNRRISNYPSFMAT
GRAPE             -----------------MQLSQCTWTFPELLKRPAFLRRSIDSISSRSRSSSKYPSFMA-
Ricinus_communi   --MQSQCTWTGTRMPLPIILKPSTFSILKHLPTKRTNLFSTRSPISNYPSLMATFSTA--
POPULUS_TRICHOC   ---------------------------------------------------------MAS--
soybean           ---------------------------MKFTPSSKFLGFSNHFHSLLAPSFSPTPKFS
Danio_rerio       ------------------------------------------------------------
arabidopsis       --------------------------MYLDINGVMIKQFSFKASLLPFSSNFRQSSA
Hordeum           ---------------------------------------------MASAPASAS
RICE              ---MNLAGFLATPATATATRHEMPLNPSSSASFLLSSLRRSLVASLRKASPAAAAALSPM
Zea_mays          ---MNLAAFSSTLATLPWYEMPSI---NSSATFSSSLLRRSLCASLRTISHMASAAAPTS
consensus         ------------------------------------------------------------

Cotton            ISSLSTHKDPVSTHDATPNITHQPVQVAKRLEKFKTTIFTQMSMLAIKHGAINLGQGFPN
GRAPE             --SASTVSAPNTEAEQTHNPPQPLQ-VAKRLEKFKTTIFTQMSMLAIKHGAINLGQGFPN
Ricinus_communi   --STTEKDAPSGQNDSTQKSQQPLQ-VAKRLEKFKTTIFTQMSSLAIKHGAINLGQGFPN
POPULUS_TRICHOC   --SPSLKDAVSTQNESTQKTQQPLQ-VAKRLEKFKTTIFTQMSSLAIKHGAINLGQGFPN
soybean           SSFSATMSTLSTQNDTVTHKTQQPLQIAKRLEKFQTTIFTQMSLLAIKHGAINLGQGFPN
Danio_rerio       ----------------------VAKRLEKFKTTIFTQMSMLAIKHGAINLGQGFPN
arabidopsis       -KIHRPIGATMTTVSTQNESTQKPVQVAKRLEKFKTTIFTQMSILAVKHGAINLGQGFPN
Hordeum           AALSTAAP---ADNGAAKPTEQRPVQVAKRLEKFKTTIFTQMSMLAVKHGAINLGQGFPN
RICE              ASASTVAAENGAAKGAAEKQQQQPVQVAKRLEKFKTTIFTQMSMLAIKHGAINLGQGFPN
Zea_mays          APVATTEN------GAAKAIEQRPVQVAERLEKFKTTIFTQMSMLAIKHGAINLGQGFPN
consensus         --------------------q----vAkRLEKFkTTIFTQMS-LAiKHGAINLGQGFPN Cotton            FDGPDFVKGAAIQAIKDGKNQYARGYGVPDFNNAIAARFKKDTGLVIDPEKEVTVTSGCT
GRAPE             FDGPEFVKEAAIQAIKDGKNQYARGYGVPDLNSAVADRFKKDTGLVVDPEKEVTVTSGCT
Ricinus_communi   FDGPEFVKEAAIQAIRDGKNQYARGYGVPDFNSAIVDRFKKDTGLVVDPEKEVTVTSGCT
POPULUS_TRICHOC   FDGPEFVKEAAIQAIKDGKNQYARGYGVPDFSSAIAERFKKDTGLVVDPEKEITVTSGCT
soybean           FDGPEFVKEAAIQAIRDGKNQYARGYGVPDLNIAIERFKKDTGLVVDPEKEITVTSGCT
Danio_rerio       FDGPDFVKEAAIQAIRDGNNQYARGYGVPDLNIAISERYKKDTGLAVDPEKEITVTSGCT
arabidopsis       FDGPDFVKEAAIQAIKDGKNQYARGYGIPQLNSATAAKFREDTGLVVDPEKEVTVTSGCT
Hordeum           FDGPDFVKDAAIEAIKAGKNQYARGYGVPELNSAVAERFLKDSGLHIDPDKEVTVTSGCT
RICE              FDGPDFVKEAAIQAINAGKNQYARGYGVPELNSAIAERFLKDSGLQVDPDKEVTVTSGCT
Zea_mays          FDGPDFVKEAAIQAINAGKNQYARGFGVPELNSAIAERFLKDSGLQVDPDKEVTVTSGCT
consensus         FDGP-FVKeAAIqAI--GkNQYARGyGvP---n-Aia-Rf-kD-GL-vDPeKE-TVTSGCT Cotton            EAIAATMLGLINPGDEVILFAPFYDSYEATLSMAGAKVKCITLCPPDFAVPIDELKSTIS
GRAPE             EAIAATMLGLINPGDEVILFAPFYDSYEATLSMAGAQIKSITLRPFDFAVPMDELKSAIS
Ricinus_communi   EAIAATILGLIDPGDEVILFAPFYDSYEATLSMAGAKIKCVTLQPFDFAVPIDELKSIIS
POPULUS_TRICHOC   EAIAATMLGLINPGDEVILFAPFYDSYEATLSMAGAKIKCITLHPFDFAVPIDELKSAIT
soybean           EAIAATMIGLINPGDEVIMFAPFYDSYEATLSMAGAKVKGITLRPFDFAVPLEELKSTIS
Danio_rerio       EAIAATVLGLINPGDEVIVFAPFYDSYEATLSMAGAKVKGITLRPFDFALPIEELKSTIS
arabidopsis       EAIAAAMLGLINPGDEVILFAPFYDSYEATLSMAGAKVKGITLRPFDFSIPLEELKAAVT
Hordeum           EAIAATILGLINPGDEVILFAPFYDSYEATLSMAGAKVKAITLRPPDFAVPLEELKAAVS
RICE              EAIAATILGLINPGDEVILFAPFYDSYEATLSMAGANVKAITLRPFDFSVPLEELKAAVS
Zea_mays          EAIAATILGLINPGDEVILFAPFYDSYEATLSMAGANVKAITLRAPDFAVPLEELEAAVS
consensus         EAIAAt-lGLInPGDEVIlFAPFYDSYEATLSMAGA--K-iTL-pPDFavP--ELk---s Cotton            KNTRAILINTPHNPTGKMFTREELNTIASLCIENDVLVFTDEVYDKLAFEMDHISMASLP
GRAPE             KNTRAILINTPHNPTGKMFTREELNVIASLCIENDVLVFTDEVYDKLAFEMDHISMASLP
Ricinus_communi   KNTRAILINTPHNPTGKMFTREELTTIASCCIENDVLVFTDEVYDKLAFEMDHISMASLP
POPULUS_TRICHOC   QDTRAVLINTPHNPTGKMFSREELSTIASLCIENDVLVFTDEVYDKLAFELDHISMASLP
soybean           KNTRAILINTPHNPTGKMFTREELNCIASLCIENDVLVFTDEVYDKLAFDMEHISMASLP
Danio_rerio       KNTRAILLNTPHNPTGKMFTREELNTIASLCIENDVLVFSDEVYDKLAFDMEHISIASLP
arabidopsis       NKTRAILMNTPHNPTGKMFTREELETIASLCIENDVLVFSDEVYDKLAFEMDHISIASLP
Hordeum           KNTRAIMINTPHNPTGKMFTREELEFIADLCKENDVLLFADEVYDKLAFEADHISMASIP
RICE              KNTRAIMINTPHNPTGKMFTREELEFIATLCKENDVLLFADEVYDKLAFEADHISMASIP
Zea_mays          KDTKAIMINTPHNPTGKMFTREELESIAALCKENDVLLFSDEVYDKLVFEADHISMASIP
consensus         k-TrAi-iNTPHNPTGKMFtrEEL--IA-1C-ENDVL-F-DEVYDKLaFe-dHISmAS-P Cotton            GMYERTVTMNSLGKTFSLTGWKIGWAIAPPHLTWGVRQAHSFLTFATSTPMQYAATVALQ
GRAPE             GMYERTVTMNSLGKTFSLTGWKIGWAIAPPHLTWGVRQAHSFLTFATSTPMQWAAATALR
Ricinus_communi   GMYERTVTLNSLGKTFSLTGWKIGWAIAPPHLTWGVRQAHAFLTFATSTPMQWAASVALR
POPULUS_TRICHOC   GMYERTVTLNSLGKTFSLTGWKIGWAIAPPHLTWGVRQAHSFLTFATSTPMQWAAAVALR
soybean           GMFERTVTLNSLGKTFSLTGWKIGWAIAPPHLSWGVRQAHAFLTFATAHPFQCAAAAALR
Danio_rerio       GMFERTVTMNSLGKTFSLTGWKIGWAIAPPHLTWGVRQAHAFLTFATASNPMQWAAAVALR
arabidopsis       GMYERTVTMNSLGKTFSLTGWKIGWAIAPPHLTWGVRQAHSYLTFATSTPAQWAAVAALK
Hordeum           GMYERTVTMNSLGKTFSLTGWKIGWAIAPPHLTWGVRQAHSFLTFATSTPMSAAAAAALR
RICE              GMYERTVTMNSLGKTFSLTGWKIGWAIAPPHLTWGVRQAHSFLTFATCTPMQAAAAAALR
Zea_mays          GMYERTVTMNSLGKTFSLTGWKIGWAIAPPHLTWGLRQAHSFLTFATCTPMQAAAAAALR
consensus         GMyERTVT-NSLGKTFSLTGWKIGWaIAPPHLtWGvRQAH-fLTFAT-tPmQ-AA--ALr
```

FIG. 3

```
Cotton            APDSYFAELKRDYMAKKAILVQGLKDVGFKVFPSSGTIFVVVDHTPFGLENDIAFCEYLI
GRAPE             APDSIYEELKRDYSAKKAILVEGLKAVGFRVYPSSGTIFVVVDHTPFGLKDDIAFCEYLI
Ricinus_communi   APDSYFEELKRDYMAKKAILVEGLKAVGFKVFPSSGTIFVVVDHTPFGLENDIAFCEHLI
POPULUS_TRICHOC   APESYFVELKRDYMAKKEILVEGLKAVGFKVFPSSGTIFVVVDHTPFGLENDIAFCEYLI
soybean           APDSYYVELKRDYMAKRAILIEGLKAVGFKVFPSSGTIFVVVDHTPFGLENDVAFCEYLV
Danio_rerio       APDSYYTELKRDYMAKRSILVEGLKAVGFKVFPSSGTIFVVVDHTPFGHENDIAFCEYLV
arabidopsis       APESYFKELKRDYNVKKETLVKGLKEVGFTVFPSSGTIFVVADHTPFGMENDVAFCEYLI
Hordeum           APDSYFEELKRDYGAKKALLVDGLKAAGFIVYPSSGTIFIMVDHTPFGFDNDVEFCEYLI
RICE              APDSIYEELRRDYGAKKALLVNGLKDAGFIVYPSSGTIFVMVDHTPFGFDNDIEFCEYLI
Zea_mays          APDSIYDELKRDYSAKKAILLEGLEAAGFIVYPSSGTIYIMVDHTPFGFDSDVEFCEYLI
consensus         APdSY--ELkRDY-aKk--Lv-GLk--GF-V-PSSGTYfv-vDHTPFG--nD--FCEyLi Cotton            KEVG--------------------------------------------AINLGQGFPN
GRAPE             KEVGVVAIPTSVFYLHPEDGKNLVRFTFCKDEGTLRAAVERMKEKLKPKQAINLGQGFPN
Ricinus_communi   KEVGVVAIPTSVFYLNPEEGKNLVRFTFCKDEGTLRTAVERMKEKLKRK-AINLGQGFPN
POPULUS_TRICHOC   KEVGVVAIPTSVFYLNPEDGKNLVRFTFCKDEGTLRAAVDRMKEKLKRK-AINLGQGFPN
soybean           KEVGVVAIPTSVFYLNPEEGKNLVRFTFCKDEETIRSAVERMKAKLRK--AINLGQGFPN
Danio_rerio       KEVGVVAIPTSVFYLNPEEGKNLVRFTFCKDEGTLRAAVDRMKEKLRK--AINLGQGFPN
arabidopsis       EEVGVVAIPTSVFYLNPEEGKNLVRFAFCKDEETLRGAIERMKQKLKRKVAINLGQGFPN
Hordeum           REVGVVAIPTSVFYLNPEDGKNLVRFTFCKDDDTLRAAVDRMKAKLRKK-AINLGQGFPN
RICE              REVGVVAIPPSVFYLNPEDGKNLVRFTFCKDDETLRAAVERMKTKLRKK-AINLGQGFPN
Zea_mays          REVGVCAIPPSVFYLDPEEGKLVRFTFSKDEGTLRAAVERLKAKLRKK-AINLGQGFPN
consensus         -EVGvvaip-svfyl-pe-gknlvrftfckd--tlr-av-rmk-kl----AINLGQGFPN Cotton            FDGPDFVKGAAIQAIKDGKNQYARGYGVPDFNNAIAARFKKDTGLVIDPEKEVTVTSGCT
GRAPE             FDGPEFVKEAAIQAIKDGKNQYARGYGVPDLNSAVADRFKKDTGLVVDPEKEVTVTSGCT
Ricinus_communi   FDGPEFVKEAAIQAIRDGKNQYARGYGVPDFNSAIVDRFKKDTGLVVDPEKEVTVTSGCT
POPULUS_TRICHOC   FDGPEFVKEAAIQAIKDGKNQYARGYGVPDFSSAIAIERFKKDTGLVVDPEKEITVTSGCT
soybean           FDGPEFVKEAAIQAIRDGKNQYARGYGVPDLNIAIAERFKKDTGLVVDPEKEITVTSGCT
Danio_rerio       FDGPDFVKEAAIQAIRDGNNQIARGYGVPDLNIAISERYKKDTGLAVDPEKEITVTSGCT
arabidopsis       FDGPDFVKEAAIQAIKDGKNQYARGYGIPQLNSAIAARFREDTGLVVDPEKEVTVTSGCT
Hordeum           FDGPDFVKDAAIEAIKAGKNQIARGYGVPELNSAVAERFLKDSGLHIDPDKEVTVTSGCT
RICE              FDGPDFVKEAAIQAINAGKNQYARGYGVPELNSAIAERFLKDSGLQVDPEKEVTVTSGCT
Zea_mays          FDGPDFVKEAAIQAINAGKNQIARGFGVPELNSAIAERFLKDSGLQVDPDKEVTVTSGCT
consensus         FDGP-FVKeAAIqAI--GkNQYARGyGvP--n-Aia-Rf-kD-GL-vDPeKE-TVTSGCT Cotton            EAIAATMLGLINPGDEVILFAPFYDSYEATLSMAGAKVKCITLCPPDFAVPIDELKSTIS
GRAPE             EAIAATMLGLINPGDEVILFAPFYDSYEATLSMAGAQIKSITLRPPDFAVPMDELKSAIS
Ricinus_communi   EAIAATILGLIDPGDEVILFAPFYDSYEATLSMAGAKIKCVTLQPPDFAVPIDELKSIIS
POPULUS_TRICHOC   EAIAATMLGLINPGDEVILFAPFYDSYEATLSMAGAKIKCITLHPPDFAVPIDELKSAIT
soybean           EAIAATMIGLINPGDEVIMFAPFYDSYEATLSMAGAKVKGITLRPPDFAVPLEELKSTIS
Danio_rerio       EAIAATVLGLINPGDEVIVFAPFYDSYEATLSMAGAKVKGITLRPPDFALPIEELKSTIS
arabidopsis       EAIAAMLGLINPGDEVILFAPFYDSYEATLSMAGAKVKGITLRPPDFSIPLEELKAAVT
Hordeum           EAIAATILGLINPGDEVILFAPFYDSYEATLSMAGANVKAITLRPPDFAVPLEELKAAVS
RICE              EAIAATILGLINPGDEVILFAPFYDSYEATLSMAGANVKAITLRPPDFSVPLEELKAAVS
Zea_mays          EAIAATILGLINPGDEVILFAPFYDSYEATLSMAGANVKAITLRAPDFAVPLEELEAAVS
consensus         EAIAAt-lGLInPGDEVIlFAPFYDSYEATLSMAGA--K-iTL-pPDFavP--ELk---s Cotton            KNTRAILINTPHNPTGKMFTREELNTIASLCIENDVLVFTDEVYDKLAFEMDHISMASLP
GRAPE             KNTRAILINTPHNPTGKMFTREELNVIASLCIENDVLVFTDEVYDKLAFEMDHISMASLP
Ricinus_communi   KNTRAILINTPHNPTGKMFTREELTTIASCCIENDVLVFTDEVYDKLAFEMDHISMASLP
POPULUS_TRICHOC   QDTRAVLINTPHNPTGKMFSREELSTIASLCIENDVLVFTDEVYDKLAFELDHISMASLP
soybean           KNTRAILINTPHNPTGKMFTREELNCIASLCIENDVLVFTDEVYDKLAFDMEHISMASLP
Danio_rerio       KNTRAILLNTPHNPTGKMFTPEELNTIASLCIENDVLVFSDEVYDKLAFDMEHISIASLP
arabidopsis       NKTRAILMNTPHNPTGKMFTREELETIASLCIENDVLVFSDEVYDKLAFEMDHISIASLP
Hordeum           KNTRAIMINTPHNPTGKMFTREELEFIADLCKENDVLLFADEVYDKLAFEADHISMASIP
RICE              KNTRAIMINTPHNPTGKMFTREELEFIATLCKENDVLLFADEVYDKLAFEADHISMASIP
Zea_mays          KDTKAIMINTPHNPTGKMFTREELESIAALCKENDVLLFSDEVYDKLVFEADHISMASIP
consensus         k-TrAi-iNTPHNPTGKMFtrEEL--IA-lC-ENDVL-F-DEVYDKLaFe-dHISmAS-P Cotton            GMYERTVTMNSLGKTFSLTGWKIGWAIAPPHLTWGVRQAHSFLTFATSTPMQYAATVALQ
GRAPE             GMYERTVTMNSLGKTFSLTGWKIGWTVAPPHLTWGVRQAHSFLTFATCTPMQWAAATALR
Ricinus_communi   GMYERTVTLNSLGKTFSLTGWKIGWAIAPPHLTWGVRQAHAFLTFATSTPMQWAASVALR
POPULUS_TRICHOC   GMYERTVTLNSLGKTFSLTGWKIGWAIAPPHLTWGVRQAHSFLTFATSTPMQWAAAVALR
soybean           GMFERTVTLNSLGKTFSLTGWKIGWAIAPPHLSWGVRQAHAPLTFATAHFFQCAAAAALR
Danio_rerio       GMFERTVTMNSLGKTFSLTGWKIGWAIAPPHLTWGVRQAHAFLTFATSNPMQWAAAVALR
arabidopsis       GMYERTVTMNSLGKTFSLTGWKIGWAIAPPHLTWGVRQAHSYLTFATSTPAQWAAVAALK
Hordeum           GMYERTVTMNSLGKTFSLTGWKIGWAIAPPHLTWGVRQAHSFLTFATSTPMQSAAAAALR
RICE              GMYERTVTMNSLGKTFSLTGWKIGWAIAPPHLTWGVRQAHSFLTFATCTPMQAAAAAALR
Zea_mays          GMYERTVTMNSLGKTFSLTGWKIGWAIAPPHLTWGLRQAHSFLTFATCTPMQAAAAAALR
consensus         GMyERTVT-NSLGKTFSLTGWKIGWaiAPPHLtWGvRQAH-fLTFAT-tPmQ-AA--ALr
```

FIG. 3 (CONT.)

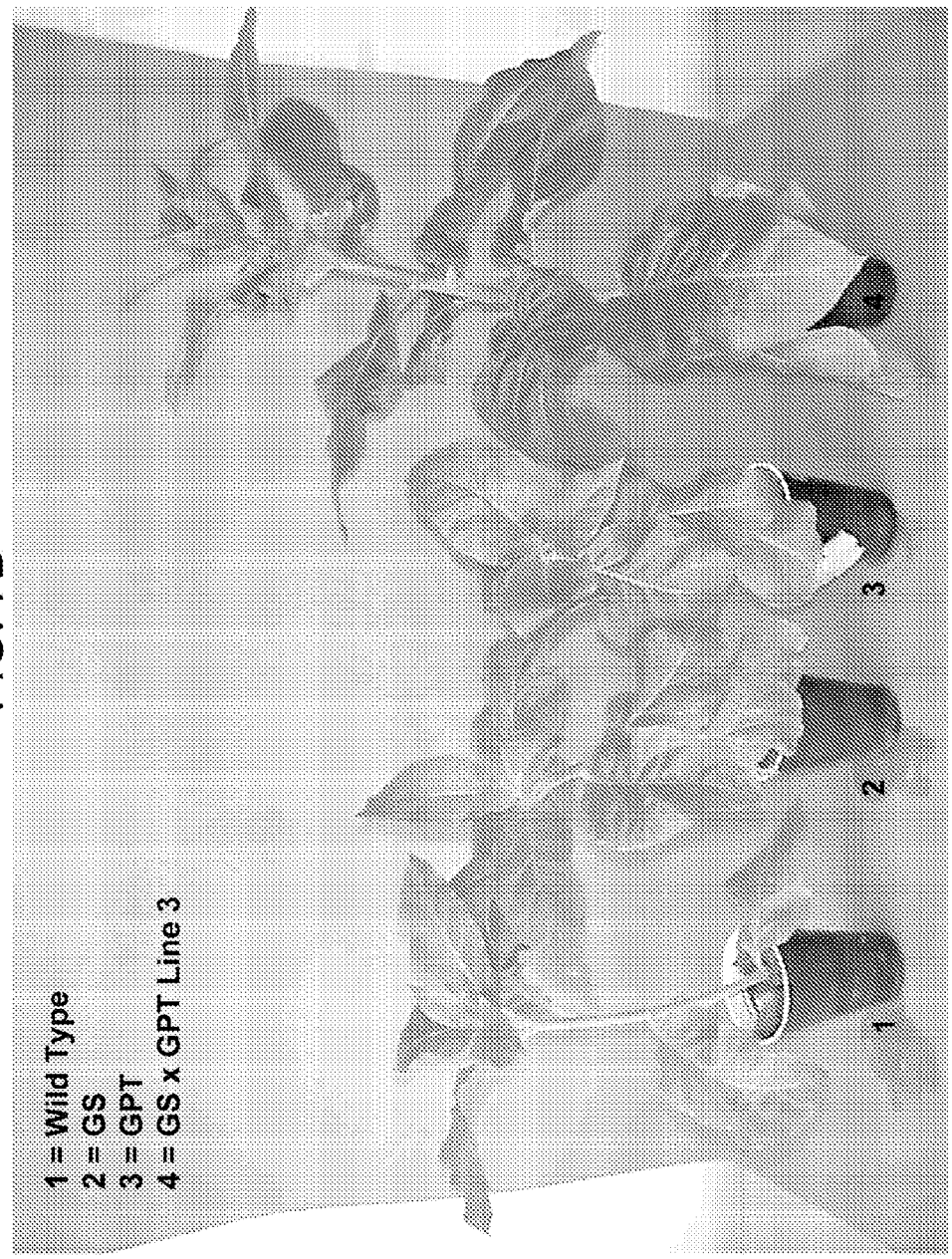

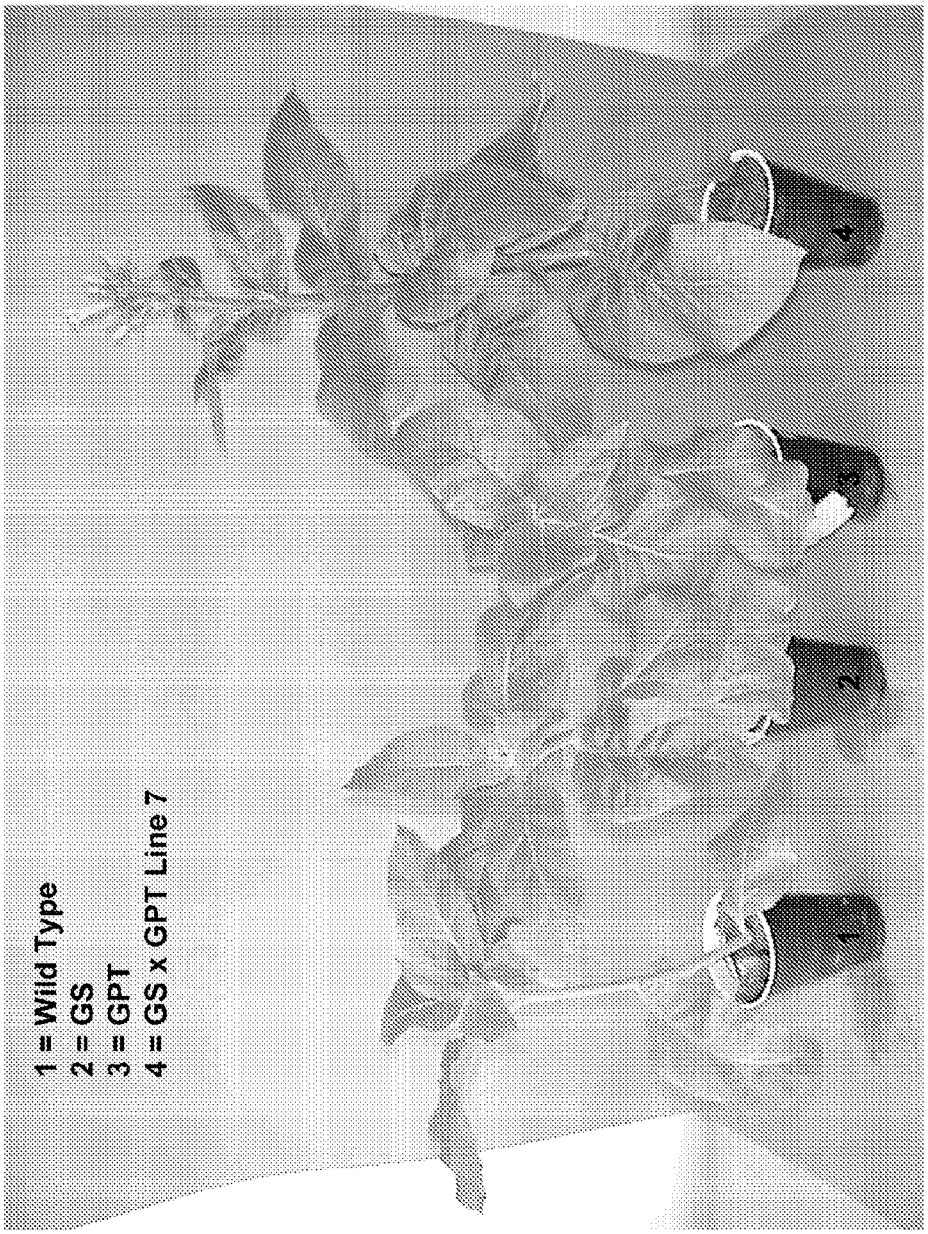

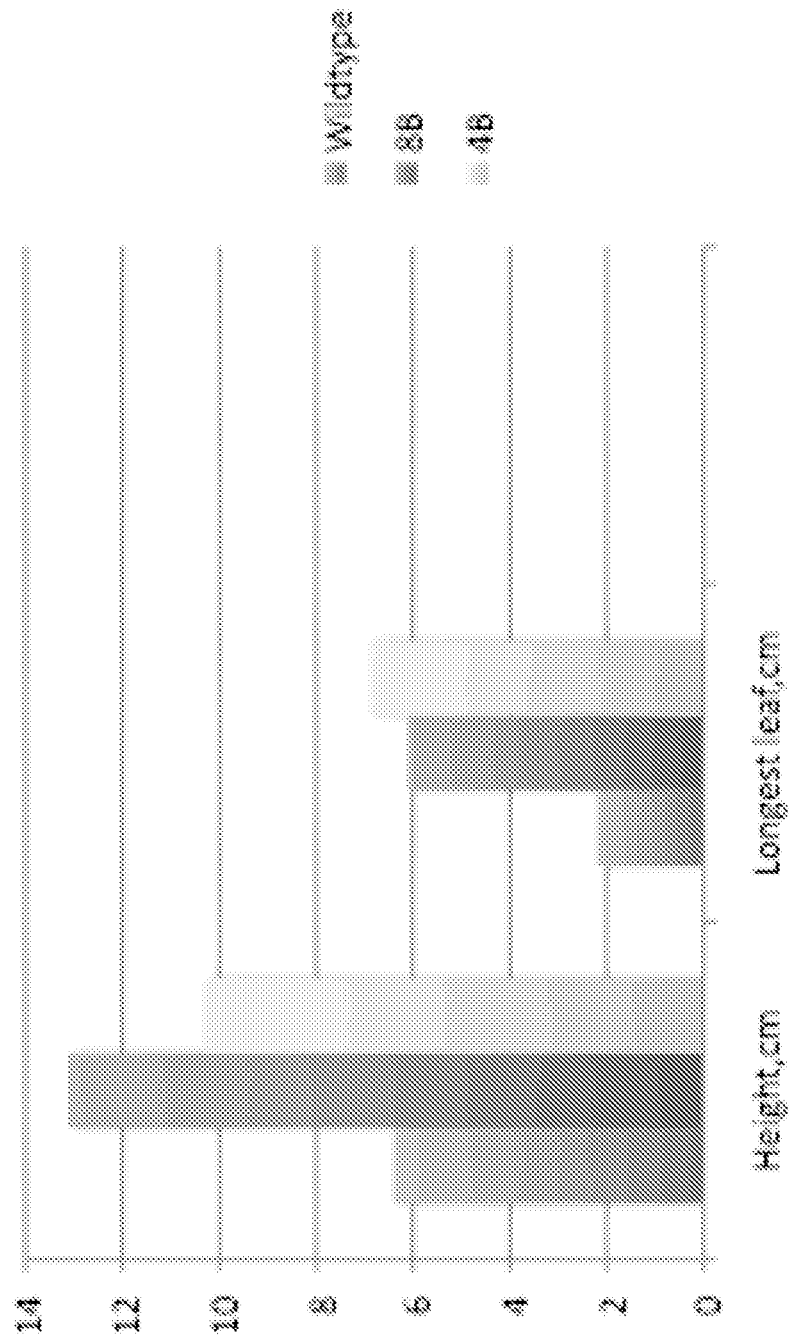

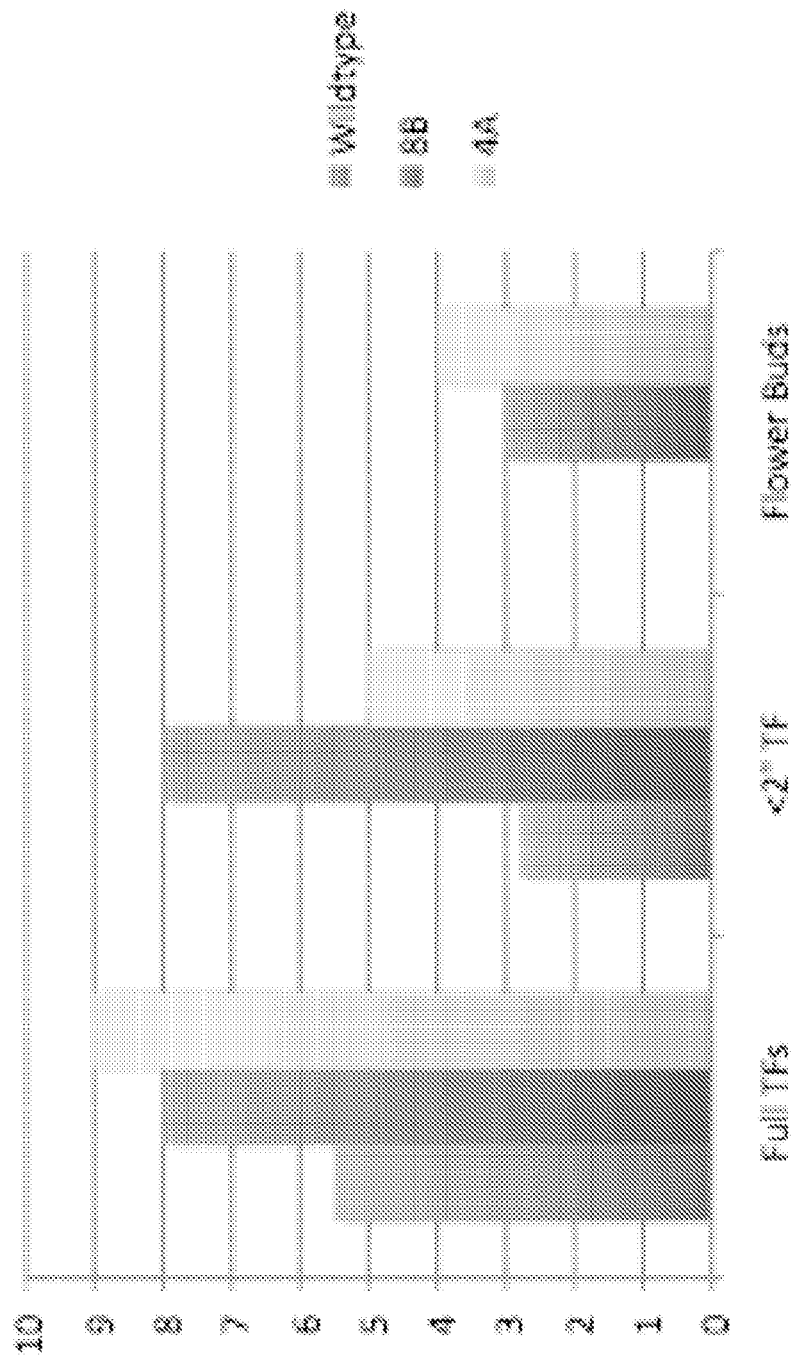

FIG. 16B
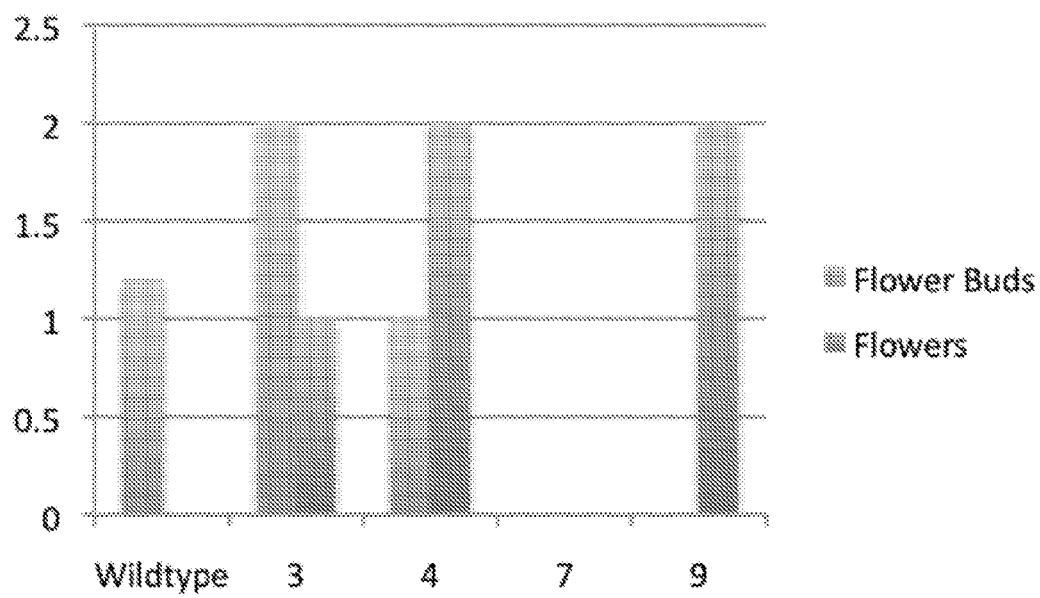
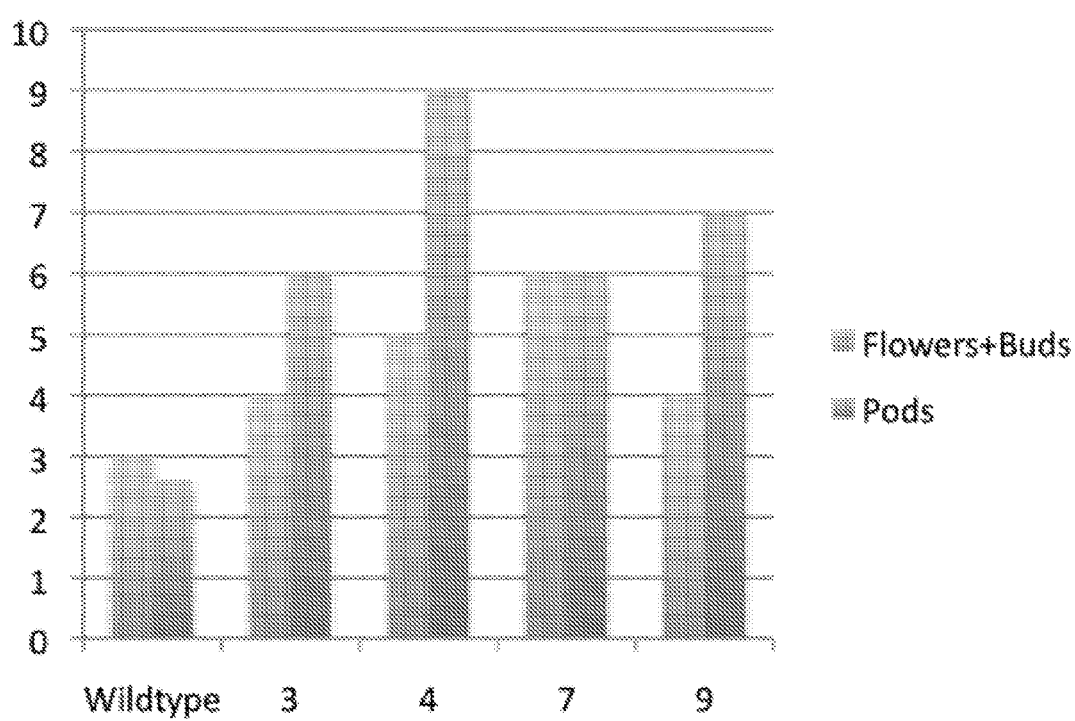

US 9,296,998 B2

NUCLEIC ACIDS ENCODING PLANT GLUTAMINE PHENYLPYRUVATE TRANSAMINASE (GPT) AND USES THEREOF

RELATED APPLICATIONS

This application is a continuation-in-part of U.S. application Ser. No. 12/551,193, filed Aug. 31, 2009, which application claims priority to U.S. Provisional Application Nos. 61/190,520 and 61/190,581, both filed on Aug. 29, 2008.

STATEMENT AS TO RIGHTS TO INVENTIONS MADE UNDER FEDERALLY SPONSORED RESEARCH OR DEVELOPMENT

This invention was made with government support under Contract No. W-7405-ENG-36 awarded by the United States Department of Energy to The Regents of The University of California, and Contract No. DE-AC52-06NA25396, awarded by the United States Department of Energy to Los Alamos National Security, LLC. The government has certain rights in this invention.

BACKGROUND OF THE INVENTION

The metabolism of carbon and nitrogen in photosynthetic organisms must be regulated in a coordinated manner to assure efficient use of plant resources and energy. Current understanding of carbon and nitrogen metabolism includes details of certain steps and metabolic pathways which are subsystems of larger systems. In photosynthetic organisms, carbon metabolism begins with $CO_2$ fixation, which proceeds via two major processes, termed C-3 and C-4 metabolism. In plants with C-3 metabolism, the enzyme ribulose bisphosphate carboxylase (RuBisCo) catalyzes the combination of $CO_2$ with ribulose bisphosphate to produce 3-phosphoglycerate, a three carbon compound (C-3) that the plant uses to synthesize carbon-containing compounds. In plants with C-4 metabolism, $CO_2$ is combined with phosphoenol pyruvate to form acids containing four carbons (C-4), in a reaction catalyzed by the enzyme phosphoenol pyruvate carboxylase. The acids are transferred to bundle sheath cells, where they are decarboxylated to release $CO_2$, which is then combined with ribulose bisphosphate in the same reaction employed by C-3 plants.

Numerous studies have found that various metabolites are important in plant regulation of nitrogen metabolism. These compounds include the organic acid malate and the amino acids glutamate and glutamine. Nitrogen is assimilated by photosynthetic organisms via the action of the enzyme glutamine synthetase (GS) which catalyzes the combination of ammonia with glutamate to form glutamine. GS plays a key role in the assimilation of nitrogen in plants by catalyzing the addition of ammonium to glutamate to form glutamine in an ATP-dependent reaction (Miflin and Habash, 2002, Journal of Experimental Botany, Vol. 53, No. 370, pp. 979-987). GS also reassimilates ammonia released as a result of photorespiration and the breakdown of proteins and nitrogen transport compounds. GS enzymes may be divided into two general classes, one representing the cytoplasmic form (GS1) and the other representing the plastidic (i.e., chloroplastic) form (GS2).

Previous work has demonstrated that increased expression levels of GS1 result in increased levels of GS activity and plant growth, although reports are inconsistent. For example, Fuentes et al. reported that CaMV S35 promoter-driven overexpression of Alfalfa GS1 (cytoplasmic form) in tobacco resulted in increased levels of GS expression and GS activity in leaf tissue, increased growth under nitrogen starvation, but no effect on growth under optimal nitrogen fertilization conditions (Fuentes et al., 2001, J. Exp. Botany 52: 1071-81). Temple et al. reported that transgenic tobacco plants overexpressing the full length Alfalfa GS1 coding sequence contained greatly elevated levels of GS transcript, and GS polypeptide which assembled into active enzyme, but did not report phenotypic effects on growth (Temple et al., 1993, Molecular and General Genetics 236: 315-325). Corruzi et al. have reported that transgenic tobacco overexpressing a pea cytosolic GS1 transgene under the control of the CaMV S35 promoter show increased GS activity, increased cytosolic GS protein, and improved growth characteristics (U.S. Pat. No. 6,107,547). Unkefer et al. have more recently reported that transgenic tobacco plants overexpressing the Alfalfa GS1 in foliar tissues, which had been screened for increased leaf-to-root GS activity following genetic segregation by selfing to achieve increased GS1 transgene copy number, were found to produce increased 2-hydroxy-5-oxoproline levels in their foliar portions, which was found to lead to markedly increased growth rates over wildtype tobacco plants (see, U.S. Pat. Nos. 6,555,500; 6,593,275; and 6,831,040).

Unkefer et al. have further described the use of 2-hydroxy-5-oxoproline (also known and referred to herein as 2-oxoglutaramate) to improve plant growth (U.S. Pat. Nos. 6,555,500; 6,593,275; 6,831,040). In particular, Unkefer et al. disclose that increased concentrations of 2-hydroxy-5-oxoproline in foliar tissues (relative to root tissues) triggers a cascade of events that result in increased plant growth characteristics. Unkefer et al. describe methods by which the foliar concentration of 2-hydroxy-5-oxoproline may be increased in order to trigger increased plant growth characteristics, specifically, by applying a solution of 2-hydroxy-5-oxoproline directly to the foliar portions of the plant and over-expressing glutamine synthetase preferentially in leaf tissues.

A number of transaminase and hydrolyase enzymes known to be involved in the synthesis of 2-hydroxy-5-oxoproline in animals have been identified in animal liver and kidney tissues (Cooper and Meister, 1977, CRC Critical Reviews in Biochemistry, pages 281-303; Meister, 1952, J. Biochem. 197: 304).

In plants, the biochemical synthesis of 2-hydroxy-5-oxoproline has been known but has been poorly characterized. Moreover, the function of 2-hydroxy-5-oxoproline in plants and the significance of its pool size (tissue concentration) are unknown. Finally, the art provides no specific guidance as to precisely what transaminase(s) or hydrolase(s) may exist and/or be active in catalyzing the synthesis of 2-hydroxy-5-oxoproline in plants, and no such plant transaminases have been reported, isolated or characterized, until the present invention.

SUMMARY OF THE INVENTION

The present invention discloses for the first time that plants contain a glutamine phenylpyruvate transaminase enzyme which is directly functional in the synthesis of the signal metabolite 2-hydroxy-5-oxoproline, and provides the protein and gene coding sequences for a number of plant GPTs as well as a highly structurally-related non-plant GPT. The invention further provides strong evidence that plant GPTs are highly conserved and are involved in directly catalyzing 2-oxoglutaramate synthesis. Until now, no plant glutamine phenylpyruvate transaminase with a defined function has been described.

The invention relates to plant glutamine phenylpyruvate transaminase (GPT) proteins, nucleic acid molecules encoding GPT proteins, and uses thereof. Defined herein are various GPT proteins and GPT gene coding sequences isolated from a number of plant species. As disclosed herein, GPT proteins share remarkable structural similarity within plant species, and are active in catalyzing the synthesis of 2-hydroxy-5-oxoproline (2-oxoglutaramate), a powerful signal metabolite which regulates the function of a large number of genes involved in the photosynthesis apparatus, carbon fixation and nitrogen metabolism.

In one aspect, the invention provides isolated nucleic acid molecules encoding GPT. Exemplary GPT polynucleotides and GPT polypeptides are provided herein. In one embodiment, the invention provides an isolated GPT polynucleotide having a sequence selected from the group consisting of (a) the nucleotide sequence of SEQ ID NO: 1; (b) a nucleotide sequence having at least 75% identity to SEQ ID NO: 1, and encoding a polypeptide having GPT activity; (c) a nucleotide sequence encoding the polypeptide of SEQ ID NO: 2, or a polypeptide having at least 75% sequence identity thereto which has GPT activity; and, (d) a nucleotide sequence encoding the polypeptide of SEQ ID NO: 2 truncated at its amino terminus by between 30 to 56 amino acid residues, or a polypeptide having at least 75% sequence identity thereto which has GPT activity. In specific embodiments, the isolated GPT polynucleotide comprises the nucleotide sequence of SEQ ID NO: 18, SEQ ID NO: 29, SEQ ID NO: 45 or SEQ ID NO: 48, or a nucleotide sequence having at least 75% identity to SEQ ID NO: 18, SEQ ID NO: 29, SEQ ID NO: 45 or SEQ ID NO: 48.

In another embodiment, the invention provides an isolated GPT polynucleotide encoding a polypeptide having an amino acid sequence selected from the group consisting of (a) SEQ ID NO: 2; SEQ ID NO: 9; SEQ ID NO: 15, SEQ ID NO: 19, SEQ ID NO: 21, SEQ ID NO 24, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 46 and SEQ ID NO: 49, and (b) an amino acid sequence that is at least 75% identical to any one of SEQ ID NO: 2; SEQ ID NO: 9; SEQ ID NO: 15, SEQ ID NO: 19, SEQ ID NO: 21, SEQ ID NO 24, SEQ ID NO: 30, SEQ ID NO:31, SEQ ID NO: 32, SEQ ID NO: 33, SEQ ID NO: 34, SEQ ID NO: 35, SEQ ID NO: 36, SEQ ID NO: 46 and SEQ ID NO: 49 and has GPT activity.

In another aspects, the invention provides a nucleic acid construct comprising a plant promoter operably linked to a GPT polynucleotide. In one embodiment, the plant promoter is a heterologous promoter. In another embodiment, the plant promoter is a heterologous tissue-specific promoter. Related aspects include a vector comprising such a nucleic acid construct, and a host cell comprising such a vector or nucleic acid construct. In one embodiment, the host cell is a plant cell. In another embodiment, the host cell is a plant cell which expresses the GPT polynucleotide. In yet another embodiment, the host cell is a plant cell which expresses the GPT polynucleotide, wherein polynucleotide so expressed has GPT activity. The invention further provides a plant organ, embryo or seed comprising such a nucleic acid construct or vector, wherein the plant organ, embryo or seed expresses the GPT polynucleotide. In one embodiment, the GPT polynucleotide expressed has GPT activity. In another aspect, the invention provides a transgenic plant comprising such a nucleic acid construct or vector, wherein the transgenic plant expresses the polynucleotide, which in one embodiment has GPT activity. Progeny and seed of such a transgenic plant, wherein the progeny or seed comprises the GPT polynucleotide, are also provided.

BRIEF DESCRIPTION OF THE DRAWINGS

FIG. 2. Multiple sequence alignment of the amino acid sequences of several putative plant, algal and animal GPT proteins, showing a high degree of structural identity and conservation (green shading indicates amino acid residues which are identical in all sequences aligned, and yellow shading indicates amino acids that are identical in all but one or two sequences aligned). This alignment compares (in order from top to bottom in each block) the plant GPTs from barley (*Hordeum vulgare*) (SEQ ID NO: 46), rice (*Orzya sativa*) (SEQ ID NO: 11), corn (*Zea mays*) (SEQ ID NO: 52), cotton (*Gossypium hirsutum*) (SEQ ID NO: 53), grape (*Vitis vinifera*) (SEQ ID NO: 9), castor oil plant (*Ricinus communis*) (SEQ ID NO: 54), California poplar (*Populus trichocarpa*) (SEQ ID NO: 55), soybean (*Glycine max*) (SEQ ID NO: 56), Zebra fish (*Danio rerio*) (SEQ ID NO: 17), arabidopsis (*Arabidopsis thaliana*) (SEQ ID NO: 2), a Bryophyte moss (*Physcomitrella patens*) (SEQ ID NO: 57), and a green algae (*Chlamydomonas* sp.) (SEQ ID NO: 58). The alignment includes the presumed amino-terminal targeting sequence, if known.

FIG. 3. Subset of the multiple sequence alignment of the of FIG. 2, showing a very high degree of structural identity and conservation (green shading indicates amino acid residues which are identical in all sequences aligned, and yellow shading indicates amino acids that are identical in all but one or two sequences aligned). This alignment includes all sequences aligned and displayed in FIG. 2 (barley (SEQ ID NO: 46), rice (SEQ ID NO: 11), corn (SEQ ID NO: 52), cotton (SEQ ID NO: 53), grape (SEQ ID NO: 9), castor oil plant (SEQ ID NO: 54), California poplar (SEQ ID NO: 55), soybean (SEQ ID NO: 56), Zebra fish (SEQ ID NO: 17), arabidopsis (SEQ ID NO: 2)), except the *Physcomitrella* and *Chlamydomonas* sequences. As will be appreciated, relative to the alignment of FIG. 2, a substantial increase in amino acid sequence identity was achieved by eliminating those two sequences, as can be seen by the increase in the number of identical residues among the ten GPT sequences aligned in this figure, nine of which are plant GPTs, and interestingly, the remaining sequence being from Zebra fish.

FIG. 7. Photographs showing comparisons of transgenic tobacco plants generated from various crosses between GS1 and GPT transgenic tobacco lines with wild type and single transgene plants. A-C: Cross 2, 3 and 7, respectively. See Example 7, infra.

DETAILED DESCRIPTION OF THE INVENTION

Definitions

Figure 1:
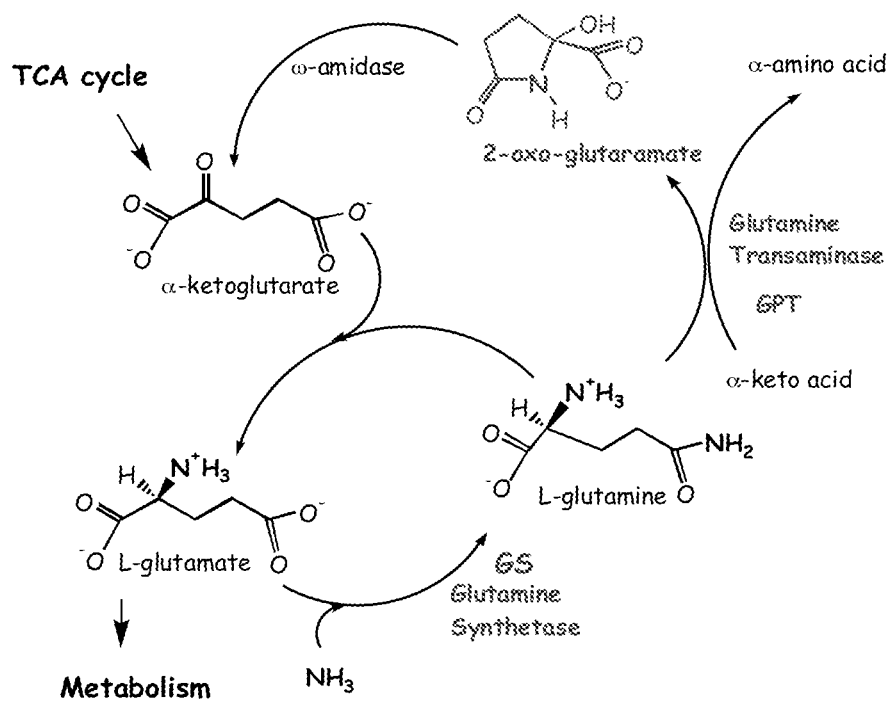
FIG. 1. Nitrogen assimilation and 2-oxoglutaramate biosynthesis: schematic of metabolic pathway.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., Molecular Cloning: A Laboratory Manual 3rd. edition (2001) Cold Spring Harbor Laboratory Press, Cold Spring Harbor, N.Y.; Current Protocols in Molecular Biology (Ausbel et al., eds., John Wiley & Sons, Inc. 2001; Transgenic Plants: Methods and Protocols (Leandro Pena, ed., Humana Press, 1$^{st}$ edition, 2004); and, *Agrobacterium* Protocols (Wan, ed., Humana Press, 2$^{nd}$ edition, 2006). As appropriate, procedures involving the use of commercially available kits and reagents are generally carried out in accordance with manufacturer defined protocols and/or parameters unless otherwise noted.

Each document, reference, patent application or patent cited in this text is expressly incorporated herein in its entirety by reference, and each should be read and considered as part of this specification. That the document, reference, patent application or patent cited in this specification is not repeated herein is merely for conciseness.

The term "nucleic acid" refers to deoxyribonucleotides or ribonucleotides and polymers thereof ("polynucleotides") in either single- or double-stranded form. Unless specifically limited, the term "polynucleotide" encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al., 1991, Nucleic Acid Res. 19: 5081; Ohtsuka et al., 1985 J. Biol. Chem. 260: 2605-2608; and Cassol et al., 1992; Rossolini et al., 1994, Mol. Cell.

Probes 8: 91-98). The term nucleic acid is used interchangeably with gene, cDNA, and mRNA encoded by a gene.

The term "promoter" refers to a nucleic acid control sequence or sequences that direct transcription of an operably linked nucleic acid. As used herein, a "plant promoter" is a promoter that functions in plants. Promoters include necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The term "plant" includes whole plants, plant organs (e.g., leaves, stems, flowers, roots, reproductive organs, embryos and parts thereof, etc.), seedlings, seeds and plant cells and progeny thereof. The class of plants which can be used in the method of the invention is generally as broad as the class of higher plants amenable to transformation techniques, including angiosperms (monocotyledonous and dicotyledonous plants), as well as gymnosperms. It includes plants of a variety of ploidy levels, including polyploid, diploid, haploid and hemizygous.

The terms "GPT polynucleotide" and "GPT nucleic acid" are used interchangeably herein, and refer to a full length or partial length polynucleotide sequence of a gene which encodes a polypeptide involved in catalyzing the synthesis of 2-oxoglutaramate, and includes polynucleotides containing both translated (coding) and un-translated sequences, as well as the complements thereof. The term "GPT coding sequence" refers to the part of the gene which is transcribed and encodes a GPT protein. The term "targeting sequence" refers to the amino terminal part of a protein which directs the protein into a subcellular compartment of a cell, such as a chloroplast in a plant cell. GPT polynucleotides are further defined by their ability to hybridize under defined conditions to the GPT polynucleotides specifically disclosed herein, or to PCR products derived therefrom.

A "GPT transgene" is a nucleic acid molecule comprising a GPT polynucleotide which is exogenous to transgenic plant, or plant embryo, organ or seed, harboring the nucleic acid molecule, or which is exogenous to an ancestor plant, or plant embryo, organ or seed thereof, of a transgenic plant harboring the GPT polynucleotide. More particularly, the exogenous GPT transgene will be heterogeneous with any GPT polynucleotide sequence present in wild-type plant, or plant embryo, organ or seed into which the GPT transgene is inserted. To this extent the scope of the heterogeneity required need only be a single nucleotide difference. However, preferably the heterogeneity will be in the order of an identity between sequences selected from the following identities: 0.01%, 0.05%, 0.1%, 0.5%, 1%, 5%, 10%, 15%, and 20%.

Exemplary GPT polynucleotides of the invention are presented herein, and include GPT coding sequences for *Arabidopsis*, Rice, Barley, Bamboo, Soybean, Grape, Clementine orange and Zebra Fish GPTs.

Partial length GPT polynucleotides include polynucleotide sequences encoding N- or C-terminal truncations of GPT, mature GPT (without targeting sequence) as well as sequences encoding domains of GPT. Exemplary GPT polynucleotides encoding N-terminal truncations of GPT include *Arabidopsis*-30, -45 and -56 constructs, in which coding sequences for the first 30, 45, and 56, respectively, amino acids of the full length GPT structure of SEQ ID NO: 2 are eliminated.

In employing the GPT polynucleotides of the invention in the generation of transformed cells and transgenic plants, one of skill will recognize that the inserted polynucleotide sequence need not be identical, but may be only "substantially identical" to a sequence of the gene from which it was derived, as further defined below. The term "GPT polynucleotide" specifically encompasses such substantially identical variants. Similarly, one of skill will recognize that because of codon degeneracy, a number of polynucleotide sequences will encode the same polypeptide, and all such polynucleotide sequences are meant to be included in the term GPT polynucleotide. In addition, the term specifically includes those sequences substantially identical (determined as described below) with an GPT polynucleotide sequence disclosed herein and that encode polypeptides that are either mutants of wild type GPT polypeptides or retain the function of the GPT polypeptide (e.g., resulting from conservative substitutions of amino acids in a GPT polypeptide). The term "GPT polynucleotide" therefore also includes such substantially identical variants.

The term "conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

Macromolecular structures such as polypeptide structures can be described in terms of various levels of organization. For a general discussion of this organization, see, e.g., Alberts et al., *Molecular Biology of the Cell* ($3^{rd}$ ed., 1994) and Cantor and Schimmel, *Biophysical Chemistry Part I: The Conformation of Biological Macromolecules* (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 25 to approximately 500 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

The term "isolated" refers to material which is substantially or essentially free from components which normally accompany the material as it is found in its native or natural state. However, the term "isolated" is not intended refer to the components present in an electrophoretic gel or other separation medium. An isolated component is free from such separation media and in a form ready for use in another application or already in use in the new application/milieu. An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or non-proteinaceous solutes. In preferred embodiments, the antibody will be purified (1) to greater than 75% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The term "heterologous" when used with reference to portions of a nucleic acid indicates that the nucleic acid comprises two or more subsequences that are not found in the same relationship to each other in nature. For instance, a nucleic acid is typically recombinantly produced, having two or more sequences from unrelated genes arranged to make a new functional nucleic acid, e.g., a nucleic acid encoding a protein from one source and a nucleic acid encoding a peptide sequence from another source. Similarly, a heterologous protein indicates that the protein comprises two or more subsequences that are not found in the same relationship to each other in nature (e.g., a fusion protein).

The terms "identical" or percent "identity," in the context of two or more nucleic acids or polypeptide sequences, refer to two or more sequences or subsequences that are the same or have a specified percentage of amino acid residues or nucleotides that are the same (i.e., about 70% identity, preferably 75%, 80%, 85%, 90%, or 95% identity over a specified region, when compared and aligned for maximum correspondence over a comparison window, or designated region as measured using a sequence comparison algorithms, or by manual alignment and visual inspection. This definition also refers to the complement of a test sequence, which has substantial sequence or subsequence complementarity when the test sequence has substantial identity to a reference sequence. This definition also refers to the complement of a test sequence, which has substantial sequence or subsequence complementarity when the test sequence has substantial identity to a reference sequence.

When percentage of sequence identity is used in reference to polypeptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the polypeptide. Where sequences differ in conservative substitutions, the percent sequence identity may be adjusted upwards to correct for the conservative nature of the substitution.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, 1981, Adv. Appl. Math. 2:482, by the homology alignment algorithm of Needleman & Wunsch, 1970, J. Mol. Biol. 48:443, by the search for similarity method of Pearson & Lipman, 1988, Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

A preferred example of algorithm that is suitable for determining percent sequence identity and sequence similarity are the BLAST and BLAST 2.0 algorithms, which are described in Altschul et al., 1977, Nuc. Acids Res. 25:3389-3402 and Altschul et al., 1990, J. Mol. Biol. 215:403-410, respectively. BLAST and BLAST 2.0 are used, typically with the default parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4 and a comparison of both strands. For amino acid sequences, the BLASTP program uses as defaults a word length of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, 1993, Proc. Nat'l. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, highly stringent conditions are selected to be about 5-10° C. lower than the thermal melting point (Tm) for the specific sequence at a defined ionic strength pH. Low stringency conditions are generally selected to be about 15-30° C. below the Tm. Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0M sodium ion, typically about 0.01 to 1.0M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cased, the nucleic acids typically hybridize under moderately stringent hybridization conditions.

Genomic DNA or cDNA comprising GPT polynucleotides may be identified in standard Southern blots under stringent conditions using the GPT polynucleotide sequences disclosed here. For this purpose, suitable stringent conditions for such hybridizations are those which include a hybridization in a buffer of 40% formamide, 1M NaCl, 1% SDS at 37° C., and at least one wash in 0.2×SSC at a temperature of at least about 50° C., usually about 55° C. to about 60° C., for 20 minutes, or equivalent conditions. A positive hybridization is at least twice background. Those of ordinary skill will readily recognize that alternative hybridization and wash conditions may be utilized to provide conditions of similar stringency.

A further indication that two polynucleotides are substantially identical is if the reference sequence, amplified by a pair of oligonucleotide primers, can then be used as a probe under stringent hybridization conditions to isolate the test sequence from a cDNA or genomic library, or to identify the test sequence in, e.g., a northern or Southern blot.

The invention relates to plant glutamine phenylpyruvate transaminase (GPT) proteins, GPT polynucleotides encoding GPT proteins, nucleic acid constructs and vectors comprising a plant promoter operably linked to a GPT polynucleotide, host cells comprising GPT polynucleotides, and uses thereof. In one embodiment, such host cells are plant cells. In another embodiment, the invention provides transgenic plants, and plant organs, embryos and seeds comprising GPT polynucleotides, which are expressed therein, as well as progeny thereof.

Defined herein are various GPT proteins and GPT gene coding sequences isolated from a number of plant species. As disclosed herein, GPT proteins share remarkable structural similarity within plant species, and are active in catalyzing the synthesis of 2-hydroxy-5-oxoproline (2-oxoglutaramate), a powerful signal metabolite which regulates the function of a large number of genes involved in the photosynthesis apparatus, carbon fixation and nitrogen metabolism. The invention provides the sequences of various GPT polynucleotides encoding GPT proteins, as well as the sequences of various GPT polypeptides which may be encoded by GPT polynucleotides, including GPTs derived from Arabidopsis, Grape, Rice, Soybean, Barley, Bamboo and a non-plant homolog from Zebra fish, all but one of which (Bamboo) have been expressed as recombinant GPTs and confirmed as having GPT activity. In addition, the beginning of the mature plant GPT structure, absent the targeting sequence, has been determined, and GPT polynucleotide constructs in which all or part of the coding sequence of the GPT targeting sequence have been deleted have been expressed in transgenic plants and/or in E. coli to establish that the encoded GPT protein is expressed as an active GPT (see Examples herein).

In addition, using the GPT polynucleotide and protein sequences disclosed herein, several additional putative GPTs have been identified, including without limitation those derived from cotton, castor, poplar, moss and algae, all of which show significant to high structural identity and homology to the aforementioned GPT protein sequences.

Presented in FIG. 2 is a multiple sequence alignment of the amino acid sequences of several putative plant, algal and animal GPT proteins, showing a high degree of structural identity and conservation. Interestingly, whereas a high degree of structural conservation is seen beginning at alignment residue 90, likely at or near the amino-terminus of a mature GPT protein following proteolytic cleavage of the target sequence (sequence beginning with VAKR in all but two sequences), little structural homology is seen in the presumed targeting sequences. With respect to the plant sequences, this may be a consequence of the natural variability in chloroplast targeting sequences among different plants. The first ten of these aligned sequences terminate (C-terminus) at alignment residue position 473-475. When individually compared (by BLAST alignment) to the Arabidopsis mature protein sequence provided in SEQ ID NO: 30, the following sequence identities and homologies (BLAST "positives", including similar amino acids) were obtained for the following mature GPT protein sequences:

| [SEQ ID] or FIG. NO. | ORIGIN | % IDENTITY | % POSITIVE |
|---|---|---|---|
| [31] | Grape | 84 | 93 |
| [32] | Rice | 83 | 91 |
| [33] | Soybean | 83 | 93 |
| [34] | Barley | 82 | 91 |
| [35] | Zebra fish | 83 | 92 |
| [36] | Bamboo | 81 | 90 |
| FIG. 2 | Corn | 79 | 90 |
| FIG. 2 | Castor | 84 | 93 |
| FIG. 2 | Poplar | 85 | 93 |

Underscoring the conserved nature of the structure of the GPT protein across most plant species, the conservation seen within the above plant species extends to the non-human putative GPTs from Zebra fish and Chlamydomonas. In the case of Zebra fish, the extent of identity is very high (83% amino acid sequence identity with the mature Arabidopsis GPT of SEQ ID NO: 30, and 92% homologous taking similar amino acid residues into account). The Zebra fish mature GPT was confirmed by expressing it in E. coli and demonstrating biological activity (synthesis of 2-oxoglutaramate).

In one group of embodiments, GPT polynucleotides encoding Arabidopsis GPTs are provided, and include GPT polynucleotides encoding the GPT proteins of SEQ ID NO: 2, SEQ ID NO: 21 and SEQ ID NO: 30. Specific embodiments include the GPT polynucleotide sequence of SEQ ID NO: 1, SEQ ID NO: 18 and SEQ ID NO: 20, as well as polynucleotides encoding the GPT amino acid sequences of SEQ ID NO: 2, SEQ ID NO: 19, SEQ ID NO: 21 and SEQ ID NO: 29.

In another group of embodiments, GPT polynucleotides encoding Grape GPTs are provided, and include GPT polynucleotides encoding the GPT proteins of SEQ ID NO: 9 and SEQ ID NO: 31. Specific embodiments include the GPT polynucleotide sequence of SEQ ID NO: 8, as well as polynucleotides encoding the GPT amino acid sequences of SEQ ID NO: 9 and SEQ ID NO: 31.

In yet another group of embodiments, GPT polynucleotides encoding Rice GPTs are provided, and include GPT polynucleotides encoding the GPT proteins of SEQ ID NO: 11 and SEQ ID NO: 32. Specific embodiments include the GPT polynucleotide sequence of SEQ ID NO:10, as well as polynucleotides encoding the GPT amino acid sequences of SEQ ID NO: 11 and SEQ ID NO: 32.

In yet another group of embodiments, GPT polynucleotides encoding Soybean GPTs are provided, and include GPT polynucleotides encoding the GPT proteins SEQ ID NO: 13, SEQ ID NO: 33 and SEQ ID NO: 33 with a further Isoleucine at the N-terminus of the sequence. Specific embodiments include the GPT polynucleotide sequence of SEQ ID NO 12, as well as polynucleotides encoding the GPT amino acid sequences of SEQ ID NO: 13, SEQ ID NO: 33 and SEQ ID NO: 33 with a further Isoleucine at the N-terminus of the sequence.

In yet another group of embodiments, GPT polynucleotides encoding Barley GPTs are provided, and include GPT polynucleotides encoding the GPT proteins of SEQ ID NO: 15 and SEQ ID NO: 34. Specific embodiments include the GPT polynucleotide sequence of SEQ ID NO: 14, as well as polynucleotides encoding the GPT amino acid sequences of SEQ ID NO: 15 and SEQ ID NO: 34.

In yet another group of embodiments, GPT polynucleotides Zebra fish Rice GPTs are provided, and include GPT polynucleotides encoding the GPT proteins of SEQ ID NO: 17 and SEQ ID NO: 35. Specific embodiments include the GPT polynucleotide sequence of SEQ ID NO: 16, as well as polynucleotides encoding the GPT amino acid sequences of SEQ ID NO: 17 and SEQ ID NO: 35.

In yet another group of embodiments, GPT polynucleotides encoding Bamboo GPTs are provided, and include GPT polynucleotides encoding the GPT proteins of SEQ ID NO: 36. Specific embodiments include a GPT polynucleotide sequence encoding the GPT amino acid sequence of SEQ ID NO: 36.

In yet another group of embodiments, GPT polynucleotides encoding Clementine GPTs are provided, and include GPT polynucleotides encoding the GPT proteins of SEQ ID NO: 36. Specific embodiments include a GPT polynucleotide sequence encoding the GPT amino acid sequence of SEQ ID NO: 36.

With the benefit of the various GPT polynucleotides exemplified herein, one of ordinary skill in the art may obtain additional GPT polynucleotides from other plant and non-plant sources using standard molecular cloning and recombinant DNA methodologies. In one approach, oligonucleotide probes based on the sequences of the GPT polynucleotides disclosed herein can be used to identify the desired gene in a cDNA or genomic DNA library. To construct genomic libraries, large segments of genomic DNA are generated by random fragmentation, e.g. using restriction endonucleases, and are ligated with vector DNA to form concatemers that can be packaged into the appropriate vector. To prepare a cDNA library, mRNA is isolated from the desired organ, such as ovules, and a cDNA library which contains the GPT gene transcript is prepared from the mRNA. Alternatively, cDNA may be prepared from mRNA extracted from other tissues in which GPT genes or homologs are expressed.

cDNA or genomic libraries may be screened using a probe based upon the sequence of a GPT polynucleotide disclosed herein. Probes may be used to hybridize with genomic DNA or cDNA sequences to isolate homologous genes in the same or different plant species. Alternatively, antibodies raised against an GPT polypeptide can be used to screen an mRNA expression library.

GPT polynucleotides may also be amplified from nucleic acid samples using nucleic acid amplification techniques, such as polymerase chain reaction (PCR), which may be used to amplify the sequences of GPT genes directly from genomic DNA, from cDNA, from genomic libraries or cDNA libraries. PCR and other amplification methods may also be useful, for example, to clone GPT polynucleotide encoding GPT proteins for expression, prepare transgene constructs and expression vectors, generate transgenic plants, make oligonucleotide probes for detecting the presence of GPT mRNA in samples, for nucleic acid sequencing, or for other purposes. For a general overview of PCR see PCR Protocols: A Guide to Methods and Applications. (Innis, M, Gelfand, D., Sninsky, J. and White, T., eds.), Academic Press, San Diego (1990).

Appropriate primers and probes for identifying GPT polynucleotides from plant tissues may be generated from the GPT polynucleotide sequences provided herein. Alignments of one or more of the GPT polynucleotides (genes) disclosed herein, and/or alignments of one or more of the GPT protein amino acid sequences disclosed herein, may be used to identify conserved regions in the GPT structure suitable for preparing the appropriate primer and probe sequences. Primers that specifically hybridize to conserved regions in one of the plant GPT polynucleotides disclosed herein may be used to amplify sequences from widely divergent plant species. Indeed, the sequence similarity seen among the several here exemplified GPT genes is very high, and many regions of perfect identity within the GPT protein primary structure are seen (see, for example, the sequence alignments shown in FIGS. 2 and 3)

GPT polynucleotides may be tested for their ability to direct the expression of a functional, biologically active GPT protein by expressing the GPT polynucleotide in a cell and assaying for GPT activity or the presence of increased levels of 2-oxoglutaramate. Assays for GPT activity and 2-oxoglutaramate are disclosed herein (see Examples). In addition, GPT polypeptides may be tested in transgenic plants, following protocols in the Examples which follow. Plants expressing a GPT transgene will show increased levels of GPT activity, higher levels of 2-oxoglutaramate, and/or enhanced growth characteristics, relative to wild type plants (see Examples following).

The GPT polynucleotides are useful in directing the expression of recombinant GPT polypeptides in recombinant expression systems, as is generally known.

The GPT polynucleotides are useful in generating transgenic plants with increased levels of GPT activity, upregulated 2-oxoglutaramate levels, and enhanced growth characteristics. As consistently shown in the examples which follow, numerous species of transgenic plants containing a GPT transgene showed enhanced growth characteristics, including increased biomass, earlier and more productive flowering, increased fruit or pod yields, larger leaf sizes, taller heights, tolerance to high salt germination and faster growth.

In order to generate the transgenic plants of the invention, the gene coding sequence for the desired transgene(s) must be incorporated into a nucleic acid construct (also interchangeably referred to herein as a/an (transgene) expression vector, expression cassette, expression construct or expressible genetic construct), which can direct the expression of the transgene sequence in transformed plant cells. Such nucleic acid constructs carrying the transgene(s) of interest may be introduced into a plant cell or cells using a number of methods known in the art, including but not limited to electroporation, DNA bombardment or biolistic approaches, microinjection, and via the use of various DNA-based vectors such as *Agrobacterium tumefaciens* and *Agrobacterium rhizogenes* vectors. Once introduced into the transformed plant cell, the nucleic acid construct may direct the expression of the incorporated transgene(s) (i.e., GPT), either in a transient or stable fashion. Stable expression is preferred, and is achieved by utilizing plant transformation vectors which are able to direct the chromosomal integration of the transgene construct. Once a plant cell has been successfully transformed, it may be cultivated to regenerate a transgenic plant.

The transgenic plants of the invention may be any vascular plant of the phylum Tracheophyta, including angiosperms and gymnosperms. Angiosperms may be a monocotyledonous (monocot) or a dicotyledonous (dicot) plant. Important monocots include those of the grass families, such as the family Poaceae and Gramineae, including plants of the genus *Avena* (*Avena sativa*, oats), genus *Hordeum* (i.e., *Hordeum vulgare*, Barley), genus *Oryza* (i.e., *Oryza sativa*, rice, cultivated rice varieties), genus *Panicum* (*Panicum* spp., *Panicum virgatum*, Switchgrass), genus *Phleum* (*Phleum pratense*, Timothy-grass), genus *Saccharum* (i.e., *Saccharum officinarum, Saccharum spontaneum*, hybrids thereof, Sugarcane), genus *Secale* (i.e., *Secale cereale*, Rye), genus *Sorghum* (*Sorghum vulgare, Sorghum*), genus *Triticum* (wheat, various classes, including *T. aestivum* and *T. durum*), genus *Fagopyrum* (buckwheat, including *F. esculentum*), genus *Triticosecale* (Triticale, various hybrids of wheat and rye), genus *Chenopodium* (quinoa, including *C. quinoa*), genus *Zea* (i.e., *Zea mays*, numerous varieties) as well as millets (i.e., *Pennisetum glaucum*) including the genus *Digitaria* (*D. exilis*).

Important dicots include those of the family Solanaceae, such as plants of the genus *Lycopersicon* (*Lycopersicon esculentum*, tomato), genus *Capiscum* (*Capsicum annuum*, peppers), genus *Solanum* (*Solanum tuberosum*, potato, *S. lycopersicum*, tomato); genus *Manihot* (cassava, *M. esculenta*), genus *Ipomoea* (sweet potato, *I. batatas*), genus *Olea* (olives, including *O. europaea*); plants of the Gossypium family (i.e., *Gossypium* spp., *G. hirsutum, G. herbaceum*, cotton); the Legumes (family Fabaceae), such as peas (*Pisum* spp, *P. sativum*), beans (*Glycine* spp., *Glycine max*(soybean); *Phaseolus vulgaris*, common beans, *Vigna radiata*, mung bean), chickpeas (*Cicer arietinum*)), lentils (*Lens culinaris*), peanuts (*Arachis hypogaea*); coconuts (*Cocos nucifera*) as well as various other important crops such as camelina (*Camelina sativa*, family Brassicaceae), citrus (*Citrus* spp, family Rutaceae), coffee (*Coffea* spp, family Rubiaceae), melon (*Cucumis* spp, family Cucurbitaceae), squash (*Cucurbita* spp, family Cucurbitaceae), roses (*Rosa* spp, family Rosaceae), sunflower (*Helianthus annuus*, family Asteraceae), sugar beets (*Beta* spp, family Amaranthaceae), including sugarbeet, *B. vulgaris*), genus *Daucus* (carrots, including *D. carota*), genus *Pastinaca* (parsnip, including *P. sativa*), genus *Raphanus* (radish, including *R. sativus*), genus *Dioscorea* (yams, including *D. rotundata* and *D. cayenensis*), genus *Armoracia* (horseradish, including *A. rusticana*), genus *Elaeis* (Oil palm, including *E. guineensis*), genus *Linum* (flax, including *L. usitatissimum*), genus *Carthamus* (safflower, including *C. tinctorius* L.), genus *Sesamum* (sesame, including *S. indicum*), genus *Vitis* (grape, including *Vitis vinifera*), and plants of the genus *Brassica* (family Brassicaceae, i.e., broccoli, brussel sprouts, cabbage, swede, turnip, rapeseed *B. napus*, and cauliflower).

Other specific plants which may be transformed to generate the transgenic plants of the invention include various other fruits and vegetables, such as apples, asparagus, avocado, banana, blackberry, blueberry, brussel sprout, cabbage, cotton, canola, carrots, radish, cucumbers, cherries, cranberries, cantaloupes, eggplant, grapefruit, lemons, limes, nectarines, oranges, peaches, pineapples, pears, plums, tangelos, tangerines, papaya, mango, strawberry, raspberry, lettuce, onion, grape, kiwi fruit, okra, parsnips, pumpkins, and spinach. In addition various flowering plants, trees and ornamental plants may be used to generate transgenic varietals, including without limitation lily, carnation, chrysanthemum, petunia, geranium, violet, gladioli, lupine, orchid and lilac.

In order to determine whether putative GPT homologs would be suitable for generating the growth-enhanced transgenic plants of the invention, one need initially express the coding sequence thereof in *E. coli* or another suitable host and determine whether the 2-oxoglutaramate signal metabolite is synthesized at increased levels (see Example 2, infra). Where such an increase is demonstrated, the coding sequence may then be introduced into both homologous plant hosts and heterologous plant hosts, and growth characteristics evaluated. Any assay that is capable of detecting 2-oxoglutaramate with specificity may be used for this purpose, including without limitation the NMR and HPLC assays described in Example 2, infra.

A large number of expression vectors suitable for driving the constitutive or induced expression of inserted genes in transformed plants are known. In addition, various transient expression vectors and systems are known. To a large extent, appropriate expression vectors are selected for use in a particular method of gene transformation (see, infra). Broadly speaking, a typical plant expression vector for generating transgenic plants will comprise the transgene of interest under the expression regulatory control of a promoter, a selectable marker for assisting in the selection of transformants, and a transcriptional terminator sequence.

More specifically, the basic elements of a nucleic acid construct for use in generating the transgenic plants of the invention are: a suitable promoter capable of directing the functional expression of the transgene(s) in a transformed plant cell, the transgene (s) (i.e., GPT coding sequence) operably linked to the promoter, preferably a suitable transcription termination sequence (i.e., nopaline synthetic enzyme gene terminator) operably linked to the transgene, and sometimes other elements useful for controlling the expression of the transgene, as well as one or more selectable marker genes suitable for selecting the desired transgenic product (i.e., antibiotic resistance genes).

Based on the results disclosed herein, it is clear that any number of GPT polynucleotides may be used to generate the transgenic plants of the invention. GPT proteins are highly conserved among various plant species, and it is evident from the experimental data disclosed herein that closely-related non-plant GPTs may be used as well (e.g., *Danio rerio* GPT).

GPT polynucleotides suitable for use as GPT transgenes in the practice of the invention may be obtained by various means, as will be appreciated by one skilled in the art, tested for the ability to direct the expression of a GPT with GPT activity in a recombinant expression system, i.e., *E. coli* (see Examples 20-23), in a transient in planta expression system (see Example 19), or in a transgenic plant (see Examples 1-18).

The invention also provides methods of generating a transgenic plant having enhanced growth and other agronomic characteristics. In one embodiment, a method of generating a transgenic plant having enhanced growth and other agronomic characteristics comprises introducing into a plant cell an expression cassette comprising a nucleic acid molecule encoding a GPT transgene, under the control of a suitable promoter capable of driving the expression of the transgene, so as to yield a transformed plant cell, and obtaining a transgenic plant which expresses the encoded GPT.

As exemplified herein, transgenic plants showing enhanced growth characteristics have been generated in two species of Tomato (see Examples 4 and 17), Pepper (Example 8), Beans (Examples 9 and 10), Cowpea (Examples 11 and 12), *Alfalfa* (Example 13), Cantaloupe (Example 14), Pumpkin (Example 15), *Arabidopsis* (Example 16) and Camilena (Example 18). These transgenic plants of the invention were generated using a variety of transformation methodologies, including *Agrobacterium*-mediated callus, floral dip, seed inoculation, pod inoculation, and direct flower inoculation, as well as combinations thereof, and via sexual crosses of, single transgene plants, as exemplified herein. Different GPT transgenes were successfully employed in generating the transgenic plants of the invention, as exemplified herein.

As *Agrobacterium tumefaciens* is the primary transformation system used to generate transgenic plants, there are numerous vectors designed for *Agrobacterium* transformation. For stable transformation, *Agrobacterium* systems utilize "binary" vectors that permit plasmid manipulation in both *E. coli* and *Agrobacterium*, and typically contain one or more selectable markers to recover transformed plants (Hellens et al., 2000, *Technical focus: A guide to Agrobacterium binary Ti vectors*. Trends Plant Sci 5:446-451). Binary vectors for use in *Agrobacterium* transformation systems typically comprise the borders of T-DNA, multiple cloning sites, replication functions for *Escherichia coli* and *A. tumefaciens*, and selectable marker and reporter genes.

So-called "super-binary" vectors provide higher transformation efficiencies, and generally comprise additional virulence genes from a Ti (Komari et al., 2006, Methods Mol. Biol. 343: 15-41). Super binary vectors are typically used in plants which exhibit lower transformation efficiencies, such as cereals. Such additional virulence genes include without limitation virB, virE, and virG (Vain et al., 2004, *The effect of additional virulence genes on transformation efficiency, transgene integration and expression in rice plants using the pGreen/pSoup dual binary vector system*. Transgenic Res. 13: 593-603; Srivatanakul et al., 2000, *Additional virulence genes influence transgene expression: transgene copy number, integration pattern and expression*. J. Plant Physiol. 157, 685-690; Park et al., 2000, *Shorter T-DNA or additional virulence genes improve Agrobacterium-mediated transformation*. Theor. Appl. Genet. 101, 1015-1020; Jin et al., 1987, *Genes responsible for the supervirulence phenotype of Agrobacterium tumefaciens A*281. J. Bacteriol. 169: 4417-4425).

In the embodiments exemplified herein (see Examples, infra), expression vectors which place the inserted transgene(s) under the control of the constitutive CaMV 35S promoter are employed. A number of expression vectors which utilize the CaMV 35S promoter are known and/or commercially available. However, numerous promoters suitable for directing the expression of the transgene are known and may be used in the practice of the invention, as further described, infra.

A large number of plant promoters, which are functional in plants, including transgenic plants, are known in the art. In constructing GPT transgene constructs, the selected promoter(s) may be constitutive, non-specific promoters such as the Cauliflower Mosaic Virus 35S ribosomal promoter (CaMV 35S promoter), which is widely employed for the expression of transgenes in plants. Examples of other strong constitutive promoters include without limitation the rice actin 1 promoter, the CaMV 19S promoter, the Ti plasmid nopaline synthase promoter, the alcohol dehydrogenase promoter and the sucrose synthase promoter.

Alternatively, in some embodiments, it may be desirable to select a promoter based upon the desired plant cells to be transformed by the transgene construct, the desired expression level of the transgene, the desired tissue or subcellular compartment for transgene expression, the developmental stage targeted, and the like.

For example, when expression in photosynthetic tissues and compartments is desired, a promoter of the ribulose bisphosphate carboxylase (RuBisCo) gene may be employed. When the expression in seeds is desired, promoters of various seed storage protein genes may be employed. For expression in fruits, a fruit-specific promoter such as tomato 2A11 may be used. Examples of other tissue specific promoters include the promoters encoding lectin (Vodkin et al., 1983, Cell 34:1023-31; Lindstrom et al., 1990, Developmental Genetics 11:160-167), corn alcohol dehydrogenase 1 (Vogel et al, 1989, J. Cell. Biochem. (Suppl. 0) 13: Part D; Dennis et al., 1984, Nucl. Acids Res., 12(9): 3983-4000), corn light harvesting complex (Simpson, 1986, Science, 233: 34-38; Bansal et al., 1992, Proc. Natl. Acad. Sci. USA, 89: 3654-3658), corn heat shock protein (Odell et al., 1985, Nature, 313: 810-812; Rochester et al., 1986, EMBO J., 5: 451-458), pea small subunit RuBP carboxylase (Poulsen et al., 1986, Mol. Gen. Genet., 205(2): 193-200; Cashmore et al., 1983, Gen. Eng. Plants, Plenum Press, New York, pp 29-38), Ti plasmid mannopine synthase and Ti plasmid nopaline synthase (Langridge et al., 1989, Proc. Natl. Acad. Sci. USA, 86: 3219-3223), petunia chalcone isomerase (Van Tunen et al., 1988, EMBO J. 7(5): 1257-1263), bean glycine rich protein 1 (Keller et al., 1989, EMBO J. 8(5): 1309-1314), truncated CaMV 35S (Odell et al., 1985, supra), potato patatin (Wenzler et al., 1989, Plant Mol. Biol. 12: 41-50), root cell (Conkling et al., 1990, Plant Physiol. 93: 1203-1211), maize zein (Reina et al., 1990, Nucl. Acids Res. 18(21): 6426; Kriz et al., 1987, Mol. Gen. Genet. 207(1): 90-98; Wandelt and Feix, 1989, Nuc. Acids Res. 17(6): 2354; Langridge and Feix, 1983, Cell 34: 1015-1022; Reina et al., 1990, Nucl. Acids Res. 18(21): 6426), globulin-1 (Belanger and Kriz, 1991, Genetics 129: 863-872), α-tubulin (Carpenter et al., 1992, Plant Cell 4(5): 557-571; Uribe et al., 1998, Plant Mol. Biol. 37(6): 1069-1078), cab (Sullivan, et al., 1989, Mol. Gen. Genet. 215(3): 431-440), PEPCase (Hudspeth and Grula, 1989, Plant Mol. Biol. 12: 579-589), R gene complex (Chandler et al., 1989, The Plant Cell 1: 1175-1183), chalcone synthase (Franken et al., 1991, EMBO J. 10(9): 2605-2612) and glutamine synthetase promoters (U.S. Pat. No. 5,391,725; Edwards et al., 1990, Proc. Natl. Acad. Sci. USA 87: 3459-3463; Brears et al., 1991, Plant J. 1(2): 235-244).

In addition to constitutive promoters, various inducible promoter sequences may be employed in cases where it is desirable to regulate transgene expression as the transgenic plant regenerates, matures, flowers, etc. Examples of such inducible promoters include promoters of heat shock genes, protection responding genes (i.e., phenylalanine ammonia lyase; see, for example Bevan et al., 1989, EMBO J. 8(7): 899-906), wound responding genes (i.e., cell wall protein genes), chemically inducible genes (i.e., nitrate reductase, chitinase) and dark inducible genes (i.e., asparagine synthetase; see, for example U.S. Pat. No. 5,256,558). Also, a number of plant nuclear genes are activated by light, including gene families encoding the major chlorophyll a/b binding proteins (cab) as well as the small subunit of ribulose-1,5-bisphosphate carboxylase (rbcS) (see, for example, Tobin and Silverthorne, 1985, Annu. Rev. Plant Physiol. 36: 569-593; Dean et al., 1989, Annu. Rev. Plant Physiol. 40: 415-439.).

Other inducible promoters include ABA- and turgor-inducible promoters, the auxin-binding protein gene promoter (Schwob et al., 1993, Plant J. 4(3): 423-432), the UDP glucose flavonoid glycosyl-transferase gene promoter (Ralston et al., 1988, Genetics 119(1): 185-197); the MPI proteinase inhibitor promoter (Cordero et al., 1994, Plant J. 6(2): 141-150), the glyceraldehyde-3-phosphate dehydrogenase gene promoter (Kohler et al., 1995, Plant Mol. Biol. 29(6): 1293-1298; Quigley et al., 1989, J. Mol. Evol. 29(5): 412-421; Martinez et al., 1989, J. Mol. Biol. 208(4): 551-565) and light inducible plastid glutamine synthetase gene from pea (U.S. Pat. No. 5,391,725; Edwards et al., 1990, supra).

For a review of plant promoters used in plant transgenic plant technology, see Potenza et al., 2004, In Vitro Cell. Devel. Biol—Plant, 40(1): 1-22. For a review of synthetic plant promoter engineering, see, for example, Venter, M., 2007, Trends Plant Sci., 12(3): 118-124.

In some embodiments, a 3' transcription termination sequence is incorporated downstream of the transgene in order to direct the termination of transcription and permit correct polyadenylation of the mRNA transcript. Suitable transcription terminators are those which are known to function in plants, including without limitation, the nopaline synthase (NOS) and octopine synthase (OCS) genes of *Agrobacterium tumefaciens*, the T7 transcript from the octopine synthase gene, the 3' end of the protease inhibitor I or II genes from potato or tomato, the CaMV 35S terminator, the tml terminator and the pea rbcS E9 terminator. In addition, a gene's native transcription terminator may be used. In specific embodiments, described by way of the Examples, infra, the nopaline synthase transcription terminator is employed.

Selectable markers are typically included in transgene expression vectors in order to provide a means for selecting transformants. While various types of markers are available, various negative selection markers are typically utilized, including those which confer resistance to a selection agent that inhibits or kills untransformed cells, such as genes which impart resistance to an antibiotic (such as kanamycin, gentamycin, anamycin, hygromycin and hygromycinB) or resistance to a herbicide (such as sulfonylurea, gulfosinate, phosphinothricin and glyphosate). Screenable markers include, for example, genes encoding β-glucuronidase (Jefferson, 1987, Plant Mol. Biol. Rep 5: 387-405), genes encoding luciferase (Ow et al., 1986, Science 234: 856-859) and various genes encoding proteins involved in the production or control of anthocyanin pigments (See, for example, U.S. Pat. No. 6,573,432). The *E. coli* glucuronidase gene (gus, gusA or uidA) has become a widely used selection marker in plant transgenics, largely because of the glucuronidase enzyme's stability, high sensitivity and ease of detection (e.g., fluorometric, spectrophotometric, various histochemical methods). Moreover, there is essentially no detectable glucuronidase in most higher plant species.

Various methods for introducing a GPT transgene expression vector construct of the invention into a plant or plant cell are well known to those skilled in the art, and any capable of transforming the target plant or plant cell may be utilized.

*Agrobacterium*-mediated transformation is perhaps the most common method utilized in plant transgenics, and protocols for *Agrobacterium*-mediated transformation of a large number of plants are extensively described in the literature (see, for example, *Agrobacterium Protocols*, Wan, ed., Humana Press, $2^{nd}$ edition, 2006). *Agrobacterium tumefaciens* is a Gram negative soil bacteria that causes tumors (Crown Gall disease) in a great many dicot species, via the insertion of a small segment of tumor-inducing DNA ("T-DNA", 'transfer DNA') into the plant cell, which is incorporated at a semi-random location into the plant genome, and which eventually may become stably incorporated there. Directly repeated DNA sequences, called T-DNA borders, define the left and the right ends of the T-DNA. The T-DNA can be physically separated from the remainder of the Ti-plasmid, creating a 'binary vector' system.

*Agrobacterium* transformation may be used for stably transforming dicots, monocots, and cells thereof (Rogers et al., 1986, Methods Enzymol., 118: 627-641; Hernalsteen et al., 1984, EMBO J., 3: 3039-3041; Hoykass-Van Slogteren et al., 1984, Nature, 311: 763-764; Grimsley et al., 1987, Nature 325: 167-1679; Boulton et al., 1989, Plant Mol. Biol. 12: 31-40; Gould et al., 1991, Plant Physiol. 95: 426-434). Various methods for introducing DNA into *Agrobacteria* are known, including electroporation, freeze/thaw methods, and triparental mating. The most efficient method of placing foreign DNA into *Agrobacterium* is via electroporation (Wise et al., 2006, *Three Methods for the Introduction of Foreign DNA into Agrobacterium, Methods in Molecular Biology*, vol. 343: *Agrobacterium* Protocols, 2/e, volume 1; Ed., Wang, Humana Press Inc., Totowa, N.J., pp. 43-53). In addition, given that a large percentage of T-DNAs do not integrate, *Agrobacterium*-mediated transformation may be used to obtain transient expression of a transgene via the transcriptional competency of unincorporated transgene construct molecules (Helens et al., 2005, Plant Methods 1:13).

A large number of *Agrobacterium* transformation vectors and methods have been described (Karimi et al., 2002, Trends Plant Sci. 7(5): 193-5), and many such vectors may be obtained commercially (for example, Invitrogen, Carlsbad, Calif.). In addition, a growing number of "open-source" *Agrobacterium* transformation vectors are available (for example, pCambia vectors; Cambia, Canberra, Australia). See, also, subsection herein on TRANSGENE CONSTRUCTS, supra; In a specific embodiment described further in the Examples, a pMON316-based vector was used in the leaf disc transformation system of Horsch et. al. (Horsch et al., 1995, Science 227:1229-1231) to generate growth enhanced transgenic tobacco and tomato plants.

Other commonly used transformation methods that may be employed in generating the transgenic plants of the invention include, without limitation, microprojectile bombardment, or biolistic transformation methods, protoplast transformation of naked DNA by calcium, polyethylene glycol (PEG) or electroporation (Paszkowski et al., 1984, EMBO J. 3: 2727-2722; Potrykus et al., 1985, Mol. Gen. Genet. 199: 169-177; Fromm et al., 1985, Proc. Nat. Acad. Sci. USA 82: 5824-5828; Shimamoto et al., 1989, Nature, 338: 274-276.

Biolistic transformation involves injecting millions of DNA-coated metal particles into target cells or tissues using a biolistic device (or "gene gun"), several kinds of which are available commercially. Once inside the cell, the DNA elutes off the particles and a portion may be stably incorporated into one or more of the cell's chromosomes (for review, see Kikkert et al., 2005, *Stable Transformation of Plant Cells by Particle Bombardment/Biolistics*, in: Methods in Molecular Biology, vol. 286: Transgenic Plants: Methods and Protocols, Ed. L. Peña, Humana Press Inc., Totowa, N.J.).

Electroporation is a technique that utilizes short, high-intensity electric fields to permeabilize reversibly the lipid bilayers of cell membranes (see, for example, Fisk and Dandekar, 2005, *Introduction and Expression of Transgenes in Plant Protoplasts*, in: Methods in Molecular Biology, vol. 286: Transgenic Plants: Methods and Protocols, Ed. L. Pena, Humana Press Inc., Totowa, N.J., pp. 79-90; Fromm et al., 1987, *Electroporation of DNA and RNA into plant protoplasts*, in Methods in Enzymology, Vol. 153, Wu and Grossman, eds., Academic Press, London, UK, pp. 351-366; Joersbo and Brunstedt, 1991, *Electroporation: mechanism and transient expression, stable transformation and biological effects in plant protoplasts*. Physiol. Plant. 81, 256-264; Bates, 1994, *Genetic transformation of plants by protoplast electroporation*. Mol. Biotech. 2: 135-145; Dillen et al., 1998, *Electroporation-mediated DNA transfer to plant protoplasts and intact plant tissues for transient gene expression assays*, in Cell Biology, Vol. 4, ed., Celis, Academic Press, London, UK, pp. 92-99). The technique operates by creating aqueous pores in the cell membrane, which are of sufficiently large size to allow DNA molecules (and other macromolecules) to enter the cell, where the transgene expression construct (as T-DNA) may be stably incorporated into plant genomic DNA, leading to the generation of transformed cells that can subsequently be regenerated into transgenic plants.

Newer transformation methods include so-called "floral dip" methods, which offer the promise of simplicity, without requiring plant tissue culture, as is the case with all other commonly used transformation methodologies (Bent et al., 2006, *Arabidopsis thaliana Floral Dip Transformation Method*, Methods Mol Biol, vol. 343: *Agrobacterium Protocols,* 2/e, volume 1; Ed., Wang, Humana Press Inc., Totowa, N.J., pp. 87-103; Clough and Bent, 1998, *Floral dip: a simplified method for Agrobacterium-mediated transformation of Arabidopsis thaliana*, Plant J. 16: 735-743). However, with the exception of *Arabidopsis*, these methods have not been widely used across a broad spectrum of different plant species. Briefly, floral dip transformation is accomplished by dipping or spraying flowering plants in with an appropriate strain of *Agrobacterium tumefaciens*. Seeds collected from these $T_0$ plants are then germinated under selection to identify transgenic $T_1$ individuals. Example 16 demonstrated floral dip inoculation of *Arabidopsis* to generate transgenic *Arabidopsis* plants.

Other transformation methods include those in which the developing seeds or seedlings of plants are transformed using vectors such as *Agrobacterium* vectors. For example, as exemplified in Example 8, such vectors may be used to transform developing seeds by injecting a suspension or mixture of the vector (i.e., *Agrobacteria*) directly into the seed cavity of developing pods (i.e., pepper pods, bean pods, pea pods and the like). Seedlings may be transformed as described for *Alfalfa* in Example 13. Germinating seeds may be transformed as described for *Camelina* in Example 18. Intra-fruit methods, in which the vector is injected into fruit or developing fruit, may be used as described for Cantaloupe melons in Example 14 and pumpkins in Example 15.

Still other transformation methods include those in which the flower structure is targeted for vector inoculation, such as the flower inoculation methods described for beans in Examples 9 and 10, peas in Examples 11 and 12 and tomatoes in Example 17.

In addition, although transgenes are most commonly inserted into the nuclear DNA of plant cells, trangenes may also be inserted into plastidic DNA (i.e., into the plastome of the chloroplast). In most flowering plants, plastids do not occur in the pollen cells, and therefore transgenic DNA incorporated within a plastome will not be passed on through propagation, thereby restricting the trait from migrating to wild type plants. Plastid transformation, however, is more complex than cell nucleus transformation, due to the presence of many thousands of plastomes per cell (as high as 10,000).

Transplastomic lines are genetically stable only if all plastid copies are modified in the same way, i.e. uniformly. This is typically achieved through repeated regeneration under certain selection conditions to eliminate untransformed plastids, by segregating transplastomic and untransformed plastids, resulting in the selection of homoplasmic cells carrying the transgene construct and the selectable marker stably integrated therein. Plastid transformation has been successfully performed in various plant species, including tobacco, potatoes, oilseed rape, rice and *Arabidopsis*.

To generate transplastomic lines carrying GPT and GS transgenes, the transgene expression cassette is inserted into flanking sequences from the plastome. Using homologous recombination, the transgene expression cassette becomes integrated into the plastome via a natural recombination process. The basic DNA delivery techniques for plastid transformation include particle bombardment of leaves or polyethylene glycol-mediated DNA transformation of protoplasts. Transplastomic plants carrying transgenes in the plastome may be expressed at very high levels, due to the fact that many plastids (i.e., chloroplasts) per cell, each carrying many copies of the plastome. This is particularly the case in foliar tissue, where a single mature leaf cell may contain over 10,000 copies of the plastome. Following a successful transformation of the plastome, the transplastomic events carry the transgene on every copy of the plastid genetic material. This can result in the transgene expression levels representing as much as half of the total protein produced in the cell.

Plastid transformation methods and vector systems are described, for example, in recent U.S. Pat. Nos. 7,528,292; 7,371,923; 7,235,711; and, 7,193,131. See also U.S. Pat. Nos. 6,680,426 and 6, 642,053.

The foregoing plant transformation methodologies may be used to introduce transgenes into a number of different plant cells and tissues, including without limitation, whole plants, tissue and organ explants including chloroplasts, flowering tissues and cells, protoplasts, meristem cells, callus, immature embryos and gametic cells such as microspores, pollen, sperm and egg cells, tissue cultured cells of any of the foregoing, any other cells from which a fertile regenerated transgenic plant may be generated. Callus is initiated from tissue sources including, but not limited to, immature embryos, seedling apical meristems, microspores and the like. Cells capable of proliferating as callus are also recipient cells for genetic transformation.

Methods of regenerating individual plants from transformed plant cells, tissues or organs are known and are described for numerous plant species.

As an illustration, transformed plantlets (derived from transformed cells or tissues) are cultured in a root-permissive growth medium supplemented with the selective agent used in the transformation strategy (i.e., an antibiotic such as kanamycin). Once rooted, transformed plantlets are then transferred to soil and allowed to grow to maturity. Upon flowering, the mature plants are preferably selfed (self-fertilized), and the resultant seeds harvested and used to grow subsequent generations. Examples 3-6 describe the regeneration of transgenic tobacco and tomato plants.

$T_0$ transgenic plants may be used to generate subsequent generations (e.g., $T_1$, $T_2$, etc.) by selfing of primary or secondary transformants, or by sexual crossing of primary or secondary transformants with other plants (transformed or untransformed). For example, as described in Example 7, infra, individual plants over expressing the *Alfalfa* GS1 gene and outperforming wildtype plants were crossed with individual plants over-expressing the *Arabidopsis* GPT gene and outperforming wildtype plants, by simple sexual crossing using manual pollen transfer. Reciprocal crosses were made such that each plant served as the male in a set of crosses and each plant served as the female in a second set of crosses. During the mature plant growth stage, the plants are typically examined for growth phenotype, $CO_2$ fixation rate, etc. (see following subsection)

Selection of Growth-Enhanced Transgenic Plants:

Transgenic plants may be selected, screened and characterized using standard methodologies. The preferred transgenic plants of the invention will exhibit one or more phenotypic characteristics indicative of enhanced growth and/or other desirable agronomic properties. Transgenic plants are typically regenerated under selective pressure in order to select transformants prior to creating subsequent transgenic plant generations. In addition, the selective pressure used may be employed beyond $T_0$ generations in order to ensure the presence of the desired transgene expression construct or cassette.

To transformed plant cells, calli, tissues or plants may be identified and isolated by selecting or screening for the genetic composition of and/or the phenotypic characteristics encoded by marker genes contained in the transgene expression construct used for the transformation. For example, selection may be conducted by growing potentially-transformed plants, tissues or cells in a growth medium containing a repressive amount of antibiotic or herbicide to which the transforming genetic construct can impart resistance. Further, the transformed plant cells, tissues and plants can be identified by screening for the activity of marker genes (i.e., β-glucuronidase) which may be present in the transgene expression construct.

Various physical and biochemical methods may be employed for identifying plants containing the desired transgene expression construct, as is well known. Examples of such methods include Southern blot analysis or various nucleic acid amplification methods (i.e., PCR) for identifying the transgene, transgene expression construct or elements thereof, Northern blotting, S1 RNase protection, reverse transcriptase PCR (RT-PCR) amplification for detecting and determining the RNA transcription products, and protein gel electrophoresis, Western blotting, immunoprecipitation, enzyme immunoassay, and the like may be used for identifying the protein encoded and expressed by the transgene.

In another approach, expression levels of genes, proteins and/or metabolic compounds that are know to be modulated by transgene expression in the target plant may be used to identify transformants. In one embodiment of the present invention, increased levels of the signal metabolite 2-oxoglutaramate may be used to screen for desirable transformants, as exemplified in the Examples. Similarly, increased levels of GPT and/or GS activity may be assayed, as exemplified in the Examples.

Ultimately, the transformed plants of the invention may be screened for enhanced growth and/or other desirable agronomic characteristics. Indeed, some degree of phenotypic screening is generally desirable in order to identify transformed lines with the fastest growth rates, the highest seed yields, etc., particularly when identifying plants for subsequent selfing, cross-breeding and back-crossing. Various parameters may be used for this purpose, including without limitation, growth rates, total fresh weights, dry weights, seed and fruit yields (number, weight), seed and/or seed pod sizes, seed pod yields (e.g., number, weight), leaf sizes, plant sizes, increased flowering, time to flowering, overall protein content (in seeds, fruits, plant tissues), specific protein content (i.e., GS), nitrogen content, free amino acid, and specific metabolic compound levels (i.e., 2-oxoglutaramate). Generally, these phenotypic measurements are compared with those obtained from a parental identical or analogous plant line, an untransformed identical or analogous plant, or an identical or analogous wild-type plant (i.e., a normal or parental plant). Preferably, and at least initially, the measurement of the chosen phenotypic characteristic(s) in the target transgenic plant is done in parallel with measurement of the same characteristic(s) in a normal or parental plant. Typically, multiple plants are used to establish the phenotypic desirability and/or superiority of the transgenic plant in respect of any particular phenotypic characteristic.

Preferably, initial transformants are selected and then used to generate $T_1$ and subsequent generations by selfing (self-fertilization), until the transgene genotype breeds true (i.e., the plant is homozygous for the transgene). In practice, this is accomplished by screening at each generation for the desired traits and selfing those individuals, often repeatedly (i.e., 3 or 4 generations). As exemplified herein, transgenic plant lines propagated through at least one sexual generation (Tobacco, *Arabidopsis*, Tomato) demonstrated higher transgene product activities compared to lines that did not have the benefit of sexual reproduction and the concomitant increase in transgene copy number.

Stable transgenic lines may be crossed and back-crossed to create varieties with any number of desired traits, including those with stacked transgenes, multiple copies of a transgene, etc. Various common breeding methods are well know to those skilled in the art (see, e.g., Breeding Methods for Cultivar Development, Wilcox J. ed., American Society of Agronomy, Madison Wis. (1987)). Additionally, stable transgenic plants may be further modified genetically, by transforming such plants with further transgenes or additional copies of the parental transgene. Also contemplated are transgenic plants created by single transformation events which introduce multiple copies of a given transgene or multiple transgenes.

EXAMPLES

Various aspects of the invention are further described and illustrated by way of the several examples which follow, none of which are intended to limit the scope of the invention.

Example 1

Isolation of *Arabidopsis* Glutamine Phenylpyruvate Transaminase (GPT) Gene

In an attempt to locate a plant enzyme that is directly involved in the synthesis of the signal metabolite 2-oxoglutaramate, applicants hypothesized that the putative plant enzyme might bear some degree of structural relationship to a human protein that had been characterized as being involved in the synthesis of 2-oxoglutaramate. The human protein, glutamine transaminase K (E.G. 2.6.1.64) (also referred in the literature as cysteine conjugate β-lyase, kyneurenine aminotransferase, glutamine phenylpyruvate transaminase, and other names), had been shown to be involved in processing of cysteine conjugates of halogenated xenobiotics (Perry et al., 1995, FEBS Letters 360:277-280). Rather than having an activity involved in nitrogen assimilation, however, human cysteine conjugate β-lyase has a detoxifying activity in humans, and in animals (Cooper and Meister, 1977, supra). Nevertheless, the potential involvement of this protein in the synthesis of 2-oxoglutaramate was of interest.

Using the protein sequence of human cysteine conjugate β-lyase, a search against the TIGR *Arabidopsis* plant database of protein sequences identified one potentially related sequence, a polypeptide encoded by a partial sequence at the *Arabidopsis* gene locus at At1q77670, sharing approximately 36% sequence homology/identity across aligned regions.

The full coding region of the gene was then amplified from an *Arabidopsis* cDNA library (Stratagene) with the following primer pair:

[SEQ ID NO: 37]
5'-CCC<u>ATCGAT</u>GTACC TGGACATAAATGGTGTGATG-3'

[SEQ ID NO: 38]
5'-GAT<u>GGTACC</u>TCAGACTTTTCTCTTAAGCTTCTGCTTC-3'

These primers were designed to incorporate Cla I (ATCGAT) and Kpn I (GGTACC) restriction sites to facilitate subsequent subcloning into expression vectors for generating transgenic plants. Takara ExTaq DNA polymerase enzyme was used for high fidelity PCR using the following conditions: initial denaturing 94° C. for 4 minutes, 30 cycles of 94° C. 30 second, annealing at 55° C. for 30 seconds, extension at 72° C. for 90 seconds, with a final extension of 72° C. for 7 minutes. The amplification product was digested with Cla I and Kpn I restriction enzymes, isolated from an agarose gel electrophoresis and ligated into vector pMon316 (Rogers, et. al. 1987 Methods in Enzymology 153:253-277) which contains the cauliflower mosaic virus (CaMV, also CMV) 35S constitutive promoter and the nopaline synthase (NOS) 3' terminator. The ligation product was transformed into DH5α cells and transformants sequenced to verify the insert.

A 1.3 kb cDNA was isolated and sequenced, and found to encode a full length protein of 440 amino acids in length, including a putative chloroplast signal sequence.

Example 2

Production of Biologically Active Recombinant *Arabidopsis* Glutamine Phenylpyruvate Transaminase (GPT)

To test whether the protein encoded by the cDNA isolated as described in Example 1, supra, is capable of catalyzing the synthesis of 2-oxoglutaramate, the cDNA was expressed in *E. coli*, purified, and assayed for its ability to synthesize 2-oxoglutaramate using a standard method.

NMR Assay for 2-Oxoglutaramate:

Briefly, the resulting purified protein was added to a reaction mixture containing 150 mM Tris-HCl, pH 8.5, 1 mM beta mercaptoethanol, 200 mM glutamine, 100 mM glyoxylate and 200 μM pyridoxal 5'-phosphate. The reaction mixture without added test protein was used as a control. Test and control reaction mixtures were incubated at 37° C. for 20 hours, and then clarified by centrifugation to remove precipitated material. Supernatants were tested for the presence and amount of 2-oxoglutaramate using $^{13}C$ NMR with authentic chemically synthesized 2-oxoglutaramate as a reference. The products of the reaction are 2-oxoglutaramate and glycine, while the substrates (glutamine and glyoxylate) diminish in abundance. The cyclic 2-oxoglutaramate gives rise to a distinctive signal allowing it to be readily distinguished from the open chain glutamine precursor.

HPLC Assay for 2-Oxoglutaramate:

An alternative assay for GPT activity uses HPLC to determine 2-oxoglutaramate production, following a modification of Calderon et al., 1985, J Bacteriol 161(2): 807-809. Briefly, a modified extraction buffer consisting of 25 mM Tris-HCl pH 8.5, 1 mM EDTA, 20 μM FAD, 10 mM Cysteine, and ~1.5% (v/v) Mercaptoethanol. Tissue samples from the test material (i.e., plant tissue) are added to the extraction buffer at approximately a 1/3 ratio (w/v), incubated for 30 minutes at 37° C., and stopped with 2000 of 20% TCA. After about 5 minutes, the assay mixture is centrifuged and the supernatant used to quantify 2-oxoglutaramate by HPLC, using an ION-300 7.8 mm ID×30 cm L column, with a mobile phase in 0.01N $H_2SO_4$, a flow rate of approximately 0.2 ml/min, at 40° C. Injection volume is approximately 20 μl, and retention time between about 38 and 39 minutes. Detection is achieved with 210 nm UV light.

Results Using NMR Assay:

This experiment revealed that the test protein was able to catalyze the synthesis of 2-oxoglutaramate. Therefore, these data indicate that the isolated cDNA encodes a glutamine phenylpyruvate transaminase that is directly involved in the synthesis of 2-oxoglutaramate in plants. Accordingly, the test protein was designated *Arabidopsis* glutamine phenylpyruvate transaminase, or "GPT".

The nucleotide sequence of the *Arabidopsis* GPT coding sequence is shown in the Table of Sequences, SEQ ID NO. 1. The translated amino acid sequence of the GPT protein is shown in SEQ ID NO. 2.

Example 3

Creation of Transgenic Tobacco Plants Over-Expressing *Arabidopsis* GPT

Generation of Plant Expression Vector pMON-PJU:

Briefly, the plant expression vector pMon316-PJU was constructed as follows. The isolated cDNA encoding *Arabidopsis* GPT (Example 1) was cloned into the ClaI-KpnI polylinker site of the pMON316 vector, which places the GPT gene under the control of the constitutive cauliflower mosaic virus (CaMV) 35S promoter and the nopaline synthase (NOS) transcriptional terminator. A kanamycin resistance gene was included to provide a selectable marker.

*Agrobacterium*-Mediated Plant Transformations:

pMON-PJU and a control vector pMon316 (without inserted DNA) were transferred to *Agrobacterium tumefaciens* strain pTiTT37ASE using a standard electroporation method (McCormac et al., 1998, Molecular Biotechnology 9:155-159), followed by plating on LB plates containing the antibiotics spectinomycin (100 micro gm/ml) and kanamycin (50 micro gm/ml). Antibiotic resistant colonies of *Agrobacterium* were examined by PCR to assure that they contained plasmid.

*Nicotiana tabacum* cv. Xanthi plants were transformed with pMON-PJU transformed *Agrobacteria* using the leaf disc transformation system of Horsch et. al. (Horsch et al., 1995, Science 227:1229-1231). Briefly, sterile leaf disks were inoculated and cultured for 2 days, then transferred to selective MS media containing 100 μg/ml kanamycin and 500 μg/ml clafaran. Transformants were confirmed by their ability to form roots in the selective media.

Generation of GPT Transgenic Tobacco Plants:

Sterile leaf segments were allowed to develop callus on Murashige & Skoog (M&S) media from which the transformant plantlets emerged. These plantlets were then transferred to the rooting-permissive selection medium (M&S medium with kanamycin as the selection agent). The healthy, and now rooted, transformed tobacco plantlets were then transferred to soil and allowed to grow to maturity and upon flowering the plants were selfed and the resultant seeds were harvested. During the growth stage the plants had been examined for growth phenotype and the $CO_2$ fixation rate was measured for many of the young transgenic plants.

Production of T1 and T2 Generation GPT Transgenic Plants:

Seeds harvested form the $T_0$ generation of the transgenic tobacco plants were germinated on M&S media containing kanamycin (100 mg/L) to enrich for the transgene. At least one fourth of the seeds did not germinate on this media (kanamycin is expected to inhibit germination of the seeds without resistance that would have been produced as a result of normal genetic segregation of the gene) and more than half of the remaining seeds were removed because of demonstrated sensitivity (even mild) to the kanamycin.

The surviving plants ($T_1$ generation) were thriving and these plants were then selfed to produce seeds for the $T_2$ generation. Seeds from the $T_1$ generation were germinated on MS media supplemented for the transformant lines with kanamycin (10 mg/liter). After 14 days they were transferred to sand and provided quarter strength Hoagland's nutrient solution supplemented with 25 mM potassium nitrate. They were allowed to grow at 24° C. with a photoperiod of 16 h light and 8 hr dark with a light intensity of 900 micromoles per meter squared per second. They were harvested 14 days after being transferred to the sand culture.

Characterization of GPT Transgenic Plants:

Harvested transgenic plants (both GPT transgenes and vector control transgenes) were analyzed for glutamine synthetase activity in root and leaf, whole plant fresh weight, total protein in root and leaf, and $CO_2$ fixation rate (Knight et al., 1988, Plant Physiol. 88: 333). Non-transformed, wild-type *A. tumefaciens* plants were also analyzed across the same parameters in order to establish a baseline control.

Figure 4:
FIG. 4. Photograph showing comparison of transgenic tobacco plants over-expressing either GS1 or GPT, compared to wild type tobacco plant. From left to right: wild type plant, *Alfalfa* GS1 transgene, *Arabidopsis* GPT transgene. See Examples 3 and 5, infra.

Growth characteristic results are tabulated below in Table I. Additionally, a photograph of the GPT transgenic plant compared to a wild type control plant is shown in FIG. 4 (together with GS1 transgenic tobacco plant, see Example 5). Across all parameters evaluated, the GPT transgenic tobacco plants showed enhanced growth characteristics. In particular, the GPT transgenic plants exhibited a greater than 50% increase in the rate of $CO_2$ fixation, and a greater than two-fold increase in glutamine synthetase activity in leaf tissue, relative to wild type control plants. In addition, the leaf-to-root GS ratio increased by almost three-fold in the transaminase transgenic plants relative to wild type control. Fresh weight and total protein quantity also increased in the transgenic plants, by about 50% and 80% (leaf), respectively, relative to the wild type control. These data demonstrate that tobacco plants overexpressing the *Arabidopsis* GPT transgene achieve significantly enhanced growth and $CO_2$ fixation rates.

TABLE I

| Protein mg/gram fresh weight | Leaf | Root |
|---|---|---|
| Wild type - control | 8.3 | 2.3 |
| Line PN1-8 a second control | 8.9 | 2.98 |
| Line PN9-9 | 13.7 | 3.2 |

TABLE I-continued

| Protein mg/gram fresh weight | Leaf | Root |
|---|---|---|
| Glutamine Synthetase activity, micromoles/min/mg protein | | |
| Wild type (Ratio of leaf:root = 4.1:1) | 4.3 | 1.1 |
| PN1-8 (Ratio of leaf:root = 4.2:1) | 5.2 | 1.3 |
| PN9-9 (Ratio of leaf:root = 10.9:1) | 10.5 | 0.97 |
| Whole Plant Fresh Weight, g | | |
| Wild type | | 21.7 |
| PN1-8 | | 26.1 |
| PN9-9 | | 33.1 |
| $CO_2$ Fixation Rate, umole/m2/sec | | |
| Wild type | | 8.4 |
| PN1-8 | | 8.9 |
| PN9-9 | | 12.9 |

Data = average of three plants
Wild type - Control plants; not regenerated or transformed.
PN1 lines were produced by regeneration after transformation using a construct without inserted gene. A control against the processes of regeneration and transformation.
PN 9 lines were produced by regeneration after transformation using a construct with the Arabidopsis GPT gene.

Example 4

Generation of Transgenic Tomato Plants Carrying *Arabidopsis* GPT Transgene

Figure 5:
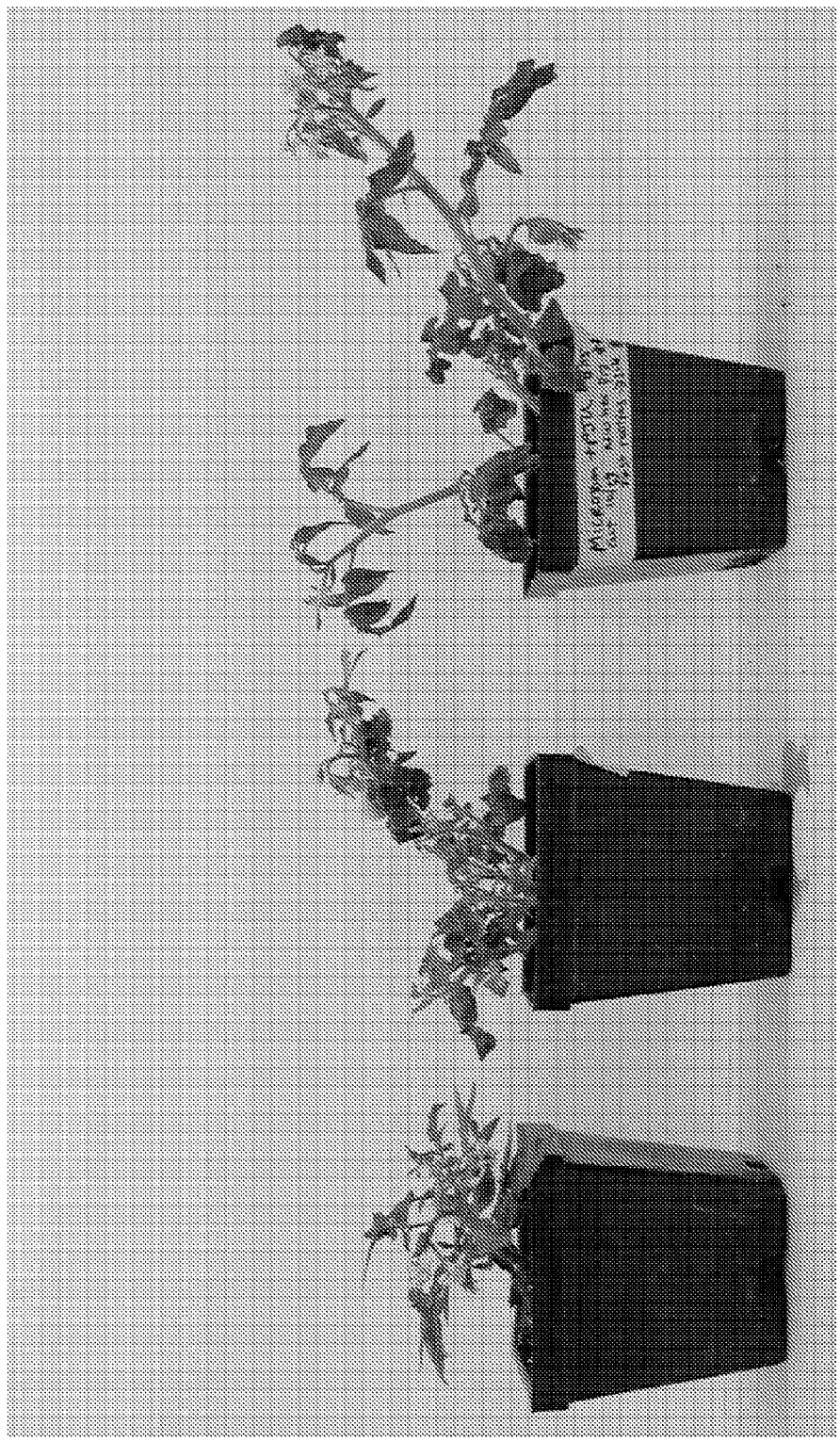
FIG. 5. Photograph showing comparison of transgenic Micro-Tom tomato plants over-expressing either GS1 or GPT, compared to wild type tomato plant. From left to right: wild type plant, *Alfalfa* GS1 transgene, *Arabidopsis* GPT transgene. See Examples 4 and 6, infra.
Figure 6A:
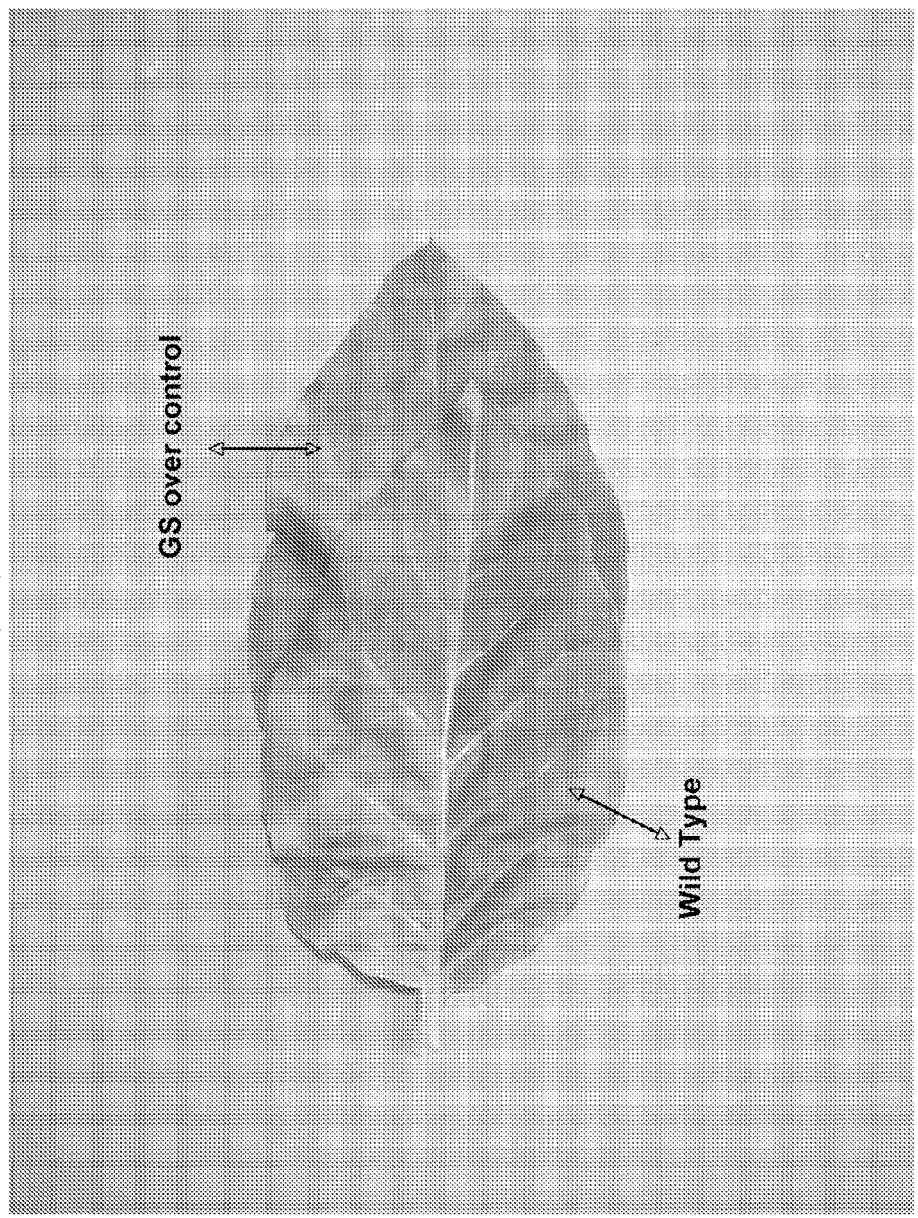
FIG. 6. Photographs showing comparisons of leaf sizes between wild type and GS1 or GPT transgenic tobacco plants. A: Comparison between leaves from GS1 transgenic tobacco (bottom leaf) and wild type (top leaf). B: Comparison between leaves from GPT transgenic tobacco (bottom leaf) and wild type (top leaf).
Figure 6B:
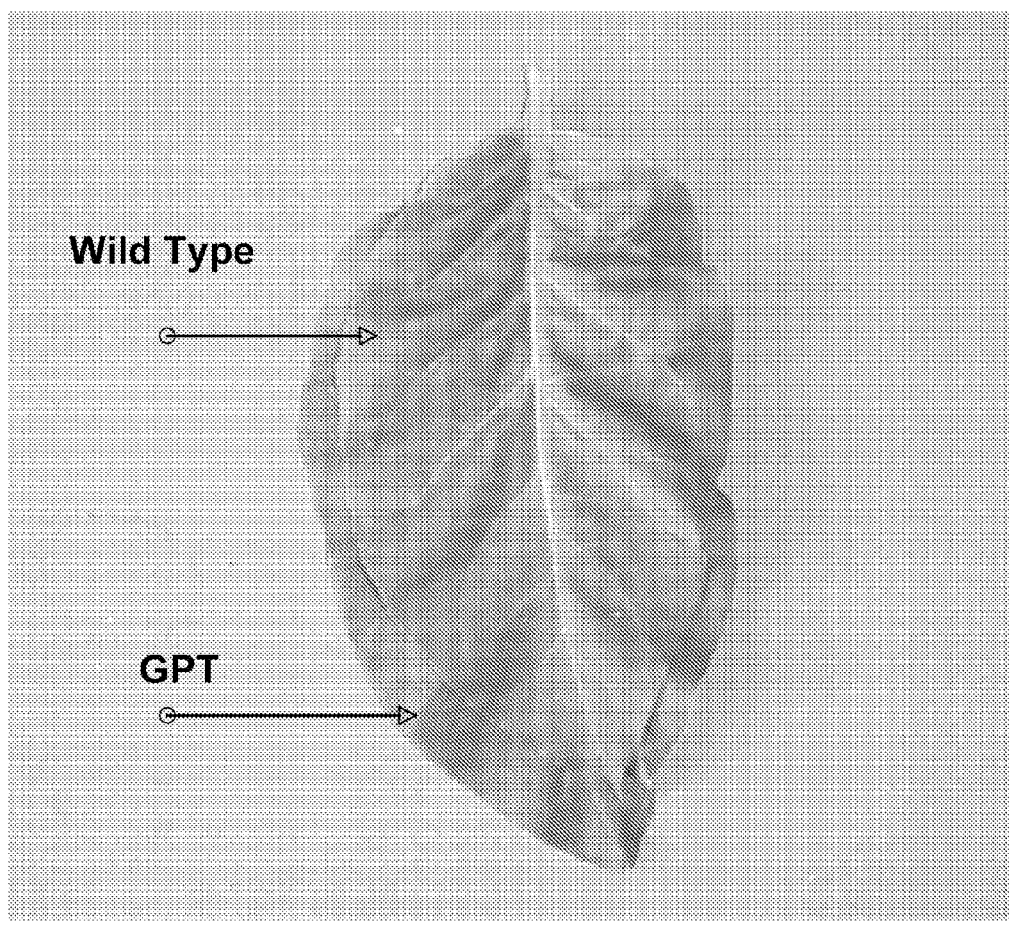

Transgenic *Lycopersicon esculentum* (Micro-Tom Tomato) plants carrying the *Arabidopsis* GPT transgene were generated using the vectors and methods described in Example 3. $T_0$ transgenic tomato plants were generated and grown to maturity. Initial growth characteristic data of the GPT transgenic tomato plants is presented in Table II. The transgenic plants showed significant enhancement of growth rate, flowering, and seed yield in relation to wild type control plants. In addition, the transgenic plants developed multiple main stems, whereas wild type plants developed with a single main stem. A photograph of a GPT transgenic tomato plant compared to a wild type plant is presented in FIG. 5 (together with GS1 transgenic tomato plants, see Example 6).

TABLE II

| Growth Characteristics | Wildtype Tomato | GPT Transgenic Tomato |
|---|---|---|
| Stem height, cm | 6.5 | 18, 12, 11 major stems |
| Stems | 1 | 3 major, 0 other |
| Buds | 2 | 16 |
| Flowers | 8 | 12 |
| Fruit | 0 | 3 |

Example 5

Generation of Transgenic Tobacco Plants Overexpressing *Alfalfa* GS1

Generation of Plant Expression Vector pGS111:
Transgenic tobacco plants overexpressing the *Alfalfa* GS1 gene were generated as previously described (Temple et al., 1993, Mol. Gen. Genetics 236: 315-325). Briefly, the plant expression vector pGS111 was constructed by inserting the entire coding sequence together with extensive regions of both the 5' and 3' untranslated regions of the *Alfalfa* GS1 gene [SEQ ID NO: 3] (DasSarma at al., 1986, Science, Vol 232, Issue 4755, 1242-1244) into pMON316 (Rogers et al., 1987, supra), placing the transgene under the control of the constitutive cauliflower mosaic virus (CaMV) 35S promoter and the nopaline synthase (NOS) transcriptional terminator. A kanamycin resistance gene was included to provide a selectable marker.

Generation of GS1 Transformants:
pGS111 was transferred to *Agrobacterium tumefaciens* strain pTiTT37ASE using triparental mating as described (Rogers et al., 1987, supra; Unkefer et al., U.S. Pat. No. 6,555,500). *Nicotiana tabacum* cv. *Xanthi* plants were transformed with pGS111 transformed *Agrobacteria* using the leaf disc transformation system of Horsch et. al. (Horsch et al., 1995, Science 227:1229-1231). Transformants were selected and regenerated on MS medium containing 100 μg/ml kanamycin. Shoots were rooted on the same medium (with kanamycin, absent hormones) and transferred to potting soil:perlite:vermiculite (3:1:1), grown to maturity, and allowed to self. Seeds were harvested from this $T_0$ generation, and subsequent generations produced by selfing and continuing selection with kanamycin. The best growth performers were used to yield a T3 progeny for crossing with the best performing GPT over-expressing lines identified as described in Example 3. A photograph of the GS1 transgenic plant compared to a wild type control plant is shown in FIG. 4 (together with GPT transgenic tobacco plant, see Example 3)

Example 6

Generation of Transgenic Tomato Plants Carrying *Alfalfa* GS1 Transgene

Transgenic *Lycopersicon esculentum* (Micro-Tom Tomato) plants carrying the *Alfalfa* GS1 transgene were generated using the vector described in Example 5 and a transformation protocol essentially as described (Sun et al., 2006. Plant Cell Physiol. 46(3) 426-31). $T_0$ transgenic tomato plants were generated and grown to maturity. Initial growth characteristic data of the GPT transgenic tomato plants is presented in Table III. The transgenic plants showed significant enhancement of growth rate, flowering, and seed yield in relation to wild type control plants. In addition, the transgenic plants developed multiple main stems, whereas wild type plants developed with a single main stem. A photograph of a GS1 transgenic tomato plant compared to a wild type plant is presented in FIG. 5 (together with GPT transgenic tomato plant, see Example 4).

TABLE III

| Growth Characteristics | Wildtype Tomato | GS1 Transgenic Tomato |
|---|---|---|
| Stem height, cm | 6.5 | 16, 7, 5 major stems |
| Stems | 1 | 3 major, 3 med, 1 sm |
| Buds | 2 | 2 |
| Flowers | 8 | 13 |
| Fruit | 0 | 4 |

Example 7

Generation of Double Transgenic Tobacco Plants Carrying GS1 and GPT Transgenes

In an effort to determine whether the combination of GS1 and GPT transgenes in a single transgenic plant might improve the extent to which growth and other agronomic characteristics may be enhanced, a number of sexual crosses between high producing lines of the single transgene (GS1 or GPT) transgenic plants were carried out. The results obtained are dramatic, as these crosses repeatedly generated progeny plants having surprising and heretofore unknown increases in growth rates, biomass yield, and seed production.

Materials and Methods:

Single-transgene, transgenic tobacco plants overexpressing GPT or GS1 were generated as described in Examples 3 and 4, respectively. Several of fastest growing $T_2$ generation GPT transgenic plant lines were crossed with the fastest growing T3 generation GS1 transgenic plant lines using reciprocal crosses. The progeny were then selected on kanamycin containing M&S media as described in Example 3, and their growth, flowering and seed yields examined.

Tissue extractions for GPT and GS activities: GPT activity was extracted from fresh plant tissue after grinding in cold 100 mM Tris-HCl, pH 7.6, containing 1 mm ethylenediaminetetraacetic, 200 mM pyridoxal phosphate and 6 mM mercaptoethanol in a ratio of 3 ml per gram of tissue. The extract was clarified by centrifugation and used in the assay. GS activity was extracted from fresh plant tissue after grinding in cold 50 mM Imidazole, pH 7.5 containing 10 mM MgCl2, and 12.5 mM mercaptoethanol in a ratio of 3 ml per gram of tissue. The extract was clarified by centrifugation and used in the assay. GPT activity was assayed as described in Calderon and Mora, 1985, Journal Bacteriology 161:807-809. GS activity was measured as described in Shapiro and Stadtmann, 1970, Methods in Enzymology 17A: 910-922. Both assays involve an incubation with substrates and cofactor at the proper pH. Detection was by HPLC.

Figure 8A:
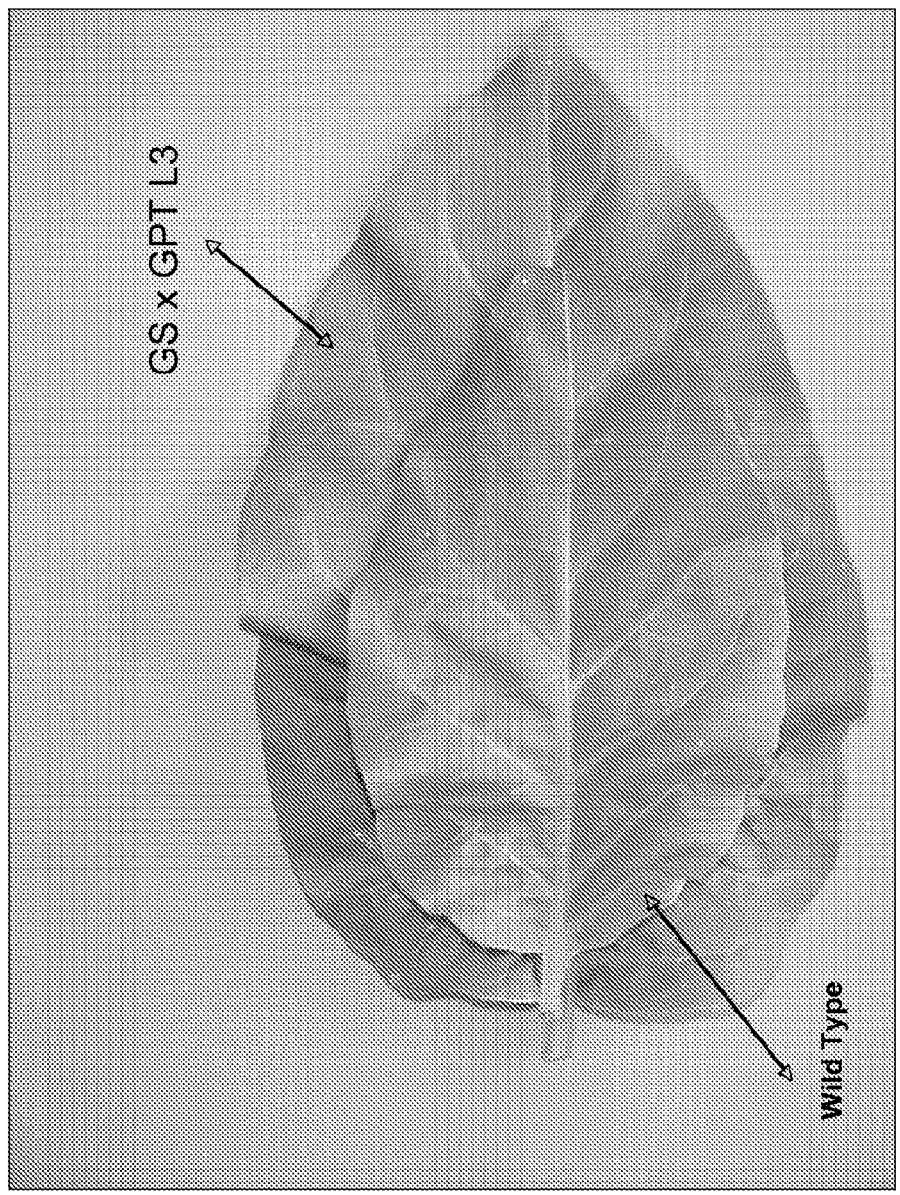
FIG. 8. Photographs showing comparisons of leaf sizes between wild, type and crosses between GS1 and GPT transgenic tobacco plants. A: Comparison between leaves from GSXGPT Cross 3 (bottom leaf) and wild type (top leaf). B: Comparison between leaves from GSXGPT Cross 7 (bottom leaf) and wild type (top leaf). See Example 7, infra.
Figure 8B:
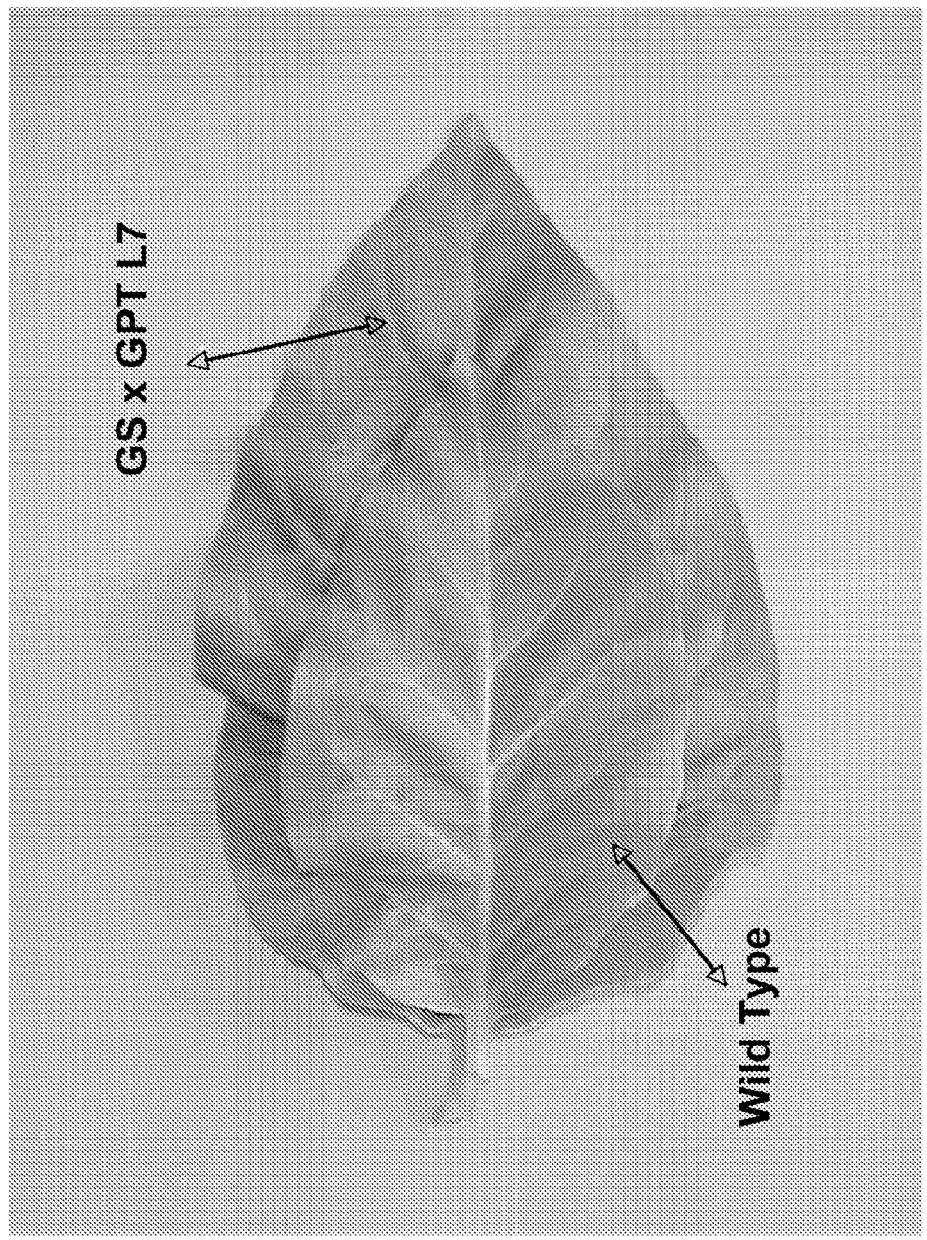

Results:

The results are presented in two ways. First, specific growth characteristics are tabulated in Tables IV.A and IV.B (biomass, seed yields, growth rate, GS activity, GPT activity, 2-oxoglutaramate activity, etc). Second, photographs of progeny plants and their leaves are shown in comparison to single-transgene and wild type plants and leaves are presented in FIG. 7 and FIG. 8, which show much larger whole plants, larger leaves, and earlier and/or more abundant flowering in comparison to the parental single-transgene plants and wild type control plants.

Referring to Table IV.A, double-transgene progeny plants form these crosses showed tremendous increases total biomass (fresh weight), with fresh weights ranging from 45-89 grams per individual progeny plant, compared to a range of only 19-24 grams per individual wild type plant, representing on average, about a two- to three-fold increase over wild type plants, and representing at the high end, an astounding four-fold increase in, biomass over wild type plants. Taking the 24 individual double-transgene progeny plants evaluated, the average individual plant biomass was about 2.75 times that of the average wild type control plant. Four of the progeny lines showed approximately 2.5 fold greater average per plant fresh weights, while two lines showed over three-fold greater fresh weights in comparison to wild type plants.

In comparison to the single-transgene parental lines, the double-transgene progeny plants also showed far more than an additive growth enhancement. Whereas GPT single-transgene lines show as much as about a 50% increase over wild type biomass, and GS1 single-transgene lines as much as a 66% increase, progeny plants averaged almost a 200% increase over wild type plants.

Similarly, the double transgene progeny plants flowered earlier and more prolifically than either the wild type or single transgene parental lines, and produced a far greater number of seed pods as well as total number of seeds per plant. Referring again to Table IV.A, on average, the double-transgene progeny produced over twice the number of seed pods produced by wild type plants, with two of the high producer plants generating over three times the number of seed pods compared to wild type. Total seed yield in progeny plants, measured on a per plant weight basis, ranged from about double to nearly quadruple the number produced in wild type plants.

TABLE IV.A

| PLANT LINE | FRESH WEIGHT g/whole plant | SEED PODS #pods/plant | SEED YIELD g/plant | LEAF | GS ACTIVITY ROOT | L/R RATIO |
|---|---|---|---|---|---|---|
| Wild Type Tobacco | | | | | | |
| Wild type 1 | 18.73 | 26 | 0.967 | | | |
| Wild type 2 | 24.33 | 24 | 1.07 | | | |
| Wild type 3 | 23.6 | 32 | 0.9 | | | |
| Wild type 4 | 18.95 | 32 | 1.125 | | | |
| WT Average | 21.4025 | 28.5 | 1.0155 | 7.75 | 1.45 | 5.34 |
| Cross 1 X1L1a x PA9-9ff | | | | | | |
| 1 | 59.21 | 62 | 2.7811 | | | |
| 2 | 65.71 | 56 | | | | |
| 3 | 55.36 | 72 | | | | |
| 4 | 46.8 | 56 | | | | |
| Cross 1 Average | 56.77 | 61.5 | | 14.98 | 1.05 | 14.27 |
| Compared to WT | +265% | +216% | +274% | +193% | −28% | +267% |
| Cross 2 PA9-2 x L9 | | | | | | |
| 1 | 70.83 | 61 | 1.76 | | | |
| 2 | 49.17 | 58 | 3.12 | | | |
| 3 | 50.23 | 90 NA | | | | |
| 4 | 45.77 | | | | | |
| Cross 2 Average | 54 | 58.3 | 2.44 | 16.32 | 1.81 | 9.02 |
| Compared to WT | +252% | +205% | +240% | +211% | +125% | +169% |
| Cross 3 PA9-9ff xL1a | | | | | | |
| 1 | 89.1 | 77 | 3.687 | | | |
| 2 | 78.18 | | | | | |

TABLE IV.A-continued

| PLANT LINE | FRESH WEIGHT g/whole plant | SEED PODS #pods/plant | SEED YIELD g/plant | LEAF | GS ACTIVITY ROOT | L/R RATIO |
|---|---|---|---|---|---|---|
| 3 | 58.34 | | | | | |
| 4 | 61.79 | | | | | |
| Cross 3 Average | 71.85 | 77 (one plant) | 3.678 (one plant) | 15.92 | 1.38 | 11.54 |
| Compared to WT | +336% | +270% | +362% | +205% | −5% | +216% |
| Cross 5 PA9-10aa x L1a | | | | | | |
| 1 | 65.34 | 45 | 2.947 | | | |
| 2 | 53.28 | 64 | 3.3314 | | | |
| 3 | 49.85 | 42 | 1.5667 | | | |
| 4 | 44.63 | 42 | 2.5013 | | | |
| Cross 5 Average | 53.275 | 48.25 | 2.86928 | 13.03 | 1.8 | 7.24 |
| Compared to WT | +244% | +169% | +283% | +168% | | |
| Cross 6 PA9-17b x L1a | | | | | | |
| 1 | 56.7 | 64 | 2.492 | | | |
| 2 | 55.05 | 66 | 2.162 | | | |
| 3 | 51.51 | 59 | 1.8572 | | | |
| 4 | 45.38 | 72 | 4.742 | | | |
| Cross 6 Average | 52.16 | 65.25 | 2.8133 | 14.1152 | 1.1124 | 13.29 |
| Compared to WT | +244% | +229% | +277% | | | |
| Cross 7 PA9-20aa x L1b | | | | | | |
| 1 | 76.26 | 67 | 2.0535 | | | |
| 2 | 66.27 | 42 | 1.505 | | | |
| 3 | 72.26 | 72 | 2.3914 | | | |
| 4 | 63.91 | 91 | 2.87 | | | |
| Cross 7 Average | 69.675 | 68 | 2.204975 | 14.12 | 1.24 | 11.39 |
| Compared to WT | +326% | +239% | +217% | | | |
| Control PA9-9ff | | | | | | |
| 1 | 32.18 | N/A | | | | |
| 2 | 32.64 | N/A | | | | |
| 3 | 34.67 | N/A | | | | |
| 4 | 25.18 | N/A | | | | |
| Average | 31.17 | N/A | | 11.57 | 1.14 | 10.15 |
| Compared to WT | +148% | | | | | |
| Control GS L1a | | | | | | |
| 1 | 41.74 | N/A | | | | |
| 2 | 36.24 | N/A | | | | |
| 3 | 33.8 | N/A | | | | |
| 4 | 30.48 | N/A | | | | |
| Average | 35.57 | N/A | | 13.15 | 1.23 | 10.69 |
| Compared to WT | +166% | | | | | |

Table IV.B shows growth rate, biomass and yield, and biochemical characteristics of Line XX (Line 3 further selfed) compared to the single transgene line expressing GS1 and wild type control tobacco. All parameters are greatly increased in the double transgenic plant (Line XX). Notably, 2-oxoglutaramate activity was almost 17-fold higher, and seed yield and foliar biomass was three-fold higher, in Line XX plants versus control plants

TABLE IV.B

| Plant Type | Specific Growth Rate mg/g/d | Foliar Biomass FWt, g | Fruit/ Flowers/ Buds | Seed Yield g | GS Activity umol/ min/gFWt | GPT Activity nmol/ h/gFwt | 2-oxoglu- taramate nmol/ gFWt | Trans Gene Assay |
|---|---|---|---|---|---|---|---|---|
| Wildtype, avg | 228 | 21.40 | 28.5 | 1.02 | 7.75 | 16.9 | 68.9 | No |
| Line 1 GS | 269 | 35.57 | NM | NM | 11.6 | NM | 414 | Yes |
| Line XX | 339 | 59.71 | 62.9 | 2.94 | 16.3 | 243.9 | 1,153.6 | Yes |

NM Not Measured

Example 8

Generation of Double Transgenic Pepper Plants Carrying GS1 and GPT Transgenes In this example, Big Jim chili pepper plants (New Mexico varietal) were transformed with the *Arabidopsis* GPT full length coding sequence of SEQ ID NO: 1 under the control of the CMV 35S promoter, and the *Arabidopsis* GS1 coding sequence included in SEQ ID NO: 6 under the control of the RuBisCo promoter, using *Agrobacterium*-mediated transfer to seed pods. After 3 days, seeds were harvested and used to generate T0 plants and screened for transformants. The resulting double-transgenic plants showed higher pod yields, faster growth rates, and greater biomass yields in comparison to the control plants.

Materials and Methods:

*Solanaceae Capisicum* Pepper plants ("Big Jim" varietal) were transformed with the *Arabidopsis* GPT full length coding sequence of SEQ ID NO: 1 under the control of the CMV 35S promoter within the expression vector pMON (see Example 3), and the *Arabidopsis* GS1 coding sequence included in SEQ ID NO: 6 under the control of the RuBisCo promoter within the expression vector pCambia 1201 (Tomato rubisco rbcS3C promoter: Kyozulka et al., 1993, Plant Physiol. 103: 991-1000; SEQ ID NO: 22; vector construct of SEQ ID NO: 6), using *Agrobacterium*-mediated transfer to seed pods.

For this and all subsequent examples, the Cambia 1201 or 1305.1 vectors were constructed according to standard cloning methods (Sambrook et al., 1989, supra, Saiki et al., 1988, Science 239: 487-491). The vector is supplied with a 35S CaMV promoter; that promoter was replaced with RcbS-3C promoter from tomato to control the expression of the target gene. The Cambia 1201 vectors contain bacterial chlorophenicol and plant hygromycin resistance selectable marker genes. The Cambia 1305.1 vectors contain bacterial chloramphenicol and hygromycin resistance selectable marker genes.

The transgene expression vectors pMON (GPT transgene) and pCambia 1201 (GS transgene) were transferred to separate *Agrobacterium tumefaciens* strain LBA4404 cultures using a standard electroporation method (McCormac et al., 1998, Molecular Biotechnology 9:155-159). Transformed *Agrobacterium* were selected on media containing 50 µg/ml of either streptomycin for pMON constructs or chloramphenicol for the Cambia constructs. Transformed *Agrobacterium* cells were grown in LB culture media containing 25 µg/ml of antibiotic for 36 hours. At the end of the 36 hr growth period cells were collected by centrifugation and cells from each transformation were resuspended in 100 ml LB broth without antibiotic.

Pepper plants were then transformed with a mixture of the resulting *Agrobacterium* cell suspensions using a transformation protocol in which the *Agrobacterium* is injected directly into the seed cavity of developing pods. Briefly, developing pods were injected with the 200 ml mixture in order to inoculate immature seeds with the *Agrobacteria* essentially as described (Wang and Waterhouse, 1997, Plant Mol. Biol. Reporter 15: 209-215). In order to induce *Agrobacteria* virulence and improve transformation efficiencies, 10 µg/ml acetosyringonone was added to the *Agrobacteria* cultures prior to pod inoculations (see, Sheikholeslam and Weeks, 1986, Plant Mol. Biol. 8: 291-298).

Using a syringe, pods were injected with a liberal quantity of the *Agrobacterium* vector mixture, and left to incubate for about 3 days. Seeds were then harvested and germinated, and developing plants observed for phenotypic characteristics including growth and antibiotic resistance. Plants carrying the transgenes were green, whereas untransformed plants showed signs of chlorosis in leaf tips. Vigorously growing transformants were further cultivated and compared to wild type pepper plants grown under identical conditions.

Figure 9:
FIG. 9. Photograph of transgenic pepper plant (right) and wild type control pepper plant (left), showing larger pepper fruit yield in the transgenic plant relative to the wild type control plant. See Example 8, infra.

Results:

The results are presented in FIG. 9 and Table V. FIG. 9 shows a photograph of a GPT+GS double transgenic pepper plant compared to a control plant grown for the same time under identical conditions. This photograph shows tremendous pepper yield in the transgenic line compared to the control plant.

Table V presents biomass yield and GS activity, as well as transgene genotyping, in the transgenic lines compared to the wild type control. Referring to Table V, double-transgene progeny plants showed tremendous increases total biomass (fresh weight), with fresh weights, ranging from 393-662 grams per individual transgenic plant, compared to an average of 328 grams per wild type plant. Transgenic line A5 produced more than twice the total biomass of the controls. Moreover, pepper yields in the transgenic lines were greatly improved over wild type plants, and were 50% greater than control plants (on average). Notably, one of the transgene lines produced twice as many peppers as the control plant average.

TABLE V

TRANSGENIC PEPPER GROWTH/BIOMASS AND REPRODUCTION

| Plant type | Biomass, Foliar Fresh Wt, g | Yield Peppers, g DWt | GS activity Umoles/min/ gFWt | Transgene Presence Assay |
|---|---|---|---|---|
| Wildtype, avg | 328.2 | 83.7 | 1.09 | Negative |
| Line A2 | 457.3 | 184.2 | 1.57 | GPT - Yes |
| Line A5 | 661.7 | 148.1 | 1.8 | GPT - Yes |
| Line B1 | 493.4 | 141.0 | 1.3 | GPT - Yes |
| Line B4 | 393.1 | 136.0 | 1.6 | GPT - Yes |
| Line C1 | 509.4 | 152.9 | 1.55 | GPT - Yes |

FWt Fresh Weight;
DWt Dry Weight

Example 9

Generation of Double Transgenic Bean Plants Carrying *Arabidopsis* GS1 and GPT Transgenes In this example, yellow wax bean plants (*Phaseolus vulgaris*) were transformed with the *Arabidopsis* GPT full length coding sequence of SEQ ID NO: 1 under the control of the CMV 35S promoter within the expression vector pCambia 1201, and the *Arabidopsis* GS1 coding sequence included in SEQ ID NO: 6 under the control of the RuBisCo promoter within the expression vector pCambia 1201, using *Agrobacterium*-mediated transfer into flowers.

Materials and Methods:

The transgene expression vectors pCambia 1201-GPT (including construct of SEQ ID NO: 27) and pCambia 1201-GS (including construct of SEQ ID NO: 6) were transferred to separate *Agrobacterium tumefaciens* strain LBA4404 cultures using a standard electroporation method (McCormac et al., 1998, Molecular Biotechnology 9:155-159). Transformed *Agrobacterium* were selected on media containing 50 µg/ml of chloramphenicol. Transformed *Agrobacterium* cells were grown in LB culture media containing 25 µg/ml of antibiotic for 36 hours. At the end of the 36 hr growth period cells were collected by centrifugation and cells from each transformation were resuspended in 100 ml LB broth without antibiotic.

Bean plants were then transformed with a mixture of the resulting *Agrobacterium* cell suspensions using a transformation protocol in which the *Agrobacteria* is injected directly into the flower structure (Yasseem, 2009, Plant Mol. Biol. Reporter 27: 20-28). In order to induce *Agrobacteria* virulence and improve transformation efficiencies, 10 µg/ml acetosyringonone was added to the *Agrobacteria* cultures prior to flower inoculation. Briefly, once flowers bloomed, the outer structure encapsulating the reproductive organs was gently opened with forceps in order to permit the introduction of the *Agrobacteria* mixture, which was added to the flower structure sufficient to flood the anthers.

Plants were grown until bean pods developed, and seeds were harvested and used to generate transgenic plants. Transgenic plants were then grown together with control bean plants under identical conditions, photographed and phenotypically characterized. Growth rates were measured for both transgenic and control plants. In this and all examples, Glutamine synthetase (GS) activity was assayed according to the methods in Shapiro and Stadtmann, 1970, Methods in Enzymology 17A: 910-922; and, Glutamine phenylpyruvate transaminase (GPT) activity was assayed according to the methods in Calderon et al., 1985, J. Bacteriol. 161: 807-809. See details in Example 7, Methods, supra.

Figure 10:
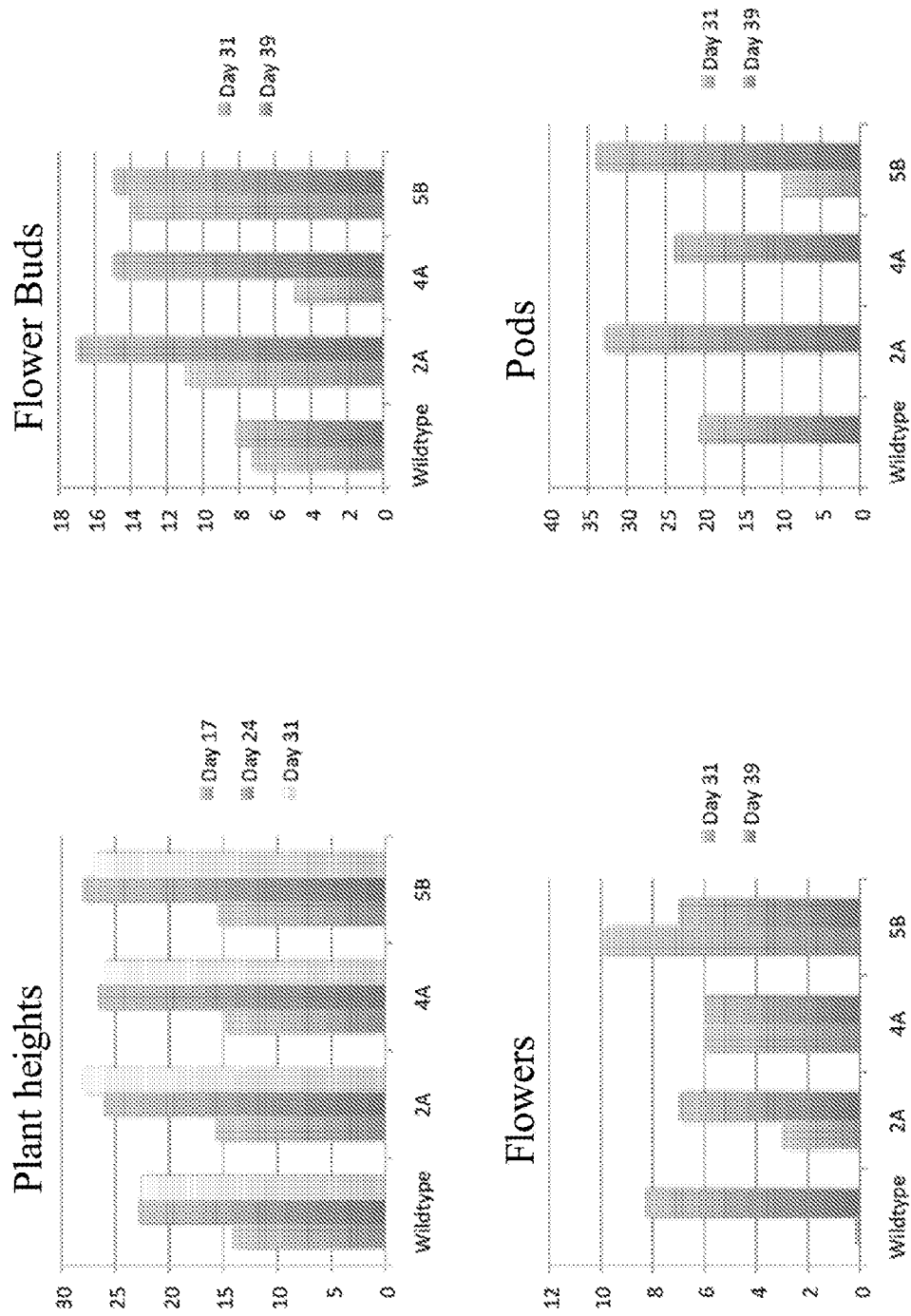
FIG. 10. Transgenic bean plants compared to wild type control bean plants (several transgenic lines expressing *Arabidopsis* GPT and GS transgenes). Upper Left: plant heights on various days; Upper right: flower bud numbers; Lower left: flower numbers; Lower right: bean pod numbers. Wildtype is the control, and lines 2A, 4A and 5B are all transgenic plant lines. See Example 9, infra.
Figure 11:
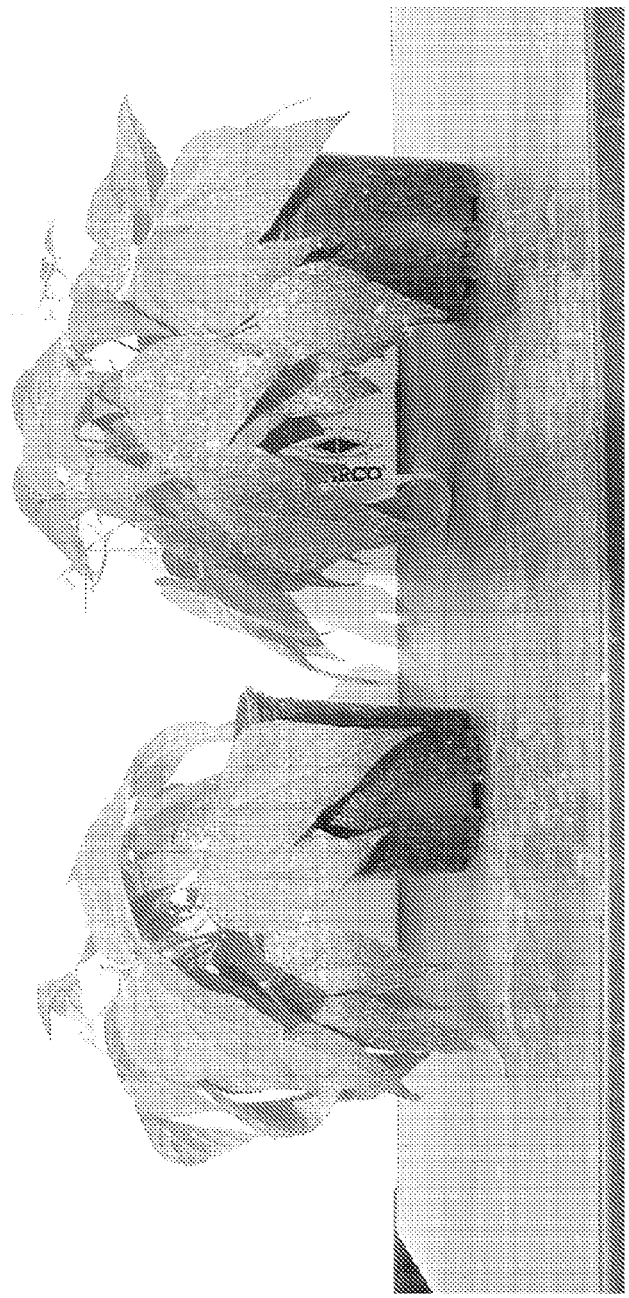
FIG. 11. Photograph of transgenic bean plant (right) and wild type control bean plant (left), showing increased growth in the transgenic plant relative to the wild type control plant. Transgenic line expressing *Arabidopsis* GPT and GS transgenes. See Example 9, infra.

Results:

The results are presented in FIG. 10, FIG. 11 and Table VI.

FIG. 10 shows GPT+GS transgenic bean line A growth rate data relative to control plants, including plant heights on various days into cultivation, as well as numbers of flower buds, flowers, and bean pods. These data show that the GPT+GS double transgenic bean plants outgrew their counterpart control plants. The transgenic plants grew taller, flowered earlier and produced more flower buds and flowers, and developed bean pods and produced more bean pods that the wild type control plants.

TABLE VI

TRANSGENIC BEANS LINE A

| Plant Type | Bean Pod Yield FWt, g | GPT Activity nmoles/h/gFWt | GS Activity umoles/min/gFWt | Antibiotic Resistance |
|---|---|---|---|---|
| Wildtype, avg | 126.6 | 101.9 | 25.2 | Negative |
| 2A | 211.5 | NM | NM | + |
| 4A | 207.7 | NM | NM | + |
| 5B | 205.7 | 984.7 | 101.3 | + |

WT Wildtype;
FWt Fresh Weight;
NM Not Measured

Table VI presents bean pod yield, GPT and GS activity, as well as antibiotic resistance status, in the transgenic lines compared to the wild type control (average of several robust control plants; control plants that did not grow well were excluded from the analyses). Referring to Table VI, double-transgene progeny plants showed substantial bean pod biomass increases (fresh pod weight) in comparison to the control plants, with bean pod biomass yields consistently above 200 grams per individual transgenic plant, compared to an average of 127 grams per wild type plant, representing an over 60% increase in pod yield in the double transgene lines relative to control plant(s).

Lastly, FIG. 11 shows a photograph of a GPT+GS double transgenic bean plant compared to a control plant grown for the same time under identical conditions, showing increased growth in the transgenic plant.

Example 10

Generation of Double Transgenic Bean Plants Carrying *Arabidopsis* GS1 and Grape GPT Transgenes In this example, yellow wax bean plants (*Phaseolus vulgaris*) were transformed with the Grape GPT full length coding sequence included in SEQ ID NO: 8 under the control of the RuBisCo promoter within the expression vector pCambia 1305.1, and the *Arabidopsis* GS1 coding sequence included in SEQ ID NO: 6 under the control of the RuBisCo promoter within the expression vector pCambia 1201, using *Agrobacterium*-mediated transfer into developing pods.

Materials and Methods:

The transgene expression vectors pCambia 1201-GPT (grape) (including construct of SEQ ID NO: 8) and pCambia 1201-GS (including construct of SEQ ID NO: 6) were transferred to separate *Agrobacterium tumefaciens* strain LBA4404 cultures using a standard electroporation method (McCormac et al., 1998, Molecular Biotechnology 9:155-159). Transformed *Agrobacterium* were selected on media containing 50 μg/ml of chloramphenicol. Transformed *Agrobacterium* cells were grown in LB culture media containing 25 μg/ml of antibiotic for 36 hours. At the end of the 36 hr growth period cells were collected by centrifugation and cells from each transformation were resuspended in 100 ml LB broth without antibiotic.

Bean plants were then transformed with a mixture of the resulting *Agrobacterium* cell suspensions using a transformation protocol in which the *Agrobacteria* is injected directly into the flower structure. In order to induce *Agrobacteria* virulence and improve transformation efficiencies, 10 μg/ml acetosyringonone was added to the *Agrobacteria* cultures prior to flower inoculation. Briefly, once flowers bloomed, the outer structure encapsulating the reproductive organs was gently opened with forceps in order to permit the introduction of the *Agrobacteria* mixture, which was added to the flower structure sufficient to flood the anthers.

Plants were grown until bean pods developed, and seeds were harvested and used to generate transgenic plants. Transgenic plants were then grown together with control bean plants under identical conditions, photographed and phenotypically characterized. Growth rates were measured for both transgenic and control plants.

Figure 12:
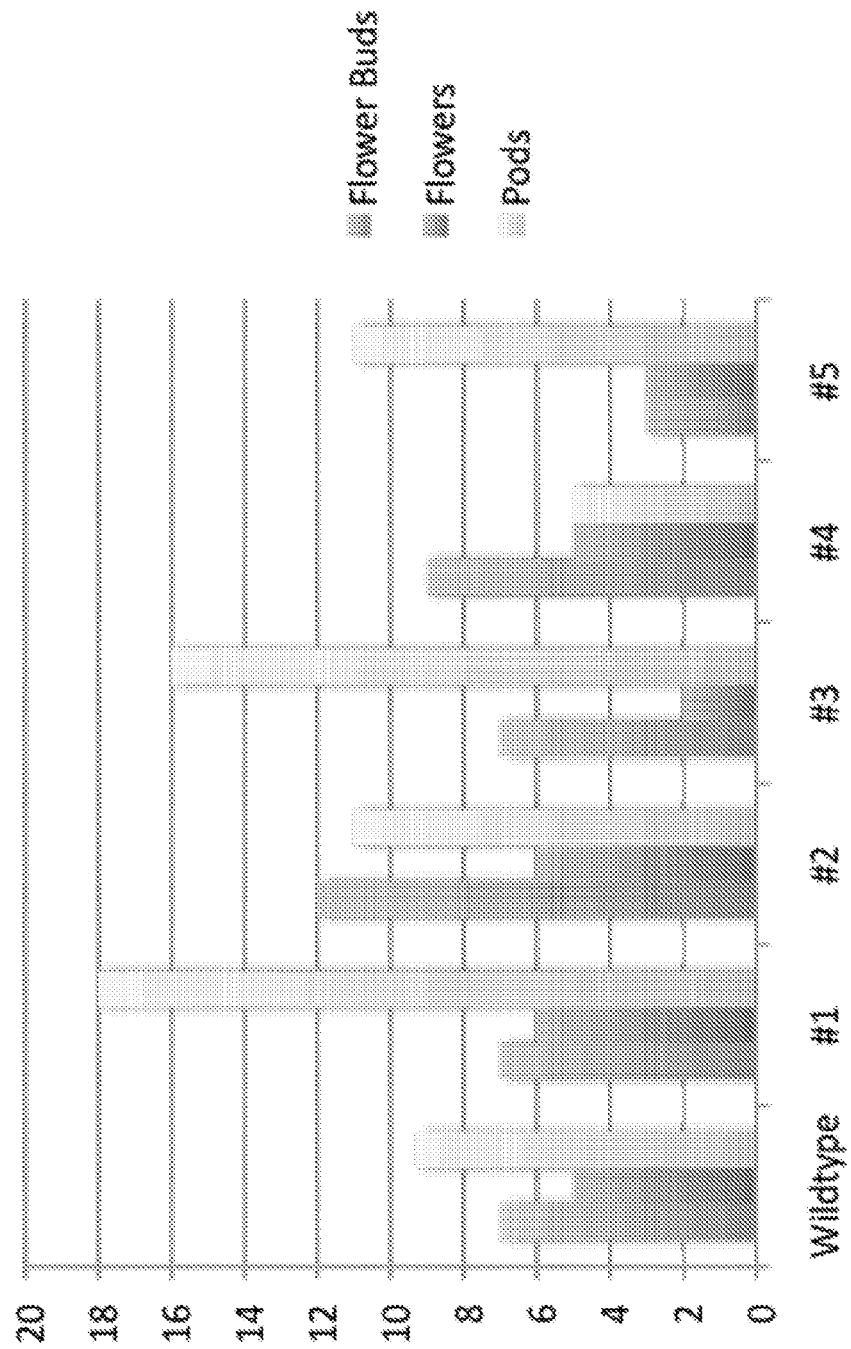
FIG. 12. Transgenic bean plants pods, flowers and flower buds compared to wild type control bean plants (transgenic line expressing grape GPT and *Arabidopsis* GS transgenes). See Example 10, infra.
Figure 13:
FIG. 13. Photograph of transgenic bean plant (right) and wild type control bean plant (left), showing increased growth in the transgenic plant relative to the wild type control plant. Transgenic line expressing Grape GPT and *Arabidopsis* GS transgenes. See Example 10, infra.

Results:

The results are presented in FIG. 12, FIG. 13 and Table VII.

FIG. 12 shows GPT+GS transgenic bean line G growth rate data relative to control plants, specifically including numbers of flower buds, flowers, and bean pods. These data show that the GPT+GS double transgenic bean plants outgrew their counterpart control plants. Notably, the transgenic plants produced substantially more bean pods that the wild type control plants.

TABLE VII

TRANSGENIC BEANS LINE G: POD YIELDS

| Plant Type | Bean Pod Yield FWt, g | Antibiotic Resistance |
|---|---|---|
| Wild type, avg | 157.9 | Negative |
| G1 | 200.5 | + |
| G2 | 178.3 | + |

WT Wildtype;
FWt Fresh Weight;
NM Not Measured

Table VII presents bean pod yield and antibiotic resistance status, in the transgenic lines compared to the wild type control (average of several robust control plants; control plants that did not grow well were excluded from the analyses). Referring to Table VII, double-transgene progeny plants showed substantial bean pod biomass increases (fresh pod weight) in comparison to the control plants, with bean pod biomass yields of 200.5 (line G1) and 178 grams (line G2) per individual transgenic plant, compared to an average of 158 grams per individual wild type plant, representing approximately a 27% increase in pod yield in the double transgene lines relative to control plants.

Lastly, FIG. 13 shows a photograph of a GPT+GS double transgenic bean plant compared to a control plant grown for the same time under identical conditions. The transgenic plant shows substantially increased size and biomass, larger leaves and a more mature flowering compared to the control plant.

Example 11

Generation of Double Transgenic Cowpea Plants Carrying *Arabidopsis* GS1 and GPT Transgenes In this example, common Cowpea plants were transformed with the *Arabidopsis* GPT full length coding sequence of SEQ ID NO: 1 under the control of the CMV 35S promoter within the expression vector pMON, and the *Arabidopsis* GS1 coding sequence included in SEQ ID NO: 6 under the control of the RuBisCo promoter within the expression vector pCambia 1201, using *Agrobacterium*-mediated transfer into flowers. Materials and methods were as in Example 9, supra.

Figure 14C:
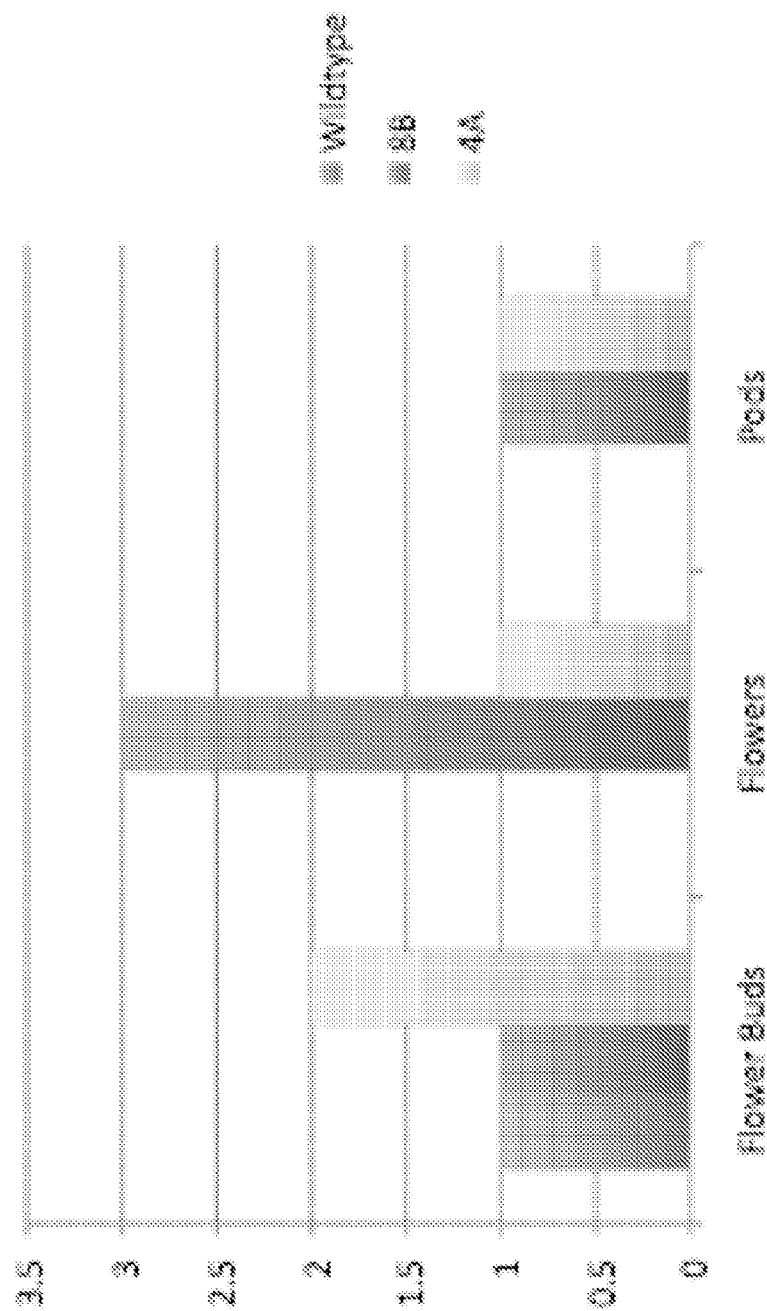
FIG. 14. Transgenic Cowpea Line A plants compared to wild type control Cowpea plants (transgenic line expressing *Arabidopsis* GPT and GS transgenes), showing that the transgenic plants grow faster and flower and set pods sooner than wild type control plants. (A) Relative height and longest leaf measurements as of May 21, (B) Relative trifolate leafs and flower buds as of June 18, (C) Relative numbers of flowers, flower buds and pea pods as of June 22. See Example 11, infra.
Figure 15:
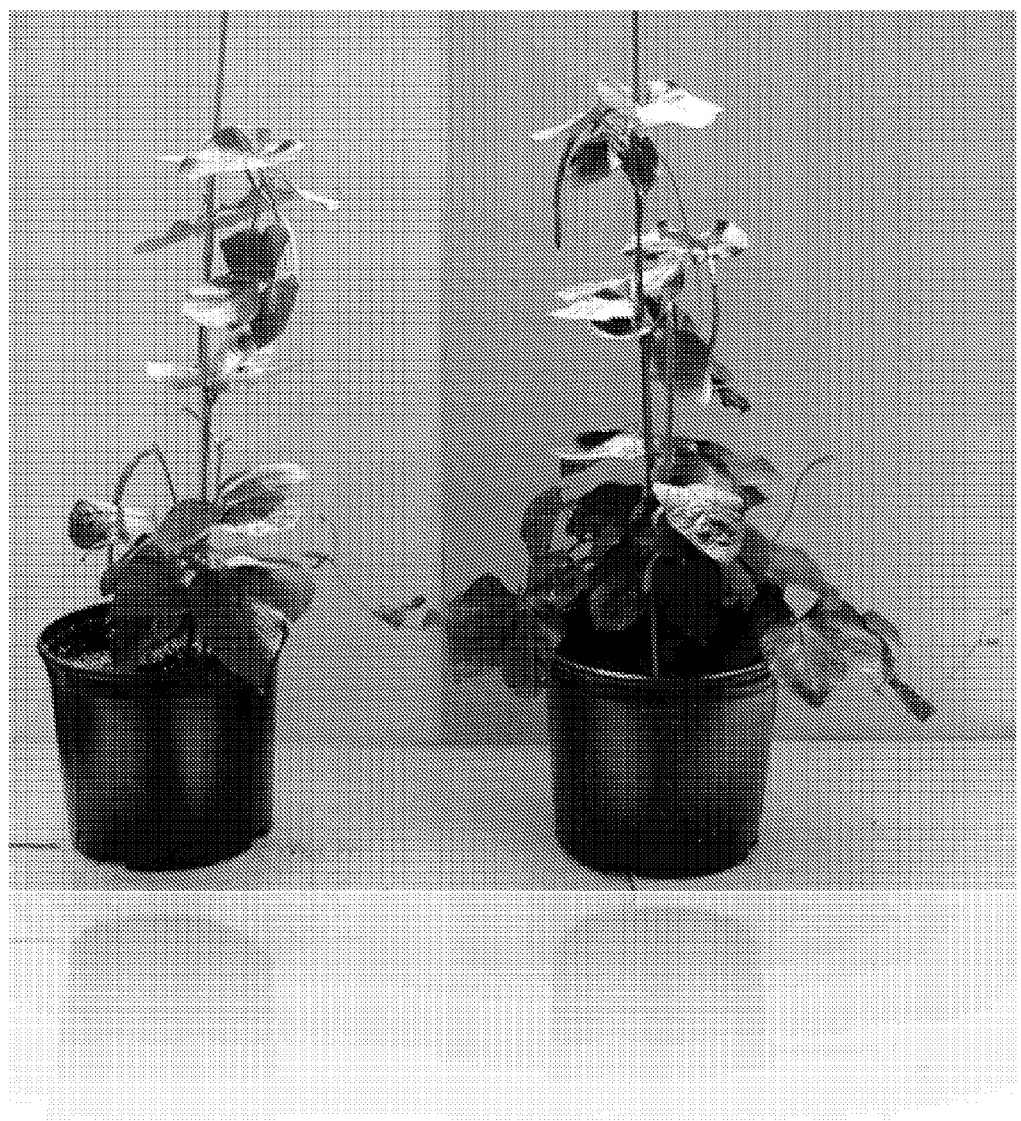
FIG. 15. Photograph of transgenic Cowpea Line A plant (right) and wild type control Cowpea plant (left), showing increased growth in the transgenic plant relative to the wild type control plant. Transgenic line expressing *Arabidopsis* GPT and GS transgenes. See Example 11, infra.

Results:

The results are presented in FIGS. 14 and 15, and Table VI. FIG. 14 shows relative growth rates for the GPT+GS transgenic Cowpea line A and wild type control Cowpea at several intervals during cultivation, including (FIG. 14A) height and longest leaf measurements, (FIG. 14B) trifolate leafs and flower buds, and (FIG. 14C) flowers, flower buds and pea pods. These data show that the GPT+GS double transgenic Cowpea plants outgrew their counterpart control plants. The transgenic plants grew faster and taller, had longer leaves, and set flowers and pods sooner than wild type control plants.

TABLE VIII

TRANSGENIC COWPEA LINE A

| Plant Type | Pea Pod Yield, FWt, g | GPT Activity nmoles/h/gFWt | GS Activity umol/min/gFWt | Antibiotic Resistance |
|---|---|---|---|---|
| Wildtype, avg | 74.7 | 44.4 | 28.3 | Negative |
| 4A | 112.8 | NM | 41.3 | + |
| 8B | 113.8 | 736.2 | 54.9 | + |

WT Wildtype;
FWt Fresh Weight;
NM Not Measured

Table VIII presents pea pod yield, GPT and GS activity, as well as antibiotic resistance status, in the transgenic lines compared to the wild type control (average of several robust control plants; control plants that did not grow well were excluded from the analyses). Referring to Table VIII, double-transgene progeny plants showed substantial pea pod biomass increases (fresh pod weight) in comparison to the control plants, with average transgenic plant pea pod biomass yields nearly 52% greater than the yields measured in control plant(s).

Lastly, FIG. 15 shows a photograph of a GPT+GS double transgenic bean plant compared to a control plant grown for the same time under identical conditions, showing increased biomass and pod yield in the transgenic plant relative to the wild type control plant.

Example 12

Generation of Double Transgenic Cowpea Plants Carrying *Arabidopsis* GS1 and Grape GPT Transgenes In this example, common Cowpea plants were transformed with the Grape GPT full length coding sequence included in SEQ ID NO: 8 under the control of the RuBisCo promoter within the expression vector pCambia 1305.1 (including construct of SEQ ID NO: 8), and the *Arabidopsis* GS1 coding sequence included in SEQ ID NO: 6 under the control of the RuBisCo promoter within the expression vector pCambia 1201 (including construct of SEQ ID NO: 6), using *Agrobacterium*-mediated transfer into flowers. Materials and methods were as in Example 11, supra.

Figure 16A:
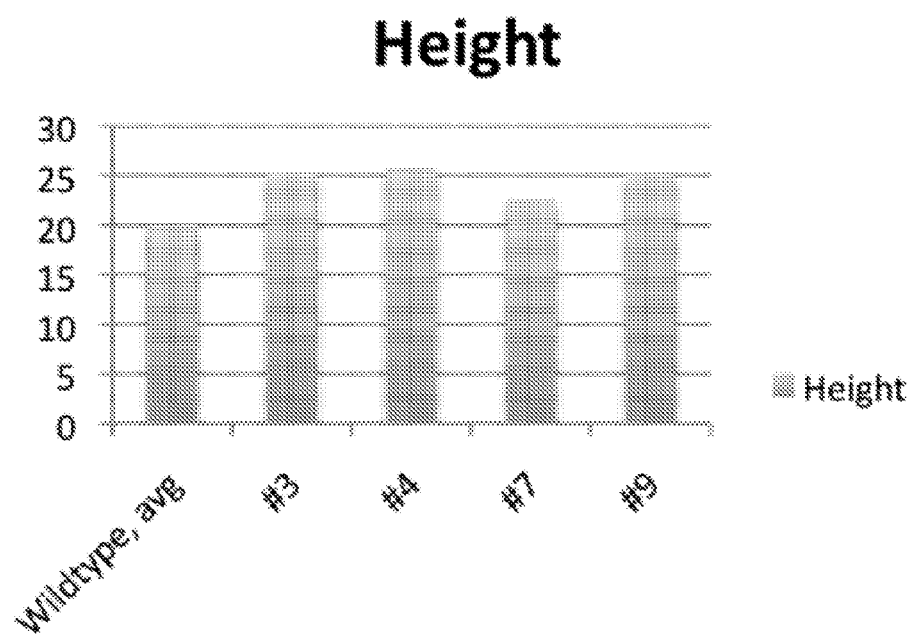
FIG. 16. Transgenic Cowpea Line G plants compared to wild type control Cowpea plants (transgenic line expressing Grape GPT and *Arabidopsis* GS transgenes), showing that the transgenic plants grow faster and flower and set pods sooner than wild type control plants. (A) plant heights, (B) flowers and pea pod numbers, (C) leaf bud and trifolate numbers. See Example 12, infra.
Figure 16C:
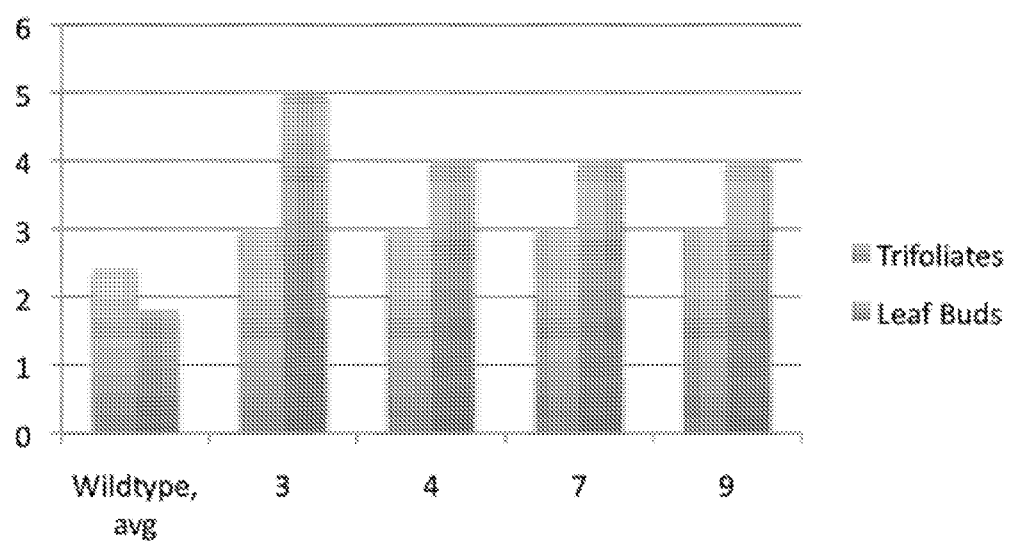
Figure 17:
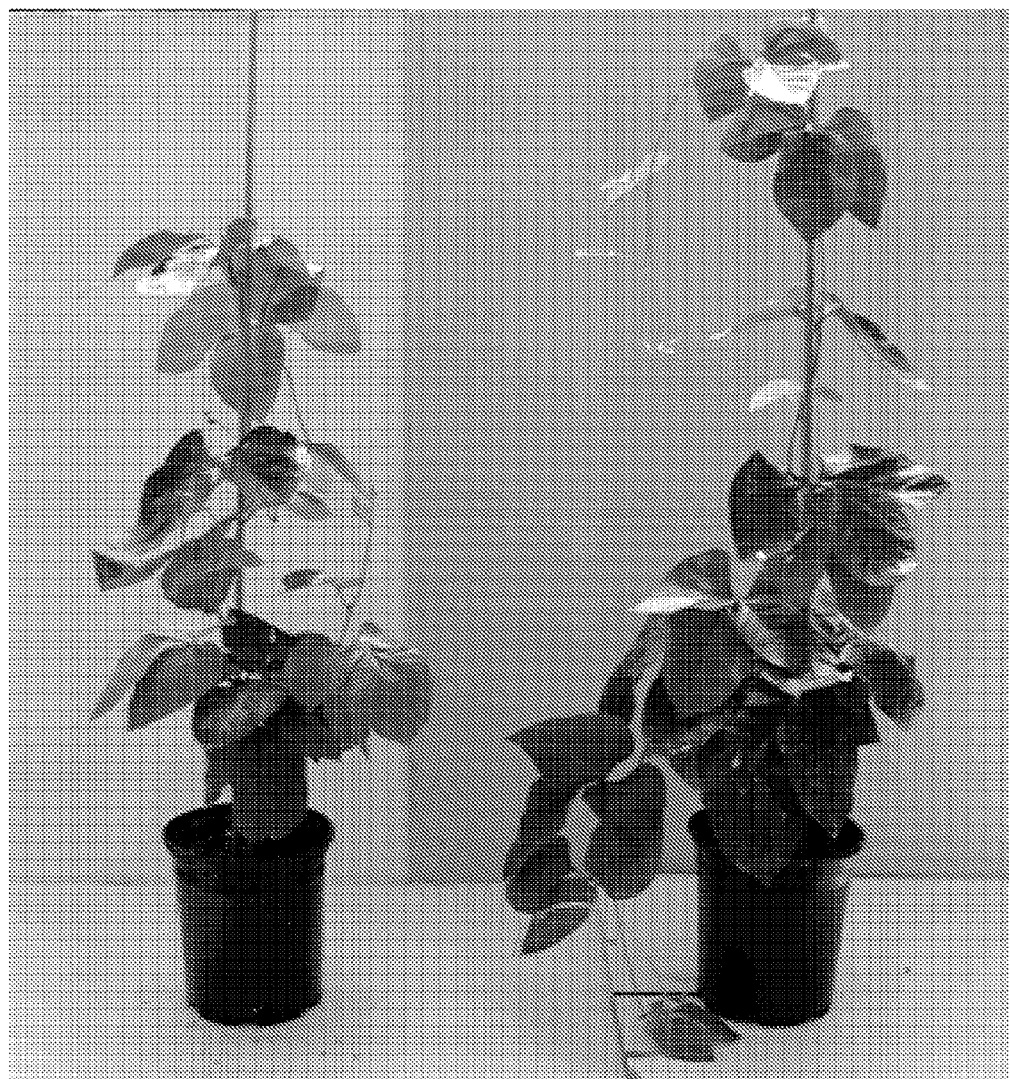
FIG. 17. Photograph of transgenic Cowpea Line G plant (right) and wild type control Cowpea plant (left), showing increased growth in the transgenic plant relative to the wild type control plant. Transgenic line expressing Grape GPT and *Arabidopsis* GS transgenes. See Example 12, infra.

Results:

The results are presented in FIGS. 16 and 17, and Table IX. FIG. 16 shows relative growth rates for the GPT+GS transgenic Cowpea line G and wild type control Cowpea. These data show that the transgenic plants are consistently higher (FIG. 16A), produce substantially more flowers, flower buds and pea pods (FIG. 16B), and develop trifolates and leaf buds faster (FIG. 16C).

TABLE IX

TRANSGENIC COWPEA LINE G

| Plant Type | Pod Yield, FWt, g | GPT Activity nmoles/h/ gFWT | GS Activity umol/min/ gFWt | Antibiotic Resistance |
|---|---|---|---|---|
| Wildtype, avg | 59.7 | 44.4 | 26.7 | Negative |
| G9 | 102.0 | 555.6 | 34.5 | + |

WT Wildtype;
FWt Fresh Weight;
NM Not Measured

Table IX presents pea pod yield, GPT and GS activity, as well as antibiotic resistance status, in the transgenic lines compared to the wild type control (average of several robust control plants; control plants that did not grow well were excluded from the analyses). Referring to Table IX, double-transgene progeny plants showed substantial pea pod biomass increases (fresh pod weight) in comparison to the control plants, with average pea pod biomass yields 70% greater in the transgenic plants compared to control plant(s).

Lastly, FIG. 17 shows a photograph of a GPT+GS double transgenic pea plant compared to a control plant grown for the same time under identical conditions, showing increased height, biomass and leaf size in the transgenic plant relative to the wild type control plant.

Example 13

Generation of Double Transgenic *Alfalfa* Plants Carrying *Arabidopsis* GS1 and GPT Transgenes In this example, *Alfalfa* plants (*Medicago sativa*, var *Ladak*) were transformed with the *Arabidopsis* GPT full length coding sequence of SEQ ID NO: 1 under the control of the CMV 35S promoter within the expression vector pMON316 (see Example 3, supra), and the *Arabidopsis* GS1 coding sequence included in SEQ ID NO: 6 under the control of the RuBisCo promoter within the expression vector pCambia 1201 (including construct of SEQ ID NO: 6), using *Agrobacterium*-mediated transfer into seedling plants. *Agrobacte*- rium vectors and mixtures were prepared for seedling inoculations as described in Example 11, supra.

Seedling Inoculations:

When *Alfalfa* seedlings were still less than about ½ inch tall, they were soaked in paper toweling that had been flooded with the *Agrobacteria* mixture containing both transgene constructs. The seedlings were left in the paper toweling for two to three days, removed and then planted in potting soil. Resulting T0 and control plants were then grown for the first 30 days in a growth chamber, thereafter cultivated in a greenhouse, and then harvested 42 days after sprouting. At this point, only the transgenic *Alfalfa* line displayed flowers, as the wild type plants only displayed immature flower buds. The plants were characterized as to flowering status and total biomass.

Results:

The results are presented in Table X. The data shows that the transgenic *Alfalfa* plants grew faster, flowered sooner, and yielded on average about a 62% biomass increase relative to the control plants.

TABLE X

TRANSGENIC ALFALFA VS. CONTROL

| Plant Type | Biomass at Sacrifice, g | Flowering Stage |
|---|---|---|
| Wildtype, avg | 6.03 | Small defined buds No buds swelling. No flowers |
| Transgene #5 | 10.38 | 4 Open flowers |
| Transgene #11 | 9.03 | Flower buds swelling |
| Transgene #13 | 9.95 | Flower buds swelling |

Example 14

Generation of Double Transgenic Cantaloupe Plants Carrying *Arabidopsis* GS1 and GPT Transgenes In this example, Cantaloupe plants (*Cucumis melo* var *common*) were transformed with the *Arabidopsis* GPT full length coding sequence of SEQ ID NO: 1 under the control of the CMV 35S promoter within the expression vector pMON316 (see Example 3, supra), and the *Arabidopsis* GS1 coding sequence included in SEQ ID NO: 6 under the control of the RuBisCo promoter within the expression vector pCambia 1201 (including construct of SEQ ID NO: 6), using *Agrobacterium*-mediated transfer via injection into developing melons. *Agrobacterium* vectors and mixtures were prepared for intra-melon inoculations as described in Example 8, supra. Inoculations into developing melons were carried out essentially as described in Example 8. The plants were characterized as to flowering status and total biomass relative to control melon plants grown under identical conditions.

Figure 18:
FIG. 18. Photograph of transgenic Cantaloupe plant (right) and wild type control Cantaloupe plant (left), showing increased growth in the transgenic plant relative to the wild type control plant. Transgenic line expressing *Arabidopsis* GPT and GS transgenes. See Example 14, infra.

The results are presented in FIG. 18 and Table XI. Referring to Table XI, the transgenic plants showed substantial foliar plant biomass increases in comparison to the control plants, with an average increase in biomass of 63%. Moreover, a tremendous increase in flower and flower bud yields was observed in all five transgenic lines. Control plants displayed no flowers and only 5 buds at sacrifice, on average. In sharp contrast, the transgenic plants displayed between 2 and 5 flowers per plant, and between 21 and 30 flower buds, per plant, indicating a substantially higher growth rate and flower yield. Increased flower yield would be expected to translate into correspondingly higher melon yields in the transgenic plants. Referring to FIG. 18 (a photograph comparing transgenic Cantaloupe plants to control Cantaloupe plants), the transgenic Cantaloupe plants show dramatically increased height, overall biomass and flowering status relative to the control plants.

TABLE XI

TRANGENIC CANTALOUPE VERSUS CONTROL

| Plant Type | Biomass Foliar FWt, g | Flowers/Flower Buds at Sacrifice | Antibiotic Resistance |
|---|---|---|---|
| Wildtype, avg | 22.8 | 0/5 | Negative |
| Line 1 | 37.0 | 3/21 | + |
| Line 2 | 35.0 | 2/30 | + |
| Line 3 | 37.1 | 3/27 | + |
| Line 4 | 40.6 | 5/26 | + |
| Line 5 | 35.7 | 4/30 | + |

FWt Fresh Weight

Example 15

Generation of Double Transgenic Pumpkin Plants Carrying *Arabidopsis* GS1 and GPT Transgenes In this example, common Pumpkin plants (*Cucurbita maxima*) were transformed with the *Arabidopsis* GPT full length coding sequence of SEQ ID NO: 1 under the control of the CMV 35S promoter within the expression vector pMON316 (see Example 3, supra), and the *Arabidopsis* GS1 coding sequence included in SEQ ID NO: 6 under the control of the RuBisCo promoter within the expression vector pCambia 1201 (including construct of SEQ ID NO: 6), using *Agrobacterium*-mediated transfer via injection into developing pumpkins, essentially as described in Example 14, supra. The transgenic and control pumpkin plants were grown under identical conditions until the emergence of flower buds in the control plants, then all plants were characterized as to flowering status and total biomass.

Figure 19:
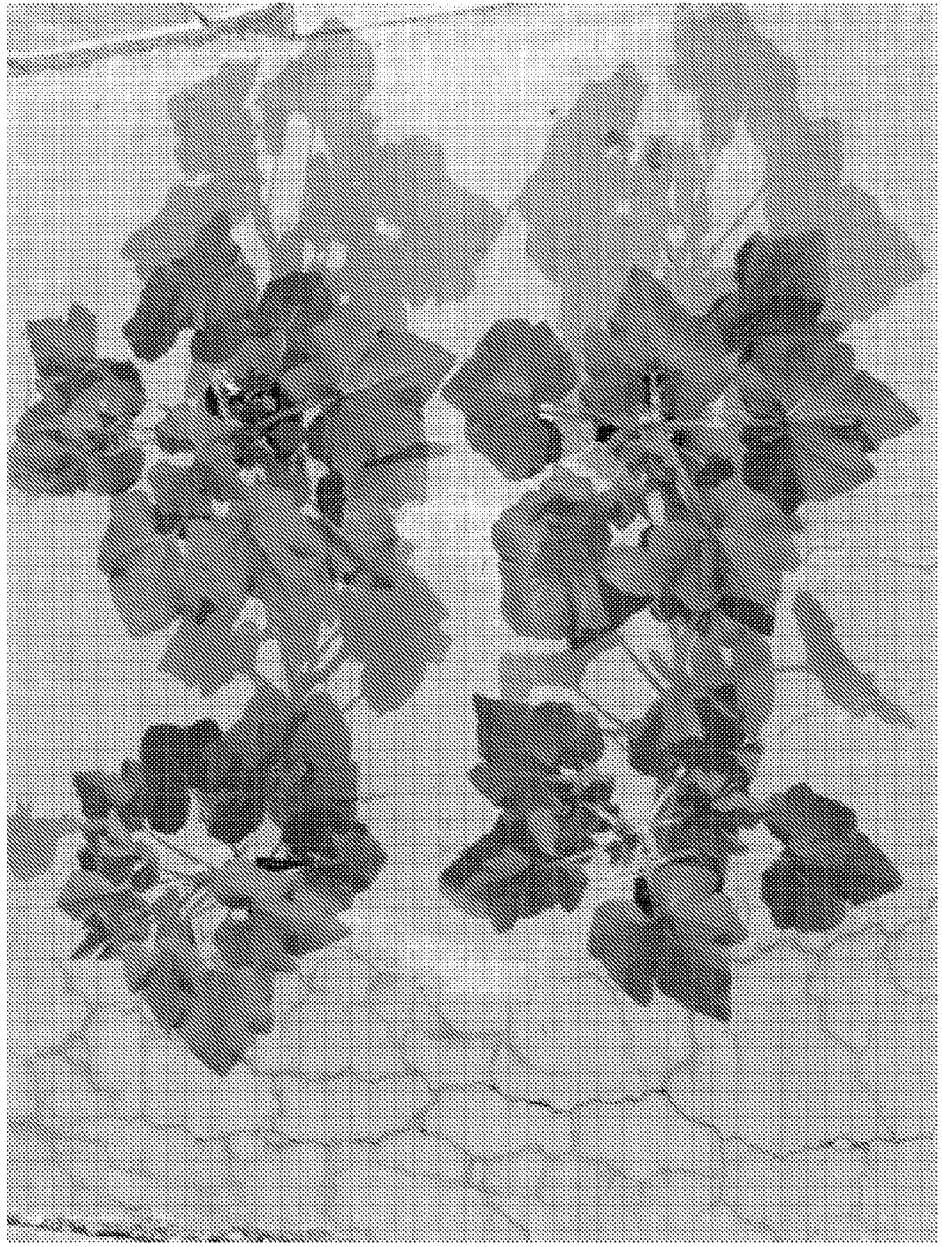
FIG. 19. Photograph of transgenic Pumpkin plants (right) and wild type control Pumpkin plants (left), showing increased growth in the transgenic plants relative to the wild type control plants. Transgenic lines expressing *Arabidopsis* GPT and GS transgenes. See Example 15, infra.

The results are presented in FIG. 19 and Table XII. Referring to Table XII, the transgenic plants showed substantial foliar plant biomass increases in comparison to the control plants, with an increase in average biomass yield of 67% over control plants. Moreover, an increase in flower bud yields was observed in four of the five transgenic lines in comparison to control. Control plants displayed only 4 buds at sacrifice (average). In contrast, four transgenic plant lines displayed between 8 and 15 flowers buds per plant, representing a two- to nearly four-fold yield increase.

TABLE XII

TRANGENIC PUMPKIN VERSUS CONTROL

| Plant Type | Biomass Foliar FWt, g | Flower Buds at Sacrifice | Antibiotic Resistance |
|---|---|---|---|
| Wildtype, avg | 47.7 | 4.2 | Negative |
| Line 1 (Photo) | 82.3 | 8 | |
| Line 2 | 74.3 | 8 | + |
| Line 3 | 80.3 | 9 | + |
| Line 4 (Photo) | 77.8 | 4 | + |
| Line 5 | 84.5 | 15 | + |

FWt Fresh Weight;

Referring to FIG. 19 (a photograph comparing transgenic pumpkin plants to control plants), the transgenic pumpkin plants show substantially increased plant size, overall biomass and leaf sizes and numbers relative to the control plants.

Example 16

Generation of Double Transgenic *Arabidopsis* Plants Carrying *Arabidopsis* GS1 and GPT Transgenes In this example, *Arabidopsis thaliana* plants were transformed with the truncated *Arabidopsis* GPT coding sequence of SEQ ID NO: 18 under the control of the CMV 35S promoter within the expression vector pMON316 (see Example 3, supra), and transgenic plants thereafter transformed with the *Arabidopsis* GS1 coding sequence included in SEQ ID NO: 6 under the control of the RuBisCo promoter within the expression vector pCambia 1201 (including construct of SEQ ID NO: 6), using *Agrobacterium*-mediated "floral dip" transfer as described (Harrison et al., 2006, Plant Methods 2:19-23; Clough and Bent, 1998, Plant J. 16:735-743). *Agrobacterium* vectors pMON316 carrying GPT and pCambia 1201 carrying GS1 were prepared as described in Examples 3 and 11, respectively.

Transformation of two different cultures of *Agrobacterium* with either a pMon 316+*Arabidopsis* GTP construct or with a Cambia 1201+*Arabidopsis* GS construct was done by electroporation using the method of Weigel and Glazebrook 2002. The transformed *Agrobacterium* were then grown under antibiotic selection, collected by centrifugation resuspended in LB broth with antibiotic and used in the floral dip of *Arabidopsis* inflorescence. Floral dipped *Arabidopsis* plants were taken to maturity and self-fertilized and seeds were collected. Seeds from twice dipped plants were first geminated on a media containing 20 ug/ml of kanamycin and by following regular selection procedures surviving seedlings were transferred to media containing 20 ug of hygromycin. Plants (3) surviving the selection process on both antibiotics were self-fertilized and seeds were collected. Seeds from the T1 generation were germinated on MS media containing 20 ug/ml of hygromycin and surviving seedlings were taken to maturity, self-fertilized and seeds collected. This seed population the T2 generation was then used for subsequent growth studies.

Figure 20:
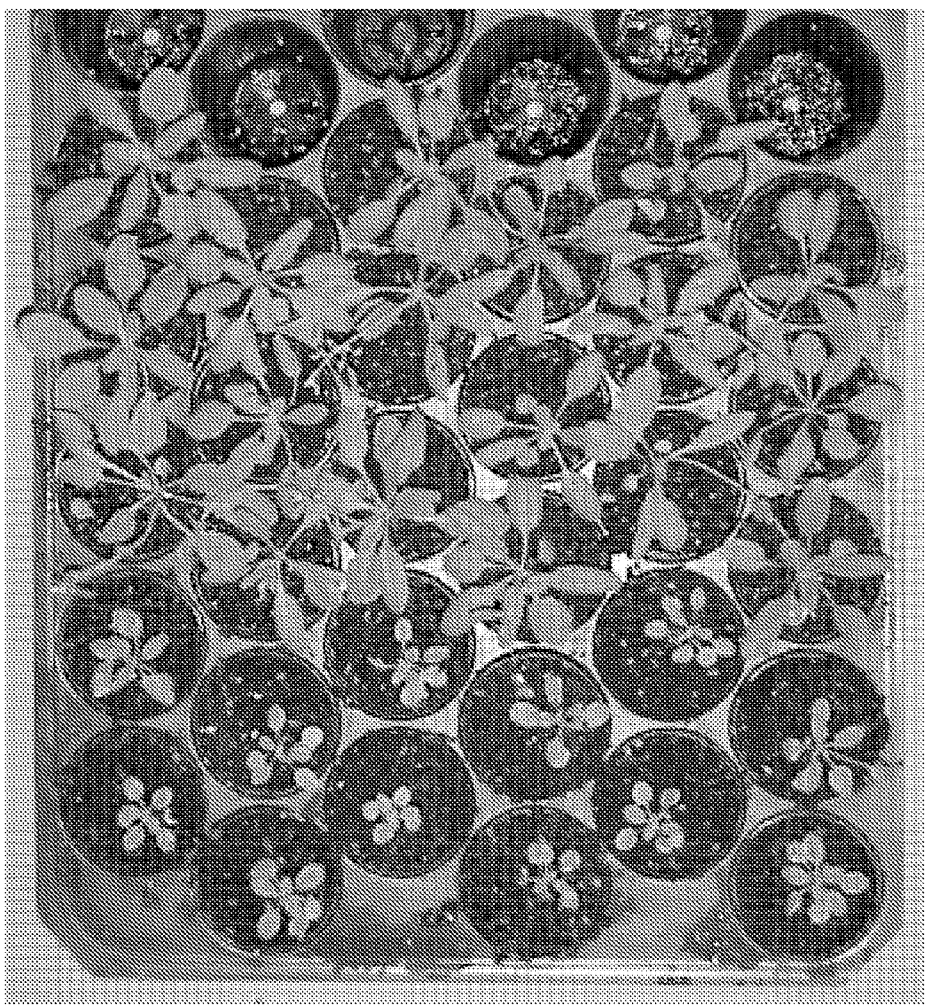
FIG. 20. Photograph of transgenic *Arabidopsis* plants (right) and wild type control *Arabidopsis* plants (left), showing increased growth in the transgenic plants relative to the wild type control plants. Transgenic lines expressing *Arabidopsis* GPT and GS transgenes. See Example 16, infra.

The results are presented in FIG. 20 and Table XIII. Referring to Table XIII, which shows data from 6 wild type and 6 transgenic *Arabidopsis* plants (averaged), the transgenic plants displayed increased levels of both GPT and GS activity. GPT activity was over twenty-fold higher than the control plants. Moreover, the transgenic plant fresh foliar weight average was well over four-fold that of the wild type control plant average. A photograph of young transgene *Arabidopsis* plants in comparison to wild type control *Arabidopsis* plants grown under identical conditions is shown in FIG. 20, and reveals a consistent and very significant growth/biomass increase in transgenic plants relative to the control plants.

TABLE XIII

TRANSGENIC *ARABIDOPSIS* VERSUS CONTROL

| Plant type | Biomass, g Fresh foliar wt | GPT Activity nmol/h/gFWt | GS Activity umol/min/ gFWt | Antibiotic Resistance |
|---|---|---|---|---|
| Wildtype, avg | 0.246 | 18.4 | 7.0 | Negative |
| Transgene | 1.106 | 395.6 | 18.2 | Positive |

Example 17

Generation of Transgenic Tomato Plants Carrying *Arabidopsis* GPT and GS1 Transgenes In this example, tomato plants (*Solanum lycopersicon*, "Money Maker" variety) were transformed with the *Arabidopsis* GPT full length coding sequence of SEQ ID NO: 1 under the control of the CMV 35S promoter within the expression vector pMON316 (see Example 3, supra), and the *Arabidopsis* GS1 coding sequence included in SEQ ID NO: 6 under the control of the RuBisCo promoter within the expression vector pCambia 1201 (including construct of SEQ ID NO: 6). Single transgene (GPT) transgenic tomato plants were generated and grown to flowering essentially as described in Example 4. The *Arabidopsis* GS1 transgene was then introduced into the single-transgene T0 plants using *Agrobacterium*-mediated transfer via injection directly into flowers (as described in Example 8). The transgenic and control tomato plants were grown under identical conditions and characterized as to growth phenotype characteristics. Resulting T0 double-transgene plants were then grown to maturity, photographed along with control tomato plants, and phenotypically characterized.

The results are presented in FIG. 21 and in Table XIX. Referring to Table XIX, double-transgene tomato plants showed substantial foliar plant biomass increases in comparison to the control plants, with an increase in average biomass yield of 45% over control. Moreover, as much as a 70% increase in tomato fruit yield was observed in the transgenic lines compared to control plants (e.g., 51 tomatoes harvested from Line 4C, versus and average of approximately 30 tomatoes from control plants). A much higher level of GPT activity was observed in the transgenic plants (e.g., line 4C displaying an approximately 32-fold higher GPT activity in comparison to the average GPT activity measured in control plants). GS activity was also higher in the transgenic plants relative to control plants (almost double in Line 4C).

Figure 21A:
FIG. 21. Transgenic tomato plants expressing *Arabidopsis* GPT and GS transgenes compared to control tomato plants. (A) Photograph of transgenic tomato plant leaves (right) vs. wild type control leaves (left) showing larger leaves in the transgenic plant. (B) Photograph of transgenic tomato plants (right) and wild type control plants (left), showing increased growth in the transgenic plants relative to the wild type control plants. See Example 17, infra.
Figure 21B:
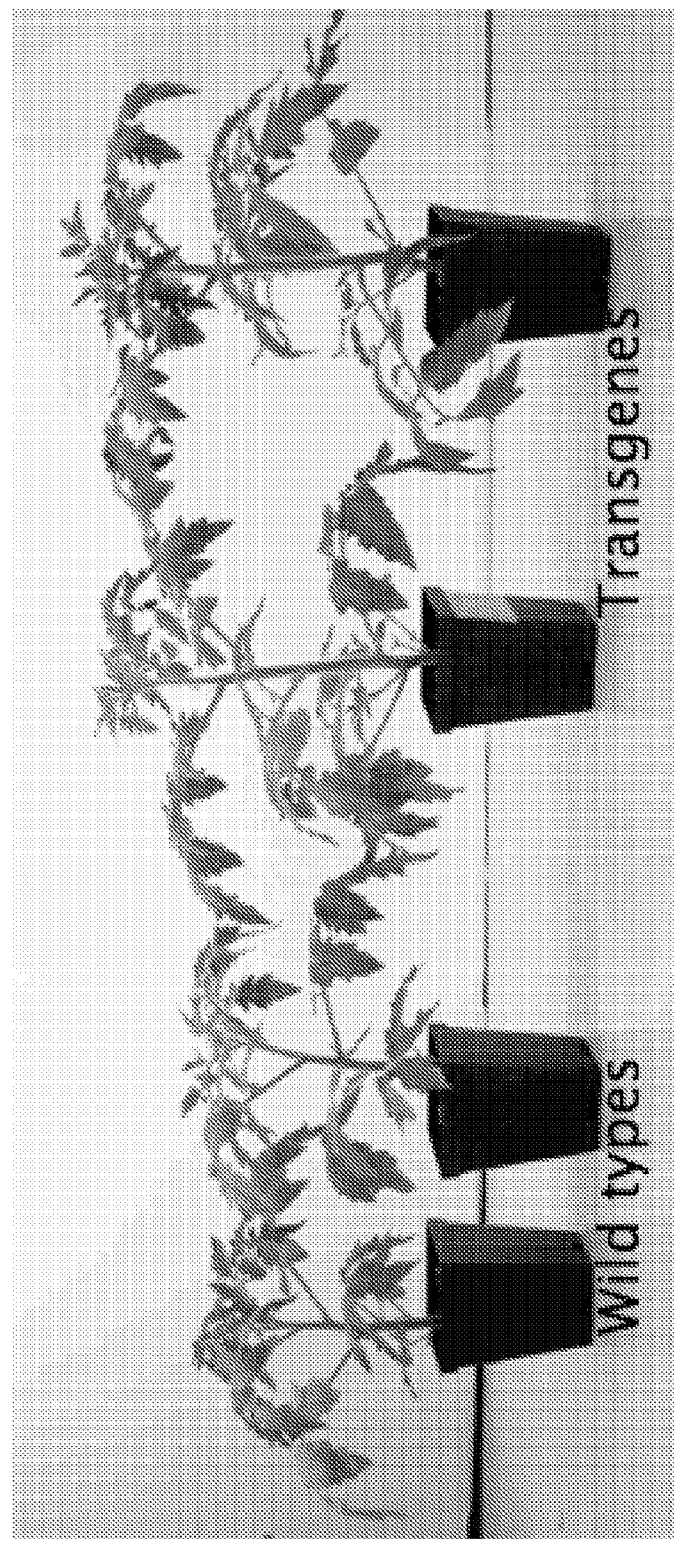

With respect to growth phenotype, and referring to FIG. 21, the transgenic tomato plants displayed substantially larger leaves compared to control plants (FIG. 21A). In addition, it can be seen that the transgenic tomato plants were substantially larger, taller and of a greater overall biomass (see FIG. 21B).

TABLE XIX

TRANSGENIC TOMATO GROWTH AND REPRODUCTION

| Plant Type | Biomass Foliar FWt, g | Total Tomatoes Harvested until Sacrifice | GPT Activity nmoles/h/ gFWt | GS Activity umoles/min/ gFWt | Transgene Presence Assay |
|---|---|---|---|---|---|
| Wildtype, avg | 891 | 30.2 | 287 | 14.27 | Negative |
| Line 6C | 1288 | 43 | 9181 | 18.3 | + |
| Line 4C | 1146 | 51 | 1718 | 26.4 | + |

Example 18

Generation of Transgenic Camilena Plants Carrying *Arabidopsis* GPT and GS1 Transgenes In this example, *Camelina* plants (*Camelina sativa*, Var MT 303) were transformed with the *Arabidopsis* GPT full length coding sequence of SEQ ID NO: 1 under the control of the RuBisCo promoter within the expression vector pCambia 1201, and the *Arabidopsis* GS1 coding sequence included in SEQ ID NO: 6 under the control of the RuBisCo promoter within the expression vector pCambia 1201, using *Agrobacterium*-mediated transfer into germinating seeds according to the method described in Chee et al., 1989, Plant Physiol. 91:

1212-1218. *Agrobacterium* vectors and mixtures were prepared for seed inoculations as described in Example 11, supra.

Transgenic and control *Camelina* plants were grown under identical conditions (30 days in a growth chamber and then moved to greenhouse cultivation) for 39 days, and characterized as to biomass, growth characteristics and flowering stage.

Figure 22:
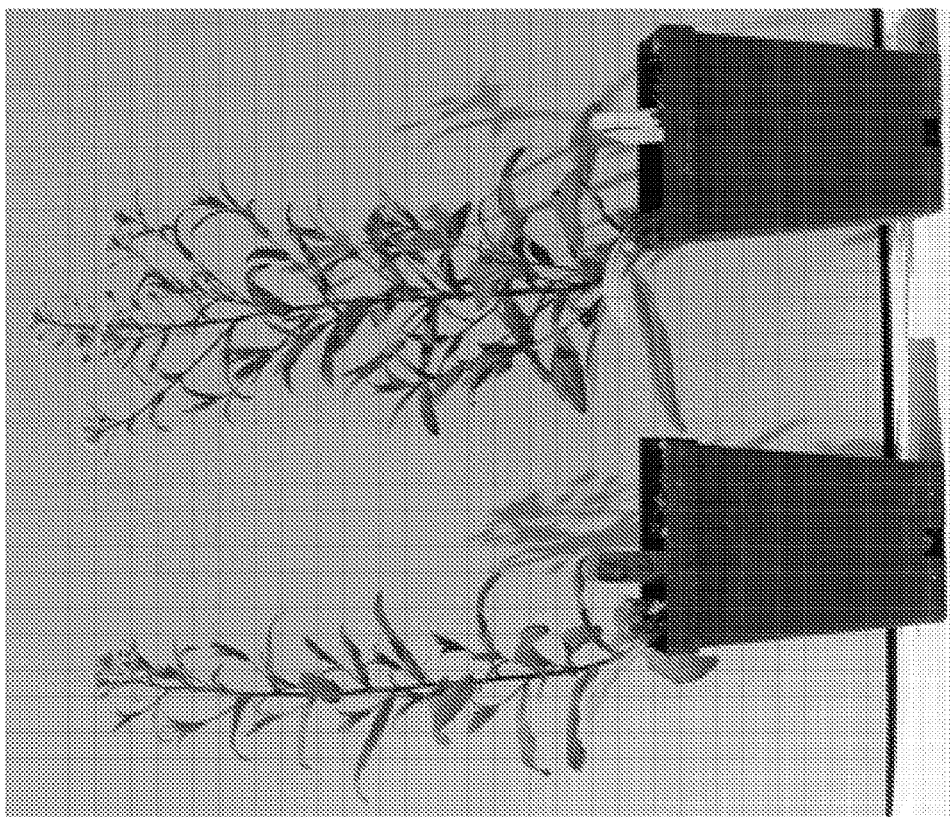
FIG. 22. Photograph of transgenic *Camelina* plant (right) and wild type control *Camelina* plant (left), showing increased growth in the transgenic plant relative to the wild type control plant. Transgenic line expressing *Arabidopsis* GPT and GS transgenes. See Example 18, infra.

The results are presented in Table XX and FIG. 22. Referring to Table XX, it can be seen that total biomass in the transgenic plants was, on average, almost double control plant biomass. Canopy diameter was also significantly improved in the transgenic plants. FIG. 22 shows a photograph of transgenic *Camelina* compared to control. The transgenic plant is noticeably larger and displays more advanced flowering.

TABLE XX

TRANSGENIC *CAMELINA* VERSUS CONTROL

| Plant Type | Height/Canopy Diameter, inches | Biomass g | Flowering Stage |
|---|---|---|---|
| Wildtype, avg | 14/4 | 8.35 | Partial flowering |
| Transgene C-1 | 15.5/5 | 16.54 | Full flowering |
| Transgene C-3 | 14/7 | 14.80 | Initial flowering |

Example 19

Activity of Barley GPT Transgene in Planta

In this example, the putative coding sequence for Barley GPT was isolated and expressed from a transgene construct using an in planta transient expression assay. Biologically active recombinant Barley GPT was produced, and catalyzed the increased synthesis of 2-oxoglutaramate, as confirmed by HPLC.

The Barley (*Hordeum vulgare*) GPT coding sequence was determined and synthesized. The DNA sequence of the Barley GPT coding sequence used in this example is provided in SEQ ID NO: 14, and the encoded GPT protein amino acid sequence is presented in SEQ ID NO: 15.

The coding sequence for Barley GPT was inserted into the 1305.1 cambia vector, and transferred to *Agrobacterium tumefaciens* strain LBA404 using a standard electroporation method (McCormac et al., 1998, Molecular Biotechnology 9:155-159), followed by plating on LB plates containing hygromycin (50 micro gm/ml). Antibiotic resistant colonies of *Agrobacterium* were selected for analysis.

The transient tobacco leaf expression assay consisted of injecting a suspension of transformed *Agrobacterium* (1.5-2.0 OD 650) into rapidly growing tobacco leaves. Intradermal injections were made in a grid across the leaf surface to assure that a significant amount of the leaf surface would be exposed to the *Agrobacterium*. The plant was then allowed to grow for 3-5 days when the tissue was extracted as described for all other tissue extractions and the GPT activity measured.

GPT activity in the inoculated leaf tissue (1217 nanomoles/gFWt/h) was three-fold the level measured in the control plant leaf tissue (407 nanomoles/gFWt/h), indicating that the *Hordeum* GPT construct directed the expression of biologically active GPT in a transgenic plant.

Example 20

Isolation and Expression of Recombinant Rice GPT Gene Coding Sequence and Analysis of Biological Activity In this example, the putative coding sequence for rice GPT was isolated and expressed in *E. coli*. Biologically active recombinant rice GPT was produced, and catalyzed the increased synthesis of 2-oxoglutaramate, as confirmed by HPLC.

Materials and Methods:

Rice GPT Coding Sequence and Expression in *E. Coli*:

The rice (*Oryza sativa*) GPT coding sequence was determined and synthesized, inserted into a PET28 vector, and expressed in *E. coli*. Briefly, *E. coli* cells were transformed with the expression vector and transformants grown overnight in LB broth diluted and grown to OD 0.4, expression induced with isopropyl-B-D-thiogalactoside (0.4 micromolar), grown for 3 hr and harvested. A total of 25×106 cells were then assayed for biological activity using the NMR assay, below. Untransformed, wild type *E. coli* cells were assayed as a control. An additional control used *E. coli* cells transformed with an empty vector.

The DNA sequence of the rice GPT coding sequence used in this example is provided in SEQ ID NO: 10, and the encoded GPT protein amino acid sequence is presented in SEQ ID NO: 11.

HPLC Assay for 2-Oxoglutaramate:

HPLC was used to determine 2-oxoglutaramate production in GPT-overexpressing *E. coli* cells, following a modification of Calderon et al., 1985, J Bacteriol 161(2): 807-809. Briefly, a modified extraction buffer consisting of 25 mM Tris-HCl pH 8.5, 1 mM EDTA, 20 µM Pyridoxal phosphate, 10 mM Cysteine, and ~1.5% (v/v) Mercaptoethanol was used. Samples (lysate from *E. coli* cells, 25×106 cells) were added to the extraction buffer at approximately a 1/3 ratio (w/v), incubated for 30 minutes at 37° C., and stopped with 200 µl of 20% TCA. After about 5 minutes, the assay mixture is centrifuged and the supernatant used to quantify 2-oxoglutaramate by HPLC, using an ION-300 7.8 mm IDx30 cm L column, with a mobile phase in 0.01N $H_2SO_4$, a flow rate of approximately 0.2 ml/min, at 40° C. Injection volume is approximately 20 µl, and retention time between about 38 and 39 minutes. Detection is achieved with 210 nm UV light.

NMR analysis comparison with authentic 2-oxoglutaramate was used to establish that the *Arabidopsis* full length sequence expresses a GPT with 2-oxoglutaramate synthesis activity. Briefly, authentic 2-oxoglutarmate (structure confirmed with NMR) made by chemical synthesis to validate the HPLC assay, above, by confirming that the product of the assay (molecule synthesized in response to the expressed GPT) and the authentic 2-oxoglutaramate elute at the same retention time. In addition, when mixed together the assay product and the authentic compound elute as a single peak. Furthermore, the validation of the HPLC assay also included monitoring the disappearance of the substrate glutamine and showing that there was a 1:1 molar stoechiometry between glutamine consumed to 2-oxoglutaramate produced. The assay procedure always included two controls, one without the enzyme added and one without the glutamine added. The first shows that the production of the 2-oxoglutaramate was dependent upon having the enzyme present, and the second shows that the production of the 2-oxoglutaramate was dependent upon the substrate glutamine.

Results:

Expression of the rice GPT coding sequence of SEQ ID NO: 10 resulted in the over-expression of recombinant GPT protein having 2-oxoglutaramate synthesis-catalyzing bioactivity. Specifically, 1.72 nanomoles of 2-oxoglutaramate activity was observed in the *E. coli* cells overexpressing the recombinant rice GPT, compared to only 0.02 nanomoles of 2-oxoglutaramate activity in control *E. coli* cells, an 86-fold activity level increase over control.

Example 21

Isolation and Expression of Recombinant Soybean GPT Gene Coding Sequence and Analysis of Biological Activity In this example, the putative coding sequence for soybean GPT was isolated and expressed in *E. coli*. Biologically active recombinant soybean GPT was produced, and catalyzed the increased synthesis of 2-oxoglutaramate, as confirmed by HPLC.

Materials and Methods:
Soybean GPT Coding Sequence and Expression in *E. Coli*:

The soybean (*Glycine max*) GPT coding sequence was determined and synthesized, inserted into a PET28 vector, and expressed in *E. coli*. Briefly, *E. coli* cells were transformed with the expression vector and transformants grown overnight in LB broth diluted and grown to OD 0.4, expression induced with isopropyl-B-D-thiogalactoside (0.4 micromolar), grown for 3 hr and harvested. A total of 25×106 cells were then assayed for biological activity using the HPLC assay, below.

Untransformed, wild type *E. coli* cells were assayed as a control. An additional control used *E coli* cells transformed with an empty vector.

The DNA sequence of the soybean GPT coding sequence used in this example is provided in SEQ ID NO: 12, and the encoded GPT protein amino acid sequence is presented in SEQ ID NO: 13.

HPLC Assay for 2-Oxoglutaramate:

HPLC was used to determine 2-oxoglutaramate production in GPT-overexpressing *E. coli* cells, as described in Example 20, supra.

Results:

Expression of the soybean GPT coding sequence of SEQ ID NO: 12 resulted in the over-expression of recombinant GPT protein having 2-oxoglutaramate synthesis-catalyzing bioactivity. Specifically, 31.9 nanomoles of 2-oxoglutaramate activity was observed in the *E. coli* cells overexpressing the recombinant soybean GPT, compared to only 0.02 nanomoles of 2-oxoglutaramate activity in control *E. coli* cells, a nearly 1.600-fold activity level increase over control.

Example 22

Isolation and Expression of Recombinant Zebra Fish GPT Gene Coding Sequence and Analysis of Biological Activity In this example, the putative coding sequence for Zebra fish GPT was isolated and expressed in *E. coli*. Biologically active recombinant Zebra fish GPT was produced, and catalyzed the increased synthesis of 2-oxoglutaramate, as confirmed by HPLC.

Materials and Methods:
Zebra Fish GPT Coding Sequence and Expression in *E. Coli*:

The Zebra fish (*Danio rerio*) GPT coding sequence was determined and synthesized, inserted into a PET28 vector, and expressed in *E. coli*. Briefly, *E. coli* cells were transformed with the expression vector and transformants grown overnight in LB broth diluted and grown to OD 0.4, expression induced with isopropyl-B-D-thiogalactoside (0.4 micromolar), grown for 3 hr and harvested. A total of 25×106 cells were then assayed for biological activity using the HPLC assay, below. Untransformed, wild type *E. coli* cells were assayed as a control. An additional control used *E coli* cells transformed with an empty vector.

The DNA sequence of the Zebra fish GPT coding sequence used in this example is provided in SEQ ID NO: 16, and the encoded GPT protein amino acid sequence is presented in SEQ ID NO: 17.

HPLC Assay for 2-Oxoglutaramate:

HPLC was used to determine 2-oxoglutaramate production in GPT-overexpressing *E. coli* cells, as described in Example 20, supra.

Results:

Expression of the Zebra fish GPT coding sequence of SEQ ID NO: 16 resulted in the over-expression of recombinant GPT protein having 2-oxoglutaramate synthesis-catalyzing bioactivity. Specifically, 28.6 nanomoles of 2-oxoglutaramate activity was observed in the *E. coli* cells overexpressing the recombinant Zebra fish GPT, compared to only 0.02 nanomoles of 2-oxoglutaramate activity in control *E. coli* cells, a more than 1,400-fold activity level increase over control.

Example 23

Generation and Expression of Recombinant Truncated *Arabidopsis* GPT Gene Coding Sequences and Analysis of Biological Activity In this example, two different truncations of the *Arabidopsis* GPT coding sequence were designed and expressed in *E. coli*, in order to evaluate the activity of GPT proteins in which the putative chloroplast signal peptide is absent or truncated. Recombinant truncated GPT proteins corresponding to the full length *Arabidopsis* GPT amino acid sequence of SEQ ID NO: 2, truncated to delete either the first 30 amino-terminal amino acid residues, or the first 45 amino-terminal amino acid residues, were successfully expressed and showed biological activity in catalyzing the increased synthesis of 2-oxoglutaramate, as confirmed by HPLC.

Materials and Methods:
Truncated *Arabidopsis* GPT Coding Sequences and Expression in *E. Coli*:

The DNA coding sequence of a truncation of the *Arabidopsis thaliana* GPT coding sequence of SEQ ID NO: 1 was designed, synthesized, inserted into a PET28 vector, and expressed in *E. coli*. The DNA sequence of the truncated *Arabidopsis* GPT coding sequence used in this example is provided in SEQ ID NO: 20 (−45 AA construct), and the corresponding truncated GPT protein amino acid sequence is provided in SEQ ID NO: 21. Briefly, *E. coli* cells were transformed with the expression vector and transformants grown overnight in LB broth diluted and grown to OD 0.4, expression induced with isopropyl-B-D-thiogalactoside (0.4 micromolar), grown for 3 hr and harvested. A total of 25×10$^6$ cells were then assayed for biological activity using HPLC as described in Example 20. Untransformed, wild type *E. coli* cells were assayed as a control. An additional control used *E coli* cells transformed with an empty vector.

Expression of the truncated −45 *Arabidopsis* GPT coding sequence of SEQ ID NO: 20 resulted in the over-expression of biologically active recombinant GPT protein (2-oxoglutaramate synthesis-catalyzing bioactivity). Specifically, 16.1 nanomoles of 2-oxoglutaramate activity was observed in the *E. coli* cells overexpressing the truncated −45 GPT, compared to only 0.02 nanomoles of 2-oxoglutaramate activity in control *E. coli* cells, a more than 800-fold activity level increase over control. For comparison, the full length *Arabidopsis* gene coding sequence expressed in the same *E. coli* assay generated 2.8 nanomoles of 2-oxoglutaramate activity, or roughly less than one-fifth the activity observed from the truncated recombinant GPT protein.

Example 24

GPT+GS Transgenic Tobacco Seed Germination Tolerates High Salt Concentrations

In this example, seeds form the double transgene tobacco line XX-3 (Cross 3 in Table 4, see Example 7) were tested in a seed germination assay designed to evaluate tolerance to high salt concentrations.
Materials and Methods:

Tobacco seeds from the wild type and XX-3 populations were surfaced sterilized (5% bleach solution for 5 minutes followed by a 10% ethanol wash for 3 minutes) and rinsed with sterile distilled water. The surface sterilized seeds were then spread on Murashige and Skoog media (10% agarose) without sucrose and containing either 0 or 200 mM NaCl. The seeds were allowed to germinate in darkness for 2 days followed by 6 days under a 16:8 photoperiod at 24° C. On day eight the rate of germination was determined by measuring the percentage of seeds from the control or transgene plants that had germinated.
Results:

The results are tabulated in Table XXI below. The rate of germination of the transgenic plant line seeds under zero salt conditions was the same as observed with wild type control plant seeds. In stark contrast, the germination rate of the transgenic plant line seeds under very high salt conditions far exceeded the rate seen in wild type control seeds. Whereas over 81% of the transgenic plant seeds had germinated under the high salt conditions, only about 9% of the wild type control plant seeds had germinated by the same time point. These data indicate that the transgenic seeds are capable of germinating very well under high salt concentrations, an important trait for plant growth in areas of increasingly high water and/or soil salinity.

TABLE XXI

TRANSGENIC TOBACCO PLANTS
GERMINATE AND TOLERATE HIGH SALT

| Plant type | Control (0 mM NaCl) % Germination | Test (200 mM NaCl)a % Germination |
|---|---|---|
| Wild type | 92, 87, 94 | 9, 11, 8 |
| Transgene line XX-3 | 92, 91, 94 | 84, 82, 78 |

Example 25

Method for Generating Transgenic Maize Plants Carrying *Hordeum* GPT and GS1 Transgenes This example provides a method for generating transgenic maize plants expressing GPT and GS1 transgenes. Maize (*Zea mays*, hybrid line Hi-II) type II callus is biolistically transformed with an expression cassette comprising the *hordeum* glutamine synthetase (GS1) coding sequence of SEQ ID NO: 40 under the control of the rice RuBisCo small subunit promoter of SEQ ID NO: 39 (expression cassette of SEQ ID NO: 42), and the *hordeum* GPT coding sequence of SEQ ID NO: 45 under the control of the corn ubiquitin (Ubil) promoter of SEQ ID NO: 44. Transformation of maize callus is achieved by particle bombardment.
Vector Constructs:

An expression cassette comprising the *hordeum* GS1 and GPT genes, under the control of the rice RuBisCo small subunit and corn ubiquitin promoters, respectively, is cloned into the plasmid pAHC25 (Christensen and Quail, 1996, Transgenic Research 5:213-218) modified to include a bar gene conferring resistance to bialophos, or a similar vector, in order to generate the transgene expression vector.
Transformation and Regeneration:

The transgene expression vector is introduced into immature zygotic embryo source callus of parent maize hybrid line Hi-II (A188xB73 origin) (Armstrong et al., 1991, Maize Genetics Coop Newsletter 65:92-93) using particle bombardment, essentially as described (Frame et al., 2000, In Vitro Cell. Dev. Biol-Plant 36:21-29; this method was developed by and is routinely used at the Iowa State University Center for Plant Transformation).

More specifically, immature zygotic embryo source callus is prepared for transformation by serial culturing on a callus-initiating medium (N6E, Songstad et al., 1996, In vitro Cell Dev. Biol.—Plant 32:179-183). Washed gold particles are coated with the plasmid construct and used to bombard the callus with a PDS 1000/He biolistic gun as described (Sanford et al., 1993, Methods in Enzymology 217: 483-509). After 7-10 days on initiation medium, the callus is then transferred to selection medium containing bialophos (N6S, Songstad et al., 1996, supra) and allowed to grow. Following the development of bialophos resistant clones, callus pieces are transferred to a regeneration medium (Armstrong and Green, 1985, Planta 164:207-214) containing bialophos and allowed to grow for several weeks. Thereafter, the resulting plantlets are transferred to regeneration medium without the selection agent, and cultivated.

Transgenic corn plants may be grown and evaluated through maturity, and seeds harvested for use in generating subsequent generations of an event. Various phenotypic characteristics may be observed in $T_0$ events, as well as in $T_1$ and subsequent generations, and used to select seed sources for the development of subsequent generations. High performing lines may be selfed to achieve trait homozygosity and/or crossed.

Example 26

Method for Generating Transgenic Rice Plants Carrying *Hordeum* GPT and GS1 Transgenes This example provides a method for generating transgenic rice plants expressing GPT and GS1 transgenes. Rice (*Oryza sativa*, Japonica cultivar Nipponbare) type II calus is transformed with the *hordeum* glutamine synthetase (GS1) coding sequence of SEQ ID NO: 40 under the control of the rice RuBisCo small subunit promoter of SEQ ID NO: 39 (expression cassette of SEQ ID NO: 42), and the *hordeum* GPT coding sequence of SEQ ID NO: 45 under the control of the corn ubiquitin (Ubil) promoter of SEQ ID NO: 44. Transformation is achieved by *Agrobacterium*-mediated transformation.

Vector Constructs:

An expression cassette comprising the *hordeum* GS1 and GPT genes, under the control of the rice RuBisCo small subunit and corn ubiquitin promoters, respectively, is cloned into base vector pTF101.1, using standard molecular cloning methodologies, to generate the transgene expression vector. Base vector pTF101.1 is a derivative of the pPZP binary vector (Hajdukiewicz et al 1994, Plant Mol. Biol. 25:989-994), which includes the right and left T-DNA border fragments from a nopaline strain of *A. tumefaciens*, a broad host origin of replication (pVS1) and a spectinomycin-resistant marker gene (aadA) for bacterial selection. The plant selectable marker gene cassette includes the phosphinothricin acetyl. transferase (bar) gene from *Streptomyces hygroscopicus* that confers resistance to the herbicides glufosinate and bialophos. The soybean vegetative storage protein terminator (Mason et al., 1993) follows the 3' end of the bar gene.

Media:

YEP Medium: 5 g/L yeast extract, 10 g/L peptone, 5 g/L $NaCl_2$, 15 g/L Bacto-agar. pH to 6.8 with NaOH. After autoclaving, the appropriate antibiotics are added to the medium when it has cooled to 50° C.

Infection Medium: N6 salts and vitamins (Chu et al., 1975, Sci. Sinica 18: 659-668), 1.5 mg/L 2,4-dichlorophenoxyacetic acid (2,4-D), 0.7 g/L L-proline, 68.4 g/L sucrose, and 36 g/L glucose (pH 5.2). This medium is filter-sterilized and stored at 4° C. Acetosyringone (AS, 100 µM) is added just prior to use (prepared from 100 µM stocks of filter-sterilized AS, dissolved in DMSO to 200 mM then diluted 1:1 with water).

Callus Induction Medium: N6 salts and vitamins, 300 mg/L casamino acids, 2.8 g/L L-proline, 30 g/L sucrose, and 4 g/L gelrite (pH 5.8). Filter sterilized N6 Vitamins and 2 mg/L 2,4-D, are added to this medium after autoclaving.

Co-cultivation Medium (make fresh): N6 salts and vitamins, 300 mg/L casamino acids, 30 g/L sucrose, 10 g/L glucose, and 4 g/L gelrite (pH 5.8). Filter sterilized N6 vitamins, acetosyringone (AS) 100 µM and 2 mg/L 2,4-D are added to this medium after autoclaving.

Selection Medium: N6 salts and vitamins, 300 mg/L casamino acids, 2.8 g/L L-proline, 30 g/L sucrose, and 4 g/L gelrite (pH 5.8). Filter sterilized N6 vitamins, 2 mg/L 2,4-D, 2 mg/L Bialaphos (Shinyo Sangyo, Japan) and 500 mg/L carbenicillin are added to this medium after autoclaving.

Regeneration Medium I: MS salts and vitamins (Murashige and Skoog, 1962), 2 g/L casamino acids, 30 g/L sucrose, 30 g/L sorbitol, and 4 g/L gelrite (pH 5.8). Filter sterilized MS vitamins, 100 mg/L cefotaxime, 100 mg/L vancomycin, 0.02 mg/L NAA (naphthaleneacetic acid), 2 mg/L kinetin (Toki, 1997, supra) and 2 mg/L Bialaphos are added to this medium after autoclaving.

Regeneration Medium II: MS Salts and vitamins, 100 mg/L myo-inositol, 30 g/L sucrose, 3 g/L gelrite, (pH 5.8).

Transformation and Regeneration:

Japonica rice cultivar Nipponbare is transformed with *Agrobacterium tumefaciens* strain EHA101 (Hood et al., 1986, J. Bacteriol. 168:1291-1301), transformed with the pTF101.1 transgene expression vector carrying the *hordeum* GS1+GPT expression cassette. The vector system pTF101.1 in EHA101 is maintained on YEP medium (An et al., 1988) containing 100 mg/L spectinomycin (for pTF101.1) and 50 mg/L kanamycin (for EHA101).

Briefly, callus tissue derived from the mature rice embryo is used as the starting material for transformation. Callus induction, co-cultivation, selection and regeneration I media are based on those of Hiei et al., 1994, The Plant Journal 6 (2):271-282.

More specifically, calli are induced as follows. First, 15-20 rice seeds are dehusked and rinsed in 10 ml of 70% Ethanol (50 ml conical tube) by vigorously shaking the tube for one minute, followed by rinsing once with sterile water. Then, 10 ml of 50% commercial bleach (5.25% hypochlorite) is added and placed on a shaker for 30 minutes (low setting). The bleach solution is then poured-off and the seeds rinsed five times with ~10 ml of sterilized water each time. With a small portion of the final rinse, the seeds are poured onto sterilized filter paper (in a sterile petri plate) and then allowed to dry. Using sterile forceps, several (i.e., 5) seeds are transferred to the surface of individual sterile petri plates containing callus induction medium. The plates are wrapped with vent tape and incubated in the light (16:8 photoperiod) at 29° C. Seeds are observed every few days and those showing signs of contamination are discarded.

After two to three weeks, developing callus is visible on the scutellum of the mature seed. Calli are then subcultured to fresh induction medium and allowed to proliferate. Four days prior to infection, the callus tissue is cut into 2-4 mm pieces and transferred to fresh induction medium.

The selection medium uses, modifications from Toki (Toki, 1997, Plant Molecular Biology Reporter 15:16-21) whereby bialophos (2 mg/L) is employed for plant selection and carbenicillin (500 mg/L) for counter selection against *Agrobacterium*. Regeneration II medium is as described (Armstrong and Green, 1985, Planta 164:207-214).

*Agrobacterium* culture is grown (i.e., for 3 days at 19° C., or 2 days at 28° C.) on YEP medium amended with spectinomycin (100 mg/L) and kanamycin (50 mg/L). An aliquot of the culture is then suspended in ~15 ml of liquid infection medium supplemented with 100 µM AS in a 50 ml conical tube (no pre-induction). The optical density is adjusted to <0.1 ($OD_{550}$=0.06-0.08) before use.

For infection, rice calli are first placed into bacteria-free infection medium+AS (50 ml conical). This pre-wash is removed and replaced with 10 ml of the prepared *Agrobacterium* suspension ($OD_{550}$<0.1). Then, the conical is fastened onto a vortex shaker (low setting) for two minutes. After infection, calli are poured out of the conical onto a stack of sterile filter paper in a 100×15 petri dish to blot dry. Then, they are transferred off the filter paper and onto the surface of co-cultivation medium with sterile forceps. Co-cultivation plates are wrapped with vent tape and incubated in the dark at 25° C. for three days. After three days of co-cultivation, the calli are washed five times with 5 ml of the liquid infection medium (no AS) supplemented with carbenicillin (500 mg/L) and vancomycin (100 mg/L). Calli are blotted dry on sterile filter paper as before. Individual callus pieces are transferred off the paper and onto selection medium containing 2 mg/L bialaphos. Selection plates are wrapped with parafilm and placed in the light at 29° C.

For selection of stable transformation events, plant tissue is cultured onto fresh selection medium every two weeks. This should be done with the aid of a microscope to look for any evidence of *Agrobacterium* overgrowth. If overgrowth is noted, the affected calli should be avoided (contaminated calli should not be transferred). The remaining tissue is then carefully transferred, preferably using newly sterilized forceps for each calli. Putative clones begin to appear after six to eight weeks on selection. A clone is recognized as white, actively growing callus and is distinguishable from the brown, unhealthy non-transformed tissue. Individual transgenic events are identified and the white, actively growing tissue is transferred to individual plates in order to produce enough tissue to take to regeneration. Regeneration of transgenic plants is accomplished by selecting new lobes of growth from the callus tissue and transferring them onto Regeneration Medium I (light, 25° C.). After two to three weeks, the maturing tissue is transferred to Regeneration Medium II for germination (light, 25° C.). When the leaves are approximately 4-6 cm long and have developed good-sized roots, the plantlets may be transferred (on an individual basis, typically 7-14 days after germination begins) to soilless mix using sterile conditions.

Transgenic rice plants may be grown and evaluated through maturity, and seeds harvested for use in generating subsequent generations of an event. Various phenotypic characteristics may be observed in $T_0$ events, as well as in $T_1$ and subsequent generations, and used to select seed sources for the development of subsequent generations. High performing lines may be selfed to achieve trait homozygosity and/or crossed.

Example 27

Method for Generating Transgenic Sugarcane Plants Carrying *Hordeum* GPT and GS1 Transgenes This example provides a method for generating transgenic sugarcane plants expressing GPT and GS1 transgenes. Sugarcane (*Saccharum* spp L) is biolistically transformed with an expression cassette comprising the *hordeum* glutamine synthetase (GS1) coding sequence of SEQ ID NO: 40 under the control of the rice RuBisCo small subunit promoter of SEQ ID NO: 39 (expression cassette of SEQ ID NO: 42), and the *hordeum* GPT coding sequence of SEQ ID NO: 45 under the control of the corn ubiquitin (Ubi1) promoter of SEQ ID NO: 44. Transformation of sugarcane callus is achieved by particle bombardment.
Vector Constructs:

An expression cassette comprising the *hordeum* GS1 and GPT genes, under the control of the rice RuBisCo small subunit and corn ubiquitin promoters, respectively, are cloned into a small plasmid well established for sugarcane expression, such as pAHC20 (Thomson et al., 1987, EMBO J. 6:2519-2523), using standard molecular cloning methodologies, to generate the transgene expression vector. The plasmid used contains a selectable marker against either the phospinothricin family of herbicides or the antibiotics geneticin or kanamycin, each of which have been shown effective (Ingelbrecht et al., 1999, Plant Physiology 119:1187-1197; Gallo-Maegher & Irvine, 1996, Crop Science 36:1367-1374).
Transformation and Regeneration:

The plasmid containing the expression cassette encoding the *hordeum* GS1 and GPT coding sequences is introduced into embryogenic callus prepared for transformation by the basic method of Gallo-Maegher and Irvine (Gallo-Maegher and Irvine, 1996, supra) and Ingelbrecht et al. (Ingelbrecht et al., 1999, supra) with the improved stimulation of shoot regeneration with thidiazuron (Gallo-Maegher et al., 2000, In vitro Cell Dev. Biol.—Plant 36:37-40). This particle bombardment method is effective in transforming sugarcane (see, for example, Gilbert et al., 2005, Crop Science 45:2060-2067; and see the foregoing references). Regenerable sugarcane varieties, such as the commercial varieties CP65-357 and CP72-1210, may be used to generate transgene events.

Briefly, 7- to 40-week old calli are bombarded with plasmid-coated tungsten or gold particles. Two days after bombardment the calli are transferred to selection medium. Four weeks later the resistant calli are transferred to shoot-induction medium containing the selection agent and sub-cultured every two weeks for approximately 12 weeks, at which time the shoots are transferred to Magenta boxes containing rooting medium with selection agent. The shoots are maintained on this medium for approximately 8 weeks, at which time those with good root development are transferred to potting mix and the adapted to atmospheric growth.

Transgenic sugarcane plants may be grown and evaluated through maturity, and seeds harvested for use in generating subsequent generations of an event. Various phenotypic characteristics may be observed in $T_0$ events, as well as in $T_1$ and subsequent generations, and used to select seed sources for the development of subsequent generations. High performing lines may be selfed to achieve trait homozygosity and/or crossed.

Example 28

Method for Generating Transgenic Wheat Plants Carrying *Hordeum* GPT and GS1 Transgenes This example provides a method for generating transgenic wheat plants expressing GPT and GS1 transgenes. Wheat (*Triticum* spp.) is biolistically transformed with an expression cassette comprising the *hordeum* glutamine synthetase (GS1) coding sequence of SEQ ID NO: 40 under the control of the rice RuBisCo small subunit promoter of SEQ ID NO: 39 (expression cassette of SEQ ID NO: 42), and the *hordeum* GPT coding sequence of SEQ ID NO: 45 under the control of the corn ubiquitin (Ubi1) promoter of SEQ ID NO: 44. Transformation of wheat callus is achieved by particle bombardment.
Vector Constructs:

An expression cassette comprising the *hordeum* GS1 and GPT genes, under the control of the rice RuBisCo small subunit and corn (maize) ubiquitin promoters, respectively, are cloned into a plasmid such as pAHC17, which contains the bar gene to provide the desired resistance to the phosphinothricin-class of herbicides for selection of transformants, using standard molecular cloning methodologies, to generate the transgene expression vector.
Transformation and Regeneration:

Wheat is transformed biolistically, and transgenic events regenerated, essentially as described (Weeks et al., 1993, Plant Physiology. 102:1077-1084; Blechl and Anderson, 1996, Nat. Biotech. 14:875-879; Okubara et. al., 2002, Theoretical and Applied Genetics. 106:74-83). These methods were developed and are routinely practiced at the US Department of Agriculture, Agricultural Research Service, Western Regional Research Center (Albany Calif.). The highly regenerable hexaploid spring wheat cultivar 'Bobwhite' is used as the source of immature embryos for bombardment with plasmid-coated particles.

Bombarded embryos are cultured without selection for 1-3 weeks in the dark on MS media before transferring them to shoot induction medium (MS media plus hormones and selection agent bialophos (1, 1.5, 2, 3 mg/L) for 2-8 weeks with subculturing weekly (Blechl et al., 2007, J Cereal Science 45:172-183). Shoots that formed are transferred to rooting medium also containing the selection agent (bialophos 3 mg/L) (Weeks et al., 1993, supra). Well-rooted plantlets are transferred to potting media and adapted to atmospheric growth conditions.

Transgenic wheat plants may be grown and evaluated through maturity, and seeds harvested for use in generating subsequent generations of an event. Various phenotypic characteristics may be observed in $T_0$ events, as well as in $T_1$ and subsequent generations, and used to select seed sources for the development of subsequent generations. High performing lines may be selfed to achieve trait homozygosity and/or crossed.

Example 29

Method for Generating Transgenic *Sorghum* Plants Carrying *Hordeum* GPT and GS1 Transgenes This example provides a method for generating transgenic *sorghum* plants expressing GPT and GS1 transgenes. *Sorghum* (*Sorghum* spp L) is transformed with *Agrobacterium* carrying an expression cassette encoding the *hordeum* glutamine synthetase (GS1) coding sequence of SEQ ID NO: 40 under the control of the rice RuBisCo subunit promoter of SEQ ID NO: 39 (expression cassette of SEQ ID NO: 42), and the *hordeum* GPT coding sequence of SEQ ID NO: 45 under the control of the corn ubiquitin (Ubil) promoter of SE ID NO: 44.

Vector Constructs:

An expression cassette comprising the *hordeum* GS1 and GPT genes, under the control of the rice RuBisCo small subunit and corn ubiquitin promoters, respectively, is cloned into a stable binary vector such as pZY101 (Vega et al 2008, Plant Cell Rep. 27:297-305), using standard molecular cloning methodologies, to generate the transgene expression vector.

Transformation and Regeneration:

*Agrobacterium*-mediated transformation and recovery of transgenic *sorghum* plants is as described (Lu et al., 2009, Plant Cell Tissue Organ Culture 99:97-108). These methods are routinely used by the University of Missouri Plant Transformation Core Facility. The public *sorghum* line, P898012, is grown as described (Lu et al., 2009, supra) and transformed with *Agrobacterium tumefaciens* strain EHA101 (Hood et al., 1986, supra) transformed with the transgene expression vector.

More specifically, *Agrobacterium* (0.3-0.4 OD) harboring the transgene expression vector is used to inoculate immature *sorghum* embryos for 5 minutes. The embryos are then transferred onto filter paper on top of their co-cultivation medium, containing acetosyringone to enhance the effectiveness of the infection. Embryos are incubated for 3-5 days and then transferred for another 4 days on resting medium (containing carbenicillin) and then transferred onto callus induction medium (with selection agent PPT) with weekly transfers. Once somatic embyrogenic cells develop they are transferred onto shooting medium (with carbenicillin and PPT) until shoots (2-5 cm long) develop. Shoots are transferred to Magenta boxes with rooting medium (with PPT) and maintained in 16 h light and 8 h darkness until 8-20 cm tall well-rooted plantlets are produced. They are then transferred to potting mix and adapted to atmospheric conditions.

Transgenic *sorghum* plants may be grown and evaluated through maturity, and seeds harvested for use in generating subsequent generations of an event. Various phenotypic characteristics may be observed in $T_0$ events, as well as in $T_1$ and subsequent generations, and used to select seed sources for the development of subsequent generations. High performing lines may be selfed to achieve trait homozygosity and/or crossed.

Example 30

Method for Generating Transgenic Switchgrass Plants Carrying *Hordeum* GPT and GS1 Transgenes This example provides a method for generating transgenic switchgrass plants expressing GPT and GS1 transgenes. Switchgrass (*Panicum virgatum*) is transformed with *Agrobacterium* carrying a transgene expression vector including an expression cassette encoding the *hordeum* glutamine synthetase (GS1) coding sequence of SEQ ID NO: 40 under the control of the rice RuBisCo small subunit promoter of SEQ ID NO: 39 (expression cassette of SEQ ID NO: 42), and the *hordeum* GPT coding sequence of SEQ ID NO: 45 under the control of the corn ubiquitin (Ubil) promoter of SE ID NO: 44.

Vector Constructs:

An expression cassette comprising the *hordeum* GS1 and GPT genes, under the control of the rice RuBisCo small subunit and corn (maize) ubiquitin promoters, respectively, is cloned into a Cambia vector thirteen hundred series (i.e., 1305.1) containing the HPT gene which provides hygromycin resistance for selection of the Switchgrass events, using standard molecular cloning methodologies, to generate the transgene expression vector.

Transformation and Regeneration:

*Agrobacterium*-mediated transformation and recovery of transgenic switchgrass plants is essentially as described (Somleva et al., 2002, Crop Science 42:2080-2087; Somleva 2006, Switchgrass (*Panicum virgatum* L.) In Methods in Molecular Biology Vol 344. *Agrobacterium* Protocols 2/e, Volume 2. Ed K. Wang Humana Press Inc., Totowa, N.J.; Xi et al 2009, Bioengineering Research 2:275-283). These methods are routinely used by the Plant Biotechnology Resource and Outreach Center at Michigan State University.

Briefly, explants of embryonic callus from the mature caryopses of the public Switchgrass cv. Alamo are transformed with *Agrobacterium tumefaciens* strain EHA105 (Hood et al., 1986, supra) carrying the transgene expression vector. *Agrobacterium* (0.8-1.0 OD) harboring the transgene expression vector and pretreated with acetosynringone is used to inoculate the switchgrass callus for 10 minutes and then co-cultivated for 4-6 days in the dark. The explants are then washed free of the *agrobacterium* and placed on selection medium containing the antibiotic timentin and hygromycin; selection requires 2-6 months. Subculturing is carried out at 4-week intervals. Regeneration is accomplished in 4-8 weeks on media containing GA3, timentin and hygromycin under a photoperiod of 16 h light and 8 dark. The plantlets are then transferred to Magenta boxes with regeneration medium containing GA3, timentin and hygromycin for another 4 weeks as before. The plants are then transferred to soil and adapted to atmospheric growth.

Transgenic switchgrass plants may be grown and evaluated through maturity, and seeds harvested for use in generating subsequent generations of an event. Various phenotypic characteristics may be observed in $T_0$ events, as well as in $T_1$ and subsequent generations, and used to select seed sources for the development of subsequent generations. High performing lines may be selfed to achieve trait homozygosity and/or crossed.

Example 31

Method for Generating Transgenic Soybean Plants Carrying *Arabidopsis* GPT and GS1 Transgenes This example provides a method for generating transgenic soybean plants expressing GPT and GS1 transgenes. Soybean (*Glycine max*) is transformed with *Agrobacterium* carrying a transgene expression vector including an expression cassette encoding the *Arabidopsis* glutamine synthetase (GS1) coding sequence of SEQ ID NO: 7 under the control of the tomato RuBisCo small subunit promoter of SEQ ID NO: 22 (expression cassette of SEQ ID NO: 47), and the *Arabidopsis* GPT coding sequence of SEQ ID NO: 1 under the control of the 35S cauliflower mosaic virus (CMV) promoter (expression cassette of SEQ ID NO: 27).

Vector Constructs:

An expression cassette comprising the *hordeum* GS1 and GPT genes, under the control of the tomato RuBisCo small subunit and 35S CMV promoters, respectively, is cloned into pTF101.1, using standard molecular cloning methodologies, to generate the transgene expression vector. pTF101.1 is a derivative of the pPZP binary vector (Hajdukiewicz et al 1994, Plant Mol. Biol. 25:989-994), which includes the right and left T-DNA border fragments from a nopaline strain of *A. tumefaciens*, a broad host origin of replication (pVS1) and a spectinomycin-resistant marker gene (aadA) for bacterial selection. The plant selectable marker gene cassette includes the phosphinothricin acetyl transferase (bar) gene from *Streptomyces hygroscopicus* that confers resistance to the herbicides glufosinate and bialophos. The soybean vegetative storage protein terminator (Mason et al., 1993) follows the 3' end of the bar gene.

Media:

YEP Solid Medium: 5 g/L Yeast extract, 10 g/L Peptone, 5 g/L $NaCl_2$, 12 g/L Bacto-agar. pH to 7.0 with NaOH. Appropriate antibiotics should be added to the medium after autoclaving. Pour into sterile 100×15 plates (~25 ml per plate).

YEP Liquid Medium: 5 g/L Yeast extract, 10 g/L Peptone, 5 g/L $NaCl_2$. pH to 7.0 with NaOH. Appropriate antibiotics should be added to the medium prior to inoculation.

Co-cultivation Medium: 1/10×B5 major salts, 1/10×B5 minor salts, 2.8 mg/L Ferrous, 3.8 mg/L NaEDTA, 30 g/L Sucrose, 3.9 g/L MES, and 4.25 g/L Noble agar (pH 5.4). Filter sterilized 1×B5 vitamins, GA3 (0.25 mg/L), BAP (1.67 mg/L), Cysteine (400 mg/L), Dithiothrietol (154.2 mg/L), and 40 mg/L acetosyringone are added to this medium after autoclaving. Pour into sterile 100×15 mm plates (~88 plates/L). When solidified, overlay the co-cultivation medium with sterile filter paper to reduce bacterial overgrowth during co-cultivation (Whatman #1, 70 mm).

Infection Medium: 1/10×B5 major salts, 1/10×B5 minor salts, 2.8 mg/L Ferrous, 3.8 mg/L NaEDTA, 30 g/L Sucrose, 3.9 g/L MES (pH 5.4). Filter sterilized 1×B5 vitamins, GA3 (0.25 mg/L), BAP (1.67 mg/L), and 40 mg/L acetosyringone are added to this medium after autoclaving.

Shoot Induction Washing Medium: 1×B5 major salts, 1×B5 minor salts, 28 mg/L Ferrous, 38 mg/L NaEDTA, 30 g/L Sucrose, and 0.59 g/L MES (pH 5.7). Filter sterilized 1×B5 vitamins, BAP (1.11 mg/L), Timentin (100 mg/L), Cefotaxime (200 mg/L), and Vancomycin (50 mg/L) are added to this medium after autoclaving.

Shoot Induction Medium I: 1×B5 major salts, 1×B5 minor salts, 28 mg/L Ferrous, 38 mg/L NaEDTA, 30 g/L Sucrose, 0.59 g/L MES, and 7 g/L Noble agar (pH 5.7). Filter sterilized 1×B5 vitamins, BAP (1.11 mg/L), Timentin (50 mg/L), Cefotaxime (200 mg/L), and Vancomycin (50 mg/L) are added to this medium after autoclaving. Pour into sterile 100×20 mm plates (26 plates/L).

Shoot Induction Medium II: 1×B5 major salts, 1×B5 minor salts, 28 mg/L Ferrous, 38 mg/L NaEDTA, 30 g/L Sucrose, 0.59 g/L MES, and 7 g/L Noble agar (pH 5.7). Filter sterilized 1×B5 vitamins, BAP (1.11 mg/L), Timentin (50 mg/L), Cefotaxime (200 mg/L), Vancomycin (50 mg/L) and Glufosinate (6 mg/L) are added to this medium after autoclaving. Pour into sterile 100×20 mm plates (26 plates/L).

Shoot Elongation Medium: 1×MS major salts, 1×MS minor salts, 28 mg/L Ferrous, 38 mg/L NaEDTA, 30 g/L Sucrose, 0.59 g/L MES, and 7 g/L Noble agar (pH 5.7). Filter sterilized 1×B5 vitamins, Asparagine (50 mg/L), L-Pyroglutamic Acid (100 mg/L), IAA (0.1 mg/L), GA3 (0.5 mg/L), Zeatin-R (1 mg/L), Timentin (50 mg/L), Cefotaxime (200 mg/L), Vancomycin (50 mg/L), and Glufosinate (6 mg/L) are added to this medium after autoclaving. Pour into sterile 100×25 mm plates (22 plates/L).

Rooting Medium: 1×MS major salts, 1×MS minor salts, 28 mg/L Ferrous, 38 mg/L NaEDTA, 20 g/L Sucrose, 0.59 g/L MES, and 7 g/L Noble agar (pH 5.6). Filter sterilized 1×B5 vitamins, Asparagine (50 mg/L), and L-Pyroglutamic Acid (100 mg/L) are added to this medium after autoclaving. Pour into sterile 150×25 mm vial (10 ml/vial).

Transformation and Regeneration:

*Agrobacterium* cultures are prepared for infecting seed explants as follows. The vector system, pTF102 in EHA101, is cultured on YEP medium (An et al., 1988) containing 100 mg/L spectinomycin (for pTF102), 50 mg/L kanamycin (for EHA101), and 25 mg/L chloramphenicol (for EHA101). 24 hours prior to infection a 2 ml culture of *Agrobacterium* is started by inoculating a loop of bacteria from the fresh YEP plate in YEP liquid medium amended with antibiotics. This culture is allowed to grow to saturation (8-10 hours) at 28° C. in a shaker incubator (~250 rpm). Then 0.2 ml of starter culture is transferred to a 1 L flask containing 250 ml of YEP medium amended with antibiotics. The culture is allowed to grow overnight at 28° C., 250 rpm to log phase (OD650=0.3-0.6 for EHA105) or late log phase (OD650=1.0-1.2 for EHA101). The *Agrobacterium* culture is then pelleted at 3,500 rpm for 10 minutes at 20° C., and the pellet resuspended in infection medium by pipetting through the pellet. Bacterial cell densities are adjusted to a final OD650=0.6 (for EHA105) or OD650=0.6 to 1.0 (for EHA101). *Agrobacteria*-containing infection medium is shaken at 60 rpm for at least 30 minutes before use.

Explants are prepared for inoculation as follows. Seeds are sterilized, ideally with a combination of bleach solution and exposure to chlorine gas. Prior to infection, (~20 hours), sees are imbibed with deionized sterile water in the dark. Imbibed soybean seeds are transferred to a sterile 100×15 petri plate for dissection. Using a scalpel (i.e., #15 blade), longitudinal cuts are made along the hilum to separate the cotyledons and remove the seed coat. The embryonic axis found at the nodal end of the cotyledons is excised, and any remaining axial shoots/buds attached to the cotyledonary node are also removed.

*Agrobacterium*-mediated transformation is conducted as follows. Half-seed explants are dissected into a 100×25 mm petri plate and 30 ml *Agrobacterium*-containing infection media added thereto, such that the explants are completely covered by the infection media. Explants are allowed to incubate at room temperature for a short period of time (i.e., 30 minutes), preferably with occasional gentle agitation.

After infection, the explants are transferred to co-cultivation medium, preferably so that the flat, axial side is touching the filter paper. These plates are typically wrapped in parafilm, and cultivated for 5 days at 24° C. under an 18:6 photoperiod. Following this co-cultivation, shoot growth is induced by first washing the explants in shoot induction washing medium at room temperature, followed by placing the explants in shoot induction medium I, such that the explants are oriented with the nodal end of the cotyledon imbedded in the medium and the regeneration region flush to the surface with flat side up (preferably at a 30-45° angle). Explants are incubated at 24° C., 18:6 photoperiod, for 14 days. Explants are thereafter transferred to shoot induction medium II and maintained under the same conditions for another 14 days.

Following shoot induction, explants are transferred to shoot elongation medium, as follows. First, cotyledons are removed from the explants. A fresh cut at the base of the shoot pad flush to the medium is made, and the explants transferred to shoot elongation medium (containing glufosinate) and incubated at 24° C., 18:6 photoperiod, for 2-8 weeks. Preferably, explant tissue is transferred to fresh shoot elongation medium every 2 weeks, and at transfer, a fresh horizontal slice at the base of the shoot pad is made.

When shoots surviving the glufosinate selection have reached ~3 cm length, they are excised from the shoot pad, briefly dipped in indole-3-butyric acid (1 mg/ml, 1-2 minutes), then transferred to rooting medium for acclimatization (i.e., in 150×25 mm glass vials with the stems of the shoots embedded approximately ½ cm into the media). When well rooted, the shoots are transferred to soil and plantlets grown at 24° C., 18:6 photoperiod, for at least one week, watering as needed. When the plantlets have at least two healthy trifoliates, an herbicide paint assay may be applied to confirm resistance to glufosinate. Briefly, using a cotton swab, Liberty herbicide (150 mg l-1) is applied to the upper leaf surface along the midrib of two leaves on two different trifoliates. Painted plants are transferred to the greenhouse and covered with a humidome. Plantlets are scored 3-5 days after painting. Resistant plantlets may be transplanted immediately to larger pots (i.e., 2 gal).

Example 32

Method for Generating Transgenic Potato Plants Carrying *Arabidopsis* GPT and GS1 Transgenes This example provides a method for generating transgenic potato plants expressing GPT and GS1 transgenes. Potato (*Solanum tuberosum*, cultivar Desiree) is transformed with *Agrobacterium* carrying a transgene expression vector including an expression cassette encoding the *Arabidopsis* glutamine synthetase (GS1) coding sequence of SEQ ID NO: 7 under the control of the tomato RuBisCo small subunit promoter of SEQ ID NO: 22 (expression cassette of SEQ ID NO: 47), and the *Arabidopsis* GPT coding sequence of SEQ ID NO: 1 under the control of the 35S cauliflower mosaic virus (CMV) promoter (expression cassette of SEQ ID NO: 27).

Vector Constructs:

An expression cassette comprising the *hordeum* GS1 and GPT genes, under the control of the tomato RuBisCo small subunit and 35S CMV promoters, respectively, is cloned into the Cambia 2201 vector which provides kanamycin resistance.

Transformation and Regeneration:

A suitable *Agrobacterium tumefaciens* strain such as UC-Riverside Agro-1 strain is employed and used for infecting potato explant tissue (see, Narvaez-Vasquez et al., 1992, Plant Mo. Biol. 20:1149-1157). Cultures are maintained at 28° C. in liquid medium containing 10 g/L Yeast extract, 10 g/L Peptone, 5 g/L NaCl$_2$, 10 mg/L kanamycin, 30 mg/L tetracycline, and 9.81 g/L Acetosyringone (50 mM). Overnight cultures are diluted with liquid MS medium (4.3 g/L MS salts, 20 g/L sucrose, 1 mg/L thiamine, 100 mg/L inositol and 7 g/L phytoagar, pH to 5.8.) to $10^8$ *Agrobacterium* cells/ml for the infection of plant tissues (co-cultivation).

Potato leaf discs or tuber discs may be used as the explants to be inoculated. Discs are pre-conditioned by incubation on feeder plates for two to three days at 25° C. under dark conditions. Pre-conditioned explants are infected with *Agrobacterium* by soaking in 20 ml of sterile liquid MS medium (supra), containing $10^8$ *Agrobacterium* cells/ml for about 20 minutes. Before or during the co-cultivation, the explants are carefully punched with a syringe needle, or scalpel blade. Then, the explants are blotted dry with sterile filter paper, and incubated again in feeder plates for another two days. Explants are then transferred to liquid medium with transgene-transformed *Agrobacterium*, and incubated for three days at 28° C. under dark conditions for calli and shoot development (development (2-4 cm) in the presence of kanamycin (100 mg/L).

Following co-cultivation, supra, the explants are washed three times with sterile liquid medium and finally rinsed with the same medium containing 500 mg/l of cefotaxime. The explants are blotted dry with sterile filter paper and placed on shoot induction medium (4.3 g/L MS salts, 10 mg/L thiamine, 1 mg/L nicotinic acid, 1 mg/L pyridxine, 100 mg/L inositol, 30 g/L sucrose, 1 mg/L zeatin, 0.5 mg/L IAA, 7 g/L phytoagar, 250 mg/L Cefotaxime, 500 mg/L Carbenicillin, 100 mg/L Kanamycin) for 4-6 weeks. Thereafter, plantlets are transferred to rooting medium (4.3 g/L MS salts, 10 mg/L thiamine, 1 mg/L nicotinic acid, 1 mg/L pyridxine, 100 mg/L inositol, 20 g/L sucrose, 50 µg/L IAA, 7 g/L phytoagar, 50 mg/L Kanamycin and 500 mg/L Vancomycin) for 3-4 weeks.

All publications, patents, and patent applications cited in this specification are herein incorporated by reference as if each individual publication or patent application were specifically and individually indicated to be incorporated by reference.

The present invention is not to be limited in scope by the embodiments disclosed herein, which are intended as single illustrations of individual aspects of the invention, and any which are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

TABLE OF SEQUENCES:

*Arabidopsis* glutamine phenylpyruvate transaminase DNA coding sequence:
SEQ ID NO: 1

ATGTACCTGGACATAAATGGTGTGATGATCAAACAGTTTAGCTTCAAAGCCTCTCTAATTTCCGACAAAG
CTCCGCCAAAATCCATCGTCCTATTTCTCCCATTCTCTTCCGGAGCCACCATGACCACAGTTTCGACTCA
GAACGAGTCTACTCAAAAACCCGTCCAGGTGGCGAAGAGATTAGAGAAGTTCAAGACTACTATTTTCACT
CAAATGAGCATATTGGCAGTTAAACATGGAGCGATCAATTTAGGCCAAGGCTTTCCCAATTTCGACGGTC
CTGATTTTGTTAAAGAAGCTGCGATCCAAGCTATTAAAGATGGTAAAAACCAGTATGCTCGTGGATACGG
CATTCCTCAGCTCAACTCTGCTATAGCTGCGCGGTTTCGTGAAGATACGGGTCTTGTTGTTGATCCTGAG
AAAGAAGTTACTGTTACATCTGGTTGCACAGAAGCCATAGCTGCAGCTATGTTGGGTTTAATAAACCCTG
GTGATGAAGTCATTCTCTTTGCACCGTTTTATGATTCCTATGAAGCAACACTCTCTATGGCTGGTGCTAA
AGTAAAAGGAATCACTTTACGTCCACCGGACTTCTCCATCCCTTTGGAAGAGCTTAAAGCTGCGGTAACT
AACAAGACTCGAGCCATCCTTATGAACACTCCGCACAACCCGACCGGGAAGATGTTCACTAGGGAGGAGC

TABLE OF SEQUENCES:

TTGAAACCATTGCATCTCTCTGCATTGAAAACGATGTGCTTGTGTTCTCGGATGAAGTATACGATAAGCT
TGCGTTTGAAATGGATCACATTTCTATAGCTTCTCTTCCCGGTATGTATGAAAGAACTGTGACCATGAAT
TCCCTGGGAAAGACTTTCTCTTTAACCGGATGGAAGATCGGCTGGCGATTGCGCCGCCTCATCTGACTT
GGGGAGTTCGACAAGCACACTCTTACCTCACATTCGCCACATCAACACCAGCACAATGGGCAGCCGTTGC
AGCTCTCAAGGCACCAGAGTCTTACTTCAAAGAGCTGAAAAGAGATTACAATGTGAAAAGGAGACTCTG
GTTAAGGGTTTGAAGGAAGTCGGATTTACAGTGTTCCCATCGAGCGGGACTTACTTTGTGGTTGCTGATC
ACACTCCATTTGGAATGGAGAACGATGTTGCTTTCTGTGAGTATCTTATTGAAGAAGTTGGGGTCGTTGC
GATCCCAACGAGCGTCTTTTATCTGAATCCAGAAGAAGGGAAGAATTTGGTTAGGTTTGCGTTCTGTAAA
GACGAAGAGACGTTGCGTGGTGCAATTGAGAGGATGAAGCAGAAGCTTAAGAGAAAAGTCTGA

Arabidopsis GPT amino acid sequence
SEQ ID NO: 2
MYLDINGVMIKQFSFKASLLPFSSNFRQSSAKIHRPIGATMTTVSTQNESTQKPVQVAKRLEKFKTTIFT
QMSILAVKHGAINLGQGFPNFDGPDFVKEAAIQAIKDGKNQYARGYGIPQLNSAIAARFREDTGLVVDPE
KEVTVTSGCTEAIAAAMLGLINPGDEVILFAPFYDSYEATLSMAGAKVKGITLRPPDFSIPLEELKAAVT
NKTRAILMNTPHNPTGKMFTREELETIASLCIENDVLVFSDEVYDKLAFEMDHISIASLPGMYERTVTMN
SLGKTFSLTGWKIGWAIAPPHLTVVGVRQAHSYLTFATSTPAQWAAVAALKAPESYFKELKRDYNVKKET
LVKGLKEVGFTVFPSSGTYFVVADHTPFGMENDVAFCEYLIEEVGVVAIPTSVFYLNPEEGKNLVRFAFC
KDEETLRGAIERMKQKLKRKV Alfalfa GS1 DNA coding sequence (upper case) with 5' and 3'
untranslated sequences (indicated in lower case).
SEQ ID NO: 3
atttccgttttcgattcatttgattcattgaatcaaatcgaatcgaatctttaggattcaatacagattc
cttagattttactaagtttgaaaccaaaaccaaaacATGTCTCTCCTTTCAGATCTTATCAACCTTGACC
TCTCCGAAACCACCGAGAAAATCATCGCCGAATACATATGGATTGGTGGATCTGGTTTGGACTTGAGGAG
CAAAGCAAGGACTCTACCAGGACCAGTTACTGACCCTTCACAGCTTCCCAAGTGGAACTATGATGGTTCC
AGCACAGGTCAAGCTCCTGGAAGAGATAGTGAAGTTATTATCTACCCCACAAGCCATTTTCAAGGACCCAT
TTAGAAGGGGTAACAATATCTTGGTTATGTGTGATGCATACACTCCAGCTGGAGAGCCCATTCCCACCAA
CAAGAGACATGCAGCTGCCAAGATTTTCAGCCATCCTGATGTTGTTGCTGAAGTACCATGGTATGGTATT
GAGCAAGAATACACCTTGTTGCAGAAAGACATCAATTGGCCTCTTGGTTGGCCAGTTGGTGGTTTTCCTG
GACCTCAGGGACCCATACTATTGTGGAGCTGGTGCTGACAAGGCATTTGGCCGTGACATTGTTGACTCACA
TTACAAAGCCTGTCTTTATGCCGGCATCAACATCAGTGGAATCAATGGTGAAGTGATGCCTGGTCAATGG
GAATTCCAAGTTGGTCCCTCAGTTGGTATCTCTGCTGGTGATGAGATATGGGTTGCTCGTTACATTTTGG
AGAGGATCACTGAGGTTGCTGGTGTGGTGCTTTCCTTTGACCCAAAACCAATTAAGGGTGATTGGAATGG
TGCTGGTGCTCACACAAATTACAGCACCAAGTCTATGAGAGAAGATGGTGGCTATGAAGTCATCTTGAAA
GCAATTGAGAAGCTTGGGAAGAAGCACAAGGAGCACATTGCTGCTTATGGAGAAGGCAACGAGCGTAGAT
TGACAGGGCGACATGAGACAGCTGACATTAACACCTTCTTATGGGGTGTTGCAAACCGTGGTGCGTCGAT
TAGAGTTGGAAGGGACACAGAGAAAGCAGGGAAAGGTTATTTCGAGGATAGGAGGCCATCATCTAACATG
GATCCATATGTTGTTACTTCCATGATTGCAGACACCACCATTCTCTGGAAACCATAAgccaccacacaca
catgcattgaagtatttgaaagtcattgttgattccgcattagaaatttggtcattgttttttctaggatt
tggatttgtgttattgttatggttcacactttgtttgtttgaatttgaggccttgttataggtttcatat
ttctttctcttgttctaagtaaatgtcagaataataatgtaat Alfalfa GS1 amino acid sequence
SEQ ID NO: 4
MSLLSDLINLDLSETTEKIIAEYIWIGGSGLDLRSKARTLPGVTDPSQLPKWNYDGSSTGQAPGEDSEV
IIYPQAIFKDPFRRGNNILVMCDAYTPAGEPIPTNKRHAAAKIFSHPDVVAEVPWYGIEQEYTLLQKDIN
WPLGWPGPQGPYYCGAGADKAFGRDIVDSHYKACLYAGINISGINGEVMPGQWEFQVGPSVGISA
GDEIWVARYILERITEVAGWLSFDPKPIKGDWNGAGAHTNYSTKSMREDGGYEVILKAIEKLGKKHKEHI
AAYGEGNERRLTGRHETADINTFLWGVANRGASIRVGRDTEKAGKGYFEDRRPSSNMDPYVVTSMIADTT
ILWKP Alfalfa GS1 DNA coding sequence (upper case) with 5' and 3'
untranslated sequences (indicated in lower case) and vector sequences
from ClaI to SmaI/SspI and SspI/SmaI to SalI/XhoI (lower case,
underlined).
SEQ ID NO: 5
<u>atcgatgaattcgagctcggtaccc</u>atttccgttttcgtttcatttgattcattgaatcaaatcgaatc
gaatctttaggattcaatacagattccttagattttactaagtttgaaaccaaaaccaaaacATGTCTCT
CCTTTCAGATCTTATCAACCTTGACCTCTCCGAAACCACCGAGAAAATCATCGCCGAATACATATGATT
GGTGGATCTGGTTTGGACTTGAGGAGCAAAGCAAGGACTCTACCAGGACCAGTTACTGACCCTTCACAGC
TTCCCAAGTGGAACTATGATGGTTCCAGCACAGGTCAAGCTCCTGGAAGAGATAGTGAAGTTATTATCTA
CCCACAAGCCATTTTCAAGGACCCATTTAGAAGGGGTAACAATATCTTGGTTATGTGTGATGCATACACT
CCAGCTGGAGAGCCCATTCCCACCAACAAGAGACATGCAGCTGCCAAGATTTTCAGCCATCCTGATGTTG
TTGCTGAAGTACCATGGTATGGTATTGAGCAAGAATACACCTTGTTGCAGAAAGACATCAATTGGCCTCT
TGGTTGGCCAGTTGGTGGTTTTCCTGGACCTCAGGGACCATACTATTGTGGAGCTGGTGCTGACAAGGCA
TTTGGCCGTGACATTGTTGACTCACATTACAAAGCCTGTCTTTATGCCGGCATCAACATCAGTGGAATCA
ATGGTGAAGTGATGCCTGGTCAATGGGAATTCCAAGTTGGTCCCTCAGTTGGTATCTCTGCTGGTGATGA
GATATGGGTTGCTCGTTACATTTTGGAGAGGATCACTGAGGTTGCTGGTGTGGTGCTTTCCTTTGACCCA
AAACCAATTAAGGGTGATTGGAATGGTGCTGGTGCTCACACAAATTACAGCACCAAGTCTATGAGAGAAG
ATGGTGGCTATGAAGTCATCTTGAAAGCAATTGAGAAGCTTGGGAAGAAGCACAAGGAGCACATTGCTGC
TTATGGAGAAGGCAACGAGCGTAGATTGACAGGGCGACATGAGACAGCTGACATTAACACCTTCTTATGG
GGTGTTGCAAACCGTGGTGCGTCGATTAGAGTTGGAAGGGACACAGAGAAAGCAGGGAAAGGTTATTTCG
AGGATAGGAGGCCATCATCTAACATGGATCCATATGTTGTTACTTCCATGATTGCAGACACCACCATTCT
CTGGAAACCATAAgccaccacacacacatgcattgaagtatttgaaagtcattgttgattccgcattaga
atttggtcattgttttttctaggatttggatttgtgttattgttatggttcacactttgtttgtttgaat -continued

TABLE OF SEQUENCES:

ttgaggccttgttataggtttcatatttctttctcttgttctaagtaaatgtcagaataataatgtaatgggatcctctagagtcgag

*Arabidopsis* GS1 coding sequence
Cambia 1201 vector + rbcS3C + *arabidopsis* GS1 Bold ATG is the start site,

SEQ ID NO: 6

AAAAAAGAAAAAAAAAACATATCTTGTTTGTCAGTATGGGAAGTTTGAGATAAGGACGAGTGAGGGGTTA
AAATTCAGTGGCCATTGATTTTGTAATGCCAAGAACCACAAAATCCAATGGTTACCATTCCTGTAAGATG
AGGTTTGCTAACTCTTTTTGTCCGTTAGATAGGAAGCCTTATCACTATATATACAAGGCGTCCTAATAAC
CTCTTAGTAACCAATTATTTCAGCA*CCATG*TCTCTGCTCTCAGATCTCGTTAACCTCAACCTCACCGAT
GCCACCGGGAAATCATCGCCGAATACATATGGATCGGTGGATCTGGAATGGATATCAGAAGCAAAGCCA
GGACACTACCAGGACCAGTGACTGATCCATCAAAGCTTCCCAAGTGGAACTACGACGGATCCAGCACCGG
TCAGGCTGCTGGAGAAGACAGTGAAGTCATTCTATACCCTCAGGCAATATTCAAGGATCCCTTCAGGAAA
GGCAACAACATCCTGGTGATGTGTGATGCTTACACACCAGCTGGTGATCCTATTCCAACCAACAAGAGGC
ACAACGCTGCTAAGATCTTCAGCCACCCCGACGTTGCCAAGGAGGAGCCTTGGTATGGGATTGAGCAAGA
ATACACTTTGATGCAAAAGGATGTGAACTGGCCAATTGGTTGGCCTGTTGGTGGCTACCCTGGCCCTCAG
GGACCTTACTACTGTGGTGTGGGAGCTGACAAAGCCATTGGTCGTGACATTGTGGATGCTCACTACAAGG
CCTGTCTTTACGCCGGTATTGGTATTTCTGGTATCAATGGAGAAGTCATGCCAGGCCAGTGGGAGTTCCA
AGTCGGCCCTGTTGAGGGTATTAGTTCTGGTGATCAAGTCTGGGTTGCTCGATACCTTCTCGAGAGGATC
ACTGAGATCTCTGGTGTAATTGTCAGCTTCGACCCGAAACCAGTCCCGGGTGACTGGAATGGAGCTGGAG
CTCACTGCAACTACAGCACTAAGACAATGAGAAACGATGGAGGATTAGAAGTGATCAAGAAAGCGATAGG
GAAGCTTCAGCTGAAACACAAAGAACACATTGCTGCTTACGGTGAAGGAAACAGCGTCGTCTCACTGGA
AAGCACGAAACCGCAGACATCAACACATTCTCTTGGGGAGTCGCGAACCGTGGAGCGTCAGTGAGAGTGG
GACGTGACACAGAGAAGGAAGGTAAAGGGTACTTCGAAGACAGAAGGCCAGCTTCTAACATGGATCCTTA
CGTTGTCACCTCCATGATCGCTGAGACGACCATACTCGGTTGA

*Arabidopsis* GS1 amino acid sequence
Vector sequences at N-terminus in italics

SEQ ID NO: 7

*MVDLRNRRTS*MSLLSDLVNLNLTDATGKIIAEYIWIGGSGMDIRSKARTLPGPVTDPSKLPKWNYDGSST
GQAAGEDSEVILYPQAIFKDPFRKGNNILVMCDAYTPAGDPIPINKRHNAAKIFSHPDVAKEEPWYGIEQ
EYTLMQKDVNWPIGWPVGGYPGPQGPYYCGVGADKAIGRDIVDAHYKACLYAGIGISGINGEVMPGQWEF
QVGPVEGISSGDQVWVARYLLERITEISGVIVSFDPKPVPGDWNGAGAHCNYSTKTMRNDGGLEVIKKAI
GKLQLKHKEHIAAYGEGNERRLTGKHETADINTFSWGVANRGASVRVGRDTEKEGKGYFEDRRPASNMDP
YVVTSMIAETTILG

Grape GPT coding DNA sequence
Showing Cambia 1305.1 with (3' end of) rbcS3C + *Vitis vinifera*
GPT (Grape). Bold ATG is the start site, parentheses are the catI
intron and the underlined actagt is the speI cloning site used to
splice in the GPT gene.

SEQ ID NO: 8

AAAAAAGAAAAAAAAAACATATCTTGTTTGTCAGTATGGGAAGTTTGAGATAAGGACGAGTGAGGGGTTA
AAATTCAGTGGCCATTGATTTTGTAATGCCAAGAACCACAAAATCCAATGGTTACCATTCCTGTAAGATG
AGGTTTGCTAACTCTTTTTGTCCGTTAGATAGGAAGCCTTATCACTATATATACAAGGCGTCCTAATAAC
CTCTTAGTAACCAATTATTTCAGCA*CCATGG* TAGATCTGAGG(GTAAATTTCTAGTTTTTCTCCTTCA
TTTTCTTGGTTAGGACCCTTTTCTCTTTTTATTTTTTTGAGCTTTGATCTTTCTTTAAACTGATCTATTT
TTTAATTGATTGGTTATGGTGTAAATATTACATAGCTTTAACTGATAATCTGATTACTTTATTTCGTGTG
TCTATGATGATGATGATAGTTACAG)AACCGACGA*ACTAGT* ATGCAGCTCTCTCAATGTACCTGGACA
TTCCCAGAGTTGCTTAAAAGACCAGCCTTTTTAAGGAGGAGTATTGATAGTATTTCGAGTAGAAGTAGGT
CCAGCTCCAAGTATCCATCTTTCATGGCGTCCGCATCAACGGTCTCCGCTCCAAATACGGAGGCTGAGCA
GACCCATAACCCCCCTCAACCTCTACAGGTTGCAAAGCGCTTGGAGAAATTCAAAACAACAATCTTTACT
CAAATGAGCATGCTTGCCATCAAACATGGAGCAATAAACCTTGGCCAAGGGTTTCCCAACTTTGATGGTC
CTGAGTTTGTCAAAGAAGCAGCAATTCAAGCCATTAAGGATGGGAAAAACCAATATGCTCGTGGATATGG
AGTTCCTGATCTCAACTCTGCTGTTGCTGATAGATTCAAGAAGGATACAGGACTCGTGGTGGACCCCGAG
AAGGAAGTTACTGTTACTTCTGGATGTACAGAAGCAATTGCTGCTACTATGCTAGGCTTGATAAATCCTG
GTGATGAGGTGATCCTCTTTGCTCCATTTTATGATTCCTATGAAGCCACTCTATCCATGGCTGGTGCCCA
AATAAAATCCATCACTTTACGTCCTCCGGATTTTGCTGTGCCCATGGATGAGCTCAAGTCTGCAATCTCA
AAGAATACCCGTGCAATCCTTATAAACACTCCCCATAACCCCACAGGAAAGATGTTCACAAGGGAGGAAC
TGAATGTGATTGCATCCCTCTGCATTGAGAATGATGTGTGGTGTTTACTGATGAAGTTTACGACAAGTT
GGCTTTCGAAATGGATCACATTTCCATGGCTTCTCTTCCTGGGATGTACGAGAGGACCGTGACTATGAAT
TCCTTAGGGAAAACTTTCTCCCTGACTGGATGGAAGATTGGTTGGACAGTAGCTCCCCCACACCTGCACA
TGGGGAGTGAGGCAAGCCCACTCATTCCTCACGTTTGCTACCTGCACCCAATGCAATGGGCAGCTGCAA
CAGCCCTCCGGGCCCCAGACTCTTACTATGAAGAGCTAAAGAGAGATTACAGTGCAAGAAGGCAATCCT
GGTGGAGGGATTGAAGGCTGTCGGTTTCAGGGTATACCCATCAAGTGGGACCTATTTTGTGGTGGTGGT
CACACCCCATTTGGGTTGAAAGACGATATTGCGTTTTGTGAGTATCTGATCAAGGAAGTTGGGGTGGTAG
CAATTCCGACAAGCGTTTTCTACTTACACCCAGAAGATGGAAAGAACCTTGTGAGGTTTACCTTCTGTAA
AGACGAGGGAACTCTGAGAGCTGCAGTTGAAAGGATGAAGGAGAAACTGAAGCCTAAACAATAGGGGCAC
GTGA

Grape GPT amino acid sequence

SEQ ID NO: 9

MVDLRNRRTSMQLSQCTWTFPELLKRPAFLRRSIDSISSRSRSSSKYPSFMASASTVSAPNTEAEQTHNP
PQPLQVAKRLEKFKTTIFTQMSMLAIKHGAINLGQGFPNFDGPEFVKEAAIQAIKDGKNQYARGYGVPDL
NSAVADRFKKDTGLWDPEKEVTVTSGCTEAIAATMLGLINPGDEVILFAPFYDSYEATLSMAGAQIKSIT

TABLE OF SEQUENCES:

```
LRPPDFAVPMDELKSAISKNTRAILINTPHNPTGKMFTREELNVIASLCIENDVLVFTDEVYDKLAFEMD
HISMASLPGMYERTVTMNSLGKTFSLTGWKIGWTVAPPHLTWGVRQAHSFLTFATCTPMQWAAATALRAP
DSYYEELKRDYSAKKAILVEGLKAVGFRVYPSSGTYFVVVDHTPFGLKDDIAFCEYLIKEVGVVAIPTSV
FYLHPEDGKNLVRFTFCKDEGTLRAAVERMKEKLKPKQ
```

Rice GPT DNA coding sequence
Rice GPT codon optimized for *E. coli* expression; untranslated sequences shown in lower case

SEQ ID NO: 10

```
atgtggATGAACCTGGCAGGCTTTCTGGCAACCCCGGCAACCGCAACCGCAACCCGTCATGAAATGCCGC
TGAACCCGAGCAGCAGCGCGAGCTTTCTGCTGAGCAGCCTGCGTCGTAGCCTGGTGGCGAGCCTGCGTAA
AGCGAGCCCGGCAGCAGCAGCAGCACTGAGCCCGATGGCAAGCGCAAGCACCGTGGCAGCAGAAAACGGT
GCAGCAAAAGCAGCAGCAGAAAAACAGCAGCAGCAGCCGGTGCAGGTGGCGAAACGTCTGGAAAAATTTA
AAACCACCATTTTTACCCAGATGAGCATGCTGGCGATTAAACATGGCGCGATTAACCTGGGCCAGGGCTT
TCCGAACTTTGATGGCCCGGATTTTGTGAAAGAAGCGGCGATTCAGGCGATTAACGCGGGCAAAAACCAG
TATGCGCGTGGCTATGGCGTGCCGGAACTGAACAGCGCGATTGCGGAACGTTTTCTGAAAGATAGCGGCC
TGCAGGTGGATCCGGAAAAAGAAGTGACCGTGACCAGCGGCTGCACCGAAGCGATTGCGGCGACCATTCT
GGGCCTGATTAACCCGGGCGATGAAGTGATTCTGTTTGCGCCGTTTTATGATAGCTATGAAGCGACCCTG
AGCATGGCGGGCGCGAACGTGAAAGCGATTACCCTGCGTCCGCCGGATTTTAGCGTGCCGCTGGAAGAAC
TGAAAGCGGCCGTGAGCAAAAACACCCGTGCGATTATGATTAACACCCCGCATAACCCGACCGGCAAAAT
GTTTACCCGTGAAGAACTGGAATTTATTGCGACCCTGTGCAAAGAAAACGATGTGCTGCTGTTTGCGGAT
GAAGTGTATGATAAACTGGCGTTTGAAGCGGATCATATTAGCATGGCGAGCATTCCGGGCATGTATGAAC
GTACCGTGACCATGAACAGCCTGGGCAAAACCTTTAGCCTGACCGGCTGGAAAATTGGCTGGGCGATTGC
GCCGCCGCATCTGACCTGGGGCGTGCGTCAGGCACATAGCTTTCTGACCTTTGCAACCTGCACCCCAACT
GATGCAGGCAGCCGCCGCAGCAGCACTGCGTGCACCGGATAGCTATTATGAAGGCGTCGTGATTATGGCG
CGAAAAAAGCGCTGCTGGTGAACGGCCTGAAAGATGCGGGCTTTATTGTGTATCCGAGCAGCGGCACCTA
TTTTGTGATGGTGGATCATACCCCGTTTGGCTTTGATAACGATATTGAATTTTGCGAATATCTGATTCGT
GAAGTGGGCGTGGTGGCGATTCCGCCGAGCGTGTTTTATCTGAACCCGGAAGATGGCAAAAACCTGGTGC
GTTTTACCTTTTGCAAAGATGATGAAACCCTGCGTGCGGCGGTGGAACGTATGAAAACCAAACTGCGTAA
AAAAAAGCTTgcggccgcactcgagcaccaccaccaccactga
```

Rice GPT amino acid sequence
Includes amino terminal amino acids MW for cloning and His tag sequences from pet28 vector in italics.

SEQ ID NO: 11

```
MWMNLAGFLATPATATATRHEMPLNPSSSASFLLSSLRRSLVASLRKASPAAAAALSPMASASTVAAENG
AAKAAAEKQQQQPVQVAKRLEKFKTTIFTQMSMLAIKHGAINLGQGFPNFDGPDFVKEAAIQAINAGKNQ
YARGYGVPELNSAIAERFLKDSGLQVDPEKEVNTSGCTEAIAATILGLINPGDEVILFAPFYDSYEATLS
MAGANVKAITLRPPDFSVPLEELKAAVSKNTRAIMINTPHNPTGKMFTREELEFIATLCKENDVLLFADE
VYDKLAFEADHISMASIPGMYERTVTMNSLGKTFSLTGWKIGWAIAPPHLTVVGVRQAHSFLTFATCTPM
QAAAAAALRAPDSYYEELRRDYGAKKALLVNGLKDAGFIVYPSSGTYFVMVDHTPFGFDNDIEFCEYLIR
EVGWAIPPSVFYLNPEDGKNLVRFTFCKDDETLRAAVERMKTKLRKKKLAAALEHHHHHH
```

Soybean GPT DNA coding sequence
TOPO 151D WITH SOYBEAN for *E. coli* expression
From starting codon. Vector sequences are italicized

SEQ ID NO: 12

```
ATGCATCATCACCATCACCATGGTAAGCCTATCCCTAACCCTCTCCTCGGTCTCGATTCTACGGAAAACC
TGTATTTTCAGGGAATTGATCCCTTCACCGCGAAACGTCTGGAAAAATTTCAGACCACCATTTTTACCCA
GATGAGCCTGCTGGCGATTAAACATGGCGCGATTAACCTGGGCCAGGGCTTTCCGAACTTTGATGGCCCG
GAATTTGTGAAAGAAGCGGCGATTCAGGCGATTCGTGATGGCAAAAACCAGTATGCGCGTGGCTATGGCG
TGCCGGATCTGAACATTGCGATTGCGGAACGTTTTAAAAAAGATACCGGCCTGGTGGTGGATCCGGAAAA
AGAAATTACCGTGACCAGCGGCTGCACCGAAGCGATTGCGGCGACCATGATTGGCCTGATTAACCCGGGC
GATGAAGTGATTATGTTTGCGCCGTTTTATGATAGCTATGAAGCGACCCTGAGCATGGCGGGCGCGAAAG
TGAAAGGCATTACCCTGCGTCCGCCGGATTTTGCGGTGCCGCTGGAAGAACTGAAAAGCACCATTAGCAA
AAACACCCGTGCGATTCTGATTAACACCCCGCATAACCCGACCGGCAAAATGTTTACCCGTGAAGAACTG
AACTGCATTGCGAGCCTGTGCATTGAAAACGATGTGCTGGTGTTTACCGATGAAGTGTATGATAAACTGG
CGTTTGATATGGAACATATTAGCATGGCGAGCCTGCCGGGCATGTTTGAACGTACCGTGACCCTGAACAG
CCTGGGCAAAACCTTTAGCCTGACCGGCTGGAAAATTGGCTGGGCGATTGCGCCGCCGCATCTGAGCTGG
GGCGTGCGTCAGGCGCATGCGTTTCTGACCTTTGCAACCGCACATCCGTTTCAGTGCGCAGCAGCAGCAG
CACTGCGTGCACCGGATAGCTATTATGTGGAACTGAAACGTGATTATATGGCGAAACGTGCGATTCTGAT
TGAAGGCCTGAAAGCGGTGGGCTTTAAAGTGTTTCCGAGCAGCGGCACCTATTTTGTGGTGGTGGATCAT
ACCCCGTTTGGCCTGGAAAACGATGTGGCGTTTTGCGAATATCTGGTGAAAGAAGTGGGCGTGGTGGCGA
TTCCGACCAGCGTGTTTTATCTGAACCCGGAAGAAGGCAAAAACCTGGTGCGTTTTACCTTTTGCAAAGA
TGAAGAAACCATTCGTAGCGCGGTGGAACGTATGAAAGCGAAACTGCGTAAAGTCGACTAA
```

Soybean GPT amino acid sequence
Translated protein product, vector sequences italicized

SEQ ID NO: 13

```
MHHHHHHGKPIPNPLLGLDSTENLYFQGIDPFTAKRLEKFQTTIFTQMSLLAIKHGAINLGQGFPNFDGP
EFVKEAAIQAIRDGKNQYARGYGVPDLNIAIAERFKKDTGLWDPEKEITVTSGCTEAIAATMIGLINPGD
EVIMFAPFYDSYEATLSMAGAKVKGITLRPPDFAVPLEELKSTISKNTRAILINTPHNPTGKMFTREELN
CIASLCIENDVLVFTDEVYDKLAFDMEHISMASLPGMFERTVTLNSLGKTFSLTGWKIGWAIAPPHLSWG
VRQAHAFLTFATAHPFQCAAAAALRAPDSYYVELKRDYMAKRAILIEGLKAVGFKVFPSSGTYFVVVDHT
PFGLENDVAFCEYLVKEVGVVAIPTSVFYLNPEEGKNLVRFTFCKDEETIRSAVERMKAKLRKVD
```

TABLE OF SEQUENCES:

Barley GPT DNA coding sequence
Coding sequence from start with intron removed

SEQ ID NO: 14

ATGGTAGATCTGAGGAACCGACGAACTAGT ATGGCATCCGCCCCCGCCTCCGCCTCCGCGGCCCTCT
CCACCGCCGCCCCCGCCGACAACGGGGCCGCCAAGCCCACGGAGCAGCGGCCGGTACAGGTGGCTAAGCG
ATTGGAGAAGTTCAAAACAACAATTTTCACACAGATGAGCATGCTCGCAGTGAAGCATGGAGCAATAAAC
CTTGGACAGGGGTTTCCCAATTTTGATGGCCCTGACTTTGTCAAAGATGCTGCTATTGAGGCTATCAAAG
CTGGAAAGAATCAGTATGCAAGAGGATATGGTGTGCCTGAATTGAACTCAGCTGTTGCTGAGAGATTTCT
CAAGGACAGTGGATTGCACATCGATCCTGATAAGGAAGTTACTGTTACATCTGGGTGCACAGAAGCAATA
GCTGCAACGATATTGGGTCTGATCAACCCTGGGGATGAAGTCATACTGTTTGCTCCATTCTATGATTCTT
ATGAGGCTACACTGTCCATGGCTGGTGCAAATGTCAAAGCCATTACACTCCGCCCTCCGGACTTTGCAGT
CCCTCTTGAAGAGCTAAAGGCTGCAGTCTCGAAGAATACCAGAGCAATAATGATTAATACACCTCACAAC
CCTACCGGGAAAATGTTCACAAGGGAGGAACTTGAGTTCATTGCTGATCTCTGCAAGGAAAATGACGTGT
TGCTCTTTGCCGATGAGGTCTACGACAAGCTGGCGTTTGAGGCGGATCACATATCAATGGCTTCTATTCC
TGGCATGTATGAGAGGACCGTCACTATGAACTCCCTGGGGAAGACGTTCTCCTTGACCGGATGGAAGATC
GGCTGGGCGATAGCACCACCGCACCTGACATGGGGCGTAAGGCAGGCACACTCCTTCCTCACATTCGCCA
CCTCCACGCCGATGCAATCAGCAGCGGCGGCGGCCCTGAGAGCACCGGACAGCTACTTTGAGGAGCTGAA
GAGGGACTACGCGCAAAGAAAGCGCTGCTGGTGGACGGGCTCAAGGCGGCGGGCTTCATCGTCTACCCT
TCGAGCGGAACCTACTTCATCATGGTCGACCACACCCCGTTCGGGTTCGACAACGACGTCGAGTTCTGCG
AGTACTTGATCCGCGAGGTCGGCGTCGTGGCCATCCCGCCAAGCGTGTTCTACCTGAACCCGGAGGACGG
GAAGAACCTGGTGAGGTTCACCTTCTGCAAGGACGACGACACGCTAAGGGCGGCGGTGGACAGGATGAAG
GCCAAGCTCAGGAAGAAATGA

Barley GPT amino acid sequence
Translated sequence from start site (intron removed)

SEQ ID NO: 15

MVDLRNRRTSMASAPASASAALSTAAPADNGAAKPTEQRPVQVAKRLEKFKTTIFTQMSMLAVKHGAINL
GQGFPNFDGPDFVKDAAIEAIKAGKNQYARGYGVPELNSAVAERFLKDSGLHIDPDKEVTVTSGCTEAIA
ATILGLINPGDEVILFAPFYDSYEATLSMAGANVKAITLRPPDFAVPLEELKAAVSKNTRAIMINTPHNP
TGKMFTREELEFIADLCKENDVLLFADEVYDKLAFEADHISMASIPGMYERTVTMNSLGKTFSLTGWKIG
WAIAPPHLTWGVRQAHSFLTFATSTPMQSAAAAALRAPDSYFEELKRDYGAKKALLVDGLKAAGFIVYPS
SGTYFIMVDHTPFGFDNDVEFCEYLIREVGVVAIPPSVFYLNPEDGKNLVRFTFCKDDDTLRAAVDRMKA
KLRKK

Zebra fish GPT DNA coding sequence
Danio rerio sequence designed for expression in E coli. Bold,
italicized nucleotides added for cloning or from pET28b vector.

SEQ ID NO: 16

ATGTCCGTGGCGAAACGTCTGGAAAAATTTAAAACCACCATTTTTACCCAGATGAGCATGCTGGCGATT
AAACATGGCGCGATTAACCTGGGCCAGGGCTTTCCGAACTTTGATGGCCCGGATTTTGTGAAAGAAGCGG
CGATTCAGGCGATTCGTGATGGCAACAACCAGTATGCGCGTGGCTATGGCGTGCCGGATCTGAACATTGC
GATTAGCGAACGTTATAAAAAAGATACCGGCCTGGCGGTGGATCCGGAAAAAGAAATTACCGTGACCAGC
GGCTGCACCGAAGCGATTGCGGCGACCGTGCTGGGCCTGATTAACCCGGGCGATGAAGTGATTGTGTTTG
CGCCGTTTTATGATAGCTATGAAGCGACCCTGAGCATGGCCGGGCGCGAAAGTGAAAGGCATTACCCTGCG
TCCGCCGGATTTTGCGCTGCCGATTGAAGAACTGAAAAGCACCATTAGCAAAAACACCCGTGCGATTCTG
CTGAACACCCCGCATAACCCGACCGGCAAAATGTTTACCCCGGAAGAACTGAACACCATTGCGAGCCTGT
GCATTGAAAACGATGTGCTGGTGTTTAGCGATGAAGTGTATGATAAACTGGCGTTTGATATGGAACATAT
TAGCATTGCGAGCCTGCCGGGCATGTTTGAACGTACCGTGACCATGAACAGCCTGGGCAAAACCTTTAGC
CTGACCGGCTGGAAAATTGGCTGGGCGATTGCGCCGCCGCATCTGACCTGGGGCGTGCGTCAGGCGCATG
CGTTTCTGACCTTTGCAACCAGCAACCCGATGCAGTGGGCAGCAGCAGTGGCACTGCGTGCACCGGATAG
CTATTATACCGAACTGAAACGTGATTATATGGCGAAACGTAGCATTCTGGTGGAAGGCCTGAAAGCGGTG
GGCTTTAAAGTGTTTCCGAGCAGCGGCACCTATTTTGTGGTGGTGGATCATACCCCGTTTGGCCATGAAA
ACGATATTGCGTTTTGCGAATATCTGGTGAAAGAAGTGGGCGTGGTGGCGATTCCGACCAGCGTGTTTTA
TCTGAACCCGGAAGAAGGCAAAAACCTGGTGCGTTTTACCTTTTGCAAAGATGAAGGCACCCTGCGTGCG
GCGGTGGATCGTATGAAAGAAAAACTGCGTAAA**GTCGACAA GCTTGCGG CCGCACTCG
AGCACCAC CACCACCA CCACTGA**

Zebra fish GPR amino acid sequence
Amino acid sequence of Danio rerio cloned and expressed in E. coli
(bold, italicized amino acids are added from vector/cloning and His
tag on C-terminus)

SEQ ID NO: 17

MS VAKRLEKFKTTIFTQMSMLAIKHGAINLGQGFPNFDGPDFVKEAAIQAIRDGNNQYARGYGVPDLN
IAISERYKKDTGLAVDPEKEITVTSGCTEAIAATVLGLINPGDEVIVFAPFYDSYEATLSMAGAKVKGIT
LRPPDFALPIEELKSTISKNTRAILLNTPHNPTGKMFTPEELNTIASLCIENDVLVFSDEVYDKLAFDME
HISIASLPGMFERTVTMNSLGKTFSLTGWKIGWAIAPPHLTWGVRQAHAFLTFATSNPMQWAAAVALRAP
DSYYTELKRDYMAKRSILVEGLKAVGFKVFPSSGTYFVVVDHTPFGHENDIAFCEYLVKEVGVVAIPTSV
FYLNPEEGKNLVRFTFCKDEGTLRAAVDRMKEKLRKVDKLAAAL EHHHHHH -

Arabidopsis truncated GPT -30 construct DNA sequence
Arabidopsis GPT coding sequence with 30 amino acids removed from the
targeting sequence.

SEQ ID NO: 18

ATGGCCAAAATCCATCGTCCTATCGGAGCCACCATGACCACAGTTTCGACTCAGAACGAGTCTACTCAA
AACCCGTCCAGGTGGCGAAGAGATTAGAGAAGTTCAAGACTACTATTTTCACTCAAATGAGCATATTGGC
AGTTAAACATGGAGCGATCAATTTAGGCCAAGGCTTTCCCAATTTCGACGGTCCTGATTTTGTTAAAGAA

TABLE OF SEQUENCES:

```
GCTGCGATCCAAGCTATTAAAGATGGTAAAAACCAGTATGCTCGTGGATACGGCATTCCTCAGCTCAACT
CTGCTATAGCTGCGCGGTTTCGTGAAGATACGGGTCTTGTTGTTGATCCTGAGAAAGAAGTTACTGTTAC
ATCTGGTTGCACAGAAGCCATAGCTGCAGCTATGTTGGGTTTAATAAACCCTGGTGATGAAGTCATTCTC
TTTGCACCGTTTTATGATTCCTATGAAGCAACACTCTCTATGGCTGGTGCTAAAGTAAAAGGAATCACTT
TACGTCCACCGGACTTCTCCATCCCTTTGGAAGAGCTTAAAGCTGCGGTAACTAACAAGACTCGAGCCAT
CCTTATGAACACTCCGCACAACCCGACCGGGAAGATGTTCACTAGGGAGGAGCTTGAAACCATTGCATCT
CTCTGCATTGAAAACGATGTGCTTGTGTTCTCGGATGAAGTATACGATAAGCTTGCGTTTGAAATGGATC
ACATTTCTATAGCTTCTCTTCCCGGTATGTATGAAAGAACTGTGACCATGAATTCCCTGGGAAAGACTTT
CTCTTTAACCGGATGGAAGATCGGCTGGGCGATTGCGCCGCCTCATCTGACTTGGGGAGTTCGACAAGCA
CACTCTTACCTCACATTCGCCACATCAACACCAGCACAATGGGCAGCCGTTGCAGCTCTCAAGGCACCAG
AGTCTTACTTCAAAGAGCTGAAAAGAGATTACAATGTGAAAAAGGAGACTCTGGTTAAGGGTTTGAAGGA
AGTCGGATTTACAGTGTTCCCATCGAGCGGGACTTACTTTGTGGTTGCTGATCACACTCCATTTGGAATG
GAGAACGATGTTGCTTTCTGTGAGTATCTTATTGAAGAAGTTGGGGTCGTTGCGATCCCAACGAGCGTCT
TTTATCTGAATCCAGAAGAAGGGAAGAATTTGGTTAGGTTTGCGTTCTGTAAAGACGAAGAGACGTTGCG
TGGTGCAATTGAGAGGATGAAGCAGAAGCTTAAGAGAAAAGTCTGA
```

*Arabidopsis* truncated GPT -30 construct amino acid sequence

SEQ ID NO: 19

```
MAKIHRPIGATMTTVSTQNESTQKPVQVAKRLEKFKTTIFTQMSILAVKHGAINLGQGFPNFDGPDFVKE
AAIQAIKDGKNQYARGYGIPQLNSAIAARFREDTGLVVDPEKEVTVTSGCTEAIAAAMLGLINPGDEVIL
FAPFYDSYEATLSMAGAKVKGITLRPPDFSIPLEELKAAVTNKTRAILMNTPHNPTGKMFTREELETIAS
LCIENDVLVFSDEVYDKLAFEMDHISIASLPGMYERTVTMNSLGKTFSLTGWKIGWAIAPPHLTVVGVRQ
AHSYLTFATSTPAQWAAVAALKAPESYFKELKRDYNVKKETLVKGLKEVGFTVFPSSGTYFWADHTPFGM
ENDVAFCEYLIEEVGVVAIPTSVFYLNPEEGKNLVRFAFCKDEETLRGAIERMKQKLKRKV
```

SEQ ID NO: 20:
*Arabidopsis* truncated GPT -45 construct DNA sequence
*Arabidopsis* GPT coding sequence with 45 residues in the targeting sequence removed

```
ATGGCGACTCAGAACGAGTCTACTCAAAAACCCGTCCAGGTGGCGAAGAGATTAGAGAAGTTCAAGACTA
CTATTTTCACTCAAATGAGCATATTGGCAGTTAAACATGGAGCGATCAATTTAGGCCAAGGCTTTCCCAA
TTTCGACGGTCCTGATTTTGTTAAAGAAGCTGCGATCCAAGCTATTAAAGATGGTAAAAACCAGTATGCT
CGTGGATACGGCATTCCTCAGCTCAACTCTGCTATAGCTGCGCGGTTTCGTGAAGATACGGGTCTTGTTG
TTGATCCTGAGAAAGAAGTTACTGTTACATCTGGTTGCACAGAAGCCATAGCTGCAGCTATGTTGGGTTT
AATAAACCCTGGTGATGAAGTCATTCTCTTTGCACCGTTTTATGATTCCTATGAAGCAACACTCTCTATG
GCTGGTGCTAAAGTAAAAGGAATCACTTTACGTCCACCGGACTTCTCCATCCCTTTGGAAGAGCTTAAAG
CTGCGGTAACTAACAAGACTCGAGCCATCCTTATGAACACTCCGCACAACCCGACCGGGAAGATGTTCAC
TAGGGAGGAGCTTGAAACCATTGCATCTCTCTGCATTGAAAACGATGTGCTTGTGTTCTCGGATGAAGTA
TACGATAAGCTTGCGTTTGAAATGGATCACATTTCTATAGCTTCTCTTCCCGGTATGTATGAAAGAACTG
TGACCATGAATTCCCTGGGAAAGACTTTCTCTTTAACCGGATGGAAGATCGGCTGGGCGATTGCGCCGCC
TCATCTGACTTGGGGAGTTCGACAAGCACACTCTTACCTCACATTCGCCACATCAACACCAGCACAATGG
GCAGCCGTTGCAGCTCTCAAGGCACCAGAGTCTTACTTCAAAGAGCTGAAAAGAGATTACAATGTGAAAA
AGGAGACTCTGGTTAAGGGTTTGAAGGAAGTCGGATTTACAGTGTTCCCATCGAGCGGGACTTACTTTGT
GGTTGCTGATCACACTCCATTTGGAATGGAGAACGATGTTGCTTTCTGTGAGTATCTTATTGAAGAAGTT
GGGGTCGTTGCGATCCCAACGAGCGTCTTTTATCTGAATCCAGAAGAAGGGAAGAATTTGGTTAGGTTTG
CGTTCTGTAAAGACGAAGAGACGTTGCGTGGTGCAATTGAGAGGATGAAGCAGAAGCTTAAGAGAAAAGT
CTGA
```

SEQ ID NO: 21:
*Arabidopsis* truncated GPT -45 construct amino acid sequence

```
MATQNESTQKPVQVAKRLEKFKTTIFTQMSILAVKHGAINLGQGFPNFDGPDFVKEAAIQAIKDGKNQYA
RGYGIPQLNSAIAARFREDTGLVVDPEKEVTVTSGCTEAIAAAMLGLINPGDEVILFAPFYDSYEATLSM
AGAKVKGITLRPPDFSIPLEELKAAVTNKTRAILMNTPHNPTGKMFTREELETIASLCIENDVLVFSDEV
YDKLAFEMDHISIASLPGMYERTVTMNSLGKTFSLTGWKIGWAIAPPHLTVVGVRQAHSYLTFATSTPAQ
WAAVAALKAPESYFKELKRDYNVKKETLVKGLKEVGFTVFPSSGTYFVVADHTPFGMENDVAFCEYLIEE
VGVVAIPTSVFYLNPEEGKNLVRFAFCKDEETLRGAIERMKQKLKRKV
```

SEQ ID NO: 22:
Tomato Rubisco promoter
TOMATO RuBisCo rbcS3C promoter sequence from KpnI to NcoI

*GGTACC*GTTTGAATCCTCCTTAAAGTTTTTCTCTGGAGAAACTGTAGTAATTTTACTTTGTTGTGTTCCC
TTCATCTTTTGAATTAATGGCATTTGTTTTAATACTAATCTGCTTCTGAAACTTGTAATGTATGTATATC
AGTTTCTTATAATTTATCCAAGTAATATCTTCCATTCTCTATGCAATTGCCTGCATAAGCTCGACAAAAG
AGTACATCAACCCCTCCTCCTCTGGACTACTCTAGCTAAACTTGAATTTCCCCTTAAGATTATGAAATTG
ATATATCCTTAACAAACGACTCCTTCTGTTGGAAAATGTAGTACTTGTCTTTCTTCTTTTGGGTATATAT
AGTTTATATACACCATACTATGTACACATCCAAGTAGAGTGGATAGGATACATGTACAAGACTTATTTG
ATTGATTGATGACTTGAGTTGCCTTAGGAGTAACAAATTCTTAGGTCAATAAATCGTTGATTTGAAATTA
ATCTCTCTGTCTTAGACAGATAGGAATTATGACTTCCAATGGTCCAGAAAGCAAAGTTCGCACTGAGGGT
ATACTTGGAATTGAGACTTGCACAGGTCCAGAAACCAAAGTTCCCATCGAGCTCTAAAATCACATCTTTG
GAATGAAATTCAATTAGAGATAAGTTGCTTCATAGCATAGGTAAAATGGAAGATGTGAAGTAACCTGCAA
TAATCAGTGAAATGACATTAATACACTAAATACTTCATATGTAATTATCCTTTCCAGGTTAACAATACTC
TATAAAGTAAGAATTATCAGAAATGGGCTCATCAAACTTTTGTACTATGTATTTCATATAAGGAAGTATA
ACTATACATAAGTGTATACACAACTTTATTCCTATTTTGTAAAGGTGGAGAGACTGTTTTCGATGGATCT
AAAGCAATATGTCTATAAAATGCATTGATATAATAATTATCTGAGAAATCCAGAATTGGCGTTGGATTA
TTTCAGCCAAATAGAAGTTTGTACCATACTTGTTGATTCCTTCTAAGTTAAGGTGAAGTATCATTCATAA
ACAGTTTTCCCCAAAGTACTACTCACCAAGTTTCCCTTTGTAGAATTAACAGTTCAAATATATGGCGCAG
AAATTACTCTATGCCCAAAACCAAACGAGAAAGAAACAAAATACAGGGGTTGCAGACTTTATTTTCGTGT
```

TAGGGTGTGTTTTTTCATGTAATTAATCAAAAAATATTATGACAAAAACATTTATACATATTTTTACTCA
ACACTCTGGGTATCAGGGTGGGTTGTGTTCGACAATCAATATGGAAAGGAAGTATTTTCCTTATTTTTTT
AGTTAATATTTTCAGTTATACCAAACATACCTTGTGATATTATTTTTAAAAATGAAAAACTCGTCAGAAA
GAAAAAGCAAAAGCAACAAAAAAATTGCAAGTATTTTTTAAAAAAGCAAAAAAAAAACATATCTTGTTTGT
CAGTATGGGAAGTTTGAGATAAGGACGAGTGAGGGGTTAAAATTCAGTGGCCATTGATTTTGTAATGCCA
AGAACCACAAAATCCAATGGTTACCATTCCTGTAAGATGAGGTTTGCTAACTCTTTTTGTCCGTTAGATA
GGAAGCCTTATCACTATATATACAAGGCGTCCTAATAACCTCTTAGTAACCAATTATTTCAGCA<u>ATGG</u>

SEQ ID NO: 23:
Bamboo GPT DNA coding sequence
ATGGCCTCCGCGGCCGTCTCCACCGTCGCCACCGCCGCCGACGGCGTCGCGAAGCCGACGGAGAAGCAGC
CGTGTACAGGTCGCAAAGCGTTTGGAAAAGTTTAAGACAACAATTTTCACACAGATGAGCATGCTTGCCA
TCAAGCATGGAGCAATAAACCTCGGCCAGGGCTTTCCGAATTTTGATGGCCCTGACTTTGTGAAAGAAGC
TGCTATTCAAGCTATCAATGCTGGGAAGAATCAGTATGCAAGAGGATATGGTGTGCCTGAACTGAACTCG
GCTGTTGCTGAAAGGTTCCTGAAGGACAGTGGCTTGCAAGTCGATCCCGAGAAGGAAGTTACTGTCACAT
CTGGGTGCACGGAAGCGATAGCTGCAACGATATTGGGTCTTATCAACCCTGGCGATGAAGTGATCTTGTT
TGCTCCATTCTATGATTCATACGAGGCTACGCTGTCGATGGCTGGTGCCAATGTAAAAGCCATTACTCTC
CGTCCTCCAGATTTTGCAGTCCCTCTTGAGGAGCTAAAGGCCACAGTCTCTAAGAACACCAGAGCGATAA
TGATAAACACACCACACAATCCTACTGGGAAAATGTTTTCTAGGGAAGAACTTGAATTCATTGCTACTCT
CTGCAAGAAAAATGATGTGTTGCTTTTTGCTGATGAGGTCTATGACAAGTTGGCATTTGAGGCAGATCAT
ATATCAATGGCTTCTATTCCTGGCATGTATGAGAGGACTGTGACTATGAACTCTCTGGGGAAGACATTCT
CTCTAACAGGATGGAAGATCGGTTGGGCAATAGCACCACCACACCTGACATGGGGTGTAAGGCAGGCACA
CTCATTCCTCACATTTGCCACCTGCACACCAATGCAATCGGCGGCGGCGGCGGCTCTTAGAGCACCAGAT
AGCTACTATGGGGAGCTGAAGAGGGATTACGGTGCAAAGAAAGCGATACTAGTCGACGGACTCAAGGCTG
CAGGTTTTATTGTTTACCCTTCAAGTGGAACATACTTTGTCATGGTCGATCACACCCCGTTTGGTTTCGA
CAATGATATTGAGTTCTGCGAGTATTTGATCCGCGAAGTCGGTGTTGTCGCCATACCACCAAGCGTATTT
TATCTCAACCCTGAGGATGGGAAGAACTTGGTGAGGTTCACCTTCTGCAAGGATGATGATACGCTGAGAG
CCGCAGTTGAGAGGATGAAGACAAAGCTCAGGAAAAAATGA SEQ ID NO: 24:
Bamboo GPT amino acid sequence
MASAAVSTVATAADGVAKPTEKQPVQVAKRLEKFKTTIFTQMSMLAIKHGAINLGQGFPNFDGPDFVKEA
AIQAINAGKNQYARGYGVPELNSAVAERFLKDSGLQVDPEKEVTVTSGCTEAIAATILGLINPGDEVILF
APFYDSYEATLSMAGANVKAITLRPPDFAVPLEELKATVSKNTRAIMINTPHNPTGKMFSREELEFIATL
CKKNDVLLFADEVYDKLAFEADHISMASIPGMYERTVTMNSLGKTFSLTGWKIGWAIAPPHLTWGVRQAH
SPLTFATCTPMQSAAAAALRAPDSYYGELKRDYGAKKAILVDGLKAAGFIVYPSSGTYFVMVDHTPFGFD
NDIEFCEYLIREVGVVAIPPSVFYLNPEDGKNLVRFTFCKDDDTLRAAVERMKTKLRKK SEQ ID NO: 25:
1305.1 + rbcS3C promoter + catI intron with rice GPT gene.
Cambia 1305.1 with (3' end of) rbcS3C + rice GPT coding sequence.
Underlined ATG is start site, parentheses are the catI intron and the
underlined actagt is the speI cloning site used to splice in the rice
gene.
AAAAAGAAAAAAAAAACATATCTTGTTTGTCAGTATGGGAAGTTTGAGATAAGGACGAGTGAGGGGTTA
AAATTCAGTGGCCATTGATTTTGTAATGCCAAGAACCACAAAATCCAATGGTTACCATTCCTGTAAGATG
AGGTTTGCTAACTCTTTTTGTCCGTTAGATAGGAAGCCTTATCACTATATATACAAGGCGTCCTAATAAC
CTCTTAGTAACCAATTATTTCAGCA<b><u>CCATGG</u></b> TAGATCTGAGG(GTAAATTTCTAGTTTTTCTCCTTC
ATTTTCTTGGTTAGGACCCTTTTCTCTTTTATTTTTTTGAGCTTTGATCTTTCTTTAAACTGATCTATT
TTTTAATTGATTGGTTATGGTGTAAATATTACATAGCTTTAACTGATAATCTGATTACTTTATTTCGTGT
GTCTATGATGATGATGATAGTTACAG)AACCGACGA<b><u>ACTAGT</u></b> ATGAATCTGGCCGGCTTTCTCGCCA
CGCCCGCGACCGCGACCGCGACGCGGCATGAGATGCCGTTAAATCCCTCCTCCTCCGCCTCCTTCCTCCT
CTCCTCGCTCCGCCGCTCGCTCGTCGCGTCGCTCCGGAAGGCCTCGCCGGCGGCGGCCGCGGCGCTCTCC
CCCATGGCCTCCGCGTCCACCGTCGCCGCCGAGAACGGCGCCGCCAAGGCGGCGGCGGAGAAGCAGCAGC
AGCAGCCTGTGCAGGTTGCAAAGCGGTTGGAAAAGTTTAAGACGACCATTTTCACACAGATGAGTATGCT
TGCCATCAAGCATGGAGCAATAAACCTTGGCCAGGGTTTTCCGAATTTCGATGGCCCTGACTTTGTAAAA
GAGGCTGCTATTCAAGCTATCAATGCTGGGAAGAATCAGTACGCAAGAGGATATGGTGTGCCTGAACTGA
ACTCAGCTATTGCTGAAAGATTCCTGAAGGACAGCGGACTGCAAGTCGATCCGGAGAAGGAAGTTACTGT
CACATCTGGATGCACAGAAGCTATAGCTGCAACAATTTTAGGTCTAATTAATCCAGGCGATGAAGTGATA
TTGTTTGCTCCATTCTATGATTCATATGAGGCTACCCTGTCAATGGCTGGTGCCAACGTAAAAGCCATTA
CTCTCCGTCCTCCAGATTTTTCAGTCCCTCTTGAAGAGCTAAAGGCTGCAGTCTCGAAGAACACCAGAGC
TATTATGATAAACACCCCGCACAATCCTACTGGGAAAATGTTTACAAGGGAAGAACTTGAGTTTATTGCC
ACTCTCTGCAAGGAAAATGATGTGCTGCTTTTTGCTGATGAGGTCTACGACAAGTTAGCTTTTGAGGCAG
ATCATATATCAATGGCTTCTATTCCTGGCATGTATGAGAGGACCGTGACCATGAACTCTCTTGGGAAGAC
ATTCTCTCTTACAGGATGGAAGATCGGTTGGGCAATCGCACCGCCACACCTGACATGGGGTAAGGCAG
GCACACTCATTCCTCACGTTTGCGACCTGCACACCAATGCAAGCAGCTGCAGCTGCAGCTCTGAGAGCAC
CAGATAGCTACTATGAGGAACTGAGGAGGGATTATGGAGCTAAGAAGGCATTGCTAGTCAACGGACTCAA
GGATGCAGGTTTCATTGTCTATCCTTCAAGTGGAACATACTTCGTCATGGTCGACCACACCCCATTTGGT
TTCGACAATGATATTGAGTTCTGCGAGTATTTGATTCGCGAAGTCGGTGTTGTCGCCATACCACCTAGTG
TATTTTATCTCAACCCTGAGGATGGGAAGAACTTGGTGAGGTTCACCTTTTGCAAGGATGATGAGACGCT
GAGAGCCGCGGTTGAGAGGATGAAGACAAAGCTCAGGAAAAAATGA

TABLE OF SEQUENCES:

SEQ ID NO: 26:
*HORDEUM* GPT SEQUENCE IN VECTOR
Cambia 1305.1 with (3' end of) rbcS3C + *hordeum* (IDI4) coding sequence.
Underlined ATG is start site, parentheses are the catI intron and the
underlined actagt is the speI cloning site used to splice in the
*hordeum* gene.
AAAAAAGAAAAAAAAAAACATATCTTGTTTGTCAGTATGGGAAGTTTGAGATAAGGACGAGTGAGGGGTTA
AAATTCAGTGGCCATTGATTTTGTAATGCCAAGAACCACAAAATCCAATGGTTACCATTCCTGTAAGATG
AGGTTTGCTAACTCTTTTTGTCCGTTAGATAGGAAGCCTTATCACTATATATACAAGGCGTCCTAATAAC
CTCTTAGTAACCAATTATTTCAGCA*CC**ATGG* TAGATCTGAGG(GTAAATTTCTAGTTTTTCTCCTTC
ATTTTCTTGGTTAGGACCCTTTTCTCTTTTTATTTTTTTGAGCTTTGATCTTTCTTTAAACTGATCTATT
TTTTAATTGATTGGTTATGGTGTAAATATTACATAGCTTTAACTGATAATCTGATTACTTTATTTCGTGT
GTCTATGATGATGATGATAGTTACAG)AACCGACGA*ACTAGT* ATGGCATCCGCCCCCGCCTCCGCCT
CCGCGGCCCTCTCCACCGCCGCCCCGCCGACAACGGGGCCGCCAAGCCACACGGAGCAGCGGCCGGTAC
AGGTGGCTAAGCGATTGGAGAAGTTCAAAACAACAATTTTCACACAGATGAGCATGCTCGCAGTGAAGCA
TGGAGCAATAAACCTTGGACAGGGGTTTCCCAATTTTGATGGCCCTGACTTTGTCAAAGATGCTGCTATT
GAGGCTATCAAAGCTGGAAAGAATCAGTATGCAAGAGGATATGGTGTGCCTGAATTGAACTCAGCTGTTG
CTGAGAGATTTCTCAAGGACAGTGGATTGCACATCGATCCTGATAAGGAAGTTACTGTTACATCTGGGTG
CACAGAAGCAATAGCTGCAACGATATTGGGTCTGATCAACCCTGGGGATGAAGTCATACTGTTTGCTCCA
TTCTATGATTCTTATGAGGCTACACTGTCCATGGCTGGTGCGAATGTCAAAGCCATTACACTCCGCCCTC
CGGACTTTGCAGTCCCTCTTGAAGAGCTAAAGGCTGCAGTCTCGAAGAATACCAGAGCAATAATGATTAA
TACACCTCACAACCCTACCGGGAAAATGTTCACAAGGGAGGAACTTGAGTTCATTGCTGATCTCTGCAAG
GAAAATGACGTGTTGCTCTTTGCCGATGAGGTCTACGACAAGCTGGCGTTTGAGGCGGATCACATATCAA
TGGCTTCTATTCCTGGCATGTATGAGAGGACCGTCACTATGAACTCCCTGGGGAAGACGTTCTCCTTGAC
CGGATGGAAGATCGGCTGGGCGATAGCACCACCGCACCTGACATGGGGCGTAAGGCAGGCACACTCCTTC
CTCACATTCGCCACCTCCACGCCGATGCAATCAGCAGCGGCGGCGGCCCTGAGAGCACCGGACAGCTACT
TGAGGAGCTGAAGAGGGACTACGGCGCAAAGAAAGCGCTGCTGGTGGACGGGCTCAAGGCGGCGGGCTT
CATCGTCTACCCTTCGAGCGGAACCTACTTCATCATGGTCGACCACACCCCGTTCGGGTTCGACAACGAC
GTCGAGTTCTGCGAGTACTTGATCCGCGAGGTCGGCGTCGTGGCCATCCCGCCAAGCGTGTTCTACCTGA
ACCCGGAGGACGGGAAGAACCTGGTGAGGTTCACCTTCTGCAAGGACGACGACACGCTAAGGGCGGCGGT
GGACAGGATGAAGGCCAAGCTCAGGAAGAAATGATTGAGGGGCGCACGTGTGA

Expression cassette, *Arabidopsis* GPT coding sequence (ATG
underlined) under control of CMV 35S promoter (italics; promoter from
Cambia 1201)
SEQ ID NO: 27
*CATGGAGTCAAAGATTCAAATAGAGGACCTAACAGAACTCGCCGTAAAGACTGGCGAACAGTTCATACAG*
*AGTCTCTTACGACTCAATGACAAGAAGAAAATCTTCGTCAACATGGTGGAGCACGACACACTTGTCTACT*
*CCAAAAATATCAAAGATACAGTCTCAGAAGACCAAAGGGCAATTGAGACTTTTCAACAAAGGGTAATATC*
*CGGAAACCTCCTCGGATTCCATTGCCCAGCTATCTGTCACTTTATTGTGAAGATAGTGGAAAAGGAAGGT*
*GGCTCCTACAAATGCCATCATTGCGATAAAGGAAAGGCCATCGTTGAAGATGCCTCTGCCGACAGTGGTC*
*CCAAAGATGGACCCCCACCCACGAGGAGCATCGTGGAAAAAGAAGACGTTCCAACCACGTCTTCAAAGCA*
*AGTGGATTGATGTGATATCTCCACTGACGTAAGGGATGACGCACAATCCCACTATCCTTCGCAAGACCCT*
*TCCTCTATATAAGGAAGTTCATTTCATTTGGAGAGAACACGGGGGACTCTTGACC*ATG TACCTGGACATA
AATGGTGTGATGATCAAACAGTTTAGCTTCAAAGCCTCTCTTCTCCCATTCTCTTCTAATTTCCGACAAA
GCTCCGCCAAAATCCATCGTCCTATCGGAGCCACCATGACCACAGTTTCGACTCAGAACGAGTCTACTCA
AAAACCCGTCCAGGTGGCGAAGAGATTAGAGAAGTTCAAGACTACTATTTTCACTCAAATGAGCATATTG
GCAGTTAAACATGGAGCGATCAATTTAGGCCAAGGCTTTCCCAATTTCGACGGTCCTGATTTTGTTAAAG
AAGCTGCGATCCAAGCTATTAAAGATGGTAAAAACCAGTATGCTCGTGGATACGGCATTCCTGAGCTCAA
CTCTGCTATAGCTGCGCGGTTTCGTGAAGATACGGGTCTTGTTGTTGATCCTGAGAAGAAGTTACTGTT
ACATCTGGTTGCACAGAAGCCATAGCTGCAGCTATGTTGGGTTTAATAAACCCTGGTGATGAAGTCATTC
TCTTTGCACCGTTTTATGATTCCTATGAAGCAACACTCTCTATGGCTGGTGCTAAAGTAAAAGGAATCAC
TTTACGTCCACCGGACTTCTCCATCCCTTTGGAAGAGCTTAAAGCTGCGGTAACTAACAAGACTCGAGCC
ATCCTTATGAACACTCCGCACAACCCGACCGGGAAGATGTTCACTAGGGAGGAGCTTGAAACCATTGCAT
CTCTCTGCATTGAAAACGATGTGCTTGTGTTCTCGGATGAAGTATACGATAAGCTTGCGTTTGAAATGGA
TCACATTTCTATAGCTTCTCTTCCCGGTATGTATGAAAGAACTGTGACCATGAATTCCCTGGGAAAGACT
TTCTCTTTAACCGGATGGAAGATCGGCTGGGCGATTGCGCCGCCTCATCTGACTTGGGGAGTTCGACAAG
CACACTCTTACCTCACATTCGCCACATCAACACCAGCACAATGGGCAGCCGTTGCAGCTCTCAAGGCACC
AGAGTCTTACTTCAAAGAGCTGAAAAGAGATTACAATGTGAAAAAGGAGACTCTGGTTAAGGGTTTGAAG
GAAGTCGGATTTACAGTGTTCCCATCGAGCGGGACTTACTTTGTGGTTGCTGATCACACTCCATTTGGAA
TGGAGAACGATGTTGCTTTCTGTGAGTATCTTATTGAAGAAGTTGGGGTCGTTGCGATCCCAACGAGCGT
CTTTTATCTGAATCCAGAAGAAGGGAAGAATTTGGTTAGGTTTGCGTTCTGTAAAGACGAAGAGACGTTG
CGTGGTGCAATTGAGGATGAAGCAGAAGCTTAAGAGAAAAGTCTGA Cambia p1305.1 with (3' end of) rbcS3C + *Arabidopsis* GPT coding
sequence. Underlined ATG is start site, parentheses are the catI
intron and the underlined actagt is the speI cloning site used to
splice in the *Arabidopsis* gene.
SEQ ID NO: 28
AAAAAAGAAAAAAAAAAACATATCTTGTTTGTCAGTATGGGAAGTTTGAGATAAGGACGAGTGAGGGGTTA
AAATTCAGTGGCCATTGATTTTGTAATGCCAAGAACCACAAAATCCAATGGTTACCATTCCTGTAAGATG
AGGTTTGCTAACTCTTTTTGTCCGTTAGATAGGAAGCCTTATCACTATATATACAAGGCGTCCTAATAAC
CTCTTAGTAACCAATTATTTCAGCA*CC**ATGG* TAGATCTGAGG(GTAAATTTCTAGTTTTTCTCCTTCA
TTTTCTTGGTTAGGACCCTTTTCTCTTTTTATTTTTTTGAGCTTTGATCTTTCTTTAAACTGATCTATTT
TTTAATTGATTGGTTATGGTGTAAATATTACATAGCTTTAACTGATAATCTGATTACTTTATTTCGTGTG
TCTATGATGATGATGATAGTTACAG)AACCGACGA*ACTAGT* ATGTACCTGGACATAAATGGTGTGAT

TABLE OF SEQUENCES:

```
GATCAAACAGTTTAGCTTCAAAGCCTCTCTTCTCCCATTCTCTTCTAATTTCCGACAAAGCTCCGCCAAA
ATCCATCGTCCTATCGGAGCCACCATGACCACAGTTTCGACTCAGAACGAGTCTACTCAAAAACCCGTCC
AGGTGGCGAAGAGATTAGAGAAGTTCAAGACTACTATTTTCACTCAAATGAGCATATTGGCAGTTAAACA
TGGAGCGATCAATTTAGGCCAAGGCTTTCCCAATTTCGACGGTCCTGATTTTGTTAAAGAAGCTGCGATC
CAAGCTATTAAAGATGGTAAAAACCAGTATGCTCGTGGATACGGCATTCCTCAGCTCAACTCTGCTATAG
CTGCGCGGTTTCGTGAAGATACGGGTCTTGTTGTTGATCCTGAGAAGAAGTTACTGTTACATCTGGTTG
CACAGAAGCCATAGCTGCAGCTATGTTGGGTTTAATAAACCCTGGTGATGAAGTCATTCTCTTTGCACCG
TTTTATGATTCCTATGAAGCAACACTCTCTATGGCTGGTGCTAAAGTAAAAGGAATCACTTTACGTCCAC
CGGACTTCTCCATCCCTTTGGAAGAGCTTAAAGCTGCGGTAACTAACAAGACTCGAGCCATCCTTATGAA
CACTCCGCACAACCCGACCGGGAAGATGTTCACTAGGGAGGAGCTTGAAACCATTGCATCTCTCTGCATT
GAAAACGATGTGCTTGTGTTCTCGGATGAAGTATACGATAAGCTTGCGTTTGAAATGGATCACATTTCTA
TAGCTTCTCTTCCCGGTATGTATGAAAGAACTGTGACCATGAATTCCCTGGGAAAGACTTTCTCTTTAAC
CGGATGGAAGATCGGCTGGGCGATTGCGCCGCCTCATCTGACTTGGGGAGTTCGACAAGCACACTCTTAC
CTCACATTCGCCACATCAACACCAGCACAATGGGCAGCCGTTGCAGCTCTCAAGGCACCAGAGTCTTACT
TCAAAGAGCTGAAAAGAGATTACAATGTGAAAAAGGAGACTCTGGTTAAGGGTTTGAAGGAAGTCGGATT
TACAGTGTTCCCATCGAGCGGGACTTACTTTGTGGTTGCTGATCACACTCCATTTGGAATGGAGAACGAT
GTTGCTTTCTGTGAGTATCTTATTGAAGAAGTTGGGGTCGTTGCGATCCCAACGAGCGTCTTTTATCTGA
ATCCAGAAGAAGGGAAGAATTTGGTTAGGTTTGCGTTCTGTAAAGACGAAGAGACGTTGCGTGGTGCAAT
TGAGAGGATGAAGCAGAAGCTTAAGAGAAAAGTCTGA
```

*Arabidpsis* GPT coding sequence (mature protein, no targeting sequence)

SEQ ID NO: 29

```
GTGGCGAAGAGATTAGAGAAGTTCAAGACTACTATTTTCACTCAAATGAGCATATTGGCAGTTAAACATG
GAGCGATCAATTTAGGCCAAGGCTTTCCCAATTTCGACGGTCCTGATTTTGTTAAAGAAGCTGCGATCCA
AGCTATTAAAGATGGTAAAAACCAGTATGCTCGTGGATACGGCATTCCTCAGCTCAACTCTGCTATAGCT
GCGCGGTTTCGTGAAGATACGGGTCTTGTTGTTGATCCTGAGAAGAAGTTACTGTTACATCTGGTTGCA
CAGAAGCCATAGCTGCAGCTATGTTGGGTTTAATAAACCCTGGTGATGAAGTCATTCTCTTTGCACCGTT
TTATGATTCCTATGAAGCAACACTCTCTATGGCTGGTGCTAAAGTAAAAGGAATCACTTTACGTCCACCG
GACTTCTCCATCCCTTTGGAAGAGCTTAAAGCTGCGGTAACTAACAAGACTCGAGCCATCCTTATGAACA
CTCCGCACAACCCGACCGGGAAGATGTTCACTAGGGAGGAGCTTGAAACCATTGCATCTCTCTGCATTGA
AAACGATGTGCTTGTGTTCTCGGATGAAGTATACGATAAGCTTGCGTTTGAAATGGATCACATTTCTATA
GCTTCTCTTCCCGGTATGTATGAAAGAACTGTGACCATGAATTCCCTGGGAAAGACTTTCTCTTTAACCG
GATGGAAGATCGGCTGGGCGATTGCGCCGCCTCATCTGACTTGGGGAGTTCGACAAGCACACTCTTACCT
CACATTCGCCACATCAACACCAGCACAATGGGCAGCCGTTGCAGCTCTCAAGGCACCAGAGTCTTACTTC
AAAGAGCTGAAAAGAGATTACAATGTGAAAAAGGAGACTCTGGTTAAGGGTTTGAAGGAAGTCGGATTTA
CAGTGTTCCCATCGAGCGGGACTTACTTTGTGGTTGCTGATCACACTCCATTTGGAATGGAGAACGATGT
TGCTTTCTGTGAGTATCTTATTGAAGAAGTTGGGGTCGTTGCGATCCCAACGAGCGTCTTTTATCTGAAT
CCAGAAGAAGGGAAGAATTTGGTTAGGTTTGCGTTCTGTAAAGACGAAGAGACGTTGCGTGGTGCAATTG
AGAGGATGAAGCAGAAGCTTAAGAGAAAAGTCTGA
```

*Arabidpsis* GPT amino acid sequence (mature protein, no targeting sequence)

SEQ ID NO: 30

```
VAKRLEKFKTTIFTQMSILAVKHGAINLGQGFPNFDGPDFVKEAAIQAIKDGKNQYARGYGIPQLNSAIA
ARFREDTGLVVDPEKEVTVTSGCTEAIAAAMLGLINPGDEVILFAPFYDSYEATLSMAGAKVKGITLRPP
DFSIPLEELKAAVTNKTRAILMNTPHNPTGKMFTREELETIASLCIENDVLVFSDEVYDKLAFEMDHISI
ASLPGMYERTVTMNSLGKTFSLTGWKIGWAIAPPHLTWGVRQAHSYLTFATSTPAQWAAVAALKAPESYF
KELKRDYNVKKETLVKGLKEVGFTVFPSSGTYFVVADHTPFGMENDVAFCEYLIEEVGVVAIPTSVFYLN
PEEGKNLVRFAFCKDEETLRGAIERMKQKLKRKV
```

Grape GPT amino acid sequence (mature protein, no targeting sequence)

SEQ ID NO: 31

```
VAKRLEKFKTTIFTQMSMLAIKHGAINLGQGFPNFDGPEFVKEAAIQAIKDGKNQYARGYGVPDLNSAVA
DRFKKDTGLWDPEKEVTVTSGCTEAIAATMLGLINPGDEVILFAPFYDSYEATLSMAGAQIKSITLRPPD
FAVPMDELKSAISKNTRAILINTPHNPTGKMFTREELNVIASLCIENDVLVFTDEVYDKLAFEMDHISMA
SLPGMYERTVTMNSLGKTFSLTGWKIGWTVAPPHLTWGVRQAHSFLTFATCTPMQWAAATALRAPDSYYE
ELKRDYSAKKAILVEGLKAVGFRVYPSSGTYFVVVDHTPFGLKDDIAFCEYLIKEVGVVAIPTSVFYLHP
EDGKNLVRFTFCKDEGTLRAAVERMKEKLKPKQ
```

Rice GPT amino acid sequence (mature protein, no targeting sequence)

SEQ ID NO: 32

```
VAKRLEKFKTTIFTQMSMLAIKHGAINLGQGFPNFDGPDFVKEAAIQAINAGKNQYARGYGVPELNSAIA
ERFLKDSGLQVDPEKEVTVTSGCTEAIAATILGLINPGDEVILFAPFYDSYEATLSMAGANVKAITLRPP
DFSVPLEELKAAVSKNTRAIMINTPHNPTGKMFTREELEFIATLCKENDVLLFADEVYDKLAFEADHISM
ASIPGMYERTVTMNSLGKTFSLTGWKIGWAIAPPHLTWGVRQAHSFLTFATCTPMQAAAAAALRAPDSYY
EELRRDYGAKKALLVNGLKDAGFIVYPSSGTYFVMVDHTPFGFDNDIEFCEYLIREVGWAIPPSVFYLNP
EDGKNLVRFTFCKDDETLRAAVERMKTKLRKK
```

Soybean GPT amino acid sequence (-1 mature protein, no targeting sequence)

SEQ ID NO: 33

```
AKRLEKFQTTIFTQMSLLAIKHGAINLGQGFPNFDGPEFVKEAAIQAIRDGKNQYARGYGVPDLNIAIAE
RFKKDTGLWDPEKEITVTSGCTEAIAATMIGLINPGDEVIMFAPFYDSYEATLSMAGAKVKGITLRPPDF
AVPLEELKSTISKNTRAILINTPHNPTGKMFTREELNCIASLCIENDVLVFTDEVYDKLAFDMEHISMAS
LPGMFERTVTLNSLGKTFSLTGWKIGWAIAPPHLSWGVRQAHAFLTFATAHPFQCAAAAALRAPDSYYVE
```

TABLE OF SEQUENCES:

LKRDYMAKRAILIEGLKAVGFKVFPSSGTYFVVVDHTPFGLENDVAFCEYLVKEVGVVAIPTSVFYLNPE
EGKNLVRFTFCKDEETIRSAVERMKAKLRKVD

Barley GPT amino acid sequence (mature protein, no targeting sequence)
SEQ ID NO: 34

VAKRLEKFKTTIFTQMSMLAVKHGAINLGQGFPNFDGPDFVKDAAIEAIKAGKNQYARGYGVPELNSAVA
ERFLKDSGLHIDPDKEVTVTSGCTEAIAATILGLINPGDEVILFAPFYDSYEATLSMAGANVKAITLRPP
DFAVPLEELKAAVSKNTRAIMINTPHNPTGKMFTREELEFIADLCKENDVLLFADEVYDKLAFEADHISM
ASIPGMYERTVTMNSLGKTFSLTGWKIGWAIAPPHLTWGVRQAHSFLTFATSTPMQSAAAAALRAPDSYF
EELKRDYGAKKALLVDGLKAAGFIVYPSSGTYFIMVDHTPFGFDNDVEFCEYLIREVGVVAIPPSVFYLN
PEDGKNLVRFTFCKDDDTLRAAVDRMKAKLRKK

Zebra fish GPT amino acid sequence (mature protein, no targeting
sequence)
SEQ ID NO: 35

VAKRLEKFKTTIFTQMSMLAIKHGAINLGQGFPNFDGPDFVKEAAIQAIRDGNNQYARGYGVPDLNIAIS
ERYKKDTGLAVDPEKEITVTSGCTEAIAATVLGLINPGDEVIVFAPFYDSYEATLSMAGAKVKGITLRPP
DFALPIEELKSTISKNTRAILLNTPHNPTGKMFTPEELNTIASLCIENDVLVFSDEVYDKLAFDMEHISI
ASLPGMFERTVTMNSLGKTFSLTGWKIGWAIAPPHLTWGVRQAHAFLTFATSNPMQWAAAVALRAPDSYY
TELKRDYMAKRSILVEGLKAVGFKVFPSSGTYFVVVDHTPFGHENDIAFCEYLVKEVGWAIPTSVFYLNP
EEGKNLVRFTFCKDEGTLRAAVDRMKEKLRK

Bamboo GPT amino acid sequence (mature protein, no targeting sequence)
SEQ ID NO: 36

VAKRLEKFKTTIFTQMSMLAIKHGAINLGQGFPNFDGPDFVKEAAIQAINAGKNQYARGYGVPELNSAVA
ERFLKDSGLQVDPEKEVTVTSGCTEAIAATILGLINPGDEVILFAPFYDSYEATLSMAGANVKAITLRPP
DFAVPLEELKATVSKNTRAIMINTPHNPTGKMFSREELEFIATLCKKNDVLLFADEVYDKLAFEADHISM
ASIPGMYERTVTMNSLGKTFSLTGWKIGWAIAPPHLTWGVRQAHSFLTFATCTPMQSAAAAALRAPDSYY
GELKRDYGAKKAILVDGLKAAGFIVYPSSGTYFVMVDHTPFGFDNDIEFCEYLIREVGVVAIPPSVFYLN
PEDGKNLVRFTFCKDDDTLRAAVERMKTKLRKK

Rice rubisco promoter deposited in NCBI GenBank: AF143510.1
PstI cloning sites in bold; NcoI cloning site in italics, catI intron
and part of Gus plus protein from Cambia 1305.1 vector in bold
underline (sequence removed and not translated), 3' terminal SpeI
cloning site in double underline. The construct also includes a PmII
1305.1 cloning site CACGTG (also cuts in rice rbsc promoter), and a
ZraI cloning site GACGTC, which can be added by PCR to clone into
PmII site of vector).
SEQ ID NO: 39

CTGCAGCAAAGAAACGTTATTAGTTGGTGCTTTTGGTGGTAGGAATGTAGTTTTCTGACAAAGTCAATTA
CTGAATATAAAAAAAATCTGCACAGCTCTGCGTCAACAGTTGTCCAAGGGATGCCTCAAAAATCTGTGCA
GATTATCAGTCGTCACGCAGAAGCAGAACATCATGGIGTGCTAGGTCAGCTTCTTGCATTGGGCCATGAA
TCCGGTTGGTTGTTAATCTCTCCTCTCTTATTCTCTTATATTAAGATGCATAACTCTTTTATGTAGTCTA
AAAAAAAATCCAGTGGATCGGATAGTAGTACGTCATGGTGCCATTAGGTACCGTTGAACCTAACAGATAT
TTATGCATGTGTATATATATAGCTATATAGACAAAATTGATGCCGATTATAGACCCAAAAGCAATAGGTA
TATATAATATAATACAGACCACACCACCAAACTAAGAATCGATCAAATAGACAAGGCATGTCTCCAAATT
GTCTTAAACTATTTCCGTAGGTTCAGCCGTTCAGGAGTCGAATCAGCCTCTGCCGGCGTTTTCTTTGCAC
GTACGACGGACACACATGGGCATACCATATAGCTGGTCCATGACATTAGGAGAGAGAACGTACGTTGA
CCTGTAGCTGAGATATAACAAGGTTGATTATAATATCACCAAACATGAAATCATCCAAGGATGACCCATA
ACTATCACTACTATAGTACTGCATCTGGTAAAAGAAATTGTATAGACTCTATTTCGAGCACTACCACATA
ACGCCTGCAATGTGACACCCTACCTATTCACTAATGTGCCTCTTCCCACACGCTTTCCACCCGTACTGCT
CACAGCTTTAAGAACCAGAACAAATGAGTAATATTAGTGTCGGTTCATGGCTAAAACCAGCACTGATGTA
CATGACCACATATGTCAAATGCTGCTTCTAGGCATGACCCGCTCTTACTAATACCTACTCATCGCTAGAA
GAATTTTCGGCTGATAAATTTTCAATTTAAGCAAGAGTTATCTGCGTTGGTTCATAACTCAAACTGATGG
CCCCAACCCATATTAGTGCAAATTTCACATATGATCATAACCTTTTCATATGAAATCGGATCGAGATGAAC
TTTATATAAACATTGTAGCTGTCGATGATACCTACAATTTTAAGTTGTTCACAACCTTTTTATTTCAAGTCA
TTTAAATGCCCAAATAGGTGTTTCAAATCTCAGATAGAAATGTTCAAAAGTAAAAAAGGTCCCTATCATA
ACATAATTGATATGTAAGTGAGTTGGAAAAAGATAAGTACGTGTGAGAGAGATCGGGGATCAAATTCTGG
TGTAATAATGTATGTATTTCAGTCATAAAAATTGGTAGCAGTAGTTGGGGCTCTGTATATATACCGGTAA
GGATGGGATGGTAGTAGAATAATTCTTTTTTGTTTTTAGTTTTTTCTGGTCCAAAATTTCAAATTTGGA
TCCCTTACTTGTACCAACTAATATTAATGAGTGTTGAGGGTAGTAGAGGTGCAACTTTACCATAATCCCT
CTGTTTCAGGTTATAAGACGTTTTGACTTTAAATTTGACCAAGTTTATGCGCAAATATAGTAATATTTAT
AATACTATATTAGTTTCATTAAATAAATAATTGAATATATTTTCATAATAAATTTGTGTTGAGTTCAAAA
TATTATTAATTTTTTCTACAAACTTGGTCAAACTTGAAGCAGTTTGACTTTGACCAAAGTCAAAACGTCT
TATAACTTGAAACGGATGGATTACTTTTTTTGTGGGGACAAGTTTACAATGTTTAATAAAGCACAATCCA
TCTTAATGTTTTCAAGCTGAATATTGTAAAATTCATGGATAAACCAGCTTCTAAATGTTTAACCGGGAAA
ATGTCGAACGACAAATTAATATTTTTAAGTGATGGGGAGTATTAATTAAGGAGTGACAACTCAACTTTCA
ATATCGTACTAAACTGTGGGATTTATTTTCTAAAATTTTATACCCTGCCAATTCACGTGTTGTAGATCTT
TTTTTTTCACTAACCGACACCAGGTATATCAATTTTATTGAATATAGCAGCAAAAAGAATGTGTTGTACT
TGTAAACAAAAAGCAAACTGTACATAAAAAAAAATGCACTCCTATATAATTAAGCTCATAAAGATCGTTT
GCTTCGTGAGGGCCCAAGTTTTGATGACCTTTTGCTTGATCTCGAAATTAAAATTTAAGTACTGTTAAGG
GAGTTCACACCACCATCAATTTTCAGCCTGAAGAAACAGTTAAACAACGACCCCGATGACCAGTCTACTG
CTCTCCACATACTAGCTGCATTATTGATCACAAAACAAAACAAACGAAATAAAAATCAGCAGCGAGAGT
GTGCAGAGAGAGACAAAGGTGATCTGGCGTGGATATCTCCCCATCCATCCTCACCCGCGCTGCCCATCAC
TCGCCGCCGCATACTCCATCATGTGGAGAGAGGAAGACGAGGACCACAGCCAGAGCCCGGGTCGAGATGC
CACCACGGCCACAACCCACGAGCCCGGCGCGACACCACCGCGCGCGCGTGAGCCAGCCACAAACGCCCGC

TABLE OF SEQUENCES:

GGATAGGCGCGCGCACGCCGGCCAATCCTACCACATCCCCGGCCTCCGCGGCTCGCGAGCGCCGCTGCCA
TCCGATCCGCTGAGTTTTGGCTATTTATACGTACCGCGGAGCCTGTGTGCAGAGCAGTGCATCTCAAGAA
GTACTCGAGCAAAGAAGGAGAGAGCTTGGTGAGCTGCAGCC*ATG*GTAGATCTGAGG**GTAAATTTCTAGTT
TTTCTCCTTCATTTTCTTGGTTAGGACCCTTTTCTCTTTTTATTTTTTTGAGCTTTGATCTTTCTTTAAA
CTGATCTATTTTTTAATTGATTGGTTATGGTGTAAATATTACATAGCTTTAACTGATAATCTGATTACTT
TATTTCGTGTGTCTATGATGATGATGATAGTTACAG**AACCGACGA<u>ACTAGT</u>

*Horeum* GS1 coding sequence

SEQ ID NO: 40

GCGCAGGCGGTTGTGCAGGCGATGCAGTGCCAGGTGGGGGTGAGGGGCAGGACGGCCGTCCCGGCGAGGC
AGCCCGCGGGCAGGGTGTGGGGCGTCAGGAGGGCCGCCCGGCCACCTCCGGGTTCAAGGTGCTGGCGCT
CGGCCCGGAGACCACCGGGGTCATCCAGAGGATGCAGCAGCTGCTCGACATGGACACCACGCCCTTCACC
GACAAGATCATCGCCGAGTACATCTGGGTTGGAGGATCTGGAATTGACCTCAGAAGCAAATCAAGGACGA
TTTCGAAGCCAGTGGAGGACCCGTCAGAGCTGCCGAAATGGAACTACGACGGATCGAGCACGGGCAGGC
TCCTGGGGAAGACAGTGAAGTCATCCTATACCCACAGGCCATATTCAAGGACCCATTCCGAGGAGGCAAC
AACATACTGGTTATCTGTGACACCTACACACCACAGGGGGAACCCATCCCTACTAACAAACGCCACATGG
CTGCACAAATCTTCAGTGACCCCAAGGTCACTTCACAAGTGCCATGGTTCGGAATCGAACAGGAGTACAC
TCTGATGCAGAGGGATGTGAACTGGCCTCTTGGCTGGCCTGTTGGAGGGTACCCTGGCCCCCAGGGTCCA
TACTACTGCGCCGTAGGATCAGACAAGTCATTTGGCCGTGACATATCAGATGCTCACTACAAGGCGTGCC
TTTACGCTGGAATTGAAATCAGTGGAACAAACGGGGAGGTCATGCCTGGTCAGTGGGAGTACCAGGTTGG
ACCCAGCGTTGGTATTGATGCAGGAGACCACATATGGGCTTCCAGATACATTCTCGAGAGAATCACGGAG
CAAGCTGGTGTGGTGCTCACCCTTGACCCAAAACCAATCCAGGGTGACTGGAACGGAGCTGGCTGCCACA
CAAACTACAGCACATTGAGCATGCGCGAGGATGGAGGTTTCGACGTGATCAAGAAGGCAATCCTGAACCT
TTCACTTCGCCATGACTTGCACATAGCCGCATATGGTGAAGGAAACGAGCGGAGGTTGACAGGGCTACAC
GAGACAGCTAGCATATCAGACTTCTCATGGGGTGTGGCGAACCGTGCTGCTCTATTCGTGTGGGGCGAG
ACACCGAGGCGAAGGGCAAAGGATACCTGGAGGACCGTCGCCCGGCCTCCAACATGGACCCGTACACCGT
GACGGCGCTGCTGGCCGAGACCACGATCCTGTGGGAGCCGACCCTCGAGGCGGAGGCCCTCGCTGCCAAG
AAGCTGGCGCTGAAGGTATGA

*Horeum* GS1 amino acid sequence

SEQ ID NO: 41

AQAVVQAMQCQVGVRGRTAVPARQPAGRVWGVRRAARATSGFKVLALGPETTGVIQRMQQLLDMDTTPFT
DKIIAEYIWVGGSGIDLRSKSRTISKPVEDPSELPKWNYDGSSTGQAPGEDSEVILYPQAIFKDPFRGGN
NILVICDTYTPQGEPIPTNKRHMAAQIFSDPKVTSQVPWFGIEQEYTLMQRDVNWPLGWPVGGYPGPQGP
YYCAVGSDKSFGRDISDAHYKACLYAGIEISGTNGEVMPGQWEYQVGPSVGIDAGDHIWASRYILERITE
QAGVVLTLDPKPIQGDWNGAGCHTNYSTLSMREDGGFDVIKKAILNLSLRHDLHIAAYGEGNERRLTGLH
ETASISDFSWGVANRGCSIRVGRDTEAKGKGYLEDRRPASNMDPYTVTALLAETTILWEPTLEAEALAAK
KLALKV

SEQ ID NO: 42:
Expression cassette combining SEQ ID NO: 39 (5') and SEQ ID NO: 40
(3'), encoding the Rice rubisco promoter, catI intron and part of Gus
plus protein, and *hordeum* GS1. Features shown as in SEQ ID NO: 39.
*Hordeum* GS1 coding sequence begins after SpeI cloning site
(double underline).
CTGCAGCAAAGAAACGTTATTAGTTGGTGCTTTTGGTGGTAGGAATGTAGTTTTCTGACAAAGTCAATTA
CTGAATATAAAAAAAATCTGCACAGCTCTGCGTCAACAGTTGTCCAAGGGATGCCTCAAAAATCTGTGCA
GATTATCAGTCGTCACGCAGAAGCAGAACATCATGGTGTGCTAGGTCAGCTTCTTGCATTGGGCCATGAA
TCCGGTTGGTTGTTAATCTCTCCTCTCTTATTCTCTTATATTAAGATGCATAACTCTTTTATGTAGTCTA
AAAAAAAATCCAGTGGATCGGATAGTAGTACGTCATGGTGCCATTAGGTACCGTTGAACCTAACAGATAT
TTATGCATGTGTATATATAGCTATATAGACAAAATTGATGCCGATTATAGACCCAAAAGCAATAGGTA
TATATAATATAACAGACCACACCACCAAACTAAGAATCGATCAAATAGACAAGGCATGTCTCCAAATT
GTCTTAAACTATTTCCGTAGGTTCAGCCGTTCAGGAGTCGAATCGAATCGACCTCTGCCGGCGTTTTCTTTGCAC
GTACGACGGACACACATGGGCATACCATATAGCTGGTCCATGACATTAGGAGAGAGAACGTACGTGTTGA
CCTGTAGCTGAGATATAACAAGGTTGATTATAATATCACCAAACATGAAATCATCCAAGGATGACCCATA
ACTATCACTACTATAGTACTGCATCTGGTAAAAGAAATTGTATAGACTCTATTTCGAGCACTACCACATA
ACGCCTGCAATGTGACACCCTACCTATTCACTAATGTGCCTCTTCCCACACGCTTTCCACCCGTACTGCT
CACAGCTTTAAGAACCAGAACAAATGAGTAATATTAGTGTCGGTTCATGGCTAAAACCAGCACTGATGTA
CATGACCACATATGTCAAATGCTGCTTCTAGGCATGACCCGCTCTTACTAATACCTACTCATCGCTAGAA
GAATTTTCGGCTGATAAATTTTCAATTTAAGCAAGAGTTATCTGCGTTGGTTCATAACTCAAACTGATGG
CCCCAACCATATTAGTGCAAATTTCACATATGATCATAACCTTTTCATATGAAATCGGATCGAGATGAAC
TTTATATAAACATTGTAGCTGTCGATGATACCTACAATTTTATAGTTCACAACCTTTTTATTTCAAGTCA
TTTAAATGCCCAAATAGGTGTTTCAAATCTCAGATAGAAATGTTCAAAAGTAAAAAAGGTCCCTATCATA
ACATAATTGATATGTAAGTGAGTTGGAAAAAGATAAGTACGTGTGAGAGAGATCGGGGATCAAATTCTGG
TGTAATAATGTATGTATTTCAGTCATAAAAATTGGTAGCAGTAGTTGGGGCTCTGTATATATACCGGTAA
GGATGGGATGGTAGTAGAATAATTCTTTTTTGTTTTTAGTTTTTTCTGGTCCAAAATTTCAAATTTGGA
TCCCTTACTTGTACCAACTAATATTAATGAGTGTTGAGGGTAGTAGAGGTGCAACTTTACCATAATCCCT
CTGTTTCAGGTTATAAGACGTTTTGACTTTAAATTTGACCAAGTTTATGCGCAAATATAGTAATATTTAT
AATACTATATTAGTTTCATTAAATAAATAATTGAATATATTTTCATAATAAATTTGTGTTGAGTTCAAAA
TATTATTAATTTTTTCTACAAACTTGGTCAAACTTGAAGCAGTTTGACTTTGACCAAAGTCAAAACGTCT
TATAACTTGAAACGGATGGATTACTTTTTTTGTGGGGACAAGTTTACAATGTTTAATAAAGCACAATCCA
TCTTAATGTTTTCAAGCTGAATATTGTAAAATTCATGGATAAACCAGCTTCTAAATGTTTAACCGGGAAA
ATGTCGAACGACAAATTAATATTTTTAAGTGATGGGGAGTATTAATTAAGGAGTGACAACTCAACTTTCA
ATATCGTACTAAACTGTGGGATTTATTTTCTAAAATTTTATACCCTGCCAATTCACGTGTTGTAGATCTT
TTTTTTTTCACTAACCGACACCAGGTATATCAATTTTATTGAATATAGCAGCAAAAGAATGTGTTGTACT
TGTAAACAAAAGCAAACTGTACATAAAAAAAAATGCACTCCTATATAATTAAGCTCATAAAGATGCTTT
GCTTCGTGAGGGCCCAAGTTTTGATGACCTTTTGCTTGATCTCGAAATTAAAATTTAAGTACTGTTAAGG

TABLE OF SEQUENCES:

```
GAGTTCACACCACCATCAATTTTCAGCCTGAAGAAACAGTTAAACAACGACCCCGATGACCAGTCTACTG
CTCTCCACATACTAGCTGCATTATTGATCACAAAACAAAACAAAACGAAATAAAAATCAGCAGCGAGAGT
GTGCAGAGAGAGACAAAGGTGATCTGGCGTGGATATCTCCCCATCCATCCTCACCCGCGCTGCCCATCAC
TCGCCGCCGCATACTCCATCATGTGGAGAGAGGAAGACGAGGACCACAGCCAGAGCCCGGGTCGAGATGC
CACCACGGCCACAACCCACGAGCCCGGCGCGACACCACCGCGCGCGCGTGAGCCAGCCACAAACGCCCGC
GGATAGGCGCGCGCACGCCGGCCAATCCTACCACATCCCCGGCCTCCGCGGCTCGCGAGCGCCGCTGCCA
TCCGATCCGCTGAGTTTTGGCTATTTATACGTACCGCGGGAGCCTGTGTGCAGAGCAGTGCATCTCAAGA
AGTACTCGAGCAAAGAAGGAGAGAGCTTGGTGAGCTGCAGCCATGGTAGATCTGAGGGTAAATTTCTAGT
TTTTCTCCTTCATTTTCTTGGTTAGGACCCTTTTCTCTTTTTATTTTTTTGAGCTTTGATCTTTCTTTAA
ACTGATCTATTTTTTAATTGATTGGTTATGGTGTAAATATTACATAGCTTTAACTGATAATCTGATTACT
TTATTTCGTGTGTCTATGATGATGATAGTTACAGAACCGACGAACTAGTGCGCAGGCGGTTGTGCAG
GCGATGCAGTGCCAGGTGGGGGTGAGGGGCAGGACGGCCGTCCCGGCGAGGCAGCCCGCGGGCAGGGTGT
GGGGCGTCAGGAGGGCCGCCCGCGCCACCTCCGGGTTCAAGGTGCTGGCGCTCGGCCCGGAGACCACCGG
GGTCATCCAGAGGATGCAGCAGCTGCTCGACATGGACACCACGCCCTTCACCGACAAGATCATCGCCGAG
TACATCTGGGTTGGAGGATCTGGAATTGACCTCAGAAGCAAATCAAGGACGATTTCGAAGCCAGTGGAGG
ACCCGTCAGAGCTGCCGAAATGGAACTACGACGGATCGAGCACGGGGCAGGCTCCTGGGGAAGACAGTGA
AGTCATCCTATACCCACAGGCCATATTCAAGGACCCATTCCGAGGAGGCAACAACATACTGGTTATCTGT
GACACCTACACACCACAGGGGGAACCCATCCCTACTAACAAACGCCACATGGCTGCACAAATCTTCAGTG
ACCCCAAGGTCACTTCACAAGTGCCATGGTTCGGAATCGAACAGGAGTACACTCTGATGCAGAGGGATGT
GAACTGGCCTCTTGGCTGGCCTGTTGGAGGGTACCCTGGCCCCCAGGGTCCATACTACTGCGCCGTAGGA
TCAGACAAGTCATTTGGCCGTGACATATCAGATGCTCACTCAAGGCGTGCCTTTACGCTGGAATTGAAA
TCAGTGGAACAAACGGGGAGGTCATGCCTGGTCAGTGGGAGTACCAGGTTGGACCCAGCGTTGGTATTGA
TGCAGGAGACCACATATGGGCTTCCAGATACATTCTCGAGAGAATCACGGAGCAAGCTGGTGTGGTGCTC
ACCCTTGACCCAAAACCAATCCAGGGTGACTGGAACGGAGCTGGCTGCCACAAACTACAGCACATTGA
GCATGCGCGAGGATGGAGGTTTCGACGTGATCAAGAAGGCAATCCTGAACCTTTCACTTCGCCATGACTT
GCACATAGCCGCATATGGTGAAGGAAACGAGCGGAGGTTGACAGGGCTACACGAGACAGCTAGCATATCA
GACTTCTCATGGGGTGTGGCGAACCGTGGCTGCTCTATTCGTGTGGGGCGAGACACCGAGGCGAAGGGCA
AAGGATACCTGGAGGACCGTCGCCCGGCCTCCAACATGGACCCGTACACCGTGACGGCGCTGCTGGCCGA
GACCACGATCCTGTGGGAGCCGACCCTCGAGGCGGAGGCCCTCGCTGCCAAGAAGCTGGCGCTGAAGGTA
TGA
```

Amino acid sequence of translation product of SEQ ID NO: 42.
Amino-terminal bold residues from Gusplus and SpeI cloning site
(intron removed)

SEQ ID NO: 43

MVDLRNRRTSAQAVVQAMQCQVGVRGRTAVPARQPAGRVWGVRRAARATSGFKVLALGPETTGVIQRMQQ
LLDMDTTPFTDKIIAEYIWVGGSGIDLRSKSRTISKPVEDPSELPKWNYDGSSTGQAPGEDSEVILYPQA
IFKDPFRGGNNILVICDTYTPQGEPIPTNKRHMAAQIFSDPKVTSQVPWFGIEQEYTLMQRDVNWPLGWP
VGGYPGPQGPYYCAVGSDKSFGRDISDAHYKACLYAGIEISGTNGEVMPGQWEYQVGPSVGIDAGDHIWA
SRYILERITEQAGWLTLDPKPIQGDWNGAGCHTNYSTLSMREDGGFDVIKKAILNLSLRHDLHIAAYGEG
NERRLTGLHETASISDFSWGVANRGCSIRVGRDTEAKGKGYLEDRRPASNMDPYTVTALLAETTILWEPT
LEAEALAAKKLALKV

Maize ubiI promoter: 5'UTR intron shown in italics, TATA box at -30
is underlined, 5' and 3' PstI cloning sites in bold

SEQ ID NO: 44

CTGCAGTGCAGCGTGACCCGGTCGTGCCCCTCTCTAGAGATAATGAGCATTGCATGTCTAAGTTATAAAA
AATTACCACATATTTTTTTGTCACACTTGTTTGAAGTGCAGTTTATCTATCTTTATACATATATTTAAA
CTTTACTCTACGAATAATATAATCTATAGTACTACAATAATATCAGTGTTTTAGAGAATCATATAAATGA
ACAGTTAGACATGGTCTAAAGGACAATTGAGTATTTTGACAACAGGACTCTACAGTTTTATCTTTTTAGT
GTGCATGTGTTCTCCTTTTTTTTTGCAAATAGCTTCACCTATATAATACTTCATCCATTTTATTAGTACA
TCCATTTAGGGTTTAGGGTTAATGGTTTTTAATAGACTAATTTTTTTAGTACATCTATTTTATTCTATTT
TAGCCTCTAAATTAAGAAAACTAAAACTCTATTTTAGTTTTTTTATTTAATAATTTAGATATAAAATAGA
ATAAAATAAAGTGACTAAAAATTAAACAAATACCCTTTAAGAAATTAAAAAACTAAGGAAACATTTTTC
TTGTTTCGAGTAGATAATGCCAGCCTGTTAAACGCCGTCGACGAGTCTAACGGACACCAACCAGCGAACC
AGCAGCGTCGCGTCGGGCCAAGCGAAGCAGACGGCACGGCATCTCTGTCGCTGCCTCTGGACCCCTCTCG
AGAGTTCCGCTCCACCGTTGGACTTGCTCCGCTGTCGGCATCCAGAAATTGCGTGGCGGAGCGGCAGACG
TGAGCCGGCACGGCAGGCGGCCTCCTCCTCCTCTCACGGCACGGCAGCTACGGGGGATTCCTTTCCCACC
GCTCCTTCGCTTTCCCTTCCTCGCCCGCCGTAATAAATAGACACCCCCTCCACACCCCTCTTTCCCCAACC
TCGTGTTGTTCGGAGCGCACACACACACAACCAGATCTCCCCCAAATCCACCCGTCGGCACCTCCGCTTC
AAGGTACGCCGCTCGTCCTCCCCCCCCCCCCTCTCTACCTTCTCTAGATCGGCGTTCCGGTCCATGGTT
*AGGGCCCGGTAGTTCTACTTCTGTTCATGTTTGTGTTAGATCCGTGTTTGTGTTAGATCCGTGCTGCTAG
CGTTCGTACACGGATGCGACCTGTACGTCAGACACGTTCTGATTGCTAACTTGCCAGTGTTTCTCTTTGG
GGAATCCTGGGATGGCTCTAGCCGTTCCGCAGACGGGATCGATTTCATGATTTTTTTTGTTTCGTTGCAT
AGGGTTTGGTTTGCCCTTTTCCTTTATTTCAATATATGCCGTGCACTTGTTTGTCGGGTCATCTTTTCAT
GCTTTTTTTTGTCTTGGTTGTGATGATGTGGTCTGGTTGGGCGGTCGTTCTAGATCGGAGTAGAATTCTG
TTTCAAACTACCTGGTGGATTTATTAATTTTGGATCTGTATGTGTGTGCCATACATATTCATAGTTACGA
ATTGAAGATGATGGATGGAAATATCGATCTAGGATAGGTATACATGTTGATGCGGGTTTACTGATGCAT
ATACAGAGATGCTTTTTGTCGCTTGGTTGTGATGATGTGGTTGGTTGGGCGGTCGTTCATTCGTTCTA
GATCGGAGTAGAATACTGTTTCAAACTACCTGGTGTATTTATTAATTTTGGAACTGTATGTGTGTGTCAT
ACATCTTCATAGTTACGAGTTTAAGATGGATGAAATATCGATCTAGGATAGGTATACATGTTGATGTGG
GTTTTACTGATGCATATACATGATGGCATATGCAGCATCTATTCATATGCTCTAACCTTGAGTACCTATC
TATTATAATAAACAAGTATGTTTTATAATTATTTTGATCTTGATATACTTGGATGATGGCATATGCAGCA
GCTATATGTGGATTTTTTAGCCCTGCCTTCATACGCTATTTATTTGCTTGGTACTGTTTCTTTTGTCGA
TGCTCACCCTGTTGTTTGGTGTTACTT*CTGCAG

TABLE OF SEQUENCES:

*Hordeum* GPT DNA coding sequence, including targeting sequence coding domain

SEQ ID NO: 45

ATGGCATCCGCCCCCGCCTCCGCCTCCGCGGCCCTCTCCACCGCCGCCCCCGCCGACAACGGGGCCGCCA
AGCCCACGGAGCAGCGGCCGGTACAGGTGGCTAAGCGATTGGAGAAGTTCAAAACAACAATTTTCACACA
GATGAGCATGCTCGCAGTGAAGCATGGAGCAATAAACCTTGGACAGGGGTTTCCCAATTTTGATGGCCCT
GACTTTGTCAAAGATGCTGCTATTGAGGCTATCAAAGCTGGAAAGAATCAGTATGCAAGAGGATATGGTG
TGCCTGAATTGAACTCAGCTGTTGCTGAGAGATTTCTCAAGGACAGTGGATTGCACATCGATCCTGATAA
GGAAGTTACTGTTACATCTGGGTGCACAGAAGCAATAGCTGCAACGATATTGGGTCTGATCAACCCTGGG
GATGAAGTCATACTGTTTGCTCCATTCTATGATTCTTATGAGGCTACACTGTCCATGGCTGGTGCGAATG
TCAAAGCCATTACACTCCGCCCTCCGGACTTTGCAGTCCCTCTTGAAGAGCTAAAGGCTGCAGTCTCGAA
GAATACCAGAGCAATAATGATTAATACACCTCACAACCCTACCGGGAAAATGTTCACAAGGGAGGAACTT
GAGTTCATTGCTGATCTCTGCAAGGAAAATGACGTGTTGCTCTTTGCCGATGAGGTCTACGACAAGCTGG
CGTTTGAGGCGGATCACATATCAATGGCTTCTATTCCTGGCATGTATGAGAGGACCGTCACTATGAACTC
CCTGGGGAAGACGTTCTCCTTGACCGGATGGAAGATCGGCTGGGCGATAGCACCACCGCACCTGACATGG
GGCGTAAGGCAGGCACACTCCTTCCTCACATTCGCCACCTCCACGCCGATGCAATCAGCAGCGGCGGCGG
CCCTGAGAGCACCGGACAGCTACTTTGAGGAGCTGAAGAGGGACTACGGCGCAAAGAAAGCGCTGCTGGT
GGACGGGCTCAAGGCGGCGGGCTTCATCGTCTACCCTTCGAGCGGAACCTACTTCATCATGGTCGACCAC
ACCCCGTTCGGGTTCGACAACGACGTCGAGTTCTGCGAGTACTTGATCCGCGAGGTCGGCGTCGTGGCCA
TCCCGCCAAGCGTGTTCTACCTGAACCCGGAGGACGGGAAGAACCTGGTGAGGTTCACCTTCTGCAAGGA
CGACGACACGCTAAGGGCGGCGGTGGACAGGATGAAGGCCAAGCTCAGGAAGAAATGA

SEQ ID NO: 46:
*Hordeum* GPT amino acid sequence, including putative targeting
sequence (in italics).

*MASAPASASAALSTAAPADNGAAKPTEQRPV*QVAKRLEKFKTTIFTQMSMLAVKHGAINLGQGFPNFDGP
DFVKDAAIEAIKAGKNQYARGYGVPELNSAVAERFLKDSGLHIDPDKEVTVTSGCTEAIAATILGLINPG
DEVILFAPFYDSYEATLSMAGANVKAITLRPPDFAVPLEELKAAVSKNTRAIMINTPHNPTGKMFTREEL
EFIADLCKENDVLLFADEVYDKLAFEADHISMASIPGMYERTVTMNSLGKTFSLTGWKIGWAIAPPHLTV
VGVRQAHSFLTFATSTPMQSAAAAALRAPDSYFEELKRDYGAKKALLVDGLKAAGFIVYPSSGTYFIMVD
HTPFGFDNDVEFCEYLIREVGVVAIPPSVFYLNPEDGKNLVRFTFCKDDDTLRAAVDRMKAKLRKK

Tomato rubisco small subunit (rbcS3C) promoter + *Arabidopsis*
GS1 DNA coding sequence; NcoI/AfIIII splice site shown in bold,
ATG start of GS1 underlined.

SEQ ID NO: 47

GTTTGAATCCTCCTTAAAGTTTTTCTCTGGAGAAACTGTAGTAATTTTACTTTGTTGTGTTCCCTTCATC
TTTTGAATTAATGGCATTTGTTTTAATACTAATCTGCTTCTGAAACTTGTAATGTATGTATATCAGTTTC
TTATAATTTATCCAAGTAATATCTTCCATTCTCTATGCAATTGCCTGCATAAGCTCGACAAAAGAGTACA
TCAACCCCTCCTCCTCTGGACTACTCTAGCTAAACTTGAATTTCCCCTTAAGATTATGAAATTGATATAT
CCTTAACAAACGACTCCTTCTGTTGGAAAATGTAGTACTTGTCTTTCTTCTTTTGGGTATATATAGTTTA
TATACACCATACTATGTACAACATCCAAGTAGAGTGAAATGGATACATGTACAAGACTTATTTGATTGAT
TGATGACTTGAGTTGCCTTAGGAGTAACAAATTCTTAGGTCAATAAATCGTTGATTTGAAATTAATCTCT
CTGTCTTAGACAGATAGGAATTATGACTTCCAATGGTCCAGAAAGCAAAGTTCGCACTGAGGGTATACTT
GGAATTGAGACTTGCACAGGTCCAGAAACCAAAGTTCCCATCGAGCTCTAAAATCACATCTTTGGAATGA
AATTCAATTAGAGATAAGTTGCTTCATAGCATAGGTAAAATGGAAGATGTGAAGTAACCTGCAATAATCA
GTGAAATGACATTAATACACTAAATACTTCATATGTAATTATCCTTTCCAGGTTAACAATACTCTATAAA
GTAAGAATTATCAGAAATGGGCTCATCAAACTTTTGTACTATGTATTTCATATAAGGAAGTATAACTATA
CATAAGTGTATACACAACTTTATTCCTATTTTGTAAAGGTGGAGAGACTGTTTTCGATGGATCTAAAGCA
ATATGTCTATAAAATGCATTGATATAATAATTATCTGAGAAAATCCAGAATTGGCGTTGGATTATTTCAG
CCAAATAGAAGTTTGTACCATACTTGTTGATTCCTTCTAAGTTAAGGTGAAGTATCATTCATAAACAGTT
TTCCCCAAAGTACTACTCACCAAGTTTCCCTTTGTAGAATTAACAGTTCAAATATATGGCGCAGAAATTA
CTCTATGCCCAAAACCAAACGAGAAAGAAACAAAATACAGGGGTTGCAGACTTTATTTTCGTGTTAGGGT
GTGTTTTTTCATGTAATTAATCAAAAAATATTATGACAAAAACATTTATACATATTTTTACTCAACACTC
TGGGTATCAGGGTGGGTTGTGTTCGACAATCAATATGGAAAGGAAGTATTTTCCTTATTTTTTTAGTTAA
TATTTTCAGTTATACCAAACATACCTTGTGATATTATTTTTAAAAATGAAAAACTCGTCAGAAAGAAAAA
GCAAAAGCAACAAAAAAATTGCAAGTATTTTTTAAAAAAGAAAAAAAAAACATATCTTGTTTGTCAGTAT
GGGAAGTTTGAGATAAGGACGAGTGAGGGGTTAAAATTCAGTGGCCATTGATTTTGTAATGCCAAGAACC
ACAAAATCCAATGGTTACCATTCCTGTAAGATGAGGTTTGCTAACTCTTTTTGTCCGTTAGATAGGAAGC
CTTATCACTATATATACAAGGCGTCCTAATAACCTCTTAGTAACCAATTATTTCAGCACCATGTCTCTGC
TCTCAGATCTCGTTAACCTCAACCTCACCGATGCCACCGGGAAAATCATCGCCGAATACATATGGATCGG
TGGATCTGGAATGGATATCAGAAGCAAAGCCAGGACACTACCAGGACCAGTGACTGATCCATCAAAGCTT
CCCAAGTGGAACTACGACGGATCCAGCACCGGTCAGGCTGCTGGAGAAGACAGTGAAGTCATTCTATACC
CTCAGGCAATATTCAAGGATCCCTTCAGGAAAGGCAACAACATCCTGGTGATGTGTGATGCTTACACACC
AGCTGGTGATCCTATTCCAACCAACAAGAGGCACAACGCTGCTAAGATCTTCAGCCACCCCGACGTTGCC
AAGGAGGAGCCTTGGTATGGGATTGAGCAAGAATACACTTTGATGCAAAAGGATGTGAACTGGCCAATTG
GTTGGCCTGTTGGTGGCTACCCTGGCCCTCAGGGACCTTACTACTGTGGTGTGGGAGCTGACAAAGCCAT
TGGTCGTGACATTGTGGATGCTCACTACAAGGCCTGTCTTTACGCCGGTATTGGTATTTCTGGTATCAAT
GGAGAAGTCATGCCAGGCCAGTGGGAGTTCCAAGTCGGCCCTGTTGAGGGTATTAGTTCTGGTGATCAAG
TCTGGGTTGCTCGATACCTTCTCGAGAGGATCACTGAGATCTCTGGTGTAATTGTCAGCTTCGACCCGAA
ACCAGTCCCGGGTGACTGGAATGGAGCTGGAGCTCACTGCAACTACAGCACTAAGACAATGAGAAACGAT
GGAGGATTAGAAGTGATCAAGAAAGCGATAGGGAAGCTTCAGCTGAAACACAAAGAACACATTGCTGCTT
ACGGTGAAGGAAACGAGCGTCGTCTCACTGGAAAGCACGAAACCGCAGACATCAACACATTCTCTTGGGG
AGTCGCGAACCGTGGAGCGTCAGTGAGAGTGGGACGTGACACAGAGAAGGAAGGTAAAGGGTACTTCGAA
GACAGAAGGCCAGCTTCTAACATGGATCCTTACGTTGTCACCTCCATGATCGCTGAGACGACCATACTCG
GTTGA

TABLE OF SEQUENCES:

SEQ ID NO: 48:
Putative Clementine orange GPT coding sequence
Derived from BioChain (Hayward, CA orange cDNA library, cat# C1634340;
Derived from clementine PCR primers:
5'-ggccacatgtccgttgctaagtgcttggagaagttta-3' (AfIIII oligo)
[SEQ ID NO: _]
5'-cgggcacgtgtcattttctcctcagcttctccttcatcct-3' (PmII oligo)
[SEQ ID NO: _]
ATG start site in bold, AfIIII oligo binding site (start of putative
mature coding sequence) is underlined; terminator sequence
italicized.
ATGCTTAAGCCGTCCGCCTTCGGGTCTTCTTTTTCTTCCTCAGCTCTGCTTTCGTTTTCGAAGCATTTGC
ATACAATAAGCATTACTGATTCTGTCAACACCAGAAGAAGAGGAATCAGTACCGCTTGCCCTAGGTACCC
TTCTCTCATGGCGAGCTTGTCCACCGTTTCCACCAATCAAAGCGACACCATCCAGAAGACCAATCTTCAG
CCTCAACAGG<u>TTGCTAAGTGCTTGGAGAAGTTT</u>AAAACTACAATCTTTACACAAATGAGTATGCTTGCCA
TCAAACATGGAGCTATAAATCTTGGTCAAGGCTTTCCCAACTTTGATGGCCCAGATTTTGTTAAAGATGC
AGCGATTCAAGCCATAAGGGATGGGAAGAATCAATATGCTCGTGGACATGGGGTTCCAGAGTTCAACTCT
GCCATTGCTTCCCGGTTTAAGAAAGATTCTGGGCTCGAGGTTGACCCTGAAAAGGAAGTTACTGTTACCT
CTGGGTGCACCGAAGCCATTGCTGCAACCATCTTAGGTTTGATTAATCCTGGAGATGAGGTGATCCTTTT
TGCACCTTTCTATGATTCCTATGAAGCTACTCTCTCCATGGCTGGTGCTAAAATTAAATGCATCACATTG
CGCCCTCCAGAATTTGCCATCCCCATTGAAGAGCTCAAGTCTACAATCTCAAAAAATACTCGTGCAATTC
TTATGAACACTCCACATAACCCCACTGGAAAGATGTTCACTAGGGAGGAACTTAATGTTATTGCATCTCT
TTGCATTGAGAATGATGTGTTGGTTTTTAGTGATGAGGTCTATGATAAGTTGGCTTTTGAAATGGATCAC
ATTTCCATAGCCTCTCTTCCTGGAATGTATGAGCGTACTGTAACCATGAATTCCTTAGGGAAGACATTCT
CTTTAACAGGGTGGAAGATCGGTGGGCAATAGCTCCACCGCACCTTACATGGGGGGTGCGGCAGGCACA
CTCTTTTCTCACGTTTGCCACATCCACTCCAATGCAGTGGGCAGCTACAGCAGCCCTTAGAGCTCCGGAG
ACGTACTATGAGGAGCTAAAGAGAGATTACTCGGCAAAGAAGGCAATTTTGGTGGAGGGATTGAATGCTG
TTGGTTTCAAGGTATTCCCATCTAGTGGGACATACTTTGTGGTTGTAGATCACACCCCATTTGGGCACGA
AACTGATATTGCAGTGAATATCTGATCAAGGAAGTTGGGGTTGTGGCAATTCCGACCAGCGTAACTTGAA
TCCAGAGGATGGAAAGAATTTGGTGAGATTTACCTTCTGCAAAGATGAAGGAACTTTGAGGTCTGCAGTT
GACAGGATGAAGGAGAAGCTGAGGAGAAAATGA SEQ ID NO: 49:
Putative Clementine orange GPT amino acid sequence; putative
mature protein sequence begins at VAK shown in bold underline.
MLKPSAFGSSFSSSALLSFSKHLHTISITDSVNTRRRGISTACPRYPSLMASLSTVSTNQSDTIQKTNLQ
PQQ<u>VAK</u>CLEKFKTTIFTQMSMLAIKHGAINLGQGFPNFDGPDFVKDAAIQAIRDGKNQYARGHGVPEFNS
AIASRFKKDSGLEVDPEKEVTVTSGCTEAIAATILGLINPGDEVILFAPFYDSYEATLSMAGAKIKCITL
RPPEFAIPIEELKSTISKNTRAILMNTPHNPTGKMFTREELNVIASLCIENDVLVFSDEVYDKLAFEMDH
ISIASLPGMYERTVTMNSLGKTFSLTGWKIGWAIAPPHLTWGVRQAHSFLTFATSTPMQWAATAALRAPE
TYYEELKRDYSAKKAILVEGLNAVGFKVFPSSGTYFVWDHTPFGHETDIAFCEYLIKEVGVVAIPTSVFY
LNPEDGKNLVRFTFCKDEGTLRSAVDRMKEKLRRK

SEQUENCE LISTING

<160> NUMBER OF SEQ ID NOS: 60

<210> SEQ ID NO 1
<211> LENGTH: 1323
<212> TYPE: DNA
<213> ORGANISM: Aradopsis thaliana

<400> SEQUENCE: 1

```
atgtacctgg acataaatgg tgtgatgatc aaacagttta gcttcaaagc ctctcttctc      60
ccattctctt ctaatttccg acaaagctcc gccaaaatcc atcgtcctat cggagccacc     120
atgaccacag tttcgactca gaacgagtct actcaaaaac ccgtccaggt ggcgaagaga     180
ttagagaagt tcaagactac tattttcact caaatgagca tattggcagt aaacatgga      240 gcgatcaatt taggccaagg ctttcccaat ttcgacggtc ctgattttgt taaagaagct     300
gcgatccaag ctattaaaga tggtaaaaac cagtatgctc gtggatacgg cattcctcag     360
ctcaactctg ctatagctgc gcggtttcgt gaagatacgg tcttgttgt tgatcctgag      420 aaagaagtta ctgttacatc tggttgcaca gaagccatag ctgcagctat gttgggttta     480 ataaccctg gtgatgaagt cattctctt gcaccgtttt atgattccta tgaagcaaca     540
```

```
ctctctatgg ctggtgctaa agtaaaagga atcactttac gtccaccgga cttctccatc    600
cctttggaag agcttaaagc tgcggtaact aacaagactc gagccatcct tatgaacact    660
ccgcacaacc cgaccgggaa gatgttcact agggaggagc ttgaaaccat tgcatctctc    720
tgcattgaaa acgatgtgct tgtgttctcg gatgaagtat acgataagct tgcgtttgaa    780
atggatcaca tttctatagc ttctcttccc ggtatgtatg aaagaactgt gaccatgaat    840
tccctgggaa agactttctc tttaaccgga tggaagatcg gctgggcgat tgcgccgcct    900
catctgactt ggggagttcg acaagcacac tcttacctca cattcgccac atcaacacca    960
gcacaatggg cagccgttgc agctctcaag gcaccagagt cttacttcaa agagctgaaa   1020
agagattaca atgtgaaaaa ggagactctg gttaagggtt tgaaggaagt cggatttaca   1080
gtgttcccat cgagcgggac ttactttgtg gttgctgatc acactccatt tggaatggag   1140
aacgatgttg ctttctgtga gtatcttatt gaagaagttg gggtcgttgc gatcccaacg   1200
agcgtctttt atctgaatcc agaagaaggg aagaatttgg ttaggtttgc gttctgtaaa   1260
gacgaagaga cgttgcgtgg tgcaattgag aggatgaagc agaagcttaa gagaaaagtc   1320
tga                                                                  1323
```

<210> SEQ ID NO 2
<211> LENGTH: 440
<212> TYPE: PRT
<213> ORGANISM: Aradopsis thaliana

<400> SEQUENCE: 2

```
Met Tyr Leu Asp Ile Asn Gly Val Met Ile Lys Gln Phe Ser Phe Lys
 1               5                  10                  15

Ala Ser Leu Leu Pro Phe Ser Ser Asn Phe Arg Gln Ser Ser Ala Lys
             20                  25                  30

Ile His Arg Pro Ile Gly Ala Thr Met Thr Thr Val Ser Thr Gln Asn
         35                  40                  45

Glu Ser Thr Gln Lys Pro Val Gln Val Ala Lys Arg Leu Glu Lys Phe
     50                  55                  60

Lys Thr Thr Ile Phe Thr Gln Met Ser Ile Leu Ala Val Lys His Gly
 65                  70                  75                  80

Ala Ile Asn Leu Gly Gln Gly Phe Pro Asn Phe Asp Gly Pro Asp Phe
                 85                  90                  95

Val Lys Glu Ala Ala Ile Gln Ala Ile Lys Asp Gly Lys Asn Gln Tyr
            100                 105                 110

Ala Arg Gly Tyr Gly Ile Pro Gln Leu Asn Ser Ala Ile Ala Ala Arg
        115                 120                 125

Phe Arg Glu Asp Thr Gly Leu Val Val Asp Pro Glu Lys Glu Val Thr
    130                 135                 140

Val Thr Ser Gly Cys Thr Glu Ala Ile Ala Ala Met Leu Gly Leu
145                 150                 155                 160

Ile Asn Pro Gly Asp Glu Val Ile Leu Phe Ala Pro Phe Tyr Asp Ser
                165                 170                 175

Tyr Glu Ala Thr Leu Ser Met Ala Gly Ala Lys Val Lys Gly Ile Thr
            180                 185                 190

Leu Arg Pro Pro Asp Phe Ser Ile Pro Leu Glu Glu Leu Lys Ala Ala
        195                 200                 205

Val Thr Asn Lys Thr Arg Ala Ile Leu Met Asn Thr Pro His Asn Pro
    210                 215                 220

Thr Gly Lys Met Phe Thr Arg Glu Glu Leu Glu Thr Ile Ala Ser Leu
```

```
225                 230                 235                 240
Cys Ile Glu Asn Asp Val Leu Val Phe Ser Asp Glu Val Tyr Asp Lys
                245                 250                 255
Leu Ala Phe Glu Met Asp His Ile Ser Ile Ala Ser Leu Pro Gly Met
                260                 265                 270
Tyr Glu Arg Thr Val Thr Met Asn Ser Leu Gly Lys Thr Phe Ser Leu
                275                 280                 285
Thr Gly Trp Lys Ile Gly Trp Ala Ile Ala Pro Pro His Leu Thr Trp
                290                 295                 300
Gly Val Arg Gln Ala His Ser Tyr Leu Thr Phe Ala Thr Ser Thr Pro
305                 310                 315                 320
Ala Gln Trp Ala Ala Val Ala Ala Leu Lys Ala Pro Glu Ser Tyr Phe
                325                 330                 335
Lys Glu Leu Lys Arg Asp Tyr Asn Val Lys Lys Glu Thr Leu Val Lys
                340                 345                 350
Gly Leu Lys Glu Val Gly Phe Thr Val Phe Pro Ser Ser Gly Thr Tyr
                355                 360                 365
Phe Val Val Ala Asp His Thr Pro Phe Gly Met Glu Asn Asp Val Ala
                370                 375                 380
Phe Cys Glu Tyr Leu Ile Glu Val Gly Val Val Ala Ile Pro Thr
385                 390                 395                 400
Ser Val Phe Tyr Leu Asn Pro Glu Glu Gly Lys Asn Leu Val Arg Phe
                405                 410                 415
Ala Phe Cys Lys Asp Glu Glu Thr Leu Arg Gly Ala Ile Glu Arg Met
                420                 425                 430
Lys Gln Lys Leu Lys Arg Lys Val
                435                 440

<210> SEQ ID NO 3
<211> LENGTH: 1374
<212> TYPE: DNA
<213> ORGANISM: Medicago sativa

<400> SEQUENCE: 3
atttccgttt tcgttttcat ttgattcatt gaatcaaatc gaatcgaatc tttaggattc      60
aatacagatt ccttagattt tactaagttt gaaaccaaaa ccaaaacatg tctctccttt     120
cagatcttat caaccttgac ctctccgaaa ccaccgagaa aatcatcgcc gaatacatat     180
ggattggtgg atctggtttg acttgagga gcaaagcaag gactctacca ggaccagtta     240
ctgacccttc acagcttccc aagtggaact atgatggttc cagcacaggt caagctcctg     300
gagaagatag tgaagttatt atctacccac aagccatttt caaggaccca tttagaaggg     360
gtaacaatat cttggttatg tgtgatgcat acactccagc tggagagccc attcccacca     420
acaagagaca tgcagctgcc aagattttca gccatcctga tgttgttgct gaagtaccat     480
ggtatggtat tgagcaagaa tacaccttgt gcagaaaga catcaattgg cctcttggtt     540
ggccagttgg tggttttcct ggacctcagg gaccatacta ttgtggagct ggtgctgaca     600
aggcatttgg ccgtgacatt gttgactcac attacaaagc ctgtctttat gccggcatca     660
acatcagtgg aatcaatggt gaagtgatgc ctggtcaatg gaattccaa gttggtccct     720 cagttggtat tctgctggg gatgagatat gggttgctcg ttacattttg gagaggatca     780
ctgaggttgc tggtgtggtg ctttcctttg acccaaaacc aattaagggt gattggaatg     840
gtgctggtgc tcacacaaat tacagcacca agtctatgag agaagatggt ggctatgaag     900
```

-continued

```
tcatcttgaa agcaattgag aagcttggga agaagcacaa ggagcacatt gctgcttatg    960
gagaaggcaa cgagcgtaga ttgacagggc gacatgagac agctgacatt aacaccttct   1020 tatgggggtgt tgcaaaccgt ggtgcgtcga ttagagttgg aagggacaca gagaaagcag   1080
ggaaaggtta tttcgaggat aggaggccat catctaacat ggatccatat gttgttactt   1140
ccatgattgc agacaccacc attctctgga aaccataagc caccacacac acatgcattg   1200
aagtatttga aagtcattgt tgattccgca ttagaatttg gtcattgttt tttctaggat   1260
ttggatttgt gttattgtta tggttcacac tttgtttgtt tgaatttgag gccttgttat   1320
aggtttcata tttctttctc ttgttctaag taaatgtcag aataataatg taat          1374
```

<210> SEQ ID NO 4
<211> LENGTH: 356
<212> TYPE: PRT
<213> ORGANISM: Medicago sativa

<400> SEQUENCE: 4

Met Ser Leu Leu Ser Asp Leu Ile Asn Leu Asp Leu Ser Glu Thr Thr
1               5                   10                  15

Glu Lys Ile Ile Ala Glu Tyr Ile Trp Ile Gly Gly Ser Gly Leu Asp
                20                  25                  30

Leu Arg Ser Lys Ala Arg Thr Leu Pro Gly Pro Val Thr Asp Pro Ser
            35                  40                  45

Gln Leu Pro Lys Trp Asn Tyr Asp Gly Ser Ser Thr Gly Gln Ala Pro
        50                  55                  60

Gly Glu Asp Ser Glu Val Ile Ile Tyr Pro Gln Ala Ile Phe Lys Asp
65                  70                  75                  80

Pro Phe Arg Arg Gly Asn Asn Ile Leu Val Met Cys Asp Ala Tyr Thr
                85                  90                  95

Pro Ala Gly Glu Pro Ile Pro Thr Asn Lys Arg His Ala Ala Ala Lys
            100                 105                 110

Ile Phe Ser His Pro Asp Val Val Ala Glu Val Pro Trp Tyr Gly Ile
        115                 120                 125

Glu Gln Glu Tyr Thr Leu Leu Gln Lys Asp Ile Asn Trp Pro Leu Gly
    130                 135                 140

Trp Pro Val Gly Gly Phe Pro Gly Pro Gln Gly Pro Tyr Tyr Cys Gly
145                 150                 155                 160

Ala Gly Ala Asp Lys Ala Phe Gly Arg Asp Ile Val Asp Ser His Tyr
                165                 170                 175

Lys Ala Cys Leu Tyr Ala Gly Ile Asn Ile Ser Gly Ile Asn Gly Glu
            180                 185                 190

Val Met Pro Gly Gln Trp Glu Phe Gln Val Gly Pro Ser Val Gly Ile
        195                 200                 205

Ser Ala Gly Asp Glu Ile Trp Val Ala Arg Tyr Ile Leu Glu Arg Ile
    210                 215                 220

Thr Glu Val Ala Gly Val Val Leu Ser Phe Asp Pro Lys Pro Ile Lys
225                 230                 235                 240

Gly Asp Trp Asn Gly Ala Gly Ala His Thr Asn Tyr Ser Thr Lys Ser
                245                 250                 255

Met Arg Glu Asp Gly Gly Tyr Glu Val Ile Leu Lys Ala Ile Glu Lys
            260                 265                 270

Leu Gly Lys Lys His Lys Glu His Ile Ala Ala Tyr Gly Glu Gly Asn
        275                 280                 285

Glu Arg Arg Leu Thr Gly Arg His Glu Thr Ala Asp Ile Asn Thr Phe 290                 295                 300
Leu Trp Gly Val Ala Asn Arg Gly Ala Ser Ile Arg Val Gly Arg Asp
305                 310                 315                 320

Thr Glu Lys Ala Gly Lys Gly Tyr Phe Glu Asp Arg Arg Pro Ser Ser
                325                 330                 335

Asn Met Asp Pro Tyr Val Val Thr Ser Met Ile Ala Asp Thr Thr Ile
                340                 345                 350

Leu Trp Lys Pro
        355

<210> SEQ ID NO 5
<211> LENGTH: 1419
<212> TYPE: DNA
<213> ORGANISM: Medicago sativa

<400> SEQUENCE: 5

| atcgatgaat | tcgagctcgg | tacccatttc | cgttttcgtt | ttcatttgat | tcattgaatc | 60 |
| aaatcgaatc | gaatctttag | gattcaatac | agattcctta | gatttactaa | agtttgaaac | 120 |
| caaaaccaaa | acatgtctct | cctttcagat | cttatcaacc | ttgacctctc | cgaaaccacc | 180 |
| gagaaaatca | tcgccgaata | catatggatt | ggtggatctg | gtttggactt | gaggagcaaa | 240 |
| gcaaggactc | taccaggacc | agttactgac | ccttcacagc | ttcccaagtg | aactatgat  | 300 |
| ggttccagca | caggtcaagc | tcctggagaa | gatagtgaag | ttattatcta | cccacaagcc | 360 |
| attttcaagg | acccatttag | aaggggtaac | aatatcttgg | ttatgtgtga | tgcatacact | 420 |
| ccagctggag | agcccattcc | caccaacaag | agacatgcag | ctgccaagat | tttcagccat | 480 |
| cctgatgttg | ttgctgaagt | accatggtat | ggtattgagc | aagaatacac | cttgttgcag | 540 |
| aaagacatca | attggcctct | tggttggcca | gttggtggtt | tcctggacc  | tcagggacca | 600 |
| tactattgtg | gagctggtgc | tgacaaggca | tttggccgtg | acattgttga | ctcacattac | 660 |
| aaagcctgtc | tttatgccgg | catcaacatc | agtggaatca | atggtgaagt | gatgcctggt | 720 |
| caatgggaat | tccaagttgg | tccctcagtt | ggtatctctg | ctggtgatga | gatatgggtt | 780 |
| gctcgttaca | ttttggagag | gatcactgag | gttgctggtg | tggtgctttc | ctttgaccca | 840 |
| aaaccaatta | agggtgattg | gaatggtgct | ggtgctcaca | caaattacag | caccaagtct | 900 |
| atgagagaag | atggtggcta | tgaagtcatc | ttgaaagcaa | ttgagaagct | tgggaagaag | 960 |
| cacaaggagc | acattgctgc | ttatggagaa | ggcaacgagc | gtagattgac | agggcgacat | 1020 |
| gagacagctg | acattaacac | cttcttatgg | ggtgttgcaa | accgtggtgc | gtcgattaga | 1080 |
| gttggaaggg | acacagagaa | agcagggaaa | ggttatttcg | aggataggag | gccatcatct | 1140 |
| aacatggatc | catatgttgt | tacttccatg | attgcagaca | ccaccattct | ctggaaacca | 1200 |
| taagccacca | cacacacatg | cattgaagta | tttgaaagtc | attgttgatt | ccgcattaga | 1260 |
| atttggtcat | tgtttttttct | aggatttgga | tttgtgttat | tgttatggtt | cacactttgt | 1320 |
| ttgtttgaat | ttgaggcctt | gttataggtt | tcatatttct | ttctcttgtt | ctaagtaaat | 1380 |
| gtcagaataa | taatgtaatg | gggatcctct | agagtcgag  |            |            | 1419 |

<210> SEQ ID NO 6
<211> LENGTH: 1302
<212> TYPE: DNA
<213> ORGANISM: Artificial Sequence
<220> FEATURE:
<223> OTHER INFORMATION: Synthetic plasmid vector sequence

<400> SEQUENCE: 6

```
aaaaaagaaa aaaaaaacat atcttgtttg tcagtatggg aagtttgaga taaggacgag      60
tgaggggtta aaattcagtg gccattgatt ttgtaatgcc aagaaccaca aaatccaatg     120
gttaccattc ctgtaagatg aggtttgcta actcttttg tccgttagat aggaagcctt     180
atcactatat atacaaggcg tcctaataac ctcttagtaa ccaattattt cagcaccatg     240
tctctgctct cagatctcgt taacctcaac ctcaccgatg ccaccgggaa atcatcgcc      300
gaatacatat ggatcggtgg atctggaatg gatatcagaa gcaaagccag gacactacca     360
ggaccagtga ctgatccatc aaagcttccc aagtggaact acgacggatc cagcaccggt     420
caggctgctg gagaagacag tgaagtcatt ctatacctc aggcaatatt caaggatccc      480
ttcaggaaag gcaacaacat cctggtgatg tgtgatgctt acacaccagc tggtgatcct     540
attccaacca acaagaggca caacgctgct aagatcttca gccaccccga cgttgccaag     600
gaggagcctt ggtatgggat tgagcaagaa tacactttga tgcaaaagga tgtgaactgg     660
ccaattggtt ggcctgttgg tggctaccct ggccctcagg gaccttacta ctgtggtgtg     720
ggagctgaca aagccattgg tcgtgacatt gtggatgctc actacaaggc ctgtctttac     780
gccggtattg gtatttctgg tatcaatgga gaagtcatgc caggccagtg ggagttccaa     840
gtcggccctg ttgagggtat tagttctggt gatcaagtct gggttgctcg ataccttctc     900
gagaggatca ctgagatctc tggtgtaatt gtcagcttcg acccgaaacc agtcccgggt     960
gactggaatg gagctggagc tcactgcaac tacagcacta gacaatgag aaacgatgga     1020
ggattagaag tgatcaagaa agcgataggg aagcttcagc tgaaacacaa agaacacatt    1080
gctgcttacg gtgaaggaaa cgagcgtcgt ctcactggaa agcacgaaac cgcagacatc    1140
aacacattct cttggggagt cgcgaaccgt ggagcgtcag tgagtggg acgtgacaca      1200
gagaaggaag gtaaagggta cttcgaagac agaaggccag cttctaacat ggatccttac    1260
gttgtcacct ccatgatcgc tgagacgacc atactcggtt ga                      1302
```

<210> SEQ ID NO 7
<211> LENGTH: 364
<212> TYPE: PRT
<213> ORGANISM: Arabidopsis thaliana
<220> FEATURE:
<221> NAME/KEY: SITE
<222> LOCATION: (1)..(9)
<223> OTHER INFORMATION: amino terminal 9 amino acids vector encoded
      sequence

<400> SEQUENCE: 7

Met Val Asp Leu Arg Asn Arg Arg Thr Ser Met Ser Leu Leu Ser Asp
1               5                   10                  15

Leu Val Asn Leu Asn Leu Thr Asp Ala Thr Gly Lys Ile Ile Ala Glu
            20                  25                  30

Tyr Ile Trp Ile Gly Gly Ser Gly Met Asp Ile Arg Ser Lys Ala Arg
        35                  40                  45

Thr Leu Pro Gly Pro Val Thr Asp Pro Ser Lys Leu Pro Lys Trp Asn
    50                  55                  60

Tyr Asp Gly Ser Ser Thr Gly Gln Ala Ala Gly Glu Asp Ser Glu Val
65                  70                  75                  80

Ile Leu Tyr Pro Gln Ala Ile Phe Lys Asp Pro Phe Arg Lys Gly Asn
                85                  90                  95

Asn Ile Leu Val Met Cys Asp Ala Tyr Thr Pro Ala Gly Asp Pro Ile
            100                 105                 110

```
Pro Thr Asn Lys Arg His Asn Ala Ala Lys Ile Phe Ser His Pro Asp
            115                 120                 125

Val Ala Lys Glu Glu Pro Trp Tyr Gly Ile Gln Glu Tyr Thr Leu
        130                 135                 140

Met Gln Lys Asp Val Asn Trp Pro Ile Gly Trp Pro Val Gly Gly Tyr
145                 150                 155                 160

Pro Gly Pro Gln Gly Pro Tyr Tyr Cys Gly Val Gly Ala Asp Lys Ala
                165                 170                 175

Ile Gly Arg Asp Ile Val Asp Ala His Tyr Lys Ala Cys Leu Tyr Ala
            180                 185                 190

Gly Ile Gly Ile Ser Gly Ile Asn Gly Glu Val Met Pro Gly Gln Trp
        195                 200                 205

Glu Phe Gln Val Gly Pro Val Glu Gly Ile Ser Ser Gly Asp Gln Val
    210                 215                 220

Trp Val Ala Arg Tyr Leu Leu Glu Arg Ile Thr Glu Ile Ser Gly Val
225                 230                 235                 240

Ile Val Ser Phe Asp Pro Lys Pro Val Pro Gly Asp Trp Asn Gly Ala
                245                 250                 255

Gly Ala His Cys Asn Tyr Ser Thr Lys Thr Met Arg Asn Asp Gly Gly
            260                 265                 270

Leu Glu Val Ile Lys Lys Ala Ile Gly Lys Leu Gln Leu Lys His Lys
        275                 280                 285

Glu His Ile Ala Ala Tyr Gly Glu Gly Asn Glu Arg Arg Leu Thr Gly
    290                 295                 300

Lys His Glu Thr Ala Asp Ile Asn Thr Phe Ser Trp Gly Val Ala Asn
305                 310                 315                 320

Arg Gly Ala Ser Val Arg Val Gly Arg Asp Thr Glu Lys Glu Gly Lys
                325                 330                 335

Gly Tyr Phe Glu Asp Arg Arg Pro Ala Ser Asn Met Asp Pro Tyr Val
            340                 345                 350

Val Thr Ser Met Ile Ala Glu Thr Thr Ile Leu Gly
        355                 360

<210> SEQ ID NO 8
<211> LENGTH: 1817
<212> TYPE: DNA
<213> ORGANISM: Artificial Sequence
<220> FEATURE:
<223> OTHER INFORMATION: Synthetic plasmid vector sequence including
      vitis vinifera GPT coding sequence

<400> SEQUENCE: 8
aaaaaagaaa aaaaaaacat atcttgtttg tcagtatggg aagtttgaga taaggacgag      60 tgagggggtta aaattcagtg gccattgatt ttgtaatgcc aagaaccaca aaatccaatg    120
gttaccattc ctgtaagatg aggtttgcta actcttttg tccgttagat aggaagcctt     180
atcactatat atacaaggcg tcctaataac ctcttagtaa ccaattattt cagcaccatg    240
gtagatctga gggtaaattt ctagttttc tccttcattt tcttggttag dacccttttc    300 tcttttatt tttttgagct tgatctttc tttaaactga tctattttt aattgattgg      360 ttatggtgta aatattacat agcttttaact gataatctga ttactttatt tcgtgtgtct  420
atgatgatga tgatagttac agaaccgacg aactagtatg cagctctctc aatgtacctg   480
gacattccca gagttgctta aaagaccagc cttttttaagg aggagtattg atagtatttc  540
gagtagaagt aggtccagct ccaagtatcc atctttcatg gcgtccgcat caacggtctc    600
```

```
cgctccaaat acggaggctg agcagaccca taaccccccct caacctctac aggttgcaaa    660
gcgcttggag aaattcaaaa caacaatctt tactcaaatg agcatgcttg ccatcaaaca    720
tggagcaata aaccttggcc aagggtttcc caactttgat ggtcctgagt ttgtcaaaga    780
agcagcaatt caagccatta aggatgggaa aaaccaatat gctcgtggat atggagttcc    840
tgatctcaac tctgctgttg ctgatagatt caagaaggat acaggactcg tggtggaccc    900
cgagaaggaa gttactgtta cttctggatg tacagaagca attgctgcta ctatgctagg    960
cttgataaat cctggtgatg aggtgatcct ctttgctcca ttttatgatt cctatgaagc   1020
cactctatcc atggctggtg cccaaataaa atccatcact ttacgtcctc cggattttgc   1080
tgtgcccatg gatgagctca gtctgcaat ctcaaagaat acccgtgcaa tccttataaa   1140
cactccccat aaccccacag gaaagatgtt cacaagggag gaactgaatg tgattgcatc   1200
cctctgcatt gagaatgatg tgttggtgtt tactgatgaa gtttacgaca agttggcttt   1260
cgaaatggat cacatttcca tggcttctct tcctgggatg tacgagagga ccgtgactat   1320
gaattcctta gggaaaactt tctccctgac tggatgaag attggttgga cagtagctcc   1380
cccacacctg acatggggag tgaggcaagc ccactcattc ctcacgtttg ctacctgcac   1440
cccaatgcaa tgggcagctg caacagcct ccgggcccca gactcttact atgaagagct   1500
aaagagagat tacagtgcaa agaaggcaat cctggtggag ggattgaagg ctgtcggttt   1560
cagggtatac ccatcaagtg ggacctattt tgtggtggtg gatcacaccc catttgggtt   1620
gaaagacgat attgcgtttt gtgagtatct gatcaaggaa gttggggtgg tagcaattcc   1680
gacaagcgtt ttctacttac acccagaaga tggaaagaac cttgtgaggt ttaccttctg   1740
taaagacgag ggaactctga gagctgcagt tgaaaggatg aaggagaaac tgaagcctaa   1800
acaatagggg cacgtga                                                  1817

<210> SEQ ID NO 9
<211> LENGTH: 459
<212> TYPE: PRT
<213> ORGANISM: Vitis vinifera

<400> SEQUENCE: 9

Met Val Asp Leu Arg Asn Arg Arg Thr Ser Met Gln Leu Ser Gln Cys
1               5                   10                  15

Thr Trp Thr Phe Pro Glu Leu Leu Lys Arg Pro Ala Phe Leu Arg Arg
            20                  25                  30

Ser Ile Asp Ser Ile Ser Ser Arg Ser Arg Ser Ser Lys Tyr Pro
        35                  40                  45

Ser Phe Met Ala Ser Ala Ser Thr Val Ser Ala Pro Asn Thr Glu Ala
    50                  55                  60

Glu Gln Thr His Asn Pro Gln Pro Leu Val Ala Lys Arg Leu
65                  70                  75                  80

Glu Lys Phe Lys Thr Thr Ile Phe Thr Gln Met Ser Met Leu Ala Ile
                85                  90                  95

Lys His Gly Ala Ile Asn Leu Gly Gln Gly Phe Pro Asn Phe Asp Gly
            100                 105                 110

Pro Glu Phe Val Lys Glu Ala Ala Ile Gln Ala Ile Lys Asp Gly Lys
        115                 120                 125

Asn Gln Tyr Ala Arg Gly Tyr Gly Val Pro Asp Leu Asn Ser Ala Val
    130                 135                 140

Ala Asp Arg Phe Lys Lys Asp Thr Gly Leu Val Val Asp Pro Glu Lys
145                 150                 155                 160
```

Glu Val Thr Val Thr Ser Gly Cys Thr Glu Ala Ile Ala Ala Thr Met
              165                 170                 175

Leu Gly Leu Ile Asn Pro Gly Asp Glu Val Ile Leu Phe Ala Pro Phe
            180                 185                 190

Tyr Asp Ser Tyr Glu Ala Thr Leu Ser Met Ala Gly Ala Gln Ile Lys
        195                 200                 205

Ser Ile Thr Leu Arg Pro Pro Asp Phe Ala Val Pro Met Asp Glu Leu
    210                 215                 220

Lys Ser Ala Ile Ser Lys Asn Thr Arg Ala Ile Leu Ile Asn Thr Pro
225                 230                 235                 240

His Asn Pro Thr Gly Lys Met Phe Thr Arg Glu Glu Leu Asn Val Ile
                245                 250                 255

Ala Ser Leu Cys Ile Glu Asn Asp Val Leu Val Phe Thr Asp Glu Val
            260                 265                 270

Tyr Asp Lys Leu Ala Phe Glu Met Asp His Ile Ser Met Ala Ser Leu
        275                 280                 285

Pro Gly Met Tyr Glu Arg Thr Val Thr Met Asn Ser Leu Gly Lys Thr
    290                 295                 300

Phe Ser Leu Thr Gly Trp Lys Ile Gly Trp Thr Val Ala Pro Pro His
305                 310                 315                 320

Leu Thr Trp Gly Val Arg Gln Ala His Ser Phe Leu Thr Phe Ala Thr
                325                 330                 335

Cys Thr Pro Met Gln Trp Ala Ala Thr Ala Leu Arg Ala Pro Asp
            340                 345                 350

Ser Tyr Tyr Glu Glu Leu Lys Arg Asp Tyr Ser Ala Lys Lys Ala Ile
        355                 360                 365

Leu Val Glu Gly Leu Lys Ala Val Gly Phe Arg Val Tyr Pro Ser Ser
    370                 375                 380

Gly Thr Tyr Phe Val Val Asp His Thr Pro Phe Gly Leu Lys Asp
385                 390                 395                 400

Asp Ile Ala Phe Cys Glu Tyr Leu Ile Lys Glu Val Gly Val Val Ala
                405                 410                 415

Ile Pro Thr Ser Val Phe Tyr Leu His Pro Glu Asp Gly Lys Asn Leu
            420                 425                 430

Val Arg Phe Thr Phe Cys Lys Asp Glu Gly Thr Leu Arg Ala Ala Val
        435                 440                 445

Glu Arg Met Lys Glu Lys Leu Lys Pro Lys Gln
    450                 455

<210> SEQ ID NO 10
<211> LENGTH: 1446
<212> TYPE: DNA
<213> ORGANISM: Artificial Sequence
<220> FEATURE:
<223> OTHER INFORMATION: Synthetic DNA encoding Oryza sativa GPT
      protein, codons optimized for expression in E. coli

<400> SEQUENCE: 10
atgtggatga acctggcagg ctttctggca accccggcaa ccgcaaccgc aacccgtcat      60
gaaatgccgc tgaacccgag cagcagcgcg agctttctgc tgagcagcct gcgtcgtagc     120
ctggtggcga gcctgcgtaa agcgagcccg gcagcagcag cagcactgag cccgatggca     180
agcgcaagca ccgtggcagc agaaaacggt gcagcaaaag cagcagcaga aaacagcag     240 cagcagccgg tgcaggtggc gaaacgtctg gaaaaattta aaccaccat ttttacccag     300

-continued

```
atgagcatgc tggcgattaa acatggcgcg attaacctgg gccagggctt tccgaacttt      360
gatggcccgg attttgtgaa agaagcggcg attcaggcga ttaacgcggg caaaaaccag      420
tatgcgcgtg gctatggcgt gccggaactg aacagcgcga ttgcggaacg ttttctgaaa      480
gatagcggcc tgcaggtgga tccggaaaaa gaagtgaccg tgaccagcgg ctgcaccgaa      540
gcgattgcgg cgaccattct gggcctgatt aacccgggcg atgaagtgat tctgtttgcg      600
ccgtttatg atagctatga agcgaccctg agcatggcgg cgcgaacgt gaaagcgatt        660
accctgcgtc cgccggattt tagcgtgccg ctggaagaac tgaaagcggc cgtgagcaaa      720
aacacccgtg cgattatgat aacaccccg cataacccga ccggcaaaat gtttacccgt      780
gaagaactgg aatttattgc gaccctgtgc aaagaaaacg atgtgctgct gtttgcggat      840
gaagtgtatg ataaactggc gtttgaagcg gatcatatta gcatggcgag cattccgggc      900
atgtatgaac gtaccgtgac catgaacagc ctgggcaaaa cctttagcct gaccggctgg      960
aaaattggct gggcgattgc gccgccgcat ctgacctggg cgtgcgtca ggcacatagc      1020
tttctgacct ttgcaacctg caccccgatg caggcagccg ccgcagcagc actgcgtgca      1080
ccggatagct attatgaaga actgcgtcgt gattatggcg cgaaaaaagc gctgctggtg      1140
aacggcctga agatgcgggg ctttattgtg tatccgagca cggcaccta ttttgtgatg       1200
gtggatcata ccccgtttgg ctttgataac gatattgaat tttgcgaata tctgattcgt      1260
gaagtgggcg tggtggcgat tccgccgagc gtgttttatc tgaacccgga agatggcaaa      1320
aacctggtgc gttttacctt ttgcaaagat gatgaaaccc tgcgtgcggc ggtggaacgt      1380
atgaaaacca aactgcgtaa aaaaaagctt gcggccgcac tcgagcacca ccaccaccac      1440
cactga                                                                1446
```

<210> SEQ ID NO 11
<211> LENGTH: 481
<212> TYPE: PRT
<213> ORGANISM: Artificial Sequence
<220> FEATURE:
<223> OTHER INFORMATION: Oryza sativa GPT protein sequence with amino-
      and carboxyl-terminal vector sequences <400> SEQUENCE: 11

```
Met Trp Met Asn Leu Ala Gly Phe Leu Ala Thr Pro Ala Thr Ala Thr
1               5                   10                  15

Ala Thr Arg His Glu Met Pro Leu Asn Pro Ser Ser Ala Ser Phe
            20                  25                  30

Leu Leu Ser Ser Leu Arg Arg Ser Leu Val Ala Ser Leu Arg Lys Ala
        35                  40                  45

Ser Pro Ala Ala Ala Ala Leu Ser Pro Met Ala Ser Ala Ser Thr
    50                  55                  60

Val Ala Ala Glu Asn Gly Ala Ala Lys Ala Ala Glu Lys Gln Gln
65                  70                  75                  80

Gln Gln Pro Val Gln Val Ala Lys Arg Leu Glu Lys Phe Lys Thr Thr
                85                  90                  95

Ile Phe Thr Gln Met Ser Met Leu Ala Ile Lys His Gly Ala Ile Asn
            100                 105                 110

Leu Gly Gln Gly Phe Pro Asn Phe Asp Gly Pro Asp Phe Val Lys Glu
        115                 120                 125

Ala Ala Ile Gln Ala Ile Asn Ala Gly Lys Asn Gln Tyr Ala Arg Gly
    130                 135                 140

Tyr Gly Val Pro Glu Leu Asn Ser Ala Ile Ala Glu Arg Phe Leu Lys
```

```
                145                 150                 155                 160
        Asp Ser Gly Leu Gln Val Asp Pro Glu Lys Glu Val Thr Val Thr Ser
                        165                 170                 175

Gly Cys Thr Glu Ala Ile Ala Ala Thr Ile Leu Gly Leu Ile Asn Pro
                        180                 185                 190

Gly Asp Glu Val Ile Leu Phe Ala Pro Phe Tyr Asp Ser Tyr Glu Ala
                        195                 200                 205

Thr Leu Ser Met Ala Gly Ala Asn Val Lys Ala Ile Thr Leu Arg Pro
                        210                 215                 220

Pro Asp Phe Ser Val Pro Leu Glu Glu Leu Lys Ala Ala Val Ser Lys
        225                 230                 235                 240

Asn Thr Arg Ala Ile Met Ile Asn Thr Pro His Asn Pro Thr Gly Lys
                        245                 250                 255

Met Phe Thr Arg Glu Glu Leu Glu Phe Ile Ala Thr Leu Cys Lys Glu
                        260                 265                 270

Asn Asp Val Leu Leu Phe Ala Asp Glu Val Tyr Asp Lys Leu Ala Phe
                        275                 280                 285

Glu Ala Asp His Ile Ser Met Ala Ser Ile Pro Gly Met Tyr Glu Arg
                        290                 295                 300

Thr Val Thr Met Asn Ser Leu Gly Lys Thr Phe Ser Leu Thr Gly Trp
        305                 310                 315                 320

Lys Ile Gly Trp Ala Ile Ala Pro Pro His Leu Thr Trp Gly Val Arg
                        325                 330                 335

Gln Ala His Ser Phe Leu Thr Phe Ala Thr Cys Thr Pro Met Gln Ala
                        340                 345                 350

Ala Ala Ala Ala Leu Arg Ala Pro Asp Ser Tyr Tyr Glu Glu Leu
                        355                 360                 365

Arg Arg Asp Tyr Gly Ala Lys Lys Ala Leu Leu Val Asn Gly Leu Lys
                        370                 375                 380

Asp Ala Gly Phe Ile Val Tyr Pro Ser Ser Gly Thr Tyr Phe Val Met
        385                 390                 395                 400

Val Asp His Thr Pro Phe Gly Phe Asp Asn Asp Ile Glu Phe Cys Glu
                        405                 410                 415

Tyr Leu Ile Arg Glu Val Gly Val Val Ala Ile Pro Pro Ser Val Phe
                        420                 425                 430

Tyr Leu Asn Pro Glu Asp Gly Lys Asn Leu Val Arg Phe Thr Phe Cys
                        435                 440                 445

Lys Asp Asp Glu Thr Leu Arg Ala Ala Val Glu Arg Met Lys Thr Lys
        450                 455                 460

Leu Arg Lys Lys Lys Leu Ala Ala Ala Leu Glu His His His His
        465                 470                 475                 480

His

<210> SEQ ID NO 12
<211> LENGTH: 1251
<212> TYPE: DNA
<213> ORGANISM: Artificial Sequence
<220> FEATURE:
<223> OTHER INFORMATION: Synthetic DNA encoding Glycine max GPT protein,
      codons optimized for expression in E. coli

<400> SEQUENCE: 12
atgcatcatc accatcacca tggtaagcct atccctaacc ctctcctcgg tctcgattct      60
acggaaaacc tgtattttca gggaattgat cccttcaccg cgaaacgtct ggaaaaattt     120
```

```
cagaccacca ttttaccca gatgagcctg ctggcgatta acatggcgc gattaacctg    180
ggccagggct ttccgaactt tgatggcccg gaatttgtga agaagcggc gattcaggcg    240
attcgtgatg gcaaaaacca gtatgcgcgt ggctatggcg tgccggatct gaacattgcg    300
attgcggaac gttttaaaaa agataccggc ctggtggtgg atccggaaaa agaaattacc    360
gtgaccagcg gctgcaccga agcgattgcg gcgaccatga ttggcctgat taacccgggc    420
gatgaagtga ttatgtttgc gccgttttat gatagctatg aagcgaccct gagcatggcg    480
ggcgcgaaag tgaaaggcat taccctgcgt ccgccggatt ttgcggtgcc gctggaagaa    540
ctgaaaagca ccattagcaa aacacccgt gcgattctga ttaacacccc gcataacccg    600
accggcaaaa tgtttacccg tgaagaactg aactgcattg cgagcctgtg cattgaaaac    660
gatgtgctgg tgtttaccga tgaagtgtat gataaactgg cgtttgatat ggaacatatt    720
agcatggcga gcctgccggg catgtttgaa cgtaccgtga ccctgaacag cctgggcaaa    780
acctttagcc tgaccggctg gaaaattggc tgggcgattg cgccgccgca tctgagctgg    840
ggcgtgcgtc aggcgcatgc gtttctgacc tttgcaaccg cacatccgtt tcagtgcgca    900
gcagcagcag cactgcgtgc accggatagc tattatgtgg aactgaaacg tgattatatg    960
gcgaaacgtg cgattctgat tgaaggcctg aaagcggtgg gctttaaagt gtttccgagc    1020
agcggcacct atttgtggt ggtggatcat accccgtttg gcctggaaaa cgatgtggcg    1080
ttttgcgaat atctggtgaa agaagtgggc gtggtggcga ttccgaccag cgtgtttat    1140
ctgaacccgg aagaaggcaa aaacctggtg cgttttacct tttgcaaaga tgaagaaacc    1200
attcgtagcg cggtggaacg tatgaaagcg aaactgcgta aagtcgacta a           1251
```

<210> SEQ ID NO 13
<211> LENGTH: 416
<212> TYPE: PRT
<213> ORGANISM: Artificial Sequence
<220> FEATURE:
<223> OTHER INFORMATION: Glycine max GPT amino acid sequence and amino-
      terminal vector sequence

<400> SEQUENCE: 13

```
Met His His His His His His Gly Lys Pro Ile Pro Asn Pro Leu Leu
1               5                   10                  15

Gly Leu Asp Ser Thr Glu Asn Leu Tyr Phe Gln Gly Ile Asp Pro Phe
            20                  25                  30

Thr Ala Lys Arg Leu Glu Lys Phe Gln Thr Thr Ile Phe Thr Gln Met
        35                  40                  45

Ser Leu Leu Ala Ile Lys His Gly Ala Ile Asn Leu Gly Gln Gly Phe
    50                  55                  60

Pro Asn Phe Asp Gly Pro Glu Phe Val Lys Glu Ala Ala Ile Gln Ala
65                  70                  75                  80

Ile Arg Asp Gly Lys Asn Gln Tyr Ala Arg Gly Tyr Gly Val Pro Asp
                85                  90                  95

Leu Asn Ile Ala Ile Ala Glu Arg Phe Lys Lys Asp Thr Gly Leu Val
            100                 105                 110

Val Asp Pro Glu Lys Glu Ile Thr Val Thr Ser Gly Cys Thr Glu Ala
        115                 120                 125

Ile Ala Ala Thr Met Ile Gly Leu Ile Asn Pro Gly Asp Glu Val Ile
    130                 135                 140

Met Phe Ala Pro Phe Tyr Asp Ser Tyr Glu Ala Thr Leu Ser Met Ala
145                 150                 155                 160
```

Gly Ala Lys Val Lys Gly Ile Thr Leu Arg Pro Pro Asp Phe Ala Val
            165                 170                 175
Pro Leu Glu Glu Leu Lys Ser Thr Ile Ser Lys Asn Thr Arg Ala Ile
        180                 185                 190
Leu Ile Asn Thr Pro His Asn Pro Thr Gly Lys Met Phe Thr Arg Glu
    195                 200                 205
Glu Leu Asn Cys Ile Ala Ser Leu Cys Ile Glu Asn Asp Val Leu Val
210                 215                 220
Phe Thr Asp Glu Val Tyr Asp Lys Leu Ala Phe Asp Met Glu His Ile
225                 230                 235                 240
Ser Met Ala Ser Leu Pro Gly Met Phe Glu Arg Thr Val Thr Leu Asn
                245                 250                 255
Ser Leu Gly Lys Thr Phe Ser Leu Thr Gly Trp Lys Ile Gly Trp Ala
            260                 265                 270
Ile Ala Pro Pro His Leu Ser Trp Gly Val Arg Gln Ala His Ala Phe
        275                 280                 285
Leu Thr Phe Ala Thr Ala His Pro Phe Gln Cys Ala Ala Ala Ala Ala
    290                 295                 300
Leu Arg Ala Pro Asp Ser Tyr Tyr Val Glu Leu Lys Arg Asp Tyr Met
305                 310                 315                 320
Ala Lys Arg Ala Ile Leu Ile Glu Gly Leu Lys Ala Val Gly Phe Lys
                325                 330                 335
Val Phe Pro Ser Ser Gly Thr Tyr Phe Val Val Val Asp His Thr Pro
            340                 345                 350
Phe Gly Leu Glu Asn Asp Val Ala Phe Cys Glu Tyr Leu Val Lys Glu
        355                 360                 365
Val Gly Val Val Ala Ile Pro Thr Ser Val Phe Tyr Leu Asn Pro Glu
    370                 375                 380
Glu Gly Lys Asn Leu Val Arg Phe Thr Phe Cys Lys Asp Glu Glu Thr
385                 390                 395                 400
Ile Arg Ser Ala Val Glu Arg Met Lys Ala Lys Leu Arg Lys Val Asp
                405                 410                 415

<210> SEQ ID NO 14
<211> LENGTH: 1278
<212> TYPE: DNA
<213> ORGANISM: Hordeum vulgare

<400> SEQUENCE: 14
atggtagatc tgaggaaccg acgaactagt atggcatccg ccccgcctc cgcctccgcg      60
gccctctcca ccgccgcccc cgccgacaac ggggccgcca agcccacgga gcagcggccg     120
gtacaggtgg ctaagcgatt ggagaagttc aaaacaacaa ttttcacaca gatgagcatg     180
ctcgcagtga agcatggagc aataaacctt ggacagggt tcccaattt tgatggccct      240
gactttgtca agatgctgc tattgaggct atcaaagctg gaaagaatca gtatgcaaga     300
ggatatggtg tgcctgaatt gaactcagct gttgctgaga gatttctcaa ggacagtgga     360
ttgcacatcg atcctgataa ggaagttact gttacatctg ggtgcacaga agcaatagct     420
gcaacgatat tgggtctgat caaccctggg gatgaagtca tactgtttgc tccattctat     480
gattcttatg aggctacact gtccatggct ggtgcgaatg tcaaagccat acactccgc     540
cctccggact tgcagtccc tcttgaagag ctaaaggctg cagtctcgaa gaataccaga     600
gcaataatga ttaatacacc tcacaaccct accgggaaaa tgttcacaag ggaggaactt     660
gagttcattg ctgatctctg caaggaaaat gacgtgttgc tctttgccga tgaggtctac     720

```
gacaagctgg cgtttgaggc ggatcacata tcaatggctt ctattcctgg catgtatgag    780
aggaccgtca ctatgaactc cctggggaag acgttctcct tgaccggatg aagatcggc     840 tgggcgatag caccaccgca cctgacatgg ggcgtaaggc aggcacactc cttcctcaca    900
ttcgccacct ccacgccgat gcaatcagca gcggcggcgg ccctgagagc accggacagc    960
tactttgagg agctgaagag ggactacggc gcaaagaaag cgctgctggt ggacgggctc   1020
aaggcggcgg gcttcatcgt ctaccctccg agcggaacct acttcatcat ggtcgaccac   1080
accccgttcg ggttcgacaa cgacgtcgag ttctgcgagt acttgatccg cgaggtcggc   1140
gtcgtggcca tcccgccaag cgtgttctac ctgaacccgg aggacgggaa gaacctggtg   1200
aggttcacct tctgcaagga cgacgacacg ctaagggcgg cggtggacag gatgaaggcc   1260
aagctcagga gaaatga                                                   1278
```

```
<210> SEQ ID NO 15
<211> LENGTH: 425
<212> TYPE: PRT
<213> ORGANISM: Hordeum vulgare

<400> SEQUENCE: 15

Met Val Asp Leu Arg Asn Arg Arg Thr Ser Met Ala Ser Ala Pro Ala
1               5                   10                  15

Ser Ala Ser Ala Ala Leu Ser Thr Ala Ala Pro Ala Asp Asn Gly Ala
            20                  25                  30

Ala Lys Pro Thr Glu Gln Arg Pro Val Gln Val Ala Lys Arg Leu Glu
        35                  40                  45

Lys Phe Lys Thr Thr Ile Phe Thr Gln Met Ser Met Leu Ala Val Lys
    50                  55                  60

His Gly Ala Ile Asn Leu Gly Gln Gly Phe Pro Asn Phe Asp Gly Pro
65                  70                  75                  80

Asp Phe Val Lys Asp Ala Ala Ile Glu Ala Ile Lys Ala Gly Lys Asn
                85                  90                  95

Gln Tyr Ala Arg Gly Tyr Gly Val Pro Glu Leu Asn Ser Ala Val Ala
            100                 105                 110

Glu Arg Phe Leu Lys Asp Ser Gly Leu His Ile Asp Pro Asp Lys Glu
        115                 120                 125

Val Thr Val Thr Ser Gly Cys Thr Glu Ala Ile Ala Ala Thr Ile Leu
    130                 135                 140

Gly Leu Ile Asn Pro Gly Asp Glu Val Ile Leu Phe Ala Pro Phe Tyr
145                 150                 155                 160

Asp Ser Tyr Glu Ala Thr Leu Ser Met Ala Gly Ala Asn Val Lys Ala
                165                 170                 175

Ile Thr Leu Arg Pro Pro Asp Phe Ala Val Pro Leu Glu Glu Leu Lys
            180                 185                 190

Ala Ala Val Ser Lys Asn Thr Arg Ala Ile Met Ile Asn Thr Pro His
        195                 200                 205

Asn Pro Thr Gly Lys Met Phe Thr Arg Glu Glu Leu Glu Phe Ile Ala
    210                 215                 220

Asp Leu Cys Lys Glu Asn Asp Val Leu Leu Phe Ala Asp Glu Val Tyr
225                 230                 235                 240

Asp Lys Leu Ala Phe Glu Ala Asp His Ile Ser Met Ala Ser Ile Pro
                245                 250                 255

Gly Met Tyr Glu Arg Thr Val Thr Met Asn Ser Leu Gly Lys Thr Phe
            260                 265                 270
```

```
Ser Leu Thr Gly Trp Lys Ile Gly Trp Ala Ile Ala Pro Pro His Leu
    275                 280                 285

Thr Trp Gly Val Arg Gln Ala His Ser Phe Leu Thr Phe Ala Thr Ser
290                 295                 300

Thr Pro Met Gln Ser Ala Ala Ala Ala Leu Arg Ala Pro Asp Ser
305                 310                 315                 320

Tyr Phe Glu Glu Leu Lys Arg Asp Tyr Gly Ala Lys Lys Ala Leu Leu
                325                 330                 335

Val Asp Gly Leu Lys Ala Ala Gly Phe Ile Val Tyr Pro Ser Ser Gly
            340                 345                 350

Thr Tyr Phe Ile Met Val Asp His Thr Pro Phe Gly Phe Asp Asn Asp
        355                 360                 365

Val Glu Phe Cys Glu Tyr Leu Ile Arg Glu Val Gly Val Val Ala Ile
370                 375                 380

Pro Pro Ser Val Phe Tyr Leu Asn Pro Glu Asp Gly Lys Asn Leu Val
385                 390                 395                 400

Arg Phe Thr Phe Cys Lys Asp Asp Thr Leu Arg Ala Ala Val Asp
                405                 410                 415

Arg Met Lys Ala Lys Leu Arg Lys Lys
                420                 425

<210> SEQ ID NO 16
<211> LENGTH: 1200
<212> TYPE: DNA
<213> ORGANISM: Artificial Sequence
<220> FEATURE:
<223> OTHER INFORMATION: Synthetic DNA encoding Danio rerio GPT protein,
      codons optimized for expression in E. coli, including 5' and 3'
      vector sequences

<400> SEQUENCE: 16
atgtccgtgg cgaaacgtct ggaaaaattt aaaaccacca tttttaccca gatgagcatg      60
ctggcgatta acatggcgc gattaacctg gccagggct ttccgaactt tgatggcccg       120
gattttgtga agaagcggc gattcaggcg attcgtgatg caacaacca gtatgcgcgt       180 ggctatggcg tgccggatct gaacattgcg attagcgaac gttataaaaa agataccggc     240
ctggcggtgg atccggaaaa agaaattacc gtgaccagcg gctgcaccga agcgattgcg     300
gcgaccgtgc tgggcctgat taacccgggc gatgaagtga ttgtgtttgc gccgtttat     360 gatagctatg aagcgaccct gagcatggcg ggcgcgaaag tgaaaggcat taccctgcgt     420
ccgccggatt ttgcgctgcc gattgaagaa ctgaaaagca ccattagcaa aacacccgt     480 gcgattctgc tgaacacccc gcataaccccg accggcaaaa tgtttacccc ggaagaactg     540
aacaccattg cgagcctgtg cattgaaaac gatgtgctgg tgtttagcga tgaagtgtat     600
gataaactgg cgtttgatat ggaacatatt agcattgcga gcctgccggg catgtttgaa     660
cgtaccgtga ccatgaacag cctgggcaaa acctttagcc tgaccggctg aaaattggc     720 tgggcgattg cgccgccgca tctgacctgg ggcgtgcgtc aggcgcatgc gtttctgacc     780
tttgcaacca gcaacccgat gcagtgggca gcagcagtgg cactgcgtgc accggatagc     840
tattataccg aactgaaacg tgattatatg gcgaaacgta gcattctggt ggaaggcctg     900
aaagcggtgg gctttaaagt gtttccgagc agcggcacct attttgtggt ggtggatcat     960
accccgtttg gccatgaaaa cgatattgcg ttttgcgaat atctggtgaa agaagtgggc    1020
gtggtggcga ttccgaccag cgtgttttat ctgaacccgg aagaaggcaa aaacctggtg    1080
```

```
cgtttaccct tttgcaaaga tgaaggcacc ctgcgtgcgg cggtggatcg tatgaaagaa    1140
aaactgcgta aagtcgacaa gcttgcggcc gcactcgagc accaccacca ccaccactga   1200
```

<210> SEQ ID NO 17
<211> LENGTH: 399
<212> TYPE: PRT
<213> ORGANISM: Danio rerio
<220> FEATURE:
<221> NAME/KEY: MISC_FEATURE
<222> LOCATION: (1)..(399)
<223> OTHER INFORMATION: Amino- and carboxy-terminal amino acids shown

<400> SEQUENCE: 17

```
Met Ser Val Ala Lys Arg Leu Glu Lys Phe Lys Thr Thr Ile Phe Thr
1               5                   10                  15

Gln Met Ser Met Leu Ala Ile Lys His Gly Ala Ile Asn Leu Gly Gln
            20                  25                  30

Gly Phe Pro Asn Phe Asp Gly Pro Asp Phe Val Lys Glu Ala Ala Ile
        35                  40                  45

Gln Ala Ile Arg Asp Gly Asn Asn Gln Tyr Ala Arg Gly Tyr Gly Val
    50                  55                  60

Pro Asp Leu Asn Ile Ala Ile Ser Glu Arg Tyr Lys Lys Asp Thr Gly
65                  70                  75                  80

Leu Ala Val Asp Pro Glu Lys Glu Ile Thr Val Thr Ser Gly Cys Thr
                85                  90                  95

Glu Ala Ile Ala Ala Thr Val Leu Gly Leu Ile Asn Pro Gly Asp Glu
            100                 105                 110

Val Ile Val Phe Ala Pro Phe Tyr Asp Ser Tyr Glu Ala Thr Leu Ser
        115                 120                 125

Met Ala Gly Ala Lys Val Lys Gly Ile Thr Leu Arg Pro Pro Asp Phe
    130                 135                 140

Ala Leu Pro Ile Glu Glu Leu Lys Ser Thr Ile Ser Lys Asn Thr Arg
145                 150                 155                 160

Ala Ile Leu Leu Asn Thr Pro His Asn Pro Thr Gly Lys Met Phe Thr
                165                 170                 175

Pro Glu Glu Leu Asn Thr Ile Ala Ser Leu Cys Ile Glu Asn Asp Val
            180                 185                 190

Leu Val Phe Ser Asp Glu Val Tyr Asp Lys Leu Ala Phe Asp Met Glu
        195                 200                 205

His Ile Ser Ile Ala Ser Leu Pro Gly Met Phe Glu Arg Thr Val Thr
    210                 215                 220

Met Asn Ser Leu Gly Lys Thr Phe Ser Leu Thr Gly Trp Lys Ile Gly
225                 230                 235                 240

Trp Ala Ile Ala Pro Pro His Leu Thr Trp Gly Val Arg Gln Ala His
                245                 250                 255

Ala Phe Leu Thr Phe Ala Thr Ser Asn Pro Met Gln Trp Ala Ala Ala
            260                 265                 270

Val Ala Leu Arg Ala Pro Asp Ser Tyr Tyr Thr Glu Leu Lys Arg Asp
        275                 280                 285

Tyr Met Ala Lys Arg Ser Ile Leu Val Glu Gly Leu Lys Ala Val Gly
    290                 295                 300

Phe Lys Val Phe Pro Ser Ser Gly Thr Tyr Phe Val Val Asp His
305                 310                 315                 320

Thr Pro Phe Gly His Glu Asn Asp Ile Ala Phe Cys Glu Tyr Leu Val
                325                 330                 335
```

Lys Glu Val Gly Val Val Ala Ile Pro Thr Ser Val Phe Tyr Leu Asn
                340                 345                 350

Pro Glu Glu Gly Lys Asn Leu Val Arg Phe Thr Phe Cys Lys Asp Glu
            355                 360                 365

Gly Thr Leu Arg Ala Ala Val Asp Arg Met Lys Glu Lys Leu Arg Lys
370                 375                 380

Val Asp Lys Leu Ala Ala Ala Leu Glu His His His His His His
385                 390                 395

<210> SEQ ID NO 18
<211> LENGTH: 1236
<212> TYPE: DNA
<213> ORGANISM: Arabidopsis thaliana

<400> SEQUENCE: 18

| | | | | | |
|---|---|---|---|---|---|
| atggccaaaa | tccatcgtcc | tatcggagcc | accatgacca | cagtttcgac | tcagaacgag | 60 |
| tctactcaaa | aacccgtcca | ggtggcgaag | agattagaga | agttcaagac | tactattttc | 120 |
| actcaaatga | gcatattggc | agttaaacat | ggagcgatca | atttaggcca | aggctttccc | 180 |
| aatttcgacg | gtcctgattt | tgttaaagaa | gctgcgatcc | aagctattaa | agatggtaaa | 240 |
| aaccagtatg | ctcgtggata | cggcattcct | cagctcaact | ctgctatagc | tgcgcggttt | 300 |
| cgtgaagata | cgggtcttgt | tgttgatcct | gagaagaag | ttactgttac | atctggttgc | 360 |
| acagaagcca | tagctgcagc | tatgttgggt | ttaataaacc | ctggtgatga | agtcattctc | 420 |
| tttgcaccgt | tttatgattc | ctatgaagca | acactctcta | tggctggtgc | taaagtaaaa | 480 |
| ggaatcactt | tacgtccacc | ggacttctcc | atccctttgg | aagagcttaa | agctgcggta | 540 |
| actaacaaga | ctcgagccat | ccttatgaac | actccgcaca | acccgaccgg | aagatgttc | 600 |
| actagggagg | agcttgaaac | cattgcatct | ctctgcattg | aaaacgatgt | gcttgtgttc | 660 |
| tcggatgaag | tatacgataa | gcttgcgttt | gaaatggatc | acatttctat | agcttctctt | 720 |
| cccggtatgt | atgaaagaac | tgtgaccatg | aattccctgg | aaagactttt | ctctttaacc | 780 |
| ggatggaaga | tcggctgggc | gattgcgccg | cctcatctga | cttggggagt | cgacaagca | 840 |
| cactcttacc | tcacattcgc | cacatcaaca | ccagcacaat | gggcagccgt | tgcagctctc | 900 |
| aaggcaccag | agtcttactt | caaagagctg | aaaagagatt | acaatgtgaa | aaggagact | 960 |
| ctggttaagg | gtttgaagga | agtcggattt | acagtgttcc | catcgagcgg | gacttacttt | 1020 |
| gtggttgctg | atcacactcc | atttggaatg | gagaacgatg | ttgctttctg | tgagtatctt | 1080 |
| attgaagaag | ttggggtcgt | tgcgatccca | acgagcgtct | tttatctgaa | tccagaagaa | 1140 |
| gggaagaatt | tggttaggtt | tgcgttctgt | aaagacgaag | agacgttgcg | tggtgcaatt | 1200 |
| gagaggatga | agcagaagct | taagagaaaa | gtctga | | | 1236 |

<210> SEQ ID NO 19
<211> LENGTH: 411
<212> TYPE: PRT
<213> ORGANISM: Arabidopsis thaliana

<400> SEQUENCE: 19

Met Ala Lys Ile His Arg Pro Ile Gly Ala Thr Met Thr Thr Val Ser
1               5                   10                  15

Thr Gln Asn Glu Ser Thr Gln Lys Pro Val Gln Val Ala Lys Arg Leu
                20                  25                  30

Glu Lys Phe Lys Thr Thr Ile Phe Thr Gln Met Ser Ile Leu Ala Val
            35                  40                  45

```
Lys His Gly Ala Ile Asn Leu Gly Gln Gly Phe Pro Asn Phe Asp Gly
 50                  55                  60

Pro Asp Phe Val Lys Glu Ala Ile Gln Ala Ile Lys Asp Gly Lys
 65                  70                  75                  80

Asn Gln Tyr Ala Arg Gly Tyr Gly Ile Pro Gln Leu Asn Ser Ala Ile
                 85                  90                  95

Ala Ala Arg Phe Arg Glu Asp Thr Gly Leu Val Val Asp Pro Glu Lys
                100                 105                 110

Glu Val Thr Val Thr Ser Gly Cys Thr Glu Ala Ile Ala Ala Met
                115                 120                 125

Leu Gly Leu Ile Asn Pro Gly Asp Glu Val Ile Leu Phe Ala Pro Phe
130                 135                 140

Tyr Asp Ser Tyr Glu Ala Thr Leu Ser Met Ala Gly Ala Lys Val Lys
145                 150                 155                 160

Gly Ile Thr Leu Arg Pro Pro Asp Phe Ser Ile Pro Leu Glu Glu Leu
                165                 170                 175

Lys Ala Ala Val Thr Asn Lys Thr Arg Ala Ile Leu Met Asn Thr Pro
                180                 185                 190

His Asn Pro Thr Gly Lys Met Phe Thr Arg Glu Glu Leu Glu Thr Ile
                195                 200                 205

Ala Ser Leu Cys Ile Glu Asn Asp Val Leu Val Phe Ser Asp Glu Val
210                 215                 220

Tyr Asp Lys Leu Ala Phe Glu Met Asp His Ile Ser Ile Ala Ser Leu
225                 230                 235                 240

Pro Gly Met Tyr Glu Arg Thr Val Thr Met Asn Ser Leu Gly Lys Thr
                245                 250                 255

Phe Ser Leu Thr Gly Trp Lys Ile Gly Trp Ala Ile Ala Pro Pro His
                260                 265                 270

Leu Thr Trp Gly Val Arg Gln Ala His Ser Tyr Leu Thr Phe Ala Thr
275                 280                 285

Ser Thr Pro Ala Gln Trp Ala Val Ala Ala Leu Lys Ala Pro Glu
290                 295                 300

Ser Tyr Phe Lys Glu Leu Lys Arg Asp Tyr Asn Val Lys Lys Glu Thr
305                 310                 315                 320

Leu Val Lys Gly Leu Lys Glu Val Gly Phe Thr Val Phe Pro Ser Ser
                325                 330                 335

Gly Thr Tyr Phe Val Val Ala Asp His Thr Pro Phe Gly Met Glu Asn
                340                 345                 350

Asp Val Ala Phe Cys Glu Tyr Leu Ile Glu Glu Val Gly Val Val Ala
                355                 360                 365

Ile Pro Thr Ser Val Phe Tyr Leu Asn Pro Glu Glu Gly Lys Asn Leu
370                 375                 380

Val Arg Phe Ala Phe Cys Lys Asp Glu Glu Thr Leu Arg Gly Ala Ile
385                 390                 395                 400

Glu Arg Met Lys Gln Lys Leu Lys Arg Lys Val
                405                 410

<210> SEQ ID NO 20
<211> LENGTH: 1194
<212> TYPE: DNA
<213> ORGANISM: Arabidopsis thaliana

<400> SEQUENCE: 20
atggcgactc agaacgagtc tactcaaaaa cccgtccagg tggcgaagag attagagaag     60
```

```
ttcaagacta ctattttcac tcaaatgagc atattggcag ttaaacatgg agcgatcaat      120
ttaggccaag ctttcccaa tttcgacggt cctgattttg ttaaagaagc tgcgatccaa       180
gctattaaag atggtaaaaa ccagtatgct cgtggatacg gcattcctca gctcaactct      240
gctatagctg cgcggtttcg tgaagatacg ggtcttgttg ttgatcctga aaagaagtt       300 actgttacat ctggttgcac agaagccata gctgcagcta tgttgggttt aataaaccct     360
ggtgatgaag tcattctctt tgcaccgttt tatgattcct atgaagcaac actctctatg     420
gctggtgcta aagtaaaagg aatcacttta cgtccaccgg acttctccat cccttttggaa   480 gagcttaaag ctgcggtaac taacaagact cgagccatcc ttatgaacac tccgcacaac    540
ccgaccggga agatgttcac tagggaggag cttgaaacca ttgcatctct ctgcattgaa    600
aacgatgtgc ttgtgttctc ggatgaagta tacgataagc ttgcgtttga aatggatcac    660
atttctatag cttctcttcc cggtatgtat gaaagaactg tgaccatgaa ttccctggga    720
aagactttct ctttaaccgg atggaagatc ggctgggcga ttgcgccgcc tcatctgact    780
tggggagttc gacaagcaca ctcttacctc acattcgcca catcaacacc agcacaatgg   840
gcagccgttg cagctctcaa ggcaccagag tcttacttca aagagctgaa aagagattac    900
aatgtgaaaa aggagactct ggttaagggt ttgaaggaag tcggatttac agtgttccca    960
tcgagcggga cttactttgt ggttgctgat cacactccat ttggaatgga aacgatgtt    1020 gctttctgtg agtatcttat tgaagaagtt ggggtcgttg cgatcccaac gagcgtcttt   1080
tatctgaatc cagaagaagg gaagaatttg gttaggtttg cgttctgtaa agacgaagag  1140
acgttgcgtg gtgcaattga gaggatgaag cagaagctta agagaaaagt ctga        1194
```

<210> SEQ ID NO 21
<211> LENGTH: 397
<212> TYPE: PRT
<213> ORGANISM: Arabidopsis thaliana

<400> SEQUENCE: 21

Met Ala Thr Gln Asn Glu Ser Thr Gln Lys Pro Val Gln Val Ala Lys
1               5                   10                  15

Arg Leu Glu Lys Phe Lys Thr Thr Ile Phe Thr Gln Met Ser Ile Leu
            20                  25                  30

Ala Val Lys His Gly Ala Ile Asn Leu Gly Gln Gly Phe Pro Asn Phe
        35                  40                  45

Asp Gly Pro Asp Phe Val Lys Glu Ala Ala Ile Gln Ala Ile Lys Asp
    50                  55                  60

Gly Lys Asn Gln Tyr Ala Arg Gly Tyr Gly Ile Pro Gln Leu Asn Ser
65                  70                  75                  80

Ala Ile Ala Ala Arg Phe Arg Glu Asp Thr Gly Leu Val Val Asp Pro
            85                  90                  95

Glu Lys Glu Val Thr Val Thr Ser Gly Cys Thr Glu Ala Ile Ala Ala
        100                 105                 110

Ala Met Leu Gly Leu Ile Asn Pro Gly Asp Glu Val Ile Leu Phe Ala
    115                 120                 125

Pro Phe Tyr Asp Ser Tyr Glu Ala Thr Leu Ser Met Ala Gly Ala Lys
    130                 135                 140

Val Lys Gly Ile Thr Leu Arg Pro Pro Asp Phe Ser Ile Pro Leu Glu
145                 150                 155                 160

Glu Leu Lys Ala Ala Val Thr Asn Lys Thr Arg Ala Ile Leu Met Asn
            165                 170                 175

```
Thr Pro His Asn Pro Thr Gly Lys Met Phe Thr Arg Glu Glu Leu Glu
            180                 185                 190

Thr Ile Ala Ser Leu Cys Ile Glu Asn Asp Val Leu Val Phe Ser Asp
        195                 200                 205

Glu Val Tyr Asp Lys Leu Ala Phe Glu Met Asp His Ile Ser Ile Ala
    210                 215                 220

Ser Leu Pro Gly Met Tyr Glu Arg Thr Val Thr Met Asn Ser Leu Gly
225                 230                 235                 240

Lys Thr Phe Ser Leu Thr Gly Trp Lys Ile Gly Trp Ala Ile Ala Pro
                245                 250                 255

Pro His Leu Thr Trp Gly Val Arg Gln Ala His Ser Tyr Leu Thr Phe
            260                 265                 270

Ala Thr Ser Thr Pro Ala Gln Trp Ala Ala Val Ala Ala Leu Lys Ala
        275                 280                 285

Pro Glu Ser Tyr Phe Lys Glu Leu Lys Arg Asp Tyr Asn Val Lys Lys
    290                 295                 300

Glu Thr Leu Val Lys Gly Leu Lys Glu Val Gly Phe Thr Val Phe Pro
305                 310                 315                 320

Ser Ser Gly Thr Tyr Phe Val Val Ala Asp His Thr Pro Phe Gly Met
                325                 330                 335

Glu Asn Asp Val Ala Phe Cys Glu Tyr Leu Ile Glu Glu Val Gly Val
            340                 345                 350

Val Ala Ile Pro Thr Ser Val Phe Tyr Leu Asn Pro Glu Glu Gly Lys
        355                 360                 365

Asn Leu Val Arg Phe Ala Phe Cys Lys Asp Glu Thr Leu Arg Gly
    370                 375                 380

Ala Ile Glu Arg Met Lys Gln Lys Leu Lys Arg Lys Val
385                 390                 395

<210> SEQ ID NO 22
<211> LENGTH: 1680
<212> TYPE: DNA
<213> ORGANISM: Lycopersicon esculentum

<400> SEQUENCE: 22
ggtaccgttt gaatcctcct taaagttttt ctctggagaa actgtagtaa ttttactttg      60
ttgtgttccc ttcatctttt gaattaatgg catttgtttt aatactaatc tgcttctgaa     120
acttgtaatg tatgtatatc agtttcttat aatttatcca agtaatatct tccattctct     180
atgcaattgc ctgcataagc tcgacaaaag agtacatcaa cccctcctcc tctggactac     240
tctagctaaa cttgaatttc cccttaagat tatgaaattg atatatcctt aacaaacgac     300
tccttctgtt ggaaaatgta gtacttgtct ttcttctttt gggtatatat agtttatata     360
caccatacta tgtacaacat ccaagtagag tgaaatggat acatgtacaa gacttatttg     420
attgattgat gacttgagtt gccttaggag taacaaattc ttaggtcaat aaatcgttga     480
tttgaaatta atctctctgt cttagacaga taggaattat gacttccaat ggtccagaaa     540
gcaaagttcg cactgagggt atacttggaa ttgagacttg cacaggtcca gaaaccaaag     600
ttcccatcga gctctaaaat cacatctttg gaatgaaatt caattagaga taagttgctt     660
catagcatag gtaaaatgga agatgtgaag taacctgcaa taatcagtga atgacatta     720 atacactaaa tacttcatat gtaattatcc tttccaggtt aacaatactc tataaagtaa     780
gaattatcag aaatgggctc atcaaacttt tgtactatgt atttcatata aggaagtata     840
actatacata agtgtataca caactttatt cctatttgt aaaggtggag agactgtttt       900
```

```
cgatggatct aaagcaatat gtctataaaa tgcattgata taataattat ctgagaaaat      960
ccagaattgg cgttggatta tttcagccaa atagaagttt gtaccatact tgttgattcc     1020
ttctaagtta aggtgaagta tcattcataa acagttttcc ccaaagtact actcaccaag     1080
tttcccttg tagaattaac agttcaaata tatggcgcag aaattactct atgcccaaaa      1140
ccaaacgaga aagaaacaaa atacagggggt tgcagacttt attttcgtgt tagggtgtgt    1200
tttttcatgt aattaatcaa aaatatttat gacaaaaaca tttatacata tttttactca     1260
acactctggg tatcagggtg ggttgtgttc gacaatcaat atggaaagga agtattttcc     1320
ttattttttt agttaatatt ttcagttata ccaaacatac cttgtgatat tattttaaa      1380
aatgaaaaac tcgtcagaaa gaaaaagcaa aagcaacaaa aaaattgcaa gtattttta     1440
aaaaagaaaa aaaaaacata tcttgtttgt cagtatggga agtttgagat aaggacgagt     1500
gaggggttaa aattcagtgg ccattgattt tgtaatgcca agaaccacaa atccaatgg      1560
ttaccattcc tgtaagatga ggtttgctaa ctctttttgt ccgttagata ggaagcctta    1620
tcactatata tacaaggcgt cctaataacc tcttagtaac caattatttc agcaccatgg    1680
```

<210> SEQ ID NO 23
<211> LENGTH: 1230
<212> TYPE: DNA
<213> ORGANISM: Phyllostachys bambusoides

<400> SEQUENCE: 23

```
atggcctccg cggccgtctc caccgtcgcc accgccgccg acggcgtcgc gaagccgacg      60
gagaagcagc cggtacaggt cgcaaagcgt ttggaaaagt ttaagacaac aattttcaca     120
cagatgagca tgcttgccat caagcatgga gcaataaacc tcggccaggg ctttccgaat     180
tttgatggcc ctgactttgt gaaagaagct gctattcaag ctatcaatgc tgggaagaat     240
cagtatgcaa gaggatatgg tgtgcctgaa ctgaactcgg ctgttgctga aaggttcctg     300
aaggacagtg gcttgcaagt cgatcccgag aaggaagtta ctgtcacatc tgggtgcacg     360
gaagcgatag ctgcaacgat attgggtctt atcaaccctg cgatgaagt gatcttgttt     420
gctccattct atgattcata cgaggctacg ctgtcgatgg ctggtgccaa tgtaaaagcc    480
attactctcc gtcctccaga ttttgcagtc cctcttgagg agctaaaggc cacagtctct    540
aagaacacca gagcgataat gataaacaca ccacacaatc ctactgggaa aatgttttct    600
agggaagaac ttgaattcat tgctactctc tgcaagaaaa atgatgtgtt gctttttgct   660
gatgaggtct atgacaagtt ggcatttgag gcagatcata tatcaatggc ttctattcct   720
ggcatgtatg agaggactgt gactatgaac tctctgggga agacattctc tctaacagga   780
tggaagatcg gttgggcaat agcaccacca cacctgacat ggggtgtaag gcaggcacac   840
tcattcctca catttgccac ctgcacacca atgcaatcgg cggcggcggc ggctcttaga   900
gcaccagata gctactatgg ggagctgaag agggattacg tgcaaagaa agcgatacta    960
gtcgacggac tcaaggctgc aggttttatt gtttacccct caagtggaac atactttgtc   1020
atggtcgatc acaccccgtt tggtttcgac aatgatattg agttctgcga gtatttgatc   1080
cgcgaagtcg gtgttgtcgc catacccacca agcgtatttt atctcaaccc tgaggatggg   1140
aagaacttgg tgaggttcac cttctgcaag gatgatgata cgctgagagc cgcagttgag   1200
aggatgaaga caaagctcag gaaaaaatga                                    1230
```

<210> SEQ ID NO 24

```
<211> LENGTH: 409
<212> TYPE: PRT
<213> ORGANISM: Phyllostachys bambusoides

<400> SEQUENCE: 24
```

```
Met Ala Ser Ala Ala Val Ser Thr Val Ala Thr Ala Ala Asp Gly Val
1               5                   10                  15

Ala Lys Pro Thr Glu Lys Gln Pro Val Gln Val Ala Lys Arg Leu Glu
            20                  25                  30

Lys Phe Lys Thr Thr Ile Phe Thr Gln Met Ser Met Leu Ala Ile Lys
        35                  40                  45

His Gly Ala Ile Asn Leu Gly Gln Gly Phe Pro Asn Phe Asp Gly Pro
    50                  55                  60

Asp Phe Val Lys Glu Ala Ala Ile Gln Ala Ile Asn Ala Gly Lys Asn
65                  70                  75                  80

Gln Tyr Ala Arg Gly Tyr Gly Val Pro Glu Leu Asn Ser Ala Val Ala
                85                  90                  95

Glu Arg Phe Leu Lys Asp Ser Gly Leu Gln Val Asp Pro Glu Lys Glu
            100                 105                 110

Val Thr Val Thr Ser Gly Cys Thr Glu Ala Ile Ala Ala Thr Ile Leu
        115                 120                 125

Gly Leu Ile Asn Pro Gly Asp Glu Val Ile Leu Phe Ala Pro Phe Tyr
    130                 135                 140

Asp Ser Tyr Glu Ala Thr Leu Ser Met Ala Gly Ala Asn Val Lys Ala
145                 150                 155                 160

Ile Thr Leu Arg Pro Pro Asp Phe Ala Val Pro Leu Glu Glu Leu Lys
                165                 170                 175

Ala Thr Val Ser Lys Asn Thr Arg Ala Ile Met Ile Asn Thr Pro His
            180                 185                 190

Asn Pro Thr Gly Lys Met Phe Ser Arg Glu Glu Leu Glu Phe Ile Ala
        195                 200                 205

Thr Leu Cys Lys Lys Asn Asp Val Leu Leu Phe Ala Asp Glu Val Tyr
    210                 215                 220

Asp Lys Leu Ala Phe Glu Ala Asp His Ile Ser Met Ala Ser Ile Pro
225                 230                 235                 240

Gly Met Tyr Glu Arg Thr Val Thr Met Asn Ser Leu Gly Lys Thr Phe
                245                 250                 255

Ser Leu Thr Gly Trp Lys Ile Gly Trp Ala Ile Ala Pro Pro His Leu
            260                 265                 270

Thr Trp Gly Val Arg Gln Ala His Ser Phe Leu Thr Phe Ala Thr Cys
        275                 280                 285

Thr Pro Met Gln Ser Ala Ala Ala Ala Leu Arg Ala Pro Asp Ser
    290                 295                 300

Tyr Tyr Gly Glu Leu Lys Arg Asp Tyr Gly Ala Lys Lys Ala Ile Leu
305                 310                 315                 320

Val Asp Gly Leu Lys Ala Ala Gly Phe Ile Val Tyr Pro Ser Ser Gly
                325                 330                 335

Thr Tyr Phe Val Met Val Asp His Thr Pro Phe Gly Phe Asp Asn Asp
            340                 345                 350

Ile Glu Phe Cys Glu Tyr Leu Ile Arg Glu Val Gly Val Val Ala Ile
        355                 360                 365

Pro Pro Ser Val Phe Tyr Leu Asn Pro Glu Asp Gly Lys Asn Leu Val
    370                 375                 380

Arg Phe Thr Phe Cys Lys Asp Asp Asp Thr Leu Arg Ala Ala Val Glu
```

```
                385                 390                 395                 400
Arg Met Lys Thr Lys Leu Arg Lys Lys
                    405

<210> SEQ ID NO 25
<211> LENGTH: 1858
<212> TYPE: DNA
<213> ORGANISM: Oryza sativa

<400> SEQUENCE: 25
aaaaaagaaa aaaaaaacat atcttgtttg tcagtatggg aagtttgaga taaggacgag      60
tgaggggtta aaattcagtg gccattgatt ttgtaatgcc aagaaccaca aaatccaatg     120
gttaccattc ctgtaagatg aggtttgcta actcttttttg tccgttagat aggaagcctt     180
atcactatat atacaaggcg tcctaataac ctcttagtaa ccaattattt cagcaccatg     240
gtagatctga gggtaaattt ctagtttttc tccttcattt tcttggttag dacccttttc     300 tcttttatt ttttgagct tgatcttttc tttaaactga tctattttttt aattgattgg      360 ttatggtgta aatattacat agctttaact gataatctga ttactttatt tcgtgtgtct     420
atgatgatga tgatagttac agaaccgacg aactagtatg aatctggccg gctttctcgc     480
cacgcccgcg accgcgaccg cgacgcggca tgagatgccg ttaaatccct cctcctccgc     540
ctccttcctc ctctcctcgc tccgccgctc gctcgtcgcg tcgctccgga aggcctcgcc     600
ggcggcggcc gcggcgctct cccccatggc ctccgcgtcc accgtcgccg ccgagaacgg     660
cgccgccaag gcggcggcgg agaagcagca gcagcagcct gtgcaggttg caaagcggtt     720
ggaaaagttt aagacgacca ttttcacaca gatgagtatg cttgccatca gcatggagc     780 aataaacctt ggccagggtt ttccgaattt cgatggccct gactttgtaa agaggctgc      840 tattcaagct atcaatgctg ggaagaatca gtacgcaaga ggatatggtg tgcctgaact     900
gaactcagct attgctgaaa gattcctgaa ggacagcgga ctgcaagtcg atccggagaa     960
ggaagttact gtcacatctg gatgcacaga agctatagct gcaacaattt taggtctaat    1020
taatccaggc gatgaagtga tattgtttgc tccattctat gattcatatg aggctaccct    1080
gtcaatggct ggtgccaacg taaaagccat tactctccgt cctccagatt tttcagtccc    1140
tcttgaagag ctaaaggctg cagtctcgaa gaacaccaga gctattatga taaacacccc    1200
gcacaatcct actgggaaaa tgtttacaag ggaagaactt gagtttattg ccactctctg    1260
caaggaaaat gatgtgctgc ttttttgctga tgaggtctac gacaagttag cttttgaggc    1320
agatcatata tcaatggctt ctattcctgg catgtatgag aggaccgtga ccatgaactc    1380
tcttgggaag acattctctc ttacaggatg gaagatcggt tgggcaatcg caccgccaca    1440
cctgacatgg ggtgtaaggc aggcacactc attcctcacg tttgcgacct gcacaccaat    1500
gcaagcagct gcagctgcag ctctgagagc accagatagc tactatgagg aactgaggag    1560
ggattatgga gctaagaagg cattgctagt caacggactc aaggatgcag gtttcattgt    1620
ctatccttca agtggaacat acttcgtcat ggtcgaccac accccatttg gtttcgacaa    1680
tgatattgag ttctgcgagt atttgattcg cgaagtcggt gttgtcgcca taccacctag    1740
tgtattttat ctcaaccctg aggatgggaa gaacttggtg aggttcacct tttgcaagga    1800
tgatgagacg ctgagagccg cggttgagag gatgaagaca aagctcagga aaaaatga     1858

<210> SEQ ID NO 26
<211> LENGTH: 1724
<212> TYPE: DNA
```

<213> ORGANISM: Artificial Sequence
<220> FEATURE:
<223> OTHER INFORMATION: Synthetic DNA encoding Hordeum vulgare GPT
      protein

<400> SEQUENCE: 26

| | | | | |
|---|---|---|---|---|
| aaaaaagaaa | aaaaaaacat | atcttgtttg | tcagtatggg | aagtttgaga taaggacgag | 60 |
| tgagggggtta | aaattcagtg | gccattgatt | ttgtaatgcc | aagaaccaca aaatccaatg | 120 |
| gttaccattc | ctgtaagatg | aggtttgcta | actctttttg | tccgttagat aggaagcctt | 180 |
| atcactatat | atacaaggcg | tcctaataac | ctcttagtaa | ccaattattt cagcaccatg | 240 |
| gtagatctga | gggtaaattt | ctagttttc | tccttcattt | tcttggttag gacccttttc | 300 |
| tcttttatt | ttttgagct | ttgatctttc | tttaaactga | tctatttttt aattgattgg | 360 |
| ttatggtgta | aatattacat | agctttaact | gataatctga | ttacttttatt tcgtgtgtct | 420 |
| atgatgatga | tgatagttac | agaaccgacg | aactagtatg | gcatccgccc ccgcctccgc | 480 |
| ctccgcggcc | ctctccaccg | ccgccccgc | cgacaacggg | gccgccaagc ccacggagca | 540 |
| gcggccggta | caggtggcta | agcgattgga | gaagttcaaa | acaacaattt tcacacagat | 600 |
| gagcatgctc | gcagtgaagc | atggagcaat | aaaccttgga | caggggtttc ccaattttga | 660 |
| tggccctgac | tttgtcaaag | atgctgctat | tgaggctatc | aaagctggaa agaatcagta | 720 |
| tgcaaggaga | tatggtgtgc | ctgaattgaa | ctcagctgtt | gctgagagat ttctcaagga | 780 |
| cagtggattg | cacatcgatc | ctgataagga | agttactgtt | acatctgggt gcacagaagc | 840 |
| aatagctgca | acgatattgg | gtctgatcaa | ccctggggat | gaagtcatac tgtttgctcc | 900 |
| attctatgat | tcttatgagg | ctacactgtc | catggctggt | gcgaatgtca aagccattac | 960 |
| actccgccct | ccggactttg | cagtccctct | tgaagagcta | aaggctgcag tctcgaagaa | 1020 |
| taccagagca | ataatgatta | atacacctca | caaccctacc | gggaaaatgt tcacaaggga | 1080 |
| ggaacttgag | ttcattgctg | atctctgcaa | ggaaaatgac | gtgttgctct ttgccgatga | 1140 |
| ggtctacgac | aagctggcgt | tgaggcgga | tcacatatca | atggcttcta ttcctggcat | 1200 |
| gtatgagagg | accgtcacta | tgaactcct | ggggaagacg | ttctccttga ccggatggaa | 1260 |
| gatcggctgg | gcgatagcac | caccgcacct | gacatggggc | gtaaggcagg cacactcctt | 1320 |
| cctcacattc | gccacctcca | cgccgatgca | atcagcagcg | gcggcggccc tgagagcacc | 1380 |
| ggacagctac | tttgaggagc | tgaagaggga | ctacggcgca | agaaagcgc tgctggtgga | 1440 |
| cgggctcaag | gcggcgggct | tcatcgtcta | cccttcgagc | ggaacctact tcatcatggt | 1500 |
| cgaccacacc | ccgttcgggt | tcgacaacga | cgtcgagttc | tgcgagtact tgatccgcga | 1560 |
| ggtcggcgtc | gtggccatcc | cgccaagcgt | gttctacctg | aacccggagg acgggaagaa | 1620 |
| cctggtgagg | ttcaccttct | gcaaggacga | cgacacgcta | agggcggcgg tggacaggat | 1680 |
| gaaggccaag | ctcaggaaga | aatgattgag | gggcgcacgt | gtga | 1724 |

<210> SEQ ID NO 27
<211> LENGTH: 1868
<212> TYPE: DNA
<213> ORGANISM: Artificial Sequence
<220> FEATURE:
<223> OTHER INFORMATION: Synthetic DNA encoding Arabidopsis thaliana GPT
      protein

<400> SEQUENCE: 27

| | | | | |
|---|---|---|---|---|
| catggagtca | aagattcaaa | tagaggacct | aacagaactc | gccgtaaaga ctggcgaaca | 60 |
| gttcatacag | agtctcttac | gactcaatga | caagaagaaa | atcttcgtca acatggtgga | 120 |

```
gcacgacaca cttgtctact ccaaaaatat caaagataca gtctcagaag accaaagggc    180
aattgagact tttcaacaaa gggtaatatc cggaaacctc ctcggattcc attgcccagc    240
tatctgtcac tttattgtga agatagtgga aaaggaaggt ggctcctaca aatgccatca    300
ttgcgataaa ggaaaggcca tcgttgaaga tgcctctgcc gacagtggtc ccaaagatgg    360
accccacccc acgaggagca tcgtggaaaa agaagacgtt ccaaccacgt cttcaaagca    420
agtggattga tgtgatatct ccactgacgt aagggatgac gcacaatccc actatccttc    480
gcaagaccct tcctctatat aaggaagttc atttcatttg gagagaacac ggggactct    540 tgaccatgta cctggacata atggtgtga tgatcaaaca gtttagcttc aaagcctctc    600
ttctcccatt ctcttctaat ttccgacaaa gctccgccaa aatccatcgt cctatcggag    660
ccaccatgac cacagtttcg actcagaacg agtctactca aaaacccgtc caggtggcga    720
agagattaga gaagttcaag actactattt tcactcaaat gagcatattg gcagttaaac    780
atggagcgat caatttaggc caaggctttc ccaatttcga cggtcctgat tttgttaaag    840
aagctgcgat ccaagctatt aaagatggta aaaaccagta tgctcgtgga tacggcattc    900
ctcagctcaa ctctgctata gctgcgcggt tcgtgaaga tacgggtctt gttgttgatc    960
ctgagaaaga agttactgtt acatctggtt gcacagaagc catagctgca gctatgttgg    1020
gtttaataaa ccctggtgat gaagtcattc tctttgcacc gttttatgat tcctatgaag    1080
caacactctc tatggctggt gctaaagtaa aaggaatcac tttacgtcca ccggacttct    1140
ccatcccttt ggaagagctt aaagctgcgg taactaacaa gactcgagcc atccttatga    1200
acactccgca caacccgacc gggaagatgt tcactaggga ggagcttgaa accattgcat    1260
ctctctgcat tgaaaacgat gtgccttgtgt tctcggatga agtatacgat aagcttgcgt    1320
ttgaaatgga tcacatttct atagcttctc ttcccggtat gtatgaaaga actgtgacca    1380
tgaattccct gggaaaagact ttctctttaa ccggatggaa gatcggctgg gcgattgcgc    1440
cgcctcatct gacttgggga gttcgacaag cacactctta cctcacattc gccacatcaa    1500
caccagcaca atgggcagcc gttgcagctc tcaaggcacc agagtcttac ttcaaagagc    1560
tgaaaagaga ttacaatgtg aaaaaggaga ctctggttaa gggtttgaag gaagtcggat    1620
ttacagtgtt cccatcgagc gggacttact ttgtggttgc tgatcacact ccatttggaa    1680
tggagaacga tgttgctttc tgtgagtatc ttattgaaga agtggggtc gttgcgatcc    1740 caacgagcgt cttttatctg aatccagaag aagggaagaa tttggttagg tttgcgttct    1800
gtaaagacga agagacgttg cgtggtgcaa ttgagaggat gaagcagaag cttaagagaa    1860
aagtctga                                                            1868
```

<210> SEQ ID NO 28
<211> LENGTH: 1780
<212> TYPE: DNA
<213> ORGANISM: Artificial Sequence
<220> FEATURE:
<223> OTHER INFORMATION: Synthetic DNA encoding Arabidopsis thaliana GPT
      protein

<400> SEQUENCE: 28

```
aaaaaagaaa aaaaaaacat atcttgtttg tcagtatggg aagtttgaga taaggacgag    60
tgaggggtta aaattcagtg gccattgatt ttgtaatgcc aagaaccaca aaatccaatg    120
gttaccattc ctgtaagatg aggtttgcta actcttttg tccgttagat aggaagcctt    180
atcactatat atacaaggcg tcctaataac ctcttagtaa ccaattattt cagcaccatg    240
```

```
gtagatctga gggtaaattt ctagtttttc tccttcattt tcttggttag gacccttttc    300 tcttttatt tttttgagct ttgatctttc tttaaactga tctatttttt aattgattgg    360
ttatggtgta aatattacat agctttaact gataatctga ttactttatt tcgtgtgtct    420
atgatgatga tgatagttac agaaccgacg aactagtatg tacctggaca taaatggtgt    480
gatgatcaaa cagtttagct tcaaagcctc tcttctccca ttctcttcta atttccgaca    540
aagctccgcc aaaatccatc gtcctatcgg agccaccatg accacagttt cgactcagaa    600
cgagtctact caaaaacccg tccaggtggc gaagagatta gagaagttca agactactat    660
tttcactcaa atgagcatat tggcagttaa acatggagcg atcaatttag gccaaggctt    720
tcccaatttc gacggtcctg attttgttaa agaagctgcg atccaagcta ttaaagatgg    780
taaaaaccag tatgctcgtg atacggcat tcctcagctc aactctgcta tagctgcgcg    840
gtttcgtgaa gatacgggtc ttgttgttga tcctgagaaa gaagttactg ttacatctgg    900
ttgcacagaa gccatagctg cagctatgtt gggtttaata aaccctggtg atgaagtcat    960
tctctttgca ccgtttatg attcctatga agcaacactc tctatggctg gtgctaaagt    1020
aaaaggaatc actttacgtc caccggactt ctccatccct ttggaagagc ttaaagctgc    1080
ggtaactaac aagactcgag ccatccttat gaacactccg cacaacccga ccgggaagat    1140
gttcactagg gaggagcttg aaaccattgc atctctctgc attgaaaacg atgtgcttgt    1200
gttctcggat gaagtatacg ataagcttgc gtttgaaatg gatcacattt ctatagcttc    1260
tcttcccggt atgtatgaaa gaactgtgac catgaattcc ctgggaaaga ctttctcttt    1320
aaccggatgg aagatcggct gggcgattgc gccgcctcat ctgacttggg gagttcgaca    1380
agcacactct tacctcacat tcgccacatc aacaccagca caatgggcag ccgttgcagc    1440
tctcaaggca ccagagtctt acttcaaaga gctgaaaaga gattacaatg tgaaaaagga    1500
gactctggtt aagggtttga aggaagtcgg atttacagtg ttcccatcga gcgggactta    1560 cttttgtggtt gctgatcaca ctccatttgg aatggagaac gatgttgctt tctgtgagta    1620
tcttattgaa gaagttgggg tcgttgcgat cccaacgagc gtcttttatc tgaatccaga    1680
agaagggaag aatttggtta ggtttgcgtt ctgtaaagac gaagagacgt tgcgtggtgc    1740
aattgagagg atgaagcaga agcttaagag aaaagtctga                         1780
```

<210> SEQ ID NO 29
<211> LENGTH: 1155
<212> TYPE: DNA
<213> ORGANISM: Arabidopsis thaliana

<400> SEQUENCE: 29

```
gtggcgaaga gattagagaa gttcaagact actattttca ctcaaatgag catattggca     60
gttaaacatg gagcgatcaa tttaggccaa ggctttccca atttcgacgg tcctgatttt    120
gttaaagaag ctgcgatcca agctattaaa gatggtaaaa accagtatgc tcgtggatac    180
ggcattcctc agctcaactc tgctatagct gcgcggtttc gtgaagatac gggtcttgtt    240
gttgatcctg agaaagaagt tactgttaca tctggttgca cagaagccat agctgcagct    300
atgttgggtt aataaaccc tggtgatgaa gtcattctct ttgcaccgtt ttatgattcc    360
tatgaagcaa cactctctat ggctggtgct aaagtaaaag gaatcacttt acgtccaccg    420
gacttctcca tcctttgga agagcttaaa gctgcggtaa ctaacaagac tcgagccatc    480
cttatgaaca ctccgcacaa cccgaccggg aagatgttca ctagggagga gcttgaaacc    540
```

```
attgcatctc tctgcattga aaacgatgtg cttgtgttct cggatgaagt atacgataag    600
cttgcgtttg aaatggatca catttctata gcttctcttc ccggtatgta tgaaagaact    660
gtgaccatga attccctggg aaagactttc tctttaaccg gatggaagat cggctgggcg    720
attgcgccgc ctcatctgac ttggggagtt cgacaagcac actcttacct cacattcgcc    780
acatcaacac cagcacaatg gcagccgtt gcagctctca aggcaccaga gtcttacttc     840
aaagagctga aaagagatta caatgtgaaa aaggagactc tggttaaggg tttgaaggaa    900
gtcggattta cagtgttccc atcgagcggg acttactttg tggttgctga tcacactcca    960 tttgaatgg agaacgatgt tgctttctgt gagtatctta ttgaagaagt tggggtcgtt    1020
gcgatcccaa cgagcgtctt ttatctgaat ccagaagaag gaagaatttt ggttaggttt    1080
gcgttctgta aagacgaaga gacgttgcgt ggtgcaattg agaggatgaa gcagaagctt    1140
aagagaaaag tctga                                                    1155
```

<210> SEQ ID NO 30
<211> LENGTH: 384
<212> TYPE: PRT
<213> ORGANISM: Arabidopsis thaliana

<400> SEQUENCE: 30

```
Val Ala Lys Arg Leu Glu Lys Phe Lys Thr Thr Ile Phe Thr Gln Met
1               5                   10                  15

Ser Ile Leu Ala Val Lys His Gly Ala Ile Asn Leu Gly Gln Gly Phe
            20                  25                  30

Pro Asn Phe Asp Gly Pro Asp Phe Val Lys Glu Ala Ala Ile Gln Ala
        35                  40                  45

Ile Lys Asp Gly Lys Asn Gln Tyr Ala Arg Gly Tyr Gly Ile Pro Gln
    50                  55                  60

Leu Asn Ser Ala Ile Ala Ala Arg Phe Arg Glu Asp Thr Gly Leu Val
65                  70                  75                  80

Val Asp Pro Glu Lys Glu Val Thr Val Thr Ser Gly Cys Thr Glu Ala
                85                  90                  95

Ile Ala Ala Ala Met Leu Gly Leu Ile Asn Pro Gly Asp Glu Val Ile
            100                 105                 110

Leu Phe Ala Pro Phe Tyr Asp Ser Tyr Glu Ala Thr Leu Ser Met Ala
        115                 120                 125

Gly Ala Lys Val Lys Gly Ile Thr Leu Arg Pro Pro Asp Phe Ser Ile
    130                 135                 140

Pro Leu Glu Glu Leu Lys Ala Ala Val Thr Asn Lys Thr Arg Ala Ile
145                 150                 155                 160

Leu Met Asn Thr Pro His Asn Pro Thr Gly Lys Met Phe Thr Arg Glu
                165                 170                 175

Glu Leu Glu Thr Ile Ala Ser Leu Cys Ile Glu Asn Asp Val Leu Val
            180                 185                 190

Phe Ser Asp Glu Val Tyr Asp Lys Leu Ala Phe Glu Met Asp His Ile
        195                 200                 205

Ser Ile Ala Ser Leu Pro Gly Met Tyr Glu Arg Thr Val Thr Met Asn
    210                 215                 220

Ser Leu Gly Lys Thr Phe Ser Leu Thr Gly Trp Lys Ile Gly Trp Ala
225                 230                 235                 240

Ile Ala Pro Pro His Leu Thr Trp Gly Val Arg Gln Ala His Ser Tyr
                245                 250                 255

Leu Thr Phe Ala Thr Ser Thr Pro Ala Gln Trp Ala Ala Val Ala Ala
```

```
                260                 265                 270
Leu Lys Ala Pro Glu Ser Tyr Phe Lys Glu Leu Lys Arg Asp Tyr Asn
            275                 280                 285

Val Lys Lys Glu Thr Leu Val Lys Gly Leu Lys Glu Val Gly Phe Thr
        290                 295                 300

Val Phe Pro Ser Ser Gly Thr Tyr Phe Val Val Ala Asp His Thr Pro
305                 310                 315                 320

Phe Gly Met Glu Asn Asp Val Ala Phe Cys Glu Tyr Leu Ile Glu Glu
                325                 330                 335

Val Gly Val Val Ala Ile Pro Thr Ser Val Phe Tyr Leu Asn Pro Glu
            340                 345                 350

Glu Gly Lys Asn Leu Val Arg Phe Ala Phe Cys Lys Asp Glu Glu Thr
        355                 360                 365

Leu Arg Gly Ala Ile Glu Arg Met Lys Gln Lys Leu Lys Arg Lys Val
370                 375                 380

<210> SEQ ID NO 31
<211> LENGTH: 384
<212> TYPE: PRT
<213> ORGANISM: Vitis vinifera

<400> SEQUENCE: 31

Val Ala Lys Arg Leu Glu Lys Phe Lys Thr Thr Ile Phe Thr Gln Met
1               5                   10                  15

Ser Met Leu Ala Ile Lys His Gly Ala Ile Asn Leu Gly Gln Gly Phe
            20                  25                  30

Pro Asn Phe Asp Gly Pro Glu Phe Val Lys Glu Ala Ala Ile Gln Ala
        35                  40                  45

Ile Lys Asp Gly Lys Asn Gln Tyr Ala Arg Gly Tyr Gly Val Pro Asp
    50                  55                  60

Leu Asn Ser Ala Val Ala Asp Arg Phe Lys Lys Asp Thr Gly Leu Val
65                  70                  75                  80

Val Asp Pro Glu Lys Glu Val Thr Val Thr Ser Gly Cys Thr Glu Ala
                85                  90                  95

Ile Ala Ala Thr Met Leu Gly Leu Ile Asn Pro Gly Asp Glu Val Ile
            100                 105                 110

Leu Phe Ala Pro Phe Tyr Asp Ser Tyr Glu Ala Thr Leu Ser Met Ala
        115                 120                 125

Gly Ala Gln Ile Lys Ser Ile Thr Leu Arg Pro Pro Asp Phe Ala Val
    130                 135                 140

Pro Met Asp Glu Leu Lys Ser Ala Ile Ser Lys Asn Thr Arg Ala Ile
145                 150                 155                 160

Leu Ile Asn Thr Pro His Asn Pro Thr Gly Lys Met Phe Thr Arg Glu
                165                 170                 175

Glu Leu Asn Val Ile Ala Ser Leu Cys Ile Glu Asn Asp Val Leu Val
            180                 185                 190

Phe Thr Asp Glu Val Tyr Asp Lys Leu Ala Phe Glu Met Asp His Ile
        195                 200                 205

Ser Met Ala Ser Leu Pro Gly Met Tyr Glu Arg Thr Val Thr Met Asn
    210                 215                 220

Ser Leu Gly Lys Thr Phe Ser Leu Thr Gly Trp Lys Ile Gly Trp Thr
225                 230                 235                 240

Val Ala Pro Pro His Leu Thr Trp Gly Val Arg Gln Ala His Ser Phe
                245                 250                 255
```

```
Leu Thr Phe Ala Thr Cys Thr Pro Met Gln Trp Ala Ala Thr Ala
            260                 265                 270

Leu Arg Ala Pro Asp Ser Tyr Tyr Glu Glu Leu Lys Arg Asp Tyr Ser
        275                 280                 285

Ala Lys Lys Ala Ile Leu Val Glu Gly Leu Lys Ala Val Gly Phe Arg
    290                 295                 300

Val Tyr Pro Ser Ser Gly Thr Tyr Phe Val Val Asp His Thr Pro
305                 310                 315                 320

Phe Gly Leu Lys Asp Asp Ile Ala Phe Cys Tyr Leu Ile Lys Glu
                325                 330                 335

Val Gly Val Val Ala Ile Pro Thr Ser Val Phe Tyr Leu His Pro Glu
            340                 345                 350

Asp Gly Lys Asn Leu Val Arg Phe Thr Phe Cys Lys Asp Glu Gly Thr
        355                 360                 365

Leu Arg Ala Ala Val Glu Arg Met Lys Glu Lys Leu Lys Pro Lys Gln
    370                 375                 380

<210> SEQ ID NO 32
<211> LENGTH: 383
<212> TYPE: PRT
<213> ORGANISM: Oryza sativa

<400> SEQUENCE: 32

Val Ala Lys Arg Leu Glu Lys Phe Lys Thr Thr Ile Phe Thr Gln Met
1               5                   10                  15

Ser Met Leu Ala Ile Lys His Gly Ala Ile Asn Leu Gly Gln Gly Phe
            20                  25                  30

Pro Asn Phe Asp Gly Pro Asp Phe Val Lys Glu Ala Ala Ile Gln Ala
        35                  40                  45

Ile Asn Ala Gly Lys Asn Gln Tyr Ala Arg Gly Tyr Gly Val Pro Glu
    50                  55                  60

Leu Asn Ser Ala Ile Ala Glu Arg Phe Leu Lys Asp Ser Gly Leu Gln
65                  70                  75                  80

Val Asp Pro Glu Lys Glu Val Thr Val Thr Ser Gly Cys Thr Glu Ala
                85                  90                  95

Ile Ala Ala Thr Ile Leu Gly Leu Ile Asn Pro Gly Asp Glu Val Ile
            100                 105                 110

Leu Phe Ala Pro Phe Tyr Asp Ser Tyr Glu Ala Thr Leu Ser Met Ala
        115                 120                 125

Gly Ala Asn Val Lys Ala Ile Thr Leu Arg Pro Pro Asp Phe Ser Val
    130                 135                 140

Pro Leu Glu Glu Leu Lys Ala Ala Val Ser Lys Asn Thr Arg Ala Ile
145                 150                 155                 160

Met Ile Asn Thr Pro His Asn Pro Thr Gly Lys Met Phe Thr Arg Glu
                165                 170                 175

Glu Leu Glu Phe Ile Ala Thr Leu Cys Lys Glu Asn Asp Val Leu Leu
            180                 185                 190

Phe Ala Asp Glu Val Tyr Asp Lys Leu Ala Phe Glu Ala Asp His Ile
        195                 200                 205

Ser Met Ala Ser Ile Pro Gly Met Tyr Glu Arg Thr Val Thr Met Asn
    210                 215                 220

Ser Leu Gly Lys Thr Phe Ser Leu Thr Gly Trp Lys Ile Gly Trp Ala
225                 230                 235                 240

Ile Ala Pro Pro His Leu Thr Trp Gly Val Arg Gln Ala His Ser Phe
                245                 250                 255
```

```
Leu Thr Phe Ala Thr Cys Thr Pro Met Gln Ala Ala Ala Ala Ala
        260                 265                 270

Leu Arg Ala Pro Asp Ser Tyr Tyr Glu Glu Leu Arg Arg Asp Tyr Gly
        275                 280                 285

Ala Lys Lys Ala Leu Leu Val Asn Gly Leu Lys Asp Ala Gly Phe Ile
        290                 295                 300

Val Tyr Pro Ser Ser Gly Thr Tyr Phe Val Met Val Asp His Thr Pro
305                 310                 315                 320

Phe Gly Phe Asp Asn Asp Ile Glu Phe Cys Glu Tyr Leu Ile Arg Glu
                325                 330                 335

Val Gly Val Val Ala Ile Pro Pro Ser Val Phe Tyr Leu Asn Pro Glu
                340                 345                 350

Asp Gly Lys Asn Leu Val Arg Phe Thr Phe Cys Lys Asp Asp Glu Thr
                355                 360                 365

Leu Arg Ala Ala Val Glu Arg Met Lys Thr Lys Leu Arg Lys Lys
        370                 375                 380
```

<210> SEQ ID NO 33
<211> LENGTH: 383
<212> TYPE: PRT
<213> ORGANISM: Glycine max

<400> SEQUENCE: 33

```
Ala Lys Arg Leu Glu Lys Phe Gln Thr Thr Ile Phe Thr Gln Met Ser
1               5                   10                  15

Leu Leu Ala Ile Lys His Gly Ala Ile Asn Leu Gly Gln Gly Phe Pro
            20                  25                  30

Asn Phe Asp Gly Pro Glu Phe Val Lys Glu Ala Ala Ile Gln Ala Ile
        35                  40                  45

Arg Asp Gly Lys Asn Gln Tyr Ala Arg Gly Tyr Gly Val Pro Asp Leu
    50                  55                  60

Asn Ile Ala Ile Ala Glu Arg Phe Lys Lys Asp Thr Gly Leu Val Val
65                  70                  75                  80

Asp Pro Glu Lys Glu Ile Thr Val Thr Ser Gly Cys Thr Glu Ala Ile
                85                  90                  95

Ala Ala Thr Met Ile Gly Leu Ile Asn Pro Gly Asp Glu Val Ile Met
            100                 105                 110

Phe Ala Pro Phe Tyr Asp Ser Tyr Glu Ala Thr Leu Ser Met Ala Gly
        115                 120                 125

Ala Lys Val Lys Gly Ile Thr Leu Arg Pro Pro Asp Phe Ala Val Pro
    130                 135                 140

Leu Glu Glu Leu Lys Ser Thr Ile Ser Lys Asn Thr Arg Ala Ile Leu
145                 150                 155                 160

Ile Asn Thr Pro His Asn Pro Thr Gly Lys Met Phe Thr Arg Glu Glu
                165                 170                 175

Leu Asn Cys Ile Ala Ser Leu Cys Ile Glu Asn Asp Val Leu Val Phe
            180                 185                 190

Thr Asp Glu Val Tyr Asp Lys Leu Ala Phe Asp Met Glu His Ile Ser
        195                 200                 205

Met Ala Ser Leu Pro Gly Met Phe Glu Arg Thr Val Thr Leu Asn Ser
    210                 215                 220

Leu Gly Lys Thr Phe Ser Leu Thr Gly Trp Lys Ile Gly Trp Ala Ile
225                 230                 235                 240

Ala Pro Pro His Leu Ser Trp Gly Val Arg Gln Ala His Ala Phe Leu
```

```
                245                 250                 255
Thr Phe Ala Thr Ala His Pro Phe Gln Cys Ala Ala Ala Ala Leu
            260                 265                 270

Arg Ala Pro Asp Ser Tyr Tyr Val Glu Leu Lys Arg Asp Tyr Met Ala
            275                 280                 285

Lys Arg Ala Ile Leu Ile Glu Gly Leu Lys Ala Val Gly Phe Lys Val
            290                 295                 300

Phe Pro Ser Ser Gly Thr Tyr Phe Val Val Asp His Thr Pro Phe
305                 310                 315                 320

Gly Leu Glu Asn Asp Val Ala Phe Cys Glu Tyr Leu Val Lys Glu Val
                325                 330                 335

Gly Val Val Ala Ile Pro Thr Ser Val Phe Tyr Leu Asn Pro Glu Glu
                340                 345                 350

Gly Lys Asn Leu Val Arg Phe Thr Phe Cys Lys Asp Glu Glu Thr Ile
                355                 360                 365

Arg Ser Ala Val Glu Arg Met Lys Ala Lys Leu Arg Lys Val Asp
                370                 375                 380

<210> SEQ ID NO 34
<211> LENGTH: 383
<212> TYPE: PRT
<213> ORGANISM: Hordeum vulgare

<400> SEQUENCE: 34

Val Ala Lys Arg Leu Glu Lys Phe Lys Thr Thr Ile Phe Thr Gln Met
1               5                   10                  15

Ser Met Leu Ala Val Lys His Gly Ala Ile Asn Leu Gly Gln Gly Phe
                20                  25                  30

Pro Asn Phe Asp Gly Pro Asp Phe Val Lys Asp Ala Ala Ile Glu Ala
                35                  40                  45

Ile Lys Ala Gly Lys Asn Gln Tyr Ala Arg Gly Tyr Gly Val Pro Glu
        50                  55                  60

Leu Asn Ser Ala Val Ala Glu Arg Phe Leu Lys Asp Ser Gly Leu His
65                  70                  75                  80

Ile Asp Pro Asp Lys Glu Val Thr Val Thr Ser Gly Cys Thr Glu Ala
                85                  90                  95

Ile Ala Ala Thr Ile Leu Gly Leu Ile Asn Pro Gly Asp Glu Val Ile
                100                 105                 110

Leu Phe Ala Pro Phe Tyr Asp Ser Tyr Glu Ala Thr Leu Ser Met Ala
        115                 120                 125

Gly Ala Asn Val Lys Ala Ile Thr Leu Arg Pro Pro Asp Phe Ala Val
        130                 135                 140

Pro Leu Glu Glu Leu Lys Ala Ala Val Ser Lys Asn Thr Arg Ala Ile
145                 150                 155                 160

Met Ile Asn Thr Pro His Asn Pro Thr Gly Lys Met Phe Thr Arg Glu
                165                 170                 175

Glu Leu Glu Phe Ile Ala Asp Leu Cys Lys Glu Asn Asp Val Leu Leu
                180                 185                 190

Phe Ala Asp Glu Val Tyr Asp Lys Leu Ala Phe Glu Ala Asp His Ile
        195                 200                 205

Ser Met Ala Ser Ile Pro Gly Met Tyr Glu Arg Thr Val Thr Met Asn
        210                 215                 220

Ser Leu Gly Lys Thr Phe Ser Leu Thr Gly Trp Lys Ile Gly Trp Ala
225                 230                 235                 240
```

```
Ile Ala Pro Pro His Leu Thr Trp Gly Val Arg Gln Ala His Ser Phe
                245                 250                 255

Leu Thr Phe Ala Thr Ser Thr Pro Met Gln Ser Ala Ala Ala Ala Ala
            260                 265                 270

Leu Arg Ala Pro Asp Ser Tyr Phe Glu Glu Leu Lys Arg Asp Tyr Gly
        275                 280                 285

Ala Lys Lys Ala Leu Leu Val Asp Gly Leu Lys Ala Ala Gly Phe Ile
    290                 295                 300

Val Tyr Pro Ser Ser Gly Thr Tyr Phe Ile Met Val Asp His Thr Pro
305                 310                 315                 320

Phe Gly Phe Asp Asn Asp Val Glu Phe Cys Glu Tyr Leu Ile Arg Glu
                325                 330                 335

Val Gly Val Val Ala Ile Pro Pro Ser Val Phe Tyr Leu Asn Pro Glu
            340                 345                 350

Asp Gly Lys Asn Leu Val Arg Phe Thr Phe Cys Lys Asp Asp Asp Thr
        355                 360                 365

Leu Arg Ala Ala Val Asp Arg Met Lys Ala Lys Leu Arg Lys Lys
    370                 375                 380

<210> SEQ ID NO 35
<211> LENGTH: 382
<212> TYPE: PRT
<213> ORGANISM: Danio rerio

<400> SEQUENCE: 35

Val Ala Lys Arg Leu Glu Lys Phe Lys Thr Thr Ile Phe Thr Gln Met
1               5                   10                  15

Ser Met Leu Ala Ile Lys His Gly Ala Ile Asn Leu Gly Gln Gly Phe
            20                  25                  30

Pro Asn Phe Asp Gly Pro Asp Phe Val Lys Glu Ala Ala Ile Gln Ala
        35                  40                  45

Ile Arg Asp Gly Asn Asn Gln Tyr Ala Arg Gly Tyr Gly Val Pro Asp
    50                  55                  60

Leu Asn Ile Ala Ile Ser Glu Arg Tyr Lys Lys Asp Thr Gly Leu Ala
65                  70                  75                  80

Val Asp Pro Glu Lys Glu Ile Thr Val Thr Ser Gly Cys Thr Glu Ala
                85                  90                  95

Ile Ala Ala Thr Val Leu Gly Leu Ile Asn Pro Gly Asp Glu Val Ile
            100                 105                 110

Val Phe Ala Pro Phe Tyr Asp Ser Tyr Glu Ala Thr Leu Ser Met Ala
        115                 120                 125

Gly Ala Lys Val Lys Gly Ile Thr Leu Arg Pro Pro Asp Phe Ala Leu
    130                 135                 140

Pro Ile Glu Glu Leu Lys Ser Thr Ile Ser Lys Asn Thr Arg Ala Ile
145                 150                 155                 160

Leu Leu Asn Thr Pro His Asn Pro Thr Gly Lys Met Phe Thr Pro Glu
                165                 170                 175

Glu Leu Asn Thr Ile Ala Ser Leu Cys Ile Glu Asn Asp Val Leu Val
            180                 185                 190

Phe Ser Asp Glu Val Tyr Asp Lys Leu Ala Phe Asp Met Glu His Ile
        195                 200                 205

Ser Ile Ala Ser Leu Pro Gly Met Phe Glu Arg Thr Val Thr Met Asn
    210                 215                 220

Ser Leu Gly Lys Thr Phe Ser Leu Thr Gly Trp Lys Ile Gly Trp Ala
225                 230                 235                 240
```

```
Ile Ala Pro Pro His Leu Thr Trp Gly Val Arg Gln Ala His Ala Phe
            245                 250                 255

Leu Thr Phe Ala Thr Ser Asn Pro Met Gln Trp Ala Ala Ala Val Ala
        260                 265                 270

Leu Arg Ala Pro Asp Ser Tyr Tyr Thr Glu Leu Lys Arg Asp Tyr Met
    275                 280                 285

Ala Lys Arg Ser Ile Leu Val Glu Gly Leu Lys Ala Val Gly Phe Lys
290                 295                 300

Val Phe Pro Ser Ser Gly Thr Tyr Phe Val Val Asp His Thr Pro
305                 310                 315                 320

Phe Gly His Glu Asn Asp Ile Ala Phe Cys Glu Tyr Leu Val Lys Glu
                325                 330                 335

Val Gly Val Val Ala Ile Pro Thr Ser Val Phe Tyr Leu Asn Pro Glu
            340                 345                 350

Glu Gly Lys Asn Leu Val Arg Phe Thr Phe Cys Lys Asp Glu Gly Thr
        355                 360                 365

Leu Arg Ala Ala Val Asp Arg Met Lys Glu Lys Leu Arg Lys
    370                 375                 380

<210> SEQ ID NO 36
<211> LENGTH: 383
<212> TYPE: PRT
<213> ORGANISM: Phyllostachys bambusoides

<400> SEQUENCE: 36

Val Ala Lys Arg Leu Glu Lys Phe Lys Thr Thr Ile Phe Thr Gln Met
1               5                   10                  15

Ser Met Leu Ala Ile Lys His Gly Ala Ile Asn Leu Gly Gln Gly Phe
            20                  25                  30

Pro Asn Phe Asp Gly Pro Asp Phe Val Lys Glu Ala Ala Ile Gln Ala
        35                  40                  45

Ile Asn Ala Gly Lys Asn Gln Tyr Ala Arg Gly Tyr Gly Val Pro Glu
    50                  55                  60

Leu Asn Ser Ala Val Ala Glu Arg Phe Leu Lys Asp Ser Gly Leu Gln
65                  70                  75                  80

Val Asp Pro Glu Lys Glu Val Thr Val Thr Ser Gly Cys Thr Glu Ala
                85                  90                  95

Ile Ala Ala Thr Ile Leu Gly Leu Ile Asn Pro Gly Asp Glu Val Ile
            100                 105                 110

Leu Phe Ala Pro Phe Tyr Asp Ser Tyr Glu Ala Thr Leu Ser Met Ala
        115                 120                 125

Gly Ala Asn Val Lys Ala Ile Thr Leu Arg Pro Pro Asp Phe Ala Val
    130                 135                 140

Pro Leu Glu Glu Leu Lys Ala Thr Val Ser Lys Asn Thr Arg Ala Ile
145                 150                 155                 160

Met Ile Asn Thr Pro His Asn Pro Thr Gly Lys Met Phe Ser Arg Glu
                165                 170                 175

Glu Leu Glu Phe Ile Ala Thr Leu Cys Lys Lys Asn Asp Val Leu Leu
            180                 185                 190

Phe Ala Asp Glu Val Tyr Asp Lys Leu Ala Phe Glu Ala Asp His Ile
        195                 200                 205

Ser Met Ala Ser Ile Pro Gly Met Tyr Glu Arg Thr Val Thr Met Asn
    210                 215                 220

Ser Leu Gly Lys Thr Phe Ser Leu Thr Gly Trp Lys Ile Gly Trp Ala
```

```
                225                 230                 235                 240
Ile Ala Pro Pro His Leu Thr Trp Gly Val Arg Gln Ala His Ser Phe
                    245                 250                 255
Leu Thr Phe Ala Thr Cys Thr Pro Met Gln Ser Ala Ala Ala Ala Ala
                    260                 265                 270
Leu Arg Ala Pro Asp Ser Tyr Tyr Gly Glu Leu Lys Arg Asp Tyr Gly
                    275                 280                 285
Ala Lys Lys Ala Ile Leu Val Asp Gly Leu Lys Ala Ala Gly Phe Ile
                290                 295                 300
Val Tyr Pro Ser Ser Gly Thr Tyr Phe Val Met Val Asp His Thr Pro
305                 310                 315                 320
Phe Gly Phe Asp Asn Asp Ile Glu Phe Cys Glu Tyr Leu Ile Arg Glu
                    325                 330                 335
Val Gly Val Val Ala Ile Pro Pro Ser Val Phe Tyr Leu Asn Pro Glu
                    340                 345                 350
Asp Gly Lys Asn Leu Val Arg Phe Thr Phe Cys Lys Asp Asp Asp Thr
                    355                 360                 365
Leu Arg Ala Ala Val Glu Arg Met Lys Thr Lys Leu Arg Lys Lys
                    370                 375                 380

<210> SEQ ID NO 37
<211> LENGTH: 34
<212> TYPE: DNA
<213> ORGANISM: Artificial Sequence
<220> FEATURE:
<223> OTHER INFORMATION: Synthetic primer sequence

<400> SEQUENCE: 37
cccatcgatg tacctggaca taaatggtgt gatg                                  34

<210> SEQ ID NO 38
<211> LENGTH: 37
<212> TYPE: DNA
<213> ORGANISM: Artificial Sequence
<220> FEATURE:
<223> OTHER INFORMATION: Synthetic primer sequence

<400> SEQUENCE: 38
gatggtacct cagactttc tcttaagctt ctgcttc                                37

<210> SEQ ID NO 39
<211> LENGTH: 2992
<212> TYPE: DNA
<213> ORGANISM: Artificial Sequence
<220> FEATURE:
<223> OTHER INFORMATION: Synthetic expression cassette

<400> SEQUENCE: 39
ctgcagcaaa gaaacgttat tagttggtgc ttttggtggt aggaatgtag ttttctgaca      60
aagtcaatta ctgaatataa aaaaaatctg cacagctctg cgtcaacagt tgtccaaggg     120
atgcctcaaa atctgtgca gattatcagt cgtcacgcag aagcagaaca tcatggtgtg     180
ctaggtcagc ttcttgcatt gggccatgaa tccggttggt tgttaatctc tcctctctta     240
ttctcttata ttaagatgca taactctttt atgtagtcta aaaaaaaatc cagtggatcg     300
gatagtagta cgtcatggtg ccattaggta ccgttgaacc taacagatat ttatgcatgt     360
gtatatatat agctatatag acaaaattga tgccgattat agacccaaaa gcaataggta     420
tatataatat aatacagacc acaccaccaa actaagaatc gatcaaatag acaaggcatg     480
```

```
tctccaaatt gtcttaaact atttccgtag gttcagccgt tcaggagtcg aatcagcctc    540
tgccggcgtt ttctttgcac gtacgacgga cacacatggg cataccatat agctggtcca    600
tgacattagg agagagaacg tacgtgttga cctgtagctg agatataaca aggttgatta    660
taatatcacc aaacatgaaa tcatccaagg atgacccata actatcacta ctatagtact    720
gcatctggta aagaaattg tatagactct atttcgagca ctaccacata acgcctgcaa     780
tgtgacaccc tacctattca ctaatgtgcc tcttcccaca cgctttccac ccgtactgct    840
cacagcttta agaaccagaa caaatgagta atattagtgt cggttcatgg ctaaaaccag    900
cactgatgta catgaccaca tatgtcaaat gctgcttcta ggcatgaccc gctcttacta    960
atacctactc atcgctagaa gaattttcgg ctgataaatt ttcaatttaa gcaagagtta   1020
tctgcgttgg ttcataactc aaactgatgg ccccaaccat attagtgcaa atttcacata   1080
tgatcataac cttttcatat gaaatcggat cgagatgaac tttatataaa cattgtagct   1140
gtcgatgata cctacaattt tatagttcac aacctttta tttcaagtca tttaaatgcc    1200
caaataggtg tttcaaatct cagatagaaa tgttcaaaag taaaaaaggt ccctatcata   1260
acataattga tatgtaagtg agttggaaaa agataagtac gtgtgagaga gatcggggat   1320
caaattctgg tgtaataatg tatgtatttc agtcataaaa attggtagca gtagttgggg   1380
ctctgtatat ataccggtaa ggatgggatg gtagtagaat aattcttttt ttgtttttag   1440 tttttctgg tccaaaattt caaatttgga tcccttactt gtaccaacta atattaatga    1500
gtgttgaggg tagtagaggt gcaactttac cataatccct ctgtttcagg ttataagacg   1560
ttttgacttt aaatttgacc aagtttatgc gcaaatatag taatatttat aatactatat   1620
tagtttcatt aaataaataa ttgaatatat tttcataata aatttgtgtt gagttcaaaa   1680
tattattaat ttttctaca aacttggtca aacttgaagc agtttgactt tgaccaaagt    1740
caaaacgtct tataacttga aacggatgga ttactttttt tgtggggaca agtttacaat   1800
gtttaataaa gcacaatcca tcttaatgtt ttcaagctga atattgtaaa attcatggat   1860
aaaccagctt ctaaatgttt aaccgggaaa atgtcgaacg acaaattaat atttttaagt   1920
gatggggagt attaattaag gagtgacaac tcaactttca atatcgtact aaactgtggg   1980
atttattttc taaaatttta taccctgcca attcacgtgt tgtagatctt ttttttcac    2040 taaccgacac caggtatatc aattttattg aatatagcag caaaagaat gtgttgtact    2100 tgtaaacaaa aagcaaactg tacataaaaa aaatgcact cctatataat taagctcata    2160
aagatgcttt gcttcgtgag ggcccaagtt ttgatgacct tttgcttgat ctcgaaatta   2220
aaatttaagt actgttaagg gagttcacac caccatcaat tttcagcctg aagaaacagt   2280
taaacaacga ccccgatgac cagtctactg ctctccacat actagctgca ttattgatca   2340
caaaacaaaa caaaacgaaa taaaaatcag cagcgagagt gtgcagagag agacaaaggt   2400
gatctggcgt ggatatctcc ccatccatcc tcacccgcgc tgcccatcac tcgccgccgc   2460
atactccatc atgtggagag aggaagacga ggaccacagc cagagcccgg gtcgagatgc   2520
caccacggcc acaacccacg agcccggcgc gacaccaccg cgcgcgcgtg agccagccac   2580
aaacgcccgc ggataggcgc gcgcacgccg gccaatccta ccacatcccc ggcctccgcg   2640
gctcgcgagc gccgctgcca tccgatccgc tgagttttgg ctatttatac gtaccgcggg   2700
agcctgtgtg cagagcagtg catctcaaga agtactcgag caaagaagga gagagcttgg   2760
tgagctgcag ccatggtaga tctgagggta aatttctagt ttttctcctt cattttcttg   2820
gttaggaccc ttttctcttt ttattttttt gagctttgat cttttctttaa actgatctat   2880
```

```
tttttaattg attggttatg gtgtaaatat tacatagctt taactgataa tctgattact    2940
ttatttcgtg tgtctatgat gatgatgata gttacagaac cgacgaacta gt           2992

<210> SEQ ID NO 40
<211> LENGTH: 1281
<212> TYPE: DNA
<213> ORGANISM: Hordeum vulgare

<400> SEQUENCE: 40
gcgcaggcgg ttgtgcaggc gatgcagtgc caggtggggg tgaggggcag acggccgtc      60 ccggcgaggc agcccgcggg cagggtgtgg ggcgtcagga gggccgcccg cgccacctcc    120
gggttcaagg tgctggcgct cggcccggag accaccgggg tcatccagag gatgcagcag    180
ctgctcgaca tggacaccac gcccttcacc gacaagatca tcgccgagta catctgggtt    240
ggaggatctg gaattgacct cagaagcaaa tcaaggacga tttcgaagcc agtggaggac    300
ccgtcagagc tgccgaaatg gaactacgac ggatcgagca cggggcaggc tcctggggaa    360
gacagtgaag tcatcctata cccacaggcc atattcaagg acccattccg aggaggcaac    420
aacatactgg ttatctgtga cacctacaca ccacaggggg aacccatccc tactaacaaa    480
cgccacatgg ctgcacaaat cttcagtgac cccaaggtca cttcacaagt gccatggttc    540
ggaatcgaac aggagtacac tctgatgcag agggatgtga actggcctct ggctggcct    600 gttggagggt accctggccc ccagggtcca tactactgcg ccgtaggatc agacaagtca    660
tttggccgtg acatatcaga tgctcactac aaggcgtgcc tttacgctgg aattgaaatc    720
agtggaacaa acggggaggt catgcctggt cagtgggagt accaggttgg acccagcgtt    780
ggtattgatg caggagacca catatgggct tccagataca ttctcgagag aatcacggag    840
caagctggtg tggtgctcac ccttgaccca aaaccaatcc agggtgactg gaacggagct    900
ggctgccaca caaactacag cacattgagc atgcgcgagg atggaggttt cgacgtgatc    960
aagaaggcaa tcctgaacct ttcacttcgc catgacttgc acatagccgc atatggtgaa   1020
ggaaacgagc ggaggttgac agggctacac gagacagcta gcatatcaga cttctcatgg   1080
ggtgtggcga accgtggctg ctctattcgt gtggggcgag acaccgaggc gaagggcaaa   1140
ggatacctgg aggaccgtcg cccggcctcc aacatggacc cgtacaccgt gacggcgctg   1200
ctggccgaga ccacgatcct gtgggagccg accctcgagg cggaggccct cgctgccaag   1260
aagctggcgc tgaaggtatg a                                             1281

<210> SEQ ID NO 41
<211> LENGTH: 426
<212> TYPE: PRT
<213> ORGANISM: Hordeum vulgare

<400> SEQUENCE: 41

Ala Gln Ala Val Val Gln Ala Met Gln Cys Gln Val Gly Val Arg Gly
1               5                   10                  15

Arg Thr Ala Val Pro Ala Arg Gln Pro Ala Gly Arg Val Trp Gly Val
            20                  25                  30

Arg Arg Ala Ala Arg Ala Thr Ser Gly Phe Lys Val Leu Ala Leu Gly
        35                  40                  45

Pro Glu Thr Thr Gly Val Ile Gln Arg Met Gln Gln Leu Leu Asp Met
    50                  55                  60

Asp Thr Thr Pro Phe Thr Asp Lys Ile Ile Ala Glu Tyr Ile Trp Val
65                  70                  75                  80
```

Gly Gly Ser Gly Ile Asp Leu Arg Ser Lys Ser Arg Thr Ile Ser Lys
                85                  90                  95

Pro Val Glu Asp Pro Ser Glu Leu Pro Lys Trp Asn Tyr Asp Gly Ser
            100                 105                 110

Ser Thr Gly Gln Ala Pro Gly Glu Asp Ser Glu Val Ile Leu Tyr Pro
        115                 120                 125

Gln Ala Ile Phe Lys Asp Pro Phe Arg Gly Gly Asn Asn Ile Leu Val
    130                 135                 140

Ile Cys Asp Thr Tyr Thr Pro Gln Gly Glu Pro Ile Pro Thr Asn Lys
145                 150                 155                 160

Arg His Met Ala Ala Gln Ile Phe Ser Asp Pro Lys Val Thr Ser Gln
                165                 170                 175

Val Pro Trp Phe Gly Ile Glu Gln Glu Tyr Thr Leu Met Gln Arg Asp
            180                 185                 190

Val Asn Trp Pro Leu Gly Trp Pro Val Gly Gly Tyr Pro Gly Pro Gln
        195                 200                 205

Gly Pro Tyr Tyr Cys Ala Val Gly Ser Asp Lys Ser Phe Gly Arg Asp
    210                 215                 220

Ile Ser Asp Ala His Tyr Lys Ala Cys Leu Tyr Ala Gly Ile Glu Ile
225                 230                 235                 240

Ser Gly Thr Asn Gly Glu Val Met Pro Gly Gln Trp Glu Tyr Gln Val
                245                 250                 255

Gly Pro Ser Val Gly Ile Asp Ala Gly Asp His Ile Trp Ala Ser Arg
            260                 265                 270

Tyr Ile Leu Glu Arg Ile Thr Glu Gln Ala Gly Val Val Leu Thr Leu
        275                 280                 285

Asp Pro Lys Pro Ile Gln Gly Asp Trp Asn Gly Ala Gly Cys His Thr
    290                 295                 300

Asn Tyr Ser Thr Leu Ser Met Arg Glu Asp Gly Gly Phe Asp Val Ile
305                 310                 315                 320

Lys Lys Ala Ile Leu Asn Leu Ser Leu Arg His Asp Leu His Ile Ala
                325                 330                 335

Ala Tyr Gly Glu Gly Asn Glu Arg Arg Leu Thr Gly Leu His Glu Thr
            340                 345                 350

Ala Ser Ile Ser Asp Phe Ser Trp Gly Val Ala Asn Arg Gly Cys Ser
        355                 360                 365

Ile Arg Val Gly Arg Asp Thr Glu Ala Lys Gly Lys Gly Tyr Leu Glu
    370                 375                 380

Asp Arg Arg Pro Ala Ser Asn Met Asp Pro Tyr Thr Val Thr Ala Leu
385                 390                 395                 400

Leu Ala Glu Thr Thr Ile Leu Trp Glu Pro Thr Leu Glu Ala Glu Ala
                405                 410                 415

Leu Ala Ala Lys Lys Leu Ala Leu Lys Val
            420                 425

<210> SEQ ID NO 42
<211> LENGTH: 4273
<212> TYPE: DNA
<213> ORGANISM: Artificial Sequence
<220> FEATURE:
<223> OTHER INFORMATION: Synthetic expression cassette

<400> SEQUENCE: 42
ctgcagcaaa gaaacgttat tagttggtgc ttttggtggt aggaatgtag ttttctgaca      60

```
aagtcaatta ctgaatataa aaaaaatctg cacagctctg cgtcaacagt tgtccaaggg      120
atgcctcaaa aatctgtgca gattatcagt cgtcacgcag aagcagaaca tcatggtgtg      180
ctaggtcagc ttcttgcatt gggccatgaa tccggttggt tgttaatctc tcctctctta      240
ttctcttata ttaagatgca taactctttt atgtagtcta aaaaaaaatc cagtggatcg      300
gatagtagta cgtcatggtg ccattaggta ccgttgaacc taacagatat ttatgcatgt      360
gtatatatat agctatatag acaaaattga tgccgattat agacccaaaa gcaataggta      420
tatataatat aatacagacc acaccaccaa actaagaatc gatcaaatag acaaggcatg      480
tctccaaatt gtcttaaact atttccgtag gttcagccgt tcaggagtcg aatcagcctc      540
tgccggcgtt ttcttttgcac gtacgacgga cacacatggg cataccatat agctggtcca      600
tgacattagg agagagaacg tacgtgttga cctgtagctg agatataaca aggttgatta      660
taatatcacc aaacatgaaa tcatccaagg atgacccata actatcacta ctatagtact      720
gcatctggta aaagaaattg tatagactct atttcgagca ctaccacata acgcctgcaa      780
tgtgacaccc tacctattca ctaatgtgcc tcttcccaca cgctttccac ccgtactgct      840
cacagcttta agaaccagaa caaatgagta atattagtgt cggttcatgg ctaaaaccag      900
cactgatgta catgaccaca tatgtcaaat gctgcttcta ggcatgaccc gctcttacta      960
atacctactc atcgctagaa gaattttcgg ctgataaatt tcaatttaa gcaagagtta     1020 tctgcgttgg ttcataactc aaactgatgg ccccaaccat attagtgcaa atttcacata     1080
tgatcataac cttttcatat gaaatcggat cgagatgaac tttatataaa cattgtagct     1140
gtcgatgata cctacaattt tatagttcac aaccttttta tttcaagtca tttaaatgcc     1200
caaataggtg tttcaaatct cagatagaaa tgttcaaaag taaaaaaggt ccctatcata     1260
acataattga tatgtaagtg agttggaaaa agataagtac gtgtgagaga gatcggggat     1320
caaattctgg tgtaataatg tatgtatttc agtcataaaa attggtagca gtagttgggg     1380
ctctgtatat ataccggtaa ggatgggatg gtagtagaat aattcttttt ttgttttag     1440 tttttctgg tccaaaattt caaatttgga tcccttactt gtaccaacta atattaatga     1500
gtgttgaggg tagtagaggt gcaactttac cataatccct ctgtttcagg ttataagacg     1560
ttttgacttt aaatttgacc aagtttatgc gcaaatatag taatatttat aatactatat     1620
tagtttcatt aaataaataa ttgaatatat tttcataata aatttgtgtt gagttcaaaa     1680
tattattaat ttttttctaca aacttggtca aacttgaagc agtttgactt tgaccaaagt     1740
caaaacgtct tataacttga aacggatgga ttactttttt tgtggggaca agttacaat      1800 gtttaataaa gcacaatcca tcttaatgtt ttcaagctga atattgtaaa attcatggat     1860
aaaccagctt ctaaatgttt aaccgggaaa atgtcgaacg acaaattaat atttttaagt     1920
gatggggagt attaattaag gagtgacaac tcaactttca atatcgtact aaactgtggg     1980
atttattttc taaaatttta taccctgcca attcacgtgt tgtagatctt ttttttcac      2040 taaccgacac caggtatatc aattttattg aatatagcag caaaagaat gtgttgtact     2100 tgtaaacaaa aagcaaactg tacataaaaa aaaatgcact cctatataat taagctcata     2160
aagatgcttt gcttcgtgag ggcccaagtt ttgatgacct tttgcttgat ctcgaaatta     2220
aaatttaagt actgttaagg gagttcacac caccatcaat tttcagcctg aagaaacagt     2280
taaacaacga ccccgatgac cagtctactg ctctccacat actagctgca ttattgatca     2340
caaaacaaaa caaaacgaaa taaaaatcag cagcgagagt gtgcagagag agacaaaggt     2400
gatctggcgt ggatatctcc ccatccatcc tcacccgcgc tgcccatcac tcgccgccgc     2460
```

```
atactccatc atgtggagag aggaagacga ggaccacagc cagagcccgg gtcgagatgc   2520
caccacggcc acaacccacg agcccggcgc gacaccaccg cgcgcgcgtg agccagccac   2580
aaacgcccgc ggataggcgc gcgcacgccg gccaatccta ccacatcccc ggcctccgcg   2640
gctcgcgagc gccgctgcca tccgatccgc tgagttttgg ctatttatac gtaccgcggg   2700
agcctgtgtg cagagcagtg catctcaaga agtactcgag caaagaagga gagagcttgg   2760
tgagctgcag ccatggtaga tctgagggta aatttctagt tttctccctt cattttcttg   2820
gttaggaccc ttttctcttt ttattttttt gagctttgat cttcctttaa actgatctat   2880
tttttaattg attggttatg gtgtaaatat tacatagctt taactgataa tctgattact   2940
ttatttcgtg tgtctatgat gatgatgata gttacagaac cgacgaacta gtgcgcaggc   3000
ggttgtgcag gcgatgcagt gccaggtggg ggtgaggggc aggacggccg tcccggcgag   3060
gcagcccgcg ggcagggtgt ggggcgtcag gagggccgcc cgcgccacct ccgggttcaa   3120
ggtgctggcg ctcggcccgg agaccaccgg ggtcatccag aggatgcagc agctgctcga   3180
catggacacc acgcccttca ccgacaagat catcgccgag tacatctggg ttggaggatc   3240
tggaattgac ctcagaagca aatcaaggac gatttcgaag ccagtggagg acccgtcaga   3300
gctgccgaaa tggaactacg acggatcgag cacggggcag gctcctgggg aagacagtga   3360
agtcatccta tacccacagg ccatattcaa ggacccattc cgaggaggca acaacatact   3420
ggttatctgt gacacctaca caccacaggg ggaacccatc cctactaaca aacgccacat   3480
ggctgcacaa atcttcagtg accccaaggt cacttcacaa gtgccatggt tcggaatcga   3540
acaggagtac actctgatgc agagggatgt gaactggcct cttggctggc ctgttggagg   3600
gtaccctggc ccccagggtc catactactg cgccgtagga tcagacaagt catttggccg   3660
tgacatatca gatgctcact acaaggcgtg cctttacgct ggaattgaaa tcagtggaac   3720
aaacggggag gtcatgcctg gtcagtggga gtaccaggtt ggacccagcg ttggtattga   3780
tgcaggagac cacatatggg cttccagata cattctcgag agaatcacgg agcaagctgg   3840
tgtggtgctc acccttgacc caaaaccaat ccagggtgac tggaacggag ctggctgcca   3900
cacaaactac agcacattga gcatgcgcga ggatggaggt ttcgacgtga tcaagaaggc   3960
aatcctgaac cttcactcc gccatgactt gcacatagcc gcatatggtg aaggaaacga   4020
gcggaggttg acagggctac acgagacagc tagcatatca gacttctcat ggggtgtggc   4080
gaaccgtggc tgctctattc gtgtggggcg agacaccgag gcgaagggca aaggatacct   4140
ggaggaccgt cgcccggcct ccaacatgga cccgtacacc gtgacggcgc tgctggccga   4200
gaccacgatc ctgtgggagc cgaccctcga ggcggaggcc ctcgctgcca agaagctggc   4260
gctgaaggta tga                                                    4273
```

<210> SEQ ID NO 43
<211> LENGTH: 436
<212> TYPE: PRT
<213> ORGANISM: Artificial Sequence
<220> FEATURE:
<223> OTHER INFORMATION: Translation product of SEQ ID NO: 42 DNA

<400> SEQUENCE: 43

Met Val Asp Leu Arg Asn Arg Arg Thr Ser Ala Gln Ala Val Val Gln
1               5                   10                  15

Ala Met Gln Cys Gln Val Gly Val Arg Gly Arg Thr Ala Val Pro Ala
            20                  25                  30

```
Arg Gln Pro Ala Gly Arg Val Trp Gly Val Arg Arg Ala Arg Ala
             35                  40                  45
Thr Ser Gly Phe Lys Val Leu Ala Leu Gly Pro Glu Thr Thr Gly Val
 50                  55                  60
Ile Gln Arg Met Gln Gln Leu Leu Asp Met Asp Thr Thr Pro Phe Thr
 65                  70                  75                  80
Asp Lys Ile Ile Ala Glu Tyr Ile Trp Val Gly Gly Ser Gly Ile Asp
                 85                  90                  95
Leu Arg Ser Lys Ser Arg Thr Ile Ser Lys Pro Val Glu Asp Pro Ser
            100                 105                 110
Glu Leu Pro Lys Trp Asn Tyr Asp Gly Ser Ser Thr Gly Gln Ala Pro
            115                 120                 125
Gly Glu Asp Ser Glu Val Ile Leu Tyr Pro Gln Ala Ile Phe Lys Asp
130                 135                 140
Pro Phe Arg Gly Gly Asn Asn Ile Leu Val Ile Cys Asp Thr Tyr Thr
145                 150                 155                 160
Pro Gln Gly Glu Pro Ile Pro Thr Asn Lys Arg His Met Ala Ala Gln
                165                 170                 175
Ile Phe Ser Asp Pro Lys Val Thr Ser Gln Val Pro Trp Phe Gly Ile
            180                 185                 190
Glu Gln Glu Tyr Thr Leu Met Gln Arg Asp Val Asn Trp Pro Leu Gly
            195                 200                 205
Trp Pro Val Gly Gly Tyr Pro Gly Pro Gln Gly Pro Tyr Tyr Cys Ala
            210                 215                 220
Val Gly Ser Asp Lys Ser Phe Gly Arg Asp Ile Ser Asp Ala His Tyr
225                 230                 235                 240
Lys Ala Cys Leu Tyr Ala Gly Ile Glu Ile Ser Gly Thr Asn Gly Glu
                245                 250                 255
Val Met Pro Gly Gln Trp Glu Tyr Gln Val Gly Pro Ser Val Gly Ile
            260                 265                 270
Asp Ala Gly Asp His Ile Trp Ala Ser Arg Tyr Ile Leu Glu Arg Ile
            275                 280                 285
Thr Glu Gln Ala Gly Val Val Leu Thr Leu Asp Pro Lys Pro Ile Gln
            290                 295                 300
Gly Asp Trp Asn Gly Ala Gly Cys His Thr Asn Tyr Ser Thr Leu Ser
305                 310                 315                 320
Met Arg Glu Asp Gly Gly Phe Asp Val Ile Lys Lys Ala Ile Leu Asn
                325                 330                 335
Leu Ser Leu Arg His Asp Leu His Ile Ala Ala Tyr Gly Glu Gly Asn
            340                 345                 350
Glu Arg Arg Leu Thr Gly Leu His Glu Thr Ala Ser Ile Ser Asp Phe
            355                 360                 365
Ser Trp Gly Val Ala Asn Arg Gly Cys Ser Ile Arg Val Gly Arg Asp
            370                 375                 380
Thr Glu Ala Lys Gly Lys Gly Tyr Leu Glu Asp Arg Arg Pro Ala Ser
385                 390                 395                 400
Asn Met Asp Pro Tyr Thr Val Thr Ala Leu Leu Ala Glu Thr Thr Ile
                405                 410                 415
Leu Trp Glu Pro Thr Leu Glu Ala Glu Ala Leu Ala Ala Lys Lys Leu
            420                 425                 430
Ala Leu Lys Val
            435
```

<210> SEQ ID NO 44
<211> LENGTH: 1992
<212> TYPE: DNA
<213> ORGANISM: Zea mays

<400> SEQUENCE: 44

```
ctgcagtgca gcgtgacccg gtcgtgcccc tctctagaga taatgagcat tgcatgtcta      60
agttataaaa aattaccaca tatttttttt gtcacacttg tttgaagtgc agtttatcta     120
tctttataca tatatttaaa ctttactcta cgaataatat aatctatagt actacaataa     180
tatcagtgtt ttagagaatc atataaatga acagttagac atggtctaaa ggacaattga     240
gtattttgac aacaggactc tacagtttta tcttttttagt gtgcatgtgt tctccttttt     300
ttttgcaaat agcttcacct atataatact tcatccattt tattagtaca tccatttagg     360
gtttagggtt aatggttttt atagactaat ttttttagta catctatttt attctatttt     420
agcctctaaa ttaagaaaac taaaactcta tttttagtttt tttatttaat aatttagata     480
taaaatagaa taaaataaag tgactaaaaa ttaaacaaat accctttaag aaattaaaaa     540
aactaaggaa acatttttct tgtttcgagt agataatgcc agcctgttaa acgccgtcga     600
cgagtctaac ggacaccaac cagcgaacca gcagcgtcgc gtcgggccaa gcgaagcaga     660
cggcacggca tctctgtcgc tgcctctgga cccctctcga gagttccgct ccaccgttgg     720
acttgctccg ctgtcggcat ccagaaattg cgtggcggag cggcagacgt gagccggcac     780
ggcaggcggc ctcctcctcc tctcacgcca cggcagctac gggggattcc tttcccaccg     840
ctccttcgct ttcccttcct cgcccgccgt aataaataga cacccctcc acaccctctt      900
tccccaacct cgtgttgttc ggagcgcaca cacacacaac cagatctccc ccaaatccac     960
ccgtcggcac ctccgcttca aggtacgccg ctcgtcctcc cccccccccc ctctctacct    1020
tctctagatc ggcgttccgg tccatggtta gggcccggta gttctacttc tgttcatgtt    1080
tgtgttagat ccgtgtttgt gttagatccg tgctgctagc gttcgtacac ggatgcgacc    1140
tgtacgtcag acacgttctg attgctaact tgccagtgtt tctctttggg gaatcctggg    1200
atggctctag ccgttccgca gacgggatcg atttcatgat tttttttgtt tcgttgcata    1260
gggtttggtt tgccctttc ctttatttca atatatgccg tgcacttgtt tgtcgggtca    1320
tcttttcatg cttttttttg tcttggttgt gatgatgtgg tctggttggg cggtcgttct    1380
agatcggagt agaattctgt ttcaaactac ctggtggatt tattaatttt ggatctgtat    1440
gtgtgtgcca tacatattca tagttacgaa ttgaagatga tggatggaaa tatcgatcta    1500
ggataggtat acatgttgat gcgggttta ctgatgcata tacagagatg cttttttgttc    1560
gcttggttgt gatgatgtgg tgtggttggg cggtcgttca ttcgttctag atcggagtag    1620
aatactgttt caaactacct ggtgtattta ttaattttgg aactgtatgt gtgtgtcata    1680
catcttcata gttacgagtt taagatggat ggaaatatcg atctaggata ggtatacatg    1740
ttgatgtggg tttactgat gcatatacat gatggcatat gcagcatcta ttcatatgct    1800
ctaaccttga gtacctatct attataataa acaagtatgt tttataatta ttttgatctt    1860
gatatacttg gatgatggca tatgcagcag ctatatgtgg atttttttag ccctgccttc    1920
atacgctatt tatttgcttg gtactgtttc ttttgtcgat gctcaccctg ttgtttggtg    1980
ttacttctgc ag                                                        1992
```

<210> SEQ ID NO 45
<211> LENGTH: 1248
<212> TYPE: DNA

<213> ORGANISM: Hordeum vulgare

<400> SEQUENCE: 45

```
atggcatccg cccccgcctc cgcctccgcg gccctctcca ccgccgcccc cgccgacaac    60
ggggccgcca agcccacgga gcagcggccg gtacaggtgg ctaagcgatt ggagaagttc   120
aaaacaacaa ttttcacaca gatgagcatg ctcgcagtga agcatggagc aataaacctt   180
ggacaggggt ttcccaattt tgatggccct gactttgtca agatgctgc tattgaggct    240
atcaaagctg gaaagaatca gtatgcaaga ggatatggtg tgcctgaatt gaactcagct   300
gttgctgaga gatttctcaa ggacagtgga ttgcacatcg atcctgataa ggaagttact   360
gttacatctg ggtgcacaga agcaatagct gcaacgatat tgggtctgat caaccctggg   420
gatgaagtca tactgtttgc tccattctat gattcttatg aggctacact gtccatggct   480
ggtgcgaatg tcaaagccat tacactccgc cctccggact ttgcagtccc tcttgaagag   540
ctaaaggctg cagtctcgaa gaataccaga gcaataatga ttaatacacc tcacaaccct   600
accgggaaaa tgttcacaag ggaggaactt gagttcattg ctgatctctg caaggaaaat   660
gacgtgttgc tctttgccga tgaggtctac gacaagctgg cgtttgaggc ggatcacata   720
tcaatggctt ctattcctgg catgtatgag aggaccgtca ctatgaactc cctggggaag   780
acgttctcct tgaccggatg aagatcggc tgggcgatag caccaccgca cctgacatgg    840
ggcgtaaggc aggcacactc cttcctcaca ttcgccacct ccacgccgat gcaatcagca   900
gcggcggcgg ccctgagagc accggacagc tactttgagg agctgaagag ggactacggc   960
gcaaagaaag cgctgctggt ggacgggctc aaggcggcgg gcttcatcgt ctacccttcg  1020
agcggaaccct acttcatcat ggtcgaccac accccgttcg ggttcgacaa cgacgtcgag  1080
ttctgcgagt acttgatccg cgaggtcggc gtcgtggcca tcccgccaag cgtgttctac  1140
ctgaacccgg aggacgggaa gaacctggtg aggttcacct tctgcaagga cgacgacacg  1200
ctaagggcgg cggtggacag gatgaaggcc aagctcagga agaaatga               1248
```

<210> SEQ ID NO 46
<211> LENGTH: 415
<212> TYPE: PRT
<213> ORGANISM: Hordeum vulgare

<400> SEQUENCE: 46

```
Met Ala Ser Ala Pro Ala Ser Ala Ala Leu Ser Thr Ala Ala
1               5                  10                  15

Pro Ala Asp Asn Gly Ala Ala Lys Pro Thr Glu Gln Arg Pro Val Gln
            20                  25                  30

Val Ala Lys Arg Leu Glu Lys Phe Lys Thr Thr Ile Phe Thr Gln Met
        35                  40                  45

Ser Met Leu Ala Val Lys His Gly Ala Ile Asn Leu Gly Gln Gly Phe
    50                  55                  60

Pro Asn Phe Asp Gly Pro Asp Phe Val Lys Asp Ala Ala Ile Glu Ala
65                  70                  75                  80

Ile Lys Ala Gly Lys Asn Gln Tyr Ala Arg Gly Tyr Gly Val Pro Glu
                85                  90                  95

Leu Asn Ser Ala Val Ala Glu Arg Phe Leu Lys Asp Ser Gly Leu His
            100                 105                 110

Ile Asp Pro Asp Lys Glu Val Thr Val Thr Ser Gly Cys Thr Glu Ala
        115                 120                 125

Ile Ala Ala Thr Ile Leu Gly Leu Ile Asn Pro Gly Asp Glu Val Ile
```

```
            130                 135                 140
Leu Phe Ala Pro Phe Tyr Asp Ser Tyr Glu Ala Thr Leu Ser Met Ala
145                 150                 155                 160

Gly Ala Asn Val Lys Ala Ile Thr Leu Arg Pro Pro Asp Phe Ala Val
                165                 170                 175

Pro Leu Glu Glu Leu Lys Ala Ala Val Ser Lys Asn Thr Arg Ala Ile
                180                 185                 190

Met Ile Asn Thr Pro His Asn Pro Thr Gly Lys Met Phe Thr Arg Glu
                195                 200                 205

Glu Leu Glu Phe Ile Ala Asp Leu Cys Lys Glu Asn Asp Val Leu Leu
                210                 215                 220

Phe Ala Asp Glu Val Tyr Asp Lys Leu Ala Phe Glu Ala Asp His Ile
225                 230                 235                 240

Ser Met Ala Ser Ile Pro Gly Met Tyr Glu Arg Thr Val Thr Met Asn
                245                 250                 255

Ser Leu Gly Lys Thr Phe Ser Leu Thr Gly Trp Lys Ile Gly Trp Ala
                260                 265                 270

Ile Ala Pro Pro His Leu Thr Trp Gly Val Arg Gln Ala His Ser Phe
                275                 280                 285

Leu Thr Phe Ala Thr Ser Thr Pro Met Gln Ser Ala Ala Ala Ala Ala
290                 295                 300

Leu Arg Ala Pro Asp Ser Tyr Phe Glu Glu Leu Lys Arg Asp Tyr Gly
305                 310                 315                 320

Ala Lys Lys Ala Leu Leu Val Asp Gly Leu Lys Ala Ala Gly Phe Ile
                325                 330                 335

Val Tyr Pro Ser Ser Gly Thr Tyr Phe Ile Met Val Asp His Thr Pro
                340                 345                 350

Phe Gly Phe Asp Asn Asp Val Glu Phe Cys Glu Tyr Leu Ile Arg Glu
                355                 360                 365

Val Gly Val Val Ala Ile Pro Pro Ser Val Phe Tyr Leu Asn Pro Glu
                370                 375                 380

Asp Gly Lys Asn Leu Val Arg Phe Thr Phe Cys Lys Asp Asp Thr
385                 390                 395                 400

Leu Arg Ala Ala Val Asp Arg Met Lys Ala Lys Leu Arg Lys Lys
                405                 410                 415

<210> SEQ ID NO 47
<211> LENGTH: 2735
<212> TYPE: DNA
<213> ORGANISM: Artificial Sequence
<220> FEATURE:
<223> OTHER INFORMATION: Synthetic expression cassette

<400> SEQUENCE: 47
gtttgaatcc tccttaaagt ttttctctgg agaaactgta gtaattttac tttgttgtgt    60
tcccttcatc ttttgaatta atggcatttg ttttaatact aatctgcttc tgaaacttgt   120
aatgtatgta tatcagtttc ttataattta tccaagtaat atcttccatt ctctatgcaa   180
ttgcctgcat aagctcgaca aaagagtaca tcaacccctc ctcctctgga ctactctagc   240
taaacttgaa tttccccctta agattatgaa attgatatat ccttaacaaa cgactccttc   300
tgttggaaaa tgtagtactt gtctttcttc ttttgggtat atatagttta tatacaccat   360
actatgtaca acatccaagt agagtgaaat ggatacatgt acaagactta tttgattgat   420
tgatgacttg agttgcctta ggagtaacaa attcttaggt caataaatcg ttgatttgaa   480
```

```
attaatctct ctgtcttaga cagataggaa ttatgacttc caatggtcca gaaagcaaag    540
ttcgcactga gggtatactt ggaattgaga cttgcacagg tccagaaacc aaagttccca    600
tcgagctcta aaatcacatc tttggaatga aattcaatta gagataagtt gcttcatagc    660
ataggtaaaa tggaagatgt gaagtaacct gcaataatca gtgaaatgac attaatacac    720
taaatacttc atatgtaatt atcctttcca ggttaacaat actctataaa gtaagaatta    780
tcagaaatgg gctcatcaaa cttttgtact atgtatttca tataaggaag tataactata    840
cataagtgta tacacaactt tattcctatt ttgtaaaggt ggagagactg ttttcgatgg    900
atctaaagca atatgtctat aaaatgcatt gatataataa ttatctgaga aaatccagaa    960
ttggcgttgg attatttcag ccaaatagaa gtttgtacca tacttgttga ttccttctaa   1020
gttaaggtga agtatcattc ataaacagtt tcccccaaag tactactcac caagtttccc   1080
tttgtagaat taacagttca aatatatggc gcagaaatta ctctatgccc aaaaccaaac   1140
gagaagaaa caaatacag gggttgcaga ctttatttc gtgttagggt gtgtttttc   1200
atgtaattaa tcaaaaata ttatgacaaa aacatttata catattttta ctcaacactc   1260
tgggtatcag ggtgggttgt gttcgacaat caatatggaa aggaagtatt ttccttattt   1320
ttttagttaa tattttcagt tataccaaac ataccttgtg atattatttt taaaaatgaa   1380
aaactcgtca gaaagaaaaa gcaaagcaa caaaaaaatt gcaagtattt tttaaaaaag   1440
aaaaaaaaaa catatcttgt ttgtcagtat gggaagtttg agataaggac gagtgagggg   1500
ttaaaattca gtggccattg attttgtaat gccaagaacc acaaaatcca atggttacca   1560
ttcctgtaag atgaggtttg ctaactcttt ttgtccgtta gataggaagc cttatcacta   1620
tatatacaag gcgtcctaat aacctcttag taaccaatta tttcagcacc atgtctctgc   1680
tctcagatct cgttaacctc aacctcaccg atgccaccgg gaaaatcatc gccgaataca   1740
tatggatcgg tggatctgga atggatatca gaagcaaagc caggacacta ccaggaccag   1800
tgactgatcc atcaaagctt cccaagtgga actacgacgg atccagcacc ggtcaggctg   1860
ctggagaaga cagtgaagtc attctatacc ctcaggcaat attcaaggat cccttcagga   1920
aaggcaacaa catcctggtg atgtgtgatg cttacacacc agctggtgat cctattccaa   1980
ccaacaagag gcacaacgct gctaagatct tcagccaccc cgacgttgcc aaggaggagc   2040
cttggtatgg gattgagcaa gaatacactt tgatgcaaaa ggatgtgaac tggccaattg   2100
gttggcctgt tggtggctac cctggccctc agggaccttaa ctactgtggt gtgggagctg   2160
acaaagccat tggtcgtgac attgtggatg ctcactacaa ggcctgtctt tacgccggta   2220
ttggtatttc tggtatcaat ggagaagtca tgccaggcca gtgggagttc caagtcggcc   2280
ctgttgaggg tattagttct ggtgatcaag tctgggttgc tcgataccttc tcgagagga   2340
tcactgagat ctctggtgta attgtcagct tcgacccgaa accagtcccg ggtgactgga   2400
atggagctgg agctcactgc aactacagca ctaagacaat gagaaacgat ggaggattag   2460
aagtgatcaa gaaagcgata gggaagcttc agctgaaaca caagaacac attgctgctt   2520
acggtgaagg aaacgagcgt cgtctcactg gaaagcacga accgcagac atcaacacat   2580
tctcttgggg agtcgcgaac cgtggagcgt cagtgagagt gggacgtgac acagagaagg   2640
aaggtaaagg gtacttcgaa gacagaaggc cagcttctaa catggatcct tacgttgtca   2700
cctccatgat cgctgagacg accatactcg gttga                              2735
```

<210> SEQ ID NO 48
<211> LENGTH: 1371

```
<212> TYPE: DNA
<213> ORGANISM: Citrus reticulata

<400> SEQUENCE: 48
atgcttaagc cgtccgcctt cgggtcttct ttttcttcct cagctctgct ttcgttttcg      60
aagcatttgc atacaataag cattactgat tctgtcaaca ccagaagaag aggaatcagt     120
accgcttgcc ctaggtaccc ttctctcatg gcgagcttgt ccaccgtttc caccaatcaa     180
agcgacacca tccagaagac caatcttcag cctcaacagg ttgctaagtg cttggagaag     240
tttaaaacta caatctttac acaaatgagt atgcttgcca tcaaacatgg agctataaat     300
cttggtcaag ctttcccaa ctttgatggc ccagattttg ttaaagatgc agcgattcaa      360
gccataaggg atgggaagaa tcaatatgct cgtggacatg gggttccaga gttcaactct     420
gccattgctt cccggtttaa gaaagattct gggctcgagg ttgaccctga aaaggaagtt     480
actgttaccT ctgggtgcac cgaagccatt gctgcaacca tcttaggttt gattaatcct     540
ggagatgagg tgatcctttt tgcacctttc tatgattcct atgaagctac tctctccatg     600
gctggtgcta aaattaaatg catcacattg cgccctccag aatttgccat ccccattgaa     660
gagctcaagt ctacaatctc aaaaaatact cgtgcaattc ttatgaacac tccacataac     720
cccactggaa agatgttcac tagggaggaa cttaatgtta ttgcatctct ttgcattgag     780
aatgatgtgt tggttttag tgatgaggtc tatgataagt tggcttttga atgggatcac     840
atttccatag cctctcttcc tggaatgtat gagcgtactg taaccatgaa ttccttaggg     900
aagacattct ctttaacagg gtggaagatc gggtgggcaa tagctccacc gcaccttaca     960
tgggggggtgc ggcaggcaca ctctttctc acgtttgcca catccactcc aatgcagtgg    1020
gcagctacag cagcccttag agctccggag acgtactatg aggagctaaa gagagattac    1080
tcggcaaaga aggcaatttt ggtggaggga ttgaatgctg ttggtttcaa ggtattccca    1140
tctagtggga catactttgt ggttgtagat cacaccccat ttgggcacga aactgatatt    1200
gcattttgtg aatatctgat caaggaagtt ggggttgtgg caattccgac cagcgtattt    1260
tacttgaatc cagaggatgg aaagaatttg gtgagattta ccttctgcaa agatgaagga    1320
actttgaggt ctgcagttga caggatgaag gagaagctga ggagaaaatg a             1371

<210> SEQ ID NO 49
<211> LENGTH: 456
<212> TYPE: PRT
<213> ORGANISM: Citrus reticulata

<400> SEQUENCE: 49

Met Leu Lys Pro Ser Ala Phe Gly Ser Ser Phe Ser Ser Ser Ala Leu
1               5                   10                  15

Leu Ser Phe Ser Lys His Leu His Thr Ile Ser Ile Thr Asp Ser Val
            20                  25                  30

Asn Thr Arg Arg Gly Ile Ser Thr Ala Cys Pro Arg Tyr Pro Ser
        35                  40                  45

Leu Met Ala Ser Leu Ser Thr Val Ser Thr Asn Gln Ser Asp Thr Ile
    50                  55                  60

Gln Lys Thr Asn Leu Gln Pro Gln Gln Val Ala Lys Cys Leu Glu Lys
65                  70                  75                  80

Phe Lys Thr Thr Ile Phe Thr Gln Met Ser Met Leu Ala Ile Lys His
                85                  90                  95

Gly Ala Ile Asn Leu Gly Gln Gly Phe Pro Asn Phe Asp Gly Pro Asp
            100                 105                 110
```

Phe Val Lys Asp Ala Ala Ile Gln Ala Ile Arg Asp Gly Lys Asn Gln
            115                 120                 125

Tyr Ala Arg Gly His Gly Val Pro Glu Phe Asn Ser Ala Ile Ala Ser
        130                 135                 140

Arg Phe Lys Lys Asp Ser Gly Leu Glu Val Asp Pro Glu Lys Glu Val
145                 150                 155                 160

Thr Val Thr Ser Gly Cys Thr Glu Ala Ile Ala Thr Ile Leu Gly
                165                 170                 175

Leu Ile Asn Pro Gly Asp Glu Val Ile Leu Phe Ala Pro Phe Tyr Asp
                180                 185                 190

Ser Tyr Glu Ala Thr Leu Ser Met Ala Gly Ala Lys Ile Lys Cys Ile
        195                 200                 205

Thr Leu Arg Pro Pro Glu Phe Ala Ile Pro Ile Glu Glu Leu Lys Ser
    210                 215                 220

Thr Ile Ser Lys Asn Thr Arg Ala Ile Leu Met Asn Thr Pro His Asn
225                 230                 235                 240

Pro Thr Gly Lys Met Phe Thr Arg Glu Glu Leu Asn Val Ile Ala Ser
                245                 250                 255

Leu Cys Ile Glu Asn Asp Val Leu Val Phe Ser Asp Glu Val Tyr Asp
        260                 265                 270

Lys Leu Ala Phe Glu Met Asp His Ile Ser Ile Ala Ser Leu Pro Gly
    275                 280                 285

Met Tyr Glu Arg Thr Val Thr Met Asn Ser Leu Gly Lys Thr Phe Ser
    290                 295                 300

Leu Thr Gly Trp Lys Ile Gly Trp Ala Ile Ala Pro Pro His Leu Thr
305                 310                 315                 320

Trp Gly Val Arg Gln Ala His Ser Phe Leu Thr Phe Ala Thr Ser Thr
                325                 330                 335

Pro Met Gln Trp Ala Ala Thr Ala Ala Leu Arg Ala Pro Glu Thr Tyr
                340                 345                 350

Tyr Glu Glu Leu Lys Arg Asp Tyr Ser Ala Lys Lys Ala Ile Leu Val
        355                 360                 365

Glu Gly Leu Asn Ala Val Gly Phe Lys Val Phe Pro Ser Ser Gly Thr
    370                 375                 380

Tyr Phe Val Val Asp His Thr Pro Phe Gly His Glu Thr Asp Ile
385                 390                 395                 400

Ala Phe Cys Glu Tyr Leu Ile Lys Glu Val Gly Val Val Ala Ile Pro
                405                 410                 415

Thr Ser Val Phe Tyr Leu Asn Pro Glu Asp Gly Lys Asn Leu Val Arg
                420                 425                 430

Phe Thr Phe Cys Lys Asp Glu Gly Thr Leu Arg Ser Ala Val Asp Arg
            435                 440                 445

Met Lys Glu Lys Leu Arg Arg Lys
    450                 455

<210> SEQ ID NO 50
<211> LENGTH: 37
<212> TYPE: DNA
<213> ORGANISM: Artificial Sequence
<220> FEATURE:
<223> OTHER INFORMATION: Synthetic primer sequence

<400> SEQUENCE: 50
ggccacatgt ccgttgctaa gtgcttggag aagttta                    37

-continued

```
<210> SEQ ID NO 51
<211> LENGTH: 40
<212> TYPE: DNA
<213> ORGANISM: Artificial Sequence
<220> FEATURE:
<223> OTHER INFORMATION: Synthetic primer sequence

<400> SEQUENCE: 51
cgggcacgtg tcatttctc ctcagcttct ccttcatcct                           40

<210> SEQ ID NO 52
<211> LENGTH: 457
<212> TYPE: PRT
<213> ORGANISM: Zea mays

<400> SEQUENCE: 52
```

Met Asn Leu Ala Ala Phe Ser Ser Thr Leu Ala Thr Leu Pro Trp Tyr
1               5                   10                  15

Glu Met Pro Ser Ile Asn Ser Ser Ala Thr Phe Ser Ser Ser Leu Leu
            20                  25                  30

Arg Arg Ser Leu Cys Ala Ser Leu Arg Thr Ile Ser His Met Ala Ser
        35                  40                  45

Ala Ala Ala Pro Thr Ser Ala Pro Val Ala Thr Thr Glu Asn Gly Ala
    50                  55                  60

Ala Lys Ala Ile Glu Gln Arg Pro Val Gln Val Ala Glu Arg Leu Glu
65                  70                  75                  80

Lys Phe Lys Thr Thr Ile Phe Thr Gln Met Ser Met Leu Ala Ile Lys
                85                  90                  95

His Gly Ala Ile Asn Leu Gly Gln Gly Phe Pro Asn Phe Asp Gly Pro
            100                 105                 110

Asp Phe Val Lys Glu Ala Ala Ile Gln Ala Ile Asn Ala Gly Lys Asn
        115                 120                 125

Gln Tyr Ala Arg Gly Phe Gly Val Pro Glu Leu Asn Ser Ala Ile Ala
    130                 135                 140

Glu Arg Phe Leu Lys Asp Ser Gly Leu Gln Val Asp Pro Asp Lys Glu
145                 150                 155                 160

Val Thr Val Thr Ser Gly Cys Thr Glu Ala Ile Ala Ala Thr Ile Leu
                165                 170                 175

Gly Leu Ile Asn Pro Gly Asp Glu Val Ile Leu Phe Ala Pro Phe Tyr
            180                 185                 190

Asp Ser Tyr Glu Ala Thr Leu Ser Met Ala Gly Ala Asn Val Lys Ala
        195                 200                 205

Ile Thr Leu Arg Ala Pro Asp Phe Ala Val Pro Leu Glu Glu Leu Glu
    210                 215                 220

Ala Ala Val Ser Lys Asp Thr Lys Ala Ile Met Ile Asn Thr Pro His
225                 230                 235                 240

Asn Pro Thr Gly Lys Met Phe Thr Arg Glu Glu Leu Glu Ser Ile Ala
                245                 250                 255

Ala Leu Cys Lys Glu Asn Asp Val Leu Leu Phe Ser Asp Glu Val Tyr
            260                 265                 270

Asp Lys Leu Val Phe Glu Ala Asp His Ile Ser Met Ala Ser Ile Pro
        275                 280                 285

Gly Met Tyr Glu Arg Thr Val Thr Met Asn Ser Leu Gly Lys Thr Phe
    290                 295                 300

Ser Leu Thr Gly Trp Lys Ile Gly Trp Ala Ile Ala Pro Pro His Leu
305                 310                 315                 320

```
Thr Trp Gly Leu Arg Gln Ala His Ser Phe Leu Thr Phe Ala Thr Cys
                325                 330                 335

Thr Pro Met Gln Ala Ala Ala Ala Ala Leu Arg Ala Pro Asp Ser
            340                 345                 350

Tyr Tyr Asp Glu Leu Lys Arg Asp Tyr Ser Ala Lys Lys Ala Ile Leu
                355                 360                 365

Leu Glu Gly Leu Glu Ala Ala Gly Phe Ile Val Tyr Pro Ser Ser Gly
            370                 375                 380

Thr Tyr Tyr Ile Met Val Asp His Thr Pro Phe Gly Phe Asp Ser Asp
385                 390                 395                 400

Val Glu Phe Cys Glu Tyr Leu Ile Arg Glu Val Gly Val Cys Ala Ile
                405                 410                 415

Pro Pro Ser Val Phe Tyr Leu Asp Pro Glu Glu Gly Lys Lys Leu Val
                420                 425                 430

Arg Phe Thr Phe Ser Lys Asp Glu Gly Thr Leu Arg Ala Ala Val Glu
                435                 440                 445

Arg Leu Lys Ala Lys Leu Arg Arg Lys
        450                 455

<210> SEQ ID NO 53
<211> LENGTH: 424
<212> TYPE: PRT
<213> ORGANISM: Gossypium hirsutum

<400> SEQUENCE: 53

Met Gln Ala Ala Glu Cys Thr Trp Thr His Phe Glu Met Leu Arg Pro
1               5                   10                  15

Leu Cys Phe Lys Ser Pro Ser Thr Thr Pro Leu Phe Phe Asn Phe Ser
                20                  25                  30

Lys His Phe Gln Lys Gly Phe Ser Asp Ser Ser Phe Phe Arg Ser Asn
            35                  40                  45

Arg Arg Ile Ser Asn Tyr Pro Ser Phe Met Ala Thr Ile Ser Ser Leu
        50                  55                  60

Ser Thr His Lys Asp Pro Val Ser Thr His Asp Ala Thr Pro Asn Ile
65                  70                  75                  80

Thr His Gln Pro Val Gln Val Ala Lys Arg Leu Glu Lys Phe Lys Thr
                85                  90                  95

Thr Ile Phe Thr Gln Met Ser Met Leu Ala Ile Lys His Gly Ala Ile
                100                 105                 110

Asn Leu Gly Gln Gly Phe Pro Asn Phe Asp Gly Pro Asp Phe Val Lys
            115                 120                 125

Gly Ala Ala Ile Gln Ala Ile Lys Asp Gly Lys Asn Gln Tyr Ala Arg
        130                 135                 140

Gly Tyr Gly Val Pro Asp Phe Asn Asn Ala Ile Ala Ala Arg Phe Lys
145                 150                 155                 160

Lys Asp Thr Gly Leu Val Ile Asp Pro Glu Lys Glu Val Thr Val Thr
                165                 170                 175

Ser Gly Cys Thr Glu Ala Ile Ala Ala Thr Met Leu Gly Leu Ile Asn
                180                 185                 190

Pro Gly Asp Glu Val Ile Leu Phe Ala Pro Phe Tyr Asp Ser Tyr Glu
            195                 200                 205

Ala Thr Leu Ser Met Ala Gly Ala Lys Val Lys Cys Ile Thr Leu Cys
        210                 215                 220

Pro Pro Asp Phe Ala Val Pro Ile Asp Glu Leu Lys Ser Thr Ile Ser
```

```
             225                 230                 235                 240
Lys Asn Thr Arg Ala Ile Leu Ile Asn Thr Pro His Asn Pro Thr Gly
                    245                 250                 255
Lys Met Phe Thr Arg Glu Glu Leu Asn Thr Ile Ala Ser Leu Cys Ile
                    260                 265                 270
Glu Asn Asp Val Leu Val Phe Thr Asp Glu Val Tyr Asp Lys Leu Ala
                    275                 280                 285
Phe Glu Met Asp His Ile Ser Met Ala Ser Leu Pro Gly Met Tyr Glu
                    290                 295                 300
Arg Thr Val Thr Met Asn Ser Leu Gly Lys Thr Phe Ser Leu Thr Gly
305                 310                 315                 320
Trp Lys Ile Gly Trp Ala Ile Ala Pro Pro His Leu Thr Trp Gly Val
                    325                 330                 335
Arg Gln Ala His Ser Phe Leu Thr Phe Ala Thr Ser Thr Pro Met Gln
                    340                 345                 350
Tyr Ala Ala Thr Val Ala Leu Gln Ala Pro Asp Ser Tyr Phe Ala Glu
                    355                 360                 365
Leu Lys Arg Asp Tyr Met Ala Lys Lys Ala Ile Leu Val Gln Gly Leu
                    370                 375                 380
Lys Asp Val Gly Phe Lys Val Phe Pro Ser Ser Gly Thr Tyr Phe Val
385                 390                 395                 400
Val Val Asp His Thr Pro Phe Gly Leu Glu Asn Asp Ile Ala Phe Cys
                    405                 410                 415
Glu Tyr Leu Ile Lys Glu Val Gly
                    420

<210> SEQ ID NO 54
<211> LENGTH: 462
<212> TYPE: PRT
<213> ORGANISM: Ricinus communis

<400> SEQUENCE: 54

Met Gln Ser Gln Cys Thr Trp Thr Gly Thr Arg Met Pro Leu Pro Ile
1               5                   10                  15
Ile Leu Lys Pro Ser Thr Phe Ser Ile Leu Lys His Leu Pro Thr Lys
                20                  25                  30
Arg Thr Asn Leu Phe Ser Thr Arg Ser Pro Ile Ser Asn Tyr Pro Ser
                35                  40                  45
Leu Met Ala Thr Phe Ser Thr Ala Ser Thr Thr Glu Lys Asp Ala Pro
            50                  55                  60
Ser Gly Gln Asn Asp Ser Thr Gln Lys Ser Gln Pro Leu Gln Val
65                  70                  75                  80
Ala Lys Arg Leu Glu Lys Phe Lys Thr Thr Ile Phe Thr Gln Met Ser
                85                  90                  95
Ser Leu Ala Ile Lys His Gly Ala Ile Asn Leu Gly Gln Gly Phe Pro
                100                 105                 110
Asn Phe Asp Gly Pro Glu Phe Val Lys Glu Ala Ala Ile Gln Ala Ile
                115                 120                 125
Arg Asp Gly Lys Asn Gln Tyr Ala Arg Gly Tyr Gly Val Pro Asp Phe
                130                 135                 140
Asn Ser Ala Ile Val Asp Arg Phe Lys Lys Asp Thr Gly Leu Val Val
145                 150                 155                 160
Asp Pro Glu Lys Glu Val Thr Val Thr Ser Gly Cys Thr Glu Ala Ile
                165                 170                 175
```

```
Ala Ala Thr Ile Leu Gly Leu Ile Asp Pro Gly Asp Glu Val Ile Leu
            180                 185                 190

Phe Ala Pro Phe Tyr Asp Ser Tyr Glu Ala Thr Leu Ser Met Ala Gly
        195                 200                 205

Ala Lys Ile Lys Cys Val Thr Leu Gln Pro Pro Asp Phe Ala Val Pro
    210                 215                 220

Ile Asp Glu Leu Lys Ser Ile Ile Ser Lys Asn Thr Arg Ala Ile Leu
225                 230                 235                 240

Ile Asn Thr Pro His Asn Pro Thr Gly Lys Met Phe Thr Arg Glu Glu
                245                 250                 255

Leu Thr Thr Ile Ala Ser Cys Cys Ile Glu Asn Asp Val Leu Val Phe
            260                 265                 270

Thr Asp Glu Val Tyr Asp Lys Leu Ala Phe Glu Met Asp His Ile Ser
        275                 280                 285

Met Ala Ser Leu Pro Gly Met Tyr Glu Arg Thr Val Thr Leu Asn Ser
    290                 295                 300

Leu Gly Lys Thr Phe Ser Leu Thr Gly Trp Lys Ile Gly Trp Ala Ile
305                 310                 315                 320

Ala Pro Pro His Leu Thr Trp Gly Val Arg Gln Ala His Ala Phe Leu
                325                 330                 335

Thr Phe Ala Thr Ser Thr Pro Met Gln Trp Ala Ala Ser Val Ala Leu
            340                 345                 350

Arg Ala Pro Asp Ser Tyr Phe Glu Glu Leu Lys Arg Asp Tyr Met Ala
        355                 360                 365

Lys Lys Ala Ile Leu Val Glu Gly Leu Lys Ala Val Gly Phe Lys Val
    370                 375                 380

Phe Pro Ser Ser Gly Thr Tyr Phe Val Val Asp His Thr Pro Phe
385                 390                 395                 400

Gly Leu Glu Asn Asp Ile Ala Phe Cys Glu His Leu Ile Lys Glu Val
                405                 410                 415

Gly Val Val Ala Ile Pro Thr Ser Val Phe Tyr Leu Asn Pro Glu Glu
            420                 425                 430

Gly Lys Asn Leu Val Arg Phe Thr Phe Cys Lys Asp Glu Gly Thr Leu
        435                 440                 445

Arg Thr Ala Val Glu Arg Met Lys Glu Lys Leu Lys Arg Lys
    450                 455                 460

<210> SEQ ID NO 55
<211> LENGTH: 409
<212> TYPE: PRT
<213> ORGANISM: Populus trichocarpa

<400> SEQUENCE: 55

Met Ala Ser Ser Pro Ser Leu Lys Asp Ala Val Ser Thr Gln Asn Glu
1               5                   10                  15

Ser Thr Gln Lys Thr Gln Gln Pro Leu Gln Val Ala Lys Arg Leu Glu
            20                  25                  30

Lys Phe Lys Thr Thr Ile Phe Thr Gln Met Ser Ser Leu Ala Ile Lys
        35                  40                  45

His Gly Ala Ile Asn Leu Gly Gln Gly Phe Pro Asn Phe Asp Gly Pro
    50                  55                  60

Glu Phe Val Lys Glu Ala Ala Ile Gln Ala Ile Lys Asp Gly Lys Asn
65                  70                  75                  80

Gln Tyr Ala Arg Gly Tyr Gly Val Pro Asp Phe Ser Ser Ala Ile Ala
                85                  90                  95
```

Glu Arg Phe Lys Lys Asp Thr Gly Leu Val Val Asp Pro Glu Lys Glu
            100                 105                 110

Ile Thr Val Thr Ser Gly Cys Thr Glu Ala Ile Ala Ala Thr Met Leu
            115                 120                 125

Gly Leu Ile Asn Pro Gly Asp Glu Val Ile Leu Phe Ala Pro Phe Tyr
130                 135                 140

Asp Ser Tyr Glu Ala Thr Leu Ser Met Ala Gly Ala Lys Ile Lys Cys
145                 150                 155                 160

Ile Thr Leu His Pro Pro Asp Phe Ala Val Pro Ile Asp Glu Leu Lys
            165                 170                 175

Ser Ala Ile Thr Gln Asp Thr Arg Ala Val Leu Ile Asn Thr Pro His
            180                 185                 190

Asn Pro Thr Gly Lys Met Phe Ser Arg Glu Glu Leu Ser Thr Ile Ala
            195                 200                 205

Ser Leu Cys Ile Glu Asn Asp Val Leu Val Phe Thr Asp Glu Val Tyr
            210                 215                 220

Asp Lys Leu Ala Phe Glu Leu Asp His Ile Ser Met Ala Ser Leu Pro
225                 230                 235                 240

Gly Met Tyr Glu Arg Thr Val Thr Leu Asn Ser Leu Gly Lys Thr Phe
            245                 250                 255

Ser Leu Thr Gly Trp Lys Ile Gly Trp Ala Ile Ala Pro His Leu
            260                 265                 270

Thr Trp Gly Val Arg Gln Ala His Ser Phe Leu Thr Phe Ala Thr Ser
            275                 280                 285

Thr Pro Met Gln Trp Ala Ala Val Ala Leu Arg Ala Pro Glu Ser
290                 295                 300

Tyr Phe Val Glu Leu Lys Arg Asp Tyr Met Ala Lys Lys Glu Ile Leu
305                 310                 315                 320

Val Glu Gly Leu Lys Ala Val Gly Phe Lys Val Phe Pro Ser Ser Gly
            325                 330                 335

Thr Tyr Phe Val Val Val Asp His Thr Pro Phe Gly Leu Glu Asn Asp
            340                 345                 350

Ile Ala Phe Cys Glu Tyr Leu Ile Lys Glu Val Gly Val Val Ala Ile
            355                 360                 365

Pro Thr Ser Val Phe Tyr Leu Asn Pro Glu Asp Gly Lys Asn Leu Val
370                 375                 380

Arg Phe Thr Phe Cys Lys Asp Glu Gly Thr Leu Arg Ala Ala Val Asp
385                 390                 395                 400

Arg Met Lys Glu Lys Leu Lys Arg Lys
            405

<210> SEQ ID NO 56
<211> LENGTH: 439
<212> TYPE: PRT
<213> ORGANISM: Glycine max

<400> SEQUENCE: 56

Met Lys Phe Thr Pro Ser Ser Lys Phe Leu Gly Phe Ser Asn His Phe
1               5                   10                  15

His Ser Leu Leu Ala Pro Ser Phe Ser Pro Thr Pro Lys Phe Ser Ser
            20                  25                  30

Ser Phe Ser Ala Thr Met Ser Thr Leu Ser Thr Gln Asn Asp Thr Val
            35                  40                  45

Thr His Lys Thr Gln Gln Pro Leu Gln Ile Ala Lys Arg Leu Glu Lys

```
            50                  55                  60
Phe Gln Thr Thr Ile Phe Thr Gln Met Ser Leu Leu Ala Ile Lys His
 65                  70                  75                  80

Gly Ala Ile Asn Leu Gly Gln Gly Phe Pro Asn Phe Asp Gly Pro Glu
                 85                  90                  95

Phe Val Lys Glu Ala Ala Ile Gln Ala Ile Arg Asp Gly Lys Asn Gln
            100                 105                 110

Tyr Ala Arg Gly Tyr Gly Val Pro Asp Leu Asn Ile Ala Ile Ala Glu
            115                 120                 125

Arg Phe Lys Lys Asp Thr Gly Leu Val Val Asp Pro Glu Lys Glu Ile
        130                 135                 140

Thr Val Thr Ser Gly Cys Thr Glu Ala Ile Ala Ala Thr Met Ile Gly
145                 150                 155                 160

Leu Ile Asn Pro Gly Asp Glu Val Ile Met Phe Ala Pro Phe Tyr Asp
                165                 170                 175

Ser Tyr Glu Ala Thr Leu Ser Met Ala Gly Ala Lys Val Lys Gly Ile
            180                 185                 190

Thr Leu Arg Pro Pro Asp Phe Ala Val Pro Leu Glu Glu Leu Lys Ser
        195                 200                 205

Thr Ile Ser Lys Asn Thr Arg Ala Ile Leu Ile Asn Thr Pro His Asn
210                 215                 220

Pro Thr Gly Lys Met Phe Thr Arg Glu Glu Leu Asn Cys Ile Ala Ser
225                 230                 235                 240

Leu Cys Ile Glu Asn Asp Val Leu Val Phe Thr Asp Glu Val Tyr Asp
                245                 250                 255

Lys Leu Ala Phe Asp Met Glu His Ile Ser Met Ala Ser Leu Pro Gly
            260                 265                 270

Met Phe Glu Arg Thr Val Thr Leu Asn Ser Leu Gly Lys Thr Phe Ser
        275                 280                 285

Leu Thr Gly Trp Lys Ile Gly Trp Ala Ile Ala Pro Pro His Leu Ser
290                 295                 300

Trp Gly Val Arg Gln Ala His Ala Phe Leu Thr Phe Ala Thr Ala His
305                 310                 315                 320

Pro Phe Gln Cys Ala Ala Ala Ala Leu Arg Ala Pro Asp Ser Tyr
                325                 330                 335

Tyr Val Glu Leu Lys Arg Asp Tyr Met Ala Lys Arg Ala Ile Leu Ile
            340                 345                 350

Glu Gly Leu Lys Ala Val Gly Phe Lys Val Phe Pro Ser Ser Gly Thr
        355                 360                 365

Tyr Phe Val Val Val Asp His Thr Pro Phe Gly Leu Glu Asn Asp Val
370                 375                 380

Ala Phe Cys Glu Tyr Leu Val Lys Glu Val Gly Val Ala Ile Pro
385                 390                 395                 400

Thr Ser Val Phe Tyr Leu Asn Pro Glu Glu Gly Lys Asn Leu Val Arg
                405                 410                 415

Phe Thr Phe Cys Lys Asp Glu Glu Thr Ile Arg Ser Ala Val Glu Arg
            420                 425                 430

Met Lys Ala Lys Leu Arg Lys
            435

<210> SEQ ID NO 57
<211> LENGTH: 418
<212> TYPE: PRT
<213> ORGANISM: Physcomitrella patens
```

<400> SEQUENCE: 57

| | | | | | | | | | | | | | | | |
|---|---|---|---|---|---|---|---|---|---|---|---|---|---|---|---|
| Met | Ala | Ser | Leu | Ser | Leu | Ser | Ile | Asn | Gly | Val | Ala | Gln | Glu | Ser | Ala |
| 1 | | | | 5 | | | | | 10 | | | | | 15 | |
| Met | Pro | Ala | Ser | Gln | Asn | Ser | Asp | Pro | Pro | Arg | Val | Gln | Val | Ala | Lys |
| | | | 20 | | | | | 25 | | | | | 30 | | |
| Arg | Leu | Glu | Gln | Phe | Lys | Thr | Thr | Ile | Phe | Thr | Glu | Ile | Ser | Ile | Leu |
| | | | 35 | | | | | 40 | | | | | 45 | | |
| Ala | Ser | Lys | His | Asn | Ala | Ile | Asn | Leu | Gly | Gln | Gly | Phe | Pro | Asn | Phe |
| | 50 | | | | | 55 | | | | | 60 | | | | |
| Asp | Gly | Pro | Glu | Phe | Val | Lys | Asn | Ala | Ala | Ile | Glu | Ala | Ile | Arg | Asp |
| 65 | | | | | 70 | | | | | 75 | | | | | 80 |
| Gly | Gly | Lys | Asn | Gln | Tyr | Ala | Arg | Gly | Phe | Gly | Val | Pro | Gln | Leu | Asn |
| | | | | 85 | | | | | 90 | | | | | 95 | |
| Ala | Ala | Ile | Ala | Glu | Ser | Phe | Asn | Lys | Glu | Ser | Gly | Ile | Val | Val | Asp |
| | | | 100 | | | | | 105 | | | | | 110 | | |
| Pro | Glu | Thr | His | Val | Thr | Val | Thr | Ser | Gly | Cys | Thr | Glu | Ala | Ile | Ala |
| | | | 115 | | | | | 120 | | | | | 125 | | |
| Ala | Thr | Val | Leu | Gly | Leu | Val | Asn | Pro | Gly | Asp | Glu | Ile | Ile | Val | Phe |
| | 130 | | | | | 135 | | | | | 140 | | | | |
| Glu | Pro | Phe | Tyr | Asp | Ser | Tyr | Gln | Ala | Thr | Val | Ser | Met | Ser | Gly | Ala |
| 145 | | | | | 150 | | | | | 155 | | | | | 160 |
| Ile | Leu | Lys | Thr | Val | Thr | Met | Arg | Ala | Pro | Glu | Phe | Ala | Val | Pro | Glu |
| | | | | 165 | | | | | 170 | | | | | 175 | |
| Glu | Glu | Leu | Arg | Ala | Ala | Phe | Ser | Ser | Lys | Thr | Arg | Ala | Ile | Leu | Val |
| | | | 180 | | | | | 185 | | | | | 190 | | |
| Asn | Thr | Pro | His | Asn | Pro | Thr | Gly | Lys | Val | Phe | Pro | Arg | His | Glu | Leu |
| | | | | 195 | | | | | 200 | | | | | 205 | |
| Glu | Leu | Ile | Ala | Ser | Leu | Cys | Lys | Glu | His | Asn | Thr | Leu | Ala | Phe | Cys |
| | 210 | | | | | 215 | | | | | 220 | | | | |
| Asp | Glu | Val | Tyr | Asn | Lys | Leu | Val | Phe | Lys | Gly | Glu | His | Val | Ser | Leu |
| 225 | | | | | 230 | | | | | 235 | | | | | 240 |
| Ala | Ser | Leu | Asp | Gly | Met | Tyr | Glu | Arg | Thr | Val | Thr | Met | Asn | Ser | Leu |
| | | | | 245 | | | | | 250 | | | | | 255 | |
| Gly | Lys | Thr | Phe | Ser | Leu | Thr | Gly | Trp | Lys | Ile | Gly | Trp | Ala | Val | Ala |
| | | | 260 | | | | | 265 | | | | | 270 | | |
| Pro | Pro | His | Leu | Thr | Arg | Gly | Ile | Arg | Leu | Ala | His | Ser | Tyr | Leu | Thr |
| | | | | 275 | | | | | 280 | | | | | 285 | |
| Phe | Ala | Thr | Ala | Thr | Pro | Leu | Gln | Trp | Ala | Ser | Val | Glu | Ala | Leu | Arg |
| | 290 | | | | | 295 | | | | | 300 | | | | |
| Ala | Pro | Asp | Ser | Phe | Tyr | Ala | Glu | Leu | Ile | Lys | Ser | Tyr | Ser | Ala | Lys |
| 305 | | | | | 310 | | | | | 315 | | | | | 320 |
| Lys | Asp | Ile | Leu | Val | Glu | Gly | Leu | Asn | Ser | Val | Gly | Phe | Glu | Val | Tyr |
| | | | | 325 | | | | | 330 | | | | | 335 | |
| Glu | Pro | Glu | Gly | Thr | Tyr | Phe | Val | Met | Val | Asp | His | Thr | Pro | Phe | Gly |
| | | | 340 | | | | | 345 | | | | | 350 | | |
| Phe | Glu | Asn | Asp | Val | Ala | Phe | Cys | Lys | Tyr | Leu | Ile | Glu | Glu | Val | Gly |
| | | | | 355 | | | | | 360 | | | | | 365 | |
| Ile | Ala | Ala | Ile | Pro | Pro | Ser | Val | Phe | Tyr | Thr | Asn | Pro | Glu | Asp | Gly |
| | 370 | | | | | 375 | | | | | 380 | | | | |
| Lys | Asn | Leu | Val | Arg | Phe | Ala | Phe | Cys | Lys | Asp | Glu | Glu | Thr | Leu | Lys |
| 385 | | | | | 390 | | | | | 395 | | | | | 400 |
| Thr | Ala | Val | Glu | Arg | Leu | Arg | Thr | Lys | Leu | Lys | Lys | Ala | Val | Ser | Leu |

Ser Ser

<210> SEQ ID NO 58
<211> LENGTH: 407
<212> TYPE: PRT
<213> ORGANISM: Chlamydomonas sp.

<400> SEQUENCE: 58

```
Met Ala Pro Pro Glu Ala Gly Ala Thr Ala Ala Glu Pro Ser Lys
1               5                   10                  15

Pro Leu Asn Glu Leu Phe Ser Ser Leu Pro Thr Thr Ile Phe Glu Val
            20                  25                  30

Met Ser Lys Leu Ala Met Glu His Ala Ser Val Asn Leu Gly Gln Gly
        35                  40                  45

Phe Pro Asp Ala Glu Gly Pro Glu Ala Met Lys Gln Ile Ala Ser Ala
    50                  55                  60

Ser Met Tyr Asp Phe His Asn Gln Tyr Pro Ser Leu Glu Gly Val Pro
65                  70                  75                  80

Glu Leu Arg Gln Ala Val Ala Ala His Ser Glu Arg Glu Gln Gly Ile
            85                  90                  95

Leu Val Asp Trp Ala Thr Glu Thr Leu Ile Thr Val Gly Ala Thr Glu
            100                 105                 110

Gly Leu Ala Ser Ala Phe Leu Gly Leu Ile Asn Pro Gly Asp Glu Val
            115                 120                 125

Ile Met Phe Asp Pro Met Tyr Asp Ser Tyr Thr Ser Met Ala Lys Arg
130                 135                 140

Ser Gly Ala Val Ile Val Pro Val Arg Leu Arg Leu Pro Asp Phe Ser
145                 150                 155                 160

Val Pro Leu Glu Glu Leu Ala Ala Val Thr Pro Arg Thr Lys Met
            165                 170                 175

Ile Met Ile Asn Thr Pro His Asn Pro Ser Gly Lys Val Phe Thr Arg
            180                 185                 190

Pro Glu Leu Glu Ala Ile Ala Glu Leu Cys Val Arg His Asp Leu Ile
            195                 200                 205

Ala Leu Ser Asp Glu Val Tyr Glu His Leu Val Phe Gly Gly Ala Ala
210                 215                 220

His Val Ser Leu Arg Ser Leu Pro Gly Met Lys Glu Arg Cys Val Arg
225                 230                 235                 240

Leu Gly Ser Ala Gly Lys Thr Phe Ser Phe Thr Ala Trp Lys Val Gly
            245                 250                 255

Trp Met Thr Gly Pro Ala Arg Leu Leu Asn Pro Ile Val Lys Ala His
            260                 265                 270

Gln Phe Leu Val Phe Thr Val Pro Ser Ser Leu Gln Arg Ala Val Ala
            275                 280                 285

His Gly Leu Asp Lys Glu Ala Asp Phe Tyr His Ser Leu Gly Pro Ser
            290                 295                 300

Leu Glu Ala Lys Arg Arg Tyr Leu Glu Ala Glu Leu Thr Ala Leu Gly
305                 310                 315                 320

Phe Asp Cys Leu Pro Ala His Gly Ala Tyr Phe Leu Val Ala Asp Phe
            325                 330                 335

Gln Arg Pro Gly Glu Asp Asp Ala Asp Phe Ala Lys Arg Leu Thr Ala
            340                 345                 350

Glu Gly Gly Val Thr Thr Ile Pro Ile Ser Gly Phe Tyr Val Gly Pro
```

```
                355                 360                 365
Arg Pro Pro Thr His Leu Val Arg Phe Cys Tyr Cys Lys Glu Asp Ile
    370                 375                 380

Lys Leu Gln Ala Ala Val Glu Arg Leu Lys Ala Tyr Val Gly Pro Gly
385                 390                 395                 400

Gly Lys Gly Ala Pro Gln Val
                405

<210> SEQ ID NO 59
<211> LENGTH: 279
<212> TYPE: PRT
<213> ORGANISM: Artificial Sequence
<220> FEATURE:
<223> OTHER INFORMATION: Consensus Sequence

<400> SEQUENCE: 59

Val Ala Lys Arg Leu Glu Lys Phe Lys Thr Thr Ile Phe Thr Gln Met
1               5                   10                  15

Ser Leu Ala Lys His Gly Ala Ile Asn Leu Gly Gln Gly Phe Pro Asn
            20                  25                  30

Phe Asp Gly Pro Phe Val Lys Ala Ala Ile Ala Ile Gly Asn Gln Tyr
        35                  40                  45

Ala Arg Gly Gly Val Pro Asn Ala Ala Arg Phe Lys Asp Gly Leu Val
    50                  55                  60

Asp Pro Lys Glu Thr Val Thr Ser Gly Cys Thr Glu Ala Ile Ala Ala
65                  70                  75                  80

Thr Leu Gly Leu Ile Asn Pro Gly Asp Glu Val Ile Phe Ala Pro Phe
                85                  90                  95

Tyr Asp Ser Tyr Glu Ala Thr Ile Ser Met Ala Gly Ala Lys Thr Leu
            100                 105                 110

Pro Asp Phe Val Pro Glu Leu Thr Arg Ala Ile Asn Thr Pro His Asn
        115                 120                 125

Pro Thr Gly Lys Met Phe Thr Arg Glu Glu Leu Ile Ala Leu Cys Glu
    130                 135                 140

Asn Asp Val Leu Phe Asp Glu Val Tyr Asp Lys Leu Phe His Ile Ser
145                 150                 155                 160

Ala Ser Pro Gly Met Glu Arg Thr Val Thr Asn Ser Leu Gly Lys Thr
                165                 170                 175

Phe Ser Leu Thr Gly Trp Lys Ile Gly Trp Ala Ala Pro Pro His Leu
            180                 185                 190

Thr Trp Gly Arg Gln Ala His Phe Leu Thr Phe Ala Thr Pro Gln Ala
        195                 200                 205

Ala Ala Leu Ala Pro Ser Tyr Glu Leu Arg Asp Tyr Ala Lys Leu Gly
    210                 215                 220

Leu Gly Phe Val Pro Ser Ser Gly Thr Tyr Phe Val Asp His Thr Pro
225                 230                 235                 240

Phe Gly Asp Phe Cys Glu Tyr Leu Glu Val Gly Val Ala Ile Pro Ser
                245                 250                 255

Val Phe Tyr Pro Glu Gly Lys Leu Val Arg Phe Phe Cys Lys Asp Thr
            260                 265                 270

Leu Ala Val Arg Lys Lys Leu
        275

<210> SEQ ID NO 60
<211> LENGTH: 319
<212> TYPE: PRT
```

```
<213> ORGANISM: Artificial Sequence
<220> FEATURE:
<223> OTHER INFORMATION: Consensus Sequence

<400> SEQUENCE: 60

Gln Val Ala Lys Arg Leu Glu Lys Phe Lys Thr Thr Ile Phe Thr Gln
1               5                   10                  15

Met Ser Leu Ala Ile Lys His Gly Ala Ile Asn Leu Gly Gln Gly Phe
                20                  25                  30

Pro Asn Phe Asp Gly Pro Phe Val Lys Glu Ala Ala Ile Gln Ala Ile
            35                  40                  45

Gly Lys Asn Gln Tyr Ala Arg Gly Tyr Gly Val Pro Asn Ala Ile Ala
        50                  55                  60

Arg Phe Lys Asp Gly Leu Val Asp Pro Glu Lys Glu Thr Val Thr Ser
65                  70                  75                  80

Gly Cys Thr Glu Ala Ile Ala Ala Thr Leu Gly Leu Ile Asn Pro Gly
                85                  90                  95

Asp Glu Val Ile Leu Phe Ala Pro Phe Tyr Asp Ser Tyr Glu Ala Thr
                100                 105                 110

Leu Ser Met Ala Gly Ala Lys Ile Thr Leu Pro Pro Asp Phe Ala Val
            115                 120                 125

Pro Glu Leu Lys Ser Lys Thr Arg Ala Ile Ile Asn Thr Pro His Asn
130                 135                 140

Pro Thr Gly Lys Met Phe Thr Arg Glu Glu Leu Ile Ala Leu Cys Glu
145                 150                 155                 160

Asn Asp Val Leu Phe Asp Glu Val Tyr Asp Lys Leu Ala Phe Glu Asp
                165                 170                 175

His Ile Ser Met Ala Ser Pro Gly Met Tyr Glu Arg Thr Val Thr Asn
            180                 185                 190

Ser Leu Gly Lys Thr Phe Ser Leu Thr Gly Trp Lys Ile Gly Trp Ala
        195                 200                 205

Ile Ala Pro Pro His Leu Thr Trp Gly Val Arg Gln Ala His Phe Leu
        210                 215                 220

Thr Phe Ala Thr Thr Pro Met Gln Ala Ala Ala Leu Arg Ala Pro Asp
225                 230                 235                 240

Ser Tyr Glu Leu Lys Arg Asp Tyr Ala Lys Lys Leu Val Gly Leu Lys
                245                 250                 255

Gly Phe Val Pro Ser Ser Gly Thr Tyr Phe Val Val Asp His Thr Pro
            260                 265                 270

Phe Gly Asn Asp Phe Cys Glu Tyr Leu Ile Glu Val Gly Val Val Ala
            275                 280                 285

Ile Pro Ser Val Phe Tyr Leu Pro Glu Gly Lys Asn Leu Val Arg Phe
        290                 295                 300

Thr Phe Cys Lys Asp Thr Leu Arg Ala Val Arg Met Lys Lys Leu
305                 310                 315
```

What is claimed is:

1. A nucleic acid construct comprising a heterologous plant promoter operably linked to an isolated polynucleotide having a sequence selected from the group consisting of (a) the nucleotide sequence of SEQ ID NO: 45; (b) a nucleotide sequence having at least 90% identity to SEQ ID NO: 45, and encoding a polypeptide having glutamine phenylpyruvate transaminase (GPT) activity; (c) a nucleotide sequence encoding the polypeptide of SEQ ID NO: 46, or a polypeptide having at least 90% sequence identity thereto which has GPT activity; and, (d) a nucleotide sequence encoding the polypeptide of SEQ ID NO: 46 truncated at its amino terminus by between 30 to 56 amino acid residues, or a polypeptide having at least 90% sequence identity thereto which has GPT activity.

2. The nucleic acid construct of claim 1 comprising the nucleotide sequence of SEQ ID NO: 45 or the nucleotide sequence which encodes a polypeptide of SEQ ID NO: 46.

3. The nucleic acid construct according to claim 1, wherein the heterologous promoter is a tissue-specific promoter.

4. A vector comprising the nucleic acid construct of claim 1.

5. A host cell comprising the nucleic acid construct of claim 1, or comprising a vector which comprises the nucleic acid construct of claim 1.

6. The host cell of claim 5, which is a plant cell.

7. The plant cell of claim 6, wherein the plant cell expresses the polynucleotide.

8. A plant organ, embryo or seed comprising the nucleic acid construct according to claim 1, wherein the plant organ, embryo or seed expresses the polynucleotide.

9. A transgenic plant comprising the nucleic acid construct of claim 1, or comprising a vector which comprises the nucleic acid construct of claim 1, wherein the transgenic plant expresses the polynucleotide.

10. A progeny of the transgenic plant according to claim 9, wherein the progeny comprises the nucleic acid construct of claim 1.

11. A nucleic acid construct comprising a heterologous plant promoter operably linked to an isolated polynucleotide having a nucleic acid sequence which is fully complementary to the isolated polynucleotide of claim 1.

12. A seed of any generation of the transgenic plant of claim 9 or a seed of a progeny of the transgenic plant according to claim 9, wherein the progeny comprises the nucleic acid construct of claim 1.

13. A plant of any generation of the seed of claim 12, wherein said plant comprises the nucleic acid construct of claim 1.

14. The plant cell of claim 7, wherein the plant cell has higher GPT activity in comparison to an analogous plant cell of a wild-type or untransformed plant.

15. The plant cell of claim 7, wherein the plant cell has a higher concentration of 2-oxoglutaramate in comparison to an analogous plant cell of a wild-type or untransformed plant.

16. The plant organ, embryo or seed of claim 8, wherein the plant organ, embryo or seed has higher GPT activity in comparison to an analogous plant organ, embryo or seed of a wild-type or untransformed plant.

17. The plant organ, embryo or seed of claim 8, wherein the plant organ, embryo or seed has a higher concentration of 2-oxoglutaramate in comparison to an analogous plant organ, embryo or seed of a wild-type or untransformed plant.

18. The transgenic plant of claim 9, wherein the transgenic plant has higher GPT activity in comparison to an analogous wild-type or untransformed plant.

19. The transgenic plant of claim 9, wherein the transgenic plant has a higher concentration of 2-oxoglutaramate in comparison to an analogous wild-type or untransformed plant.

20. The transgenic plant of claim 9, wherein the transgenic plant displays increased biomass yield when compared to an analogous wild-type or untransformed plant.

21. The transgenic plant of claim 9, wherein the transgenic plant has at least one increased growth characteristic selected from the group consisting of increased biomass, earlier flowering, earlier budding, increased plant height, increased flowering, increased budding, larger leaves, increased fruit or pod yield, and increased seed yield.

22. The transgenic plant of claim 9, wherein the transgenic plant has an increased leaf-to-root ratio of glutamine synthetase activity in comparison to an analogous wild-type or untransformed plant.

23. The nucleic acid construct according to claim 1, wherein the heterologous promoter is a constitutive promoter.

* * * * *